US011473083B2

(12) United States Patent
Polydoro Ofengeim et al.

(10) Patent No.: US 11,473,083 B2
(45) Date of Patent: Oct. 18, 2022

(54) COMPOSITIONS AND METHODS FOR DECREASING TAU EXPRESSION

(71) Applicant: NOVARTIS AG, Basel (CH)

(72) Inventors: Manuela Polydoro Ofengeim, Brookline, MA (US); Jan Weiler, Newton, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/383,452

(22) Filed: Dec. 19, 2016

(65) Prior Publication Data

US 2017/0175116 A1 Jun. 22, 2017

Related U.S. Application Data

(60) Provisional application No. 62/270,165, filed on Dec. 21, 2015.

(51) Int. Cl.
*C12N 15/113* (2010.01)
*A61K 31/711* (2006.01)
*A61K 31/7115* (2006.01)
*A61K 48/00* (2006.01)
*A61K 31/7125* (2006.01)

(52) U.S. Cl.
CPC ........ *C12N 15/113* (2013.01); *A61K 31/7125* (2013.01); *C12N 2310/11* (2013.01); *C12N 2310/315* (2013.01); *C12N 2310/321* (2013.01); *C12N 2310/322* (2013.01); *C12N 2310/3341* (2013.01); *C12N 2310/341* (2013.01); *C12N 2310/346* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 5,627,274 A | 5/1997 | Dominski | |
| 5,665,593 A | 9/1997 | Dominski | |
| 5,789,573 A | 8/1998 | Baker | |
| 5,837,853 A | 11/1998 | Shiratsuchi | |
| 5,916,808 A | 6/1999 | Dominski | |
| 5,976,879 A | 11/1999 | Dominski | |
| 6,071,694 A | 6/2000 | Shiratsuchi | |
| 6,200,768 B1 | 3/2001 | Biernat | |
| 6,248,559 B1 | 6/2001 | Shiratsuchi | |
| 6,350,868 B1 | 2/2002 | Hiller | |
| 6,451,991 B1 | 9/2002 | Martin et al. | |
| 6,475,723 B2 | 11/2002 | Goate | |
| 6,664,443 B1 | 12/2003 | McGowan | |
| 7,176,290 B2 | 2/2007 | Mandelkow | |
| 7,250,496 B2 | 7/2007 | Bentwich | |
| 7,312,035 B2 | 12/2007 | Makeev | |
| 7,408,027 B1 | 8/2008 | Mandelkow | |
| 7,442,516 B2 | 10/2008 | Ishiguro | |
| 7,618,814 B2 | 11/2009 | Bentwich | |
| 7,687,616 B1 | 3/2010 | Bentwich | |
| 7,696,334 B1 | 4/2010 | Bentwich | |
| 7,696,342 B1 | 4/2010 | Bentwich | |
| 7,759,478 B1 | 7/2010 | Bentwich | |
| 7,790,867 B2 | 9/2010 | Bentwich | |
| 7,807,816 B2 | 10/2010 | Fletcher | |
| 7,833,513 B2 | 11/2010 | De La Monte | |
| 7,838,657 B2 | 11/2010 | Singh | |
| 7,888,497 B2 | 2/2011 | Bentwich | |
| 7,901,882 B2 | 3/2011 | Davies | |
| 7,906,326 B2 | 3/2011 | Bentwich | |
| 8,039,608 B1 | 10/2011 | Bentwich | |
| 8,084,598 B1 | 12/2011 | Bentwich | |
| 8,110,560 B2 | 2/2012 | Singh | |
| 8,163,896 B1 | 4/2012 | Bentwich | |
| 8,207,316 B1 | 6/2012 | Bentwich | |
| 8,258,109 B2 | 9/2012 | Freier | |
| 8,329,890 B2 | 12/2012 | Davidson | |
| 8,361,980 B2 | 1/2013 | Abrahamsen | |
| 8,404,659 B2 | 3/2013 | Abrahamsen | |
| 8,501,703 B2 | 8/2013 | Dean | |
| 8,586,559 B2 | 11/2013 | Singh | |
| 8,637,483 B2 | 1/2014 | Meloni | |
| 8,709,716 B2 | 4/2014 | Davies | |
| 8,791,088 B2 | 7/2014 | Freier | |
| 8,871,729 B2 | 10/2014 | Gomez-Acebo Gullon | |
| 9,034,837 B2 | 5/2015 | Lanford | |
| 9,084,813 B2 | 7/2015 | Roberson | |
| 9,145,557 B2 | 9/2015 | Udesen | |
| 9,157,081 B2 | 10/2015 | Kopczynski | |
| 2002/0010947 A1 | 1/2002 | Abraham | |
| 2002/0026651 A1 | 2/2002 | Goate | |
| 2002/0052331 A1 | 5/2002 | Baker | |

(Continued)

FOREIGN PATENT DOCUMENTS

EP 0616032 A2 9/1994
EP 2578692 A1 4/2013

(Continued)

OTHER PUBLICATIONS

Exiqon, 2' O-Methyl bases, downloaded Jul. 6, 2018, p. 1.*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
IDT, Antisense Technologies, downloaded Jul. 6, 2018, pp. 1-11.*
Mazur et al, Brain pharmacology of intrathecal antisense oligonucleotides revealed through multimodal imaging,Insight. 2019, pp. 1-19.*

(Continued)

*Primary Examiner* — Maria Marvich

(74) *Attorney, Agent, or Firm* — Yichen Liu

(57) ABSTRACT

Provided herein are compositions and methods for decreasing tau mRNA and protein expression. These compositions and methods are useful in treating tau-related diseases and disorders.

10 Claims, 14 Drawing Sheets

Specification includes a Sequence Listing.

(56) References Cited

U.S. PATENT DOCUMENTS

| | | |
|---|---|---|
| 2002/0058637 A1 | 5/2002 | Shiratsuchi |
| 2002/0188106 A1 | 12/2002 | Mandelkow |
| 2004/0186071 A1 | 9/2004 | Malik |
| 2004/0219515 A1 | 11/2004 | Bentwich |
| 2004/0241854 A1 | 12/2004 | Davidson |
| 2005/0130924 A1 | 6/2005 | Gaarde |
| 2005/0181460 A1 | 8/2005 | Imagawa |
| 2005/0222399 A1 | 10/2005 | Bentwich |
| 2005/0244851 A1 | 11/2005 | Blume |
| 2006/0051770 A1 | 3/2006 | Makeev |
| 2006/0257851 A1 | 11/2006 | Bentwich |
| 2007/0031823 A1 | 2/2007 | Bentwich |
| 2007/0042380 A1 | 2/2007 | Bentwich |
| 2007/0042437 A1 | 2/2007 | Wands |
| 2007/0048756 A1 | 3/2007 | Shapero |
| 2007/0050146 A1* | 3/2007 | Bentwich ............ C12N 15/111 702/19 |
| 2007/0077553 A1 | 4/2007 | Bentwich |
| 2007/0106066 A1 | 5/2007 | Cherkasky |
| 2007/0134655 A1* | 6/2007 | Bentwich ............ C12N 15/113 435/6.1 |
| 2007/0161589 A1 | 7/2007 | Siwkowski |
| 2007/0243546 A1 | 10/2007 | Davies |
| 2007/0292408 A1 | 12/2007 | Singh |
| 2008/0176812 A1 | 7/2008 | Miller |
| 2008/0188428 A1 | 8/2008 | Bentwich |
| 2008/0249058 A1 | 10/2008 | Mucke |
| 2009/0176728 A1 | 7/2009 | Anton |
| 2009/0280110 A1 | 11/2009 | King |
| 2010/0021914 A1 | 1/2010 | Moeller |
| 2010/0087511 A1 | 4/2010 | Singh |
| 2011/0039332 A1 | 2/2011 | Sakurada |
| 2011/0166037 A1 | 7/2011 | Davies |
| 2011/0244561 A1 | 10/2011 | Davidson |
| 2012/0165394 A1 | 6/2012 | Singh |
| 2012/0184031 A1 | 7/2012 | Bennett |
| 2012/0198573 A1 | 8/2012 | Mucke |
| 2012/0295819 A1* | 11/2012 | Leamon ............ C12Q 1/6806 506/26 |
| 2013/0079505 A1 | 3/2013 | Moeller |
| 2013/0130231 A1 | 5/2013 | Bentwich |
| 2014/0005374 A1 | 1/2014 | Dean |
| 2014/0010861 A1 | 1/2014 | Bancel et al. |
| 2014/0065171 A1 | 3/2014 | Bursulaya |
| 2014/0065206 A1 | 3/2014 | Roberson |
| 2014/0066492 A1 | 3/2014 | Singh |
| 2014/0142160 A1 | 5/2014 | Lee |
| 2014/0171373 A1 | 6/2014 | Le Naour |
| 2014/0309282 A1 | 10/2014 | Freier |
| 2014/0315977 A1 | 10/2014 | Bestwick |
| 2014/0323544 A1 | 10/2014 | Bestwick |
| 2014/0329881 A1 | 11/2014 | Bestwick |
| 2014/0350067 A1 | 11/2014 | Meloni |
| 2015/0018223 A1 | 1/2015 | Hall |
| 2015/0038352 A1 | 2/2015 | Davies |
| 2015/0104468 A1 | 4/2015 | Bursulaya |
| 2015/0259418 A1 | 9/2015 | Barth et al. |
| 2015/0275205 A1 | 10/2015 | Miller et al. |
| 2016/0145617 A1* | 5/2016 | Kordasiewicz ........ C07H 21/02 514/44 A |
| 2016/0237427 A1* | 8/2016 | Olson .................... A61P 25/28 |
| 2017/0035860 A1* | 2/2017 | Flynn ................. A61K 38/465 |
| 2017/0137814 A1* | 5/2017 | Weiler ................. C12N 15/113 |

FOREIGN PATENT DOCUMENTS

| | | |
|---|---|---|
| WO | 9110671 A1 | 7/1991 |
| WO | 1993011231 A1 | 6/1993 |
| WO | 9426887 A1 | 11/1994 |
| WO | 9745437 A1 | 12/1997 |
| WO | 9957129 A1 | 11/1999 |
| WO | 0064262 A1 | 11/2000 |
| WO | 0153340 A2 | 7/2001 |
| WO | 02055681 A2 | 7/2002 |
| WO | 2004003134 A2 | 1/2004 |
| WO | 2004013280 A2 | 2/2004 |
| WO | 2004016655 A1 | 2/2004 |
| WO | 04044123 A2 | 5/2004 |
| WO | 04048511 A2 | 6/2004 |
| WO | 2004058940 A2 | 7/2004 |
| WO | 2005017143 A1 | 2/2005 |
| WO | 2006060753 A2 | 6/2006 |
| WO | 2007028065 A2 | 3/2007 |
| WO | 2007047913 A2 | 4/2007 |
| WO | 07107789 A2 | 9/2007 |
| WO | 2007107789 A2 | 9/2007 |
| WO | 2007112753 A2 | 10/2007 |
| WO | 2007112754 A2 | 10/2007 |
| WO | 2007123723 A2 | 11/2007 |
| WO | 2008002620 A2 | 1/2008 |
| WO | 2008124066 A1 | 10/2008 |
| WO | 2009109665 A1 | 9/2009 |
| WO | 2010122538 A1 | 10/2010 |
| WO | 2011057350 A1 | 5/2011 |
| WO | 2011094645 A1 | 8/2011 |
| WO | 2011117353 A1 | 9/2011 |
| WO | 2012065143 A1 | 5/2012 |
| WO | 2012069059 A1 | 5/2012 |
| WO | 2012087983 A1 | 6/2012 |
| WO | 13013165 A2 | 1/2013 |
| WO | 2013148260 A1 | 10/2013 |
| WO | 2013148283 A1 | 10/2013 |
| WO | 13184514 A1 | 12/2013 |
| WO | 2014100714 A1 | 6/2014 |
| WO | 2014153220 A2 | 9/2014 |
| WO | 2014153236 A1 | 9/2014 |
| WO | 2014153240 A2 | 9/2014 |
| WO | 14201306 A1 | 12/2014 |
| WO | 2015010135 A2 | 1/2015 |
| WO | 15068075 A2 | 5/2015 |
| WO | 16019063 A1 | 2/2016 |
| WO | 16126995 A | 8/2016 |
| WO | 16127000 A1 | 8/2016 |
| WO | 16127002 A1 | 8/2016 |
| WO | WO 2016126995 * | 8/2016 |

OTHER PUBLICATIONS

Godfrey et al., Delivery is key: lessons learnt from developing splice-switching antisense therapies, EMBO Mol Med (2017) 9: 545-557.*

Gao etal, Tau in neurodegenerative disease, Ann Transl Med 2018;6(10):175, pp. 1-3.*

Jafar et al., The atlas of RNase H antisense oligonucleotide distribution and activity in the CNS of rodents and non-human primates following central administration, bioRxiv, 2020, pp. 1-35.*

Lee et al, Recent tau-targeted clinical strategies for the treatment of Alzheimer's disease, FutureMed. Chem. (2019) 11(15), 1845-1848.*

Weingarten, Murray D., et al., "A Protein Factor Essential for Microtubule Assembly", Proc. Nat. Acad. Sci. USA, 72(5):1852-1862, (1975).

Andreadis, Athena, et al., "Structure and Novel Exons of the Human tau Gene", Biochemistry, 31:10626-10633, (1992).

Miller, Victor M., et al., "Allele-specific silencing of dominant disease genes", Proc. Nat. Acad. Sci. USA, 100(12):7195-7200, (2003).

Caceres & Kosik, "Inhibition of neurite polarity by tau antisense oligonucleotides in primary cerebellar neurons", Nature, 343:461-463, (1990).

Caceres, A., et al., "The Effect of Tau Antisense Oligonucleotides on Neurite Formation of Cultured Cerebellar Macroneurons", Jounral of Neuroscience, 11(6):1515-1523, (1991).

Pizzi, M., et al., "Antisense Strategy Unravels Tau Proteins as Molecular Risk Factors for Glutamate-Induced Neurodegeneration", Cellular and Molecular Neurobiology, 14(5):569-578, (1994).

Pizzi, M., et al., "Inhibition of Glutamate-induced Neurotoxicity by a Tau Antisense Oligonucleotide in Primary culture of Rat Cerebellar Granule Cells", European Journal of Neuroscience, 7:1603-1613, (1995).

(56) References Cited

OTHER PUBLICATIONS

Memo, "Application of Antisense Technology for Studying the Functional Role of Tau Proteins in Neural Plasticity", Antisense Strategies for the Study of Receptor Mechanisms, Chapter 12, pp. 189-199, (1996).

* cited by examiner

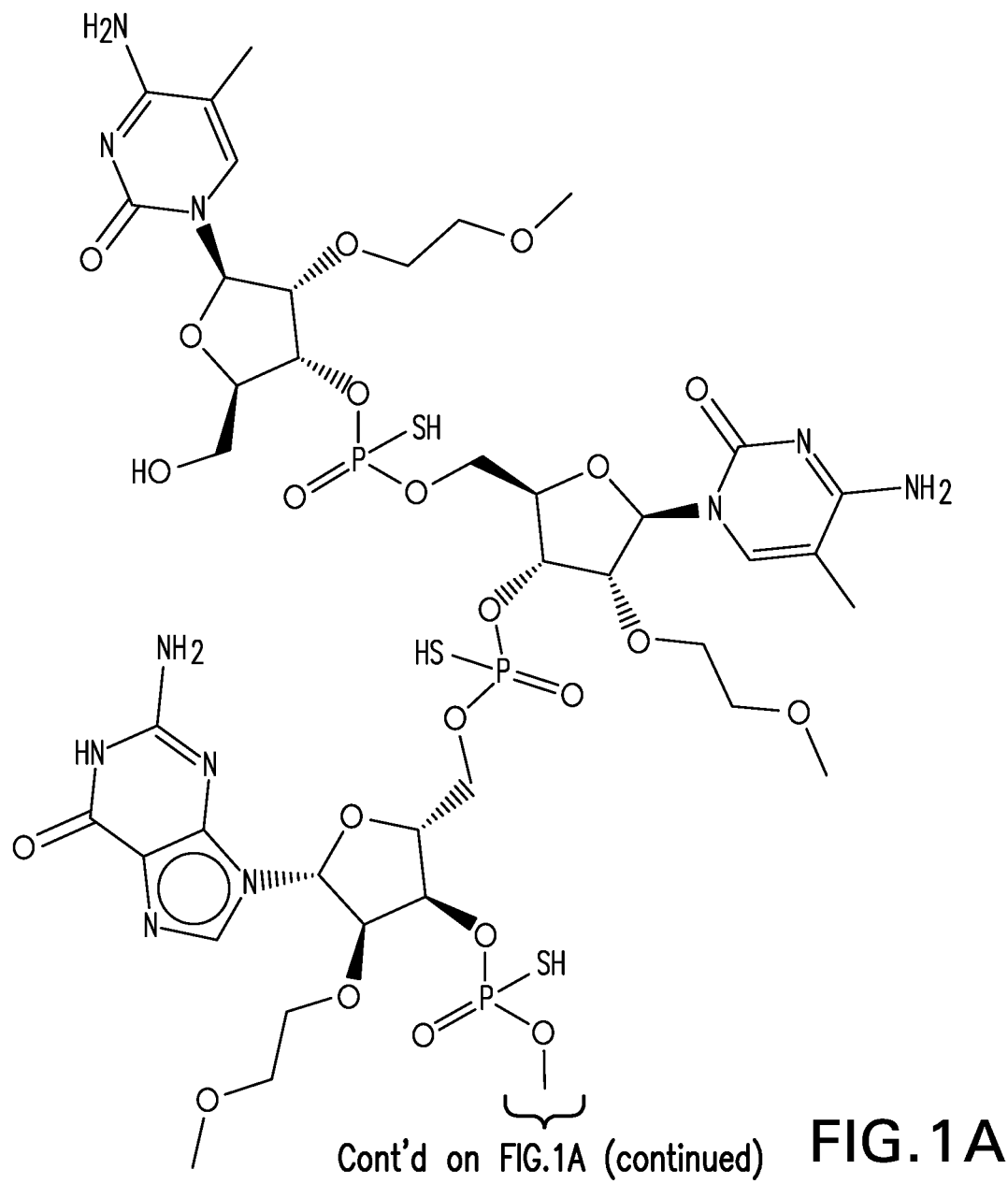
Cont'd on FIG.1A (continued)    FIG.1A

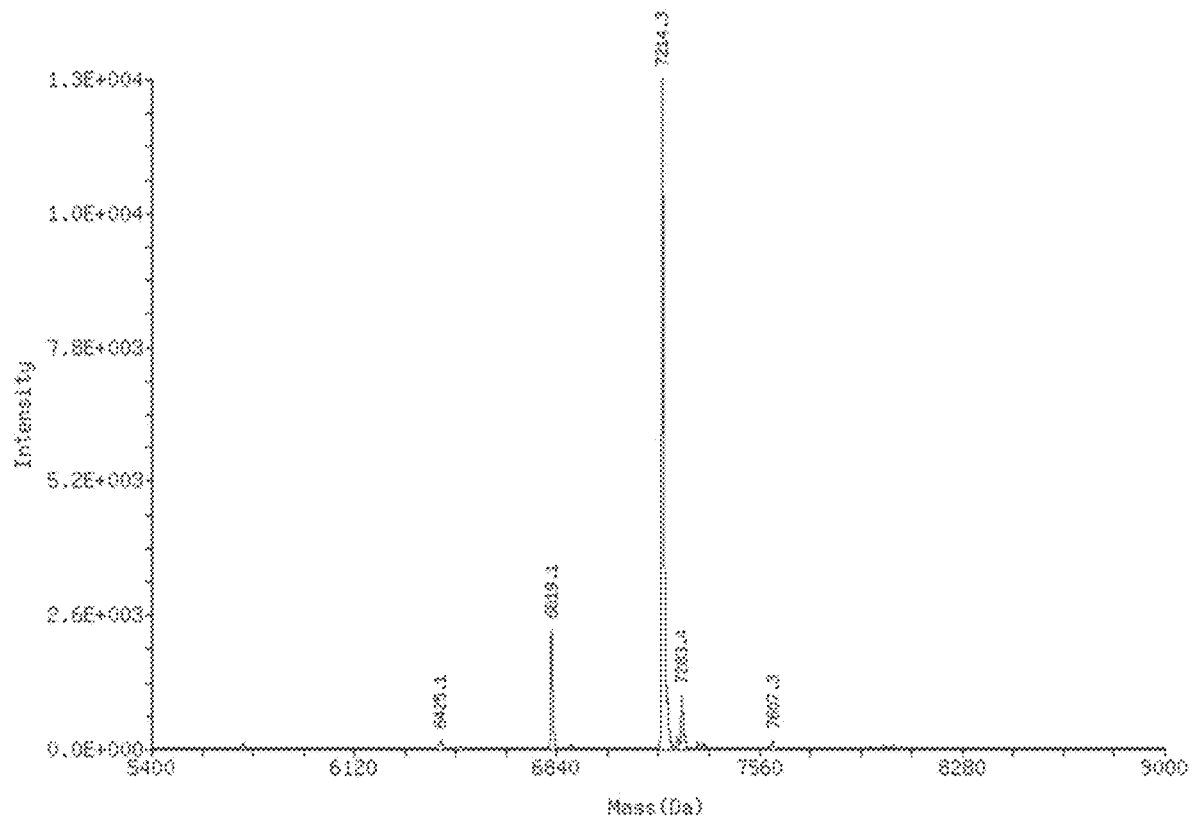

FIG. 2A Forebrain Isoforms Transcripts RT-PCR

FIG. 2B Forebrain Isoforms Western Blot

FIG. 2C Human Tau distribution Immunohistochemistry

FIG. 2D Tau mRNA knock-down 4 weeks after ASO treatment in Cortex

FIG. 2E Tau protein knockdown 4 weeks after ASO treatment in Hippocampus

COMPOSITIONS AND METHODS FOR DECREASING TAU EXPRESSION

CROSS-REFERENCE TO RELATED APPLICATIONS

This application claims the benefit of U.S. Provisional Application No. 62/270,165, filed Dec. 21, 2015, which is incorporated by reference herein in its entirety.

TECHNICAL FIELD

The present invention provides compositions and methods for decreasing tau mRNA and protein expression. These compositions and methods are useful for treating tau-associated diseases.

BACKGROUND

Tau is a microtubule-associated protein that stabilizes microtubules and facilitates axonal transport. Tau protein interacts with tubulin to stabilize the microtubules and promote tubulin assembly into microtubules. The microtubule network is involved in many important cellular processes, including forming cytoskeleton and maintaining the structure and morphology of the cell, and providing platforms for intracellular transport of vesicles, organelles and macromolecules. Since binding of tau to microtubules stabilizes the microtubules, tau is a key mediator of these cellular processes.

At least six tau isoforms exist in human brain, ranging from 352-441 amino acid residues long. The tau isoforms are derived from a single gene MAPT (microtubule-associated protein tau) located on chromosome 17. MAPT transcript undergoes complex, regulated alternative splicing, giving rise to multiple mRNA species. Exons 2 and 3 of MAPT encode a 29- or 58-amino acid sequence respectively, and thus alternative splicing of exons 2 and/or 3 leads to inclusion of zero, one, or two copies of the N-terminal 29 amino acid acidic domain, which are referred to as 0N, 1N, or 2N tau, respectively. Exon 10 of MAPT encodes a microtubule-binding domain, thus inclusion of exon 10 leads to the presence of an additional microtubule-binding domain. Since there are three microtubule-binding domains elsewhere in tau, the tau isoforms that include exon 10 are referred to as "4R tau," which means the tau protein with four repeats of microtubule-binding domain. The tau isoforms without exon 10 are referred to as "3R tau", which means the tau protein with three repeats of microtubule-binding domain. The 4R tau isoforms presumably bind microtubules better than the 3R tau isoforms since they have one more microtubule-binding domain. The ratio of 3R tau to 4R tau is developmentally regulated, with fetal tissues expressing exclusively 3R tau and adult human tissues expressing approximately equal levels of 3R tau and 4R tau.

Tau is a phosphoprotein with approximately 85 potential phosphorylation sites (Ser, Thr, or Tyr) on the longest tau isoform (Pedersen and Sigurdsson, Trends in Molecular Medicine 2015, 21 (6): 394). Phosphorylation has been reported on approximately half of these sites in normal tau proteins. Tau is dynamically phosphorylated and dephosphorylated during the cell cycle. Tau can only associate with microtubules in its dephosphorylated form, and thus phosphorylation of tau acts as a direct microtubule association-dissociation switch within the neuron. Under pathological conditions, tau protein becomes hyperphosphorylated, resulting in a loss of tubulin binding and destabilization of microtubules, followed by the aggregation and deposition of tau in pathogenic neurofibrillary tangles. Protease cleavage fragments of tau (Asp13. Glu391, and Asp421) have also been identified in neurofibrillary tangles.

SUMMARY OF THE INVENTION

Provided herein are antisense oligonucleotides targeting human microtubule-associated protein tau (MAPT), compositions comprising the antisense oligonucleotides, and methods for decreasing tau mRNA and protein expression using these antisense oligonucleotides. The compositions and methods provided herein are useful in treating tau-associated diseases.

In one aspect, provided herein are oligonucleotides comprising a nucleobase sequence that has at least 70% (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any of the nucleobase sequences provided in Tables 2-17, wherein C in any of the nucleobase sequences is either cytosine or 5-methylcytosine, and wherein at least one nucleotide of the oligonucleotide has a 2'-modification. These oligonucleotides are antisense oligonucleotides targeting human MAPT. The 2'-modification can be selected from the group consisting of 2'-fluoro, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyl-oxyethyl (2'-O-DMAEOE), and 2'-O—N-methylacetamido (2'-O-NMA). In some embodiments, the 2'-modification is 2'-O-methoxyethyl (2'-O-MOE). In some embodiments, each C in any of the nucleobase sequences is 5-methylcytosine.

In some embodiments, the antisense oligonucleotides provided herein are 12 to 30 nucleobases in length. For example, an antisense oligonucleotide targeting MAPT can comprise 12, 13, 14, 15, 16, 17, 18, 19, 20, 21, 22, 23, 24, 25, 26, 27, 28, 29, or 30 nucleobases. In some embodiments, the antisense oligonucleotides targeting MAPT are 12 to 25 nucleobases in length. For example, an antisense oligonucleotide targeting MAPT can comprise 12, 13, 14, 15, 16, 17, 18, 19, 20, 21, 22, 23, 24, or 25 nucleobases. In some embodiments, the antisense oligonucleotides targeting MAPT are 15 to 20 nucleobases in length. For example, an antisense oligonucleotide targeting MAPT can comprise 15, 16, 17, 18, 19, or 20 nucleobases.

In some embodiments, the antisense oligonucleotides targeting MAPT provided herein are steric blockers. Such antisense oligonucleotides decrease tau mRNA and/or protein expression independent of RNAse H. The internucleoside linkage of steric blockers can be either phosphodiester or phosphorothioate linkages. In some embodiments, the antisense oligonucleotides targeting MAPT provided herein are steric blockers comprising a nucleobase sequence that has at least 70% (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any of the sequences provided in Tables 2-8, wherein C in any of the nucleobase sequences is either cytosine or 5-methylcytosine, and wherein each nucleotide of the oligonucleotide has a 2'-modification. In some embodiments, an antisense oligonucleotide targeting MAPT comprises a nucleobase sequence that has at least 80% sequence identity to any of the sequences provided in Tables 2-8. In some embodiments, an antisense oligonucleotide targeting MAPT comprises a nucleobase sequence that has at least 90% sequence identity to any of the nucleobase sequences provided in Tables 2-8. In some embodiments, an antisense oligonucleotide targeting MAPT comprises any of the nucleobase sequences provided in Tables 2-8. In some embodiments, an antisense oligonucleotide targeting MAPT consists of any of the nucleobase sequences provided in Tables 2-8. In some embodiments, each C in any of the nucleobase sequences is 5-methylcytosine.

In some embodiments, an antisense oligonucleotide targeting MAPT has 2'-O-MOE modification at each nucleotide subunit.

In some embodiments, an antisense oligonucleotide targeting MAPT comprises a linker attached to the 3' end of the oligonucleotide through a phosphate bridge, and the oligonucleotide has any of the following structures:

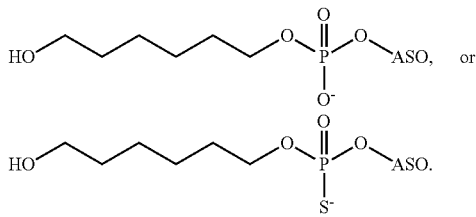

In some embodiments, the antisense oligonucleotides targeting MAPT provided herein are gapmers, which have a central gap segment of contiguous 2'-deoxyribonucleotides, positioned between two wing segments on the 5' and 3' ends (also called 5' wing and 3' wing respectively). Such antisense oligonucleotides decrease tau mRNA and/or protein expression by activating RNAse H. The internucleoside linkage of gapmers can be phosphorothioate or phosphodiester linkages. In some embodiments, the gapmers comprise a stretch of at least five (e.g., 5, 6, 7, 8, 9, 10, 11, 12) contiguous 2'-deoxyribonucleotides and the 5' and 3' wing segments comprise one or more 2'-modified nucleotides. In some embodiments, such an oligonucleotide comprises at least seven (e.g., 7, 8, 9, 10, 11, 12) contiguous 2'-deoxyribonucleotides. In some embodiments, such an oligonucleotide comprises ten contiguous 2'-deoxyribonucleotides. The 2'-modification can be selected from the group consisting of 2'-fluoro, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In some embodiments, the gapmers comprise 2'-O-MOE modified nucleotide in the 5' wing and 3' wing.

In some embodiments, the gapmers targeting tau are 5-10-5 gapmers that are 20 nucleosides in length, wherein the central gap segment comprises ten contiguous 2'-deoxynucleosides, flanked by 5' wing and 3' wing, each wing comprising five nucleosides each with a 2'-O-MOE modification.

In some embodiments, the antisense oligonucleotides targeting MAPT provided herein are gapmers comprising a nucleobase sequence that has at least 70% (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any of the sequences provided in Tables 9-15 and 17, wherein C in any of the nucleobase sequences is either cytosine or 5-methylcytosine, and wherein at least one nucleotide of the oligonucleotide has a 2'-modification. In some embodiments, an antisense oligonucleotide targeting MAPT comprises a nucleobase sequence that has at least 80% sequence identity to any of the sequences provided in Tables 9-15 and 17. In some embodiments, an antisense oligonucleotide targeting MAPT comprises a nucleobase sequence that has at least 90% sequence identity to any of the nucleobase sequences provided in Tables 9-15 and 17. In some embodiments, an antisense oligonucleotide targeting MAPT comprises any of the nucleobase sequences provided in Tables 9-15 and 17. In some embodiments, an antisense oligonucleotide targeting MAPT consists of any of the nucleobase sequences provided in Tables 9-15 and 17. In some embodiments, the antisense oligonucleotides targeting MAPT provided herein are 5-10-5 gapmers that comprise any of the nucleobase sequences provided in any of Tables 9-15 and 17, wherein the first to fifth nucleotides each comprise a 2'-O-MOE modified nucleoside, wherein the sixth to fifteenth nucleotides each comprise a 2'-deoxynucleoside, and wherein the sixteenth to twentieth nucleotides each comprise a 2'-O-MOE modified nucleoside. In some embodiments, each C in any of the nucleobase sequences is 5-methylcytosine.

In some embodiments, the antisense oligonucleotide targeting MAPT comprises a nucleobase sequence selected from any one of SEQ ID NOs: 208, 284, 285, 313, 329, 335, 366, 384, 386, 405, 473, and 474. In some embodiments, the antisense oligonucleotide targeting MAPT comprises a nucleobase sequence that has at least 90% (e.g., 90%, 91%, 92%, 93%, 94%, 95%, 96%, 97%, 98%, 99%, or 100%) sequence identity to SEQ ID NO: 284. In some embodiments, the antisense oligonucleotide targeting MAPT comprises SEQ ID NO: 284. In some embodiments, the antisense oligonucleotide targeting MAPT comprises a nucleobase sequence that has at least 906, (e.g., 90%, 91%, 92%, 93%, 94%, 95%, 96%, 97%, 98%, 99%, or 100%) sequence identity to SEQ ID NO: 285 or 208. In some embodiments, the antisense oligonucleotide targeting MAPT comprises SEQ ID NO: 285 or 208.

In another aspect, provided herein are oligonucleotides comprising a nucleobase sequence that is complementary to at least 12 contiguous nucleobases of any one of SEQ ID NOs: 487-506, with 1, 2, or 3 mismatches, wherein at least one nucleotide of the oligonucleotide has a 2'-modification. These oligonucleotides are antisense oligonucleotides targeting MAPT. In some embodiments, such an oligonucleotide comprises a nucleobase sequence that is 100% complementary to at least 12 contiguous nucleobases of any one of SEQ ID NOs: 487-506. In some embodiments, such an oligonucleotide comprises one or more 5-methylcytosines. In some embodiments, such an oligonucleotide has a 2'-modification. The 2'-modification can be selected from the group consisting of 2'-fluoro, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In some embodiments, the 2'-modification is 2'-O-methoxyethyl (2'-O-MOE). In some embodiments, such an oligonucleotide comprises at least five (e.g., 5, 6, 7, 8, 9, 10, 11, 12) contiguous 2'-deoxyribonucleotides. In some embodiments, such an oligonucleotide comprises at least seven (e.g., 7, 8, 9, 10, 11, 12) contiguous 2'-deoxyribonucleotides. In some embodiments, such an oligonucleotide comprises ten contiguous 2'-deoxyribonucleotides.

In some embodiments, the antisense oligonucleotides targeting MAPT provided herein are capable of decreasing tau mRNA or protein expression level by at least 30% in vitro.

In some embodiments, the antisense oligonucleotides targeting MAPT provided herein are capable of decreasing tau mRNA or protein expression level by at least 30% in vivo.

In another aspect, provided herein are compositions comprising any of the antisense oligonucleotides described herein and a pharmaceutically acceptable carrier.

In a further aspect, provided herein are methods of decreasing tau expression level in a subject, e.g., a subject afflicted with or susceptible to a tau-associated disease, by administering to the subject a therapeutically effective amount of any of the antisense oligonucleotides described herein. In some embodiments, such methods can include administering a second agent to the subject. In some embodiments, the antisense oligonucleotide targeting MAPT can be administered to the subject through an intrathecal, intracranial, intranasal, oral, intravenous, or subcutaneous route. In some embodiments, the subject is a human.

Also provided are antisense oligonucleotides as described herein for use in treating a tau-associated disease in a subject in need thereof, e.g., a subject afflicted with or susceptible to a tau-associated disease. Use of the antisense oligonucleotides or pharmaceutical composition described herein to treat a tau-associated disease in a subject in need thereof is also included. The present disclosure also includes use of the antisense oligonucleotides described herein in the manufacture of a medicament for use in the treatment of a tau-associated disease in a subject in need thereof.

The tau-associated disease can be selected from Alzheimer's disease (AD), amyotrophic lateral sclerosis/parkinsonism-dementia complex (ALS-PDC), argyrophilic grain dementia (AGD). British type amyloid angiopathy, cerebral amyloid angiopathy, chronic traumatic encephalopathy (CTE), corticobasal degeneration (CBD), Creutzfeldt-Jakob disease (CJD), dementia pugilistica, diffuse neurofibrillary tangles with calcification, Down's syndrome, Dravet's Syndrome, epilepsy, frontotemporal dementia (FTD), frontotemporal dementia with parkinsonism linked to chromosome 17 (FTDP-17), frontotemporal lobar degeneration, ganglioglioma, gangliocytoma, Gerstmann-Straussler-Scheinker disease, Hallervorden-Spatz disease, Huntington's disease, inclusion body myositis, lead encephalopathy, Lytico-Bodig disease, meningioangiomatosis, multiple system atrophy, myotonic dystrophy, Niemann-Pick disease type C (NP-C), non-Guamanian motor neuron disease with neurofibrillary tangles, Pick's disease (PiD), postencephalitic parkinsonism, prion protein cerebral amyloid angiopathy, progressive subcortical gliosis, progressive supranuclear palsy (PSP), subacute sclerosing panencephalitis, tangle only dementia. Tangle-predominant dementia, multi-infarct dementia, ischemic stroke, or tuberous sclerosis.

BRIEF DESCRIPTION OF THE DRAWINGS

FIGS. 1A-1E show physical characterization of antisense oligonucleotide targeting MAPT. FIG. 1A shows the structure of antisense oligonucleotide (ASO) comprising SEQ ID NO: 284, with formula $C_{230}H_{321}N_{72}O_{120}P_{19}S_{19}$ and expected molecular weight of 7212.3 Da. FIG. 1A-1 to FIG. 1A-4 show enlarged view of FIG. 1A. FIG. 1B shows the liquid chromatography-mass spectrometry (LC-MS) data of ASO comprising SEQ ID NO: 284, with a measured peak mass of 7214.3. FIG. 1C shows the deconvolution peak report of LC-MS for ASO comprising SEQ ID NO: 284. FIG. 1D shows the LC-MS data of ASO comprising SEQ ID NO: 285, with a measured peak mass of 7232.5. FIG. 1E shows the deconvolution peak report of LC-MS for ASO comprising SEQ ID NO: 285.

FIG. 2A is representative RT-PCR results showing that all six human tau transcripts were found in the forebrain of the hTau BAC transgenic mice (transgenic line 510, two month old female mice). Exons 2, 3 and 10 are alternatively spliced, resulting in six tau isoforms: 2−3−10−; 2+3−10−; 2+3+10−; 2−3−10+; 2+3−10+; 2+3+10+. 4R represents tau isoforms with exon 10, 3R represents tau isoforms without exon 10; 0N represents tau isoforms with neither exon 2 nor exon 3; 1N represents tau isoforms with either exon 2 or exon3; 2N represents tau isoforms with both exon 2 and exon 3. FIG. 2B is a representative Western blot showing six tau protein isoforms ranging from 352-441 amino acids with molecular weights of 48-67 kD. They differ in (1) inclusion of zero, one or two inserts of a 29 amino acid N-terminal part (0N, 1N, or 2N), or (2) inclusion of three or four microtubule binding domain (3R or 4R). FIG. 2C is a representative immunohistochemistry image showing normal axonal distribution of human tau in the brain of hTau BAC transgenic mouse, as stained by a human tau specific antibody. FIG. 2D is a bar graph showing tau mRNA knockdown in the cortex of hTau BAC transgenic mouse 4 weeks after a single treatment of an antisense oligonucleotide comprising SEQ ID NO: 285. FIG. 2E is a representative Western blot showing tau protein knockdown in the hippocampus of hTau BAC transgenic mouse 4 weeks after a single treatment of an antisense oligonucleotide comprising SEQ ID NO: 285.

FIG. 3 is a set of in situ hybridization images showing wide brain distribution of the antisense oligonucleotide of SEQ ID NO: 285 in hTau BAC transgenic mice.

DETAILED DESCRIPTION

Figure 1:
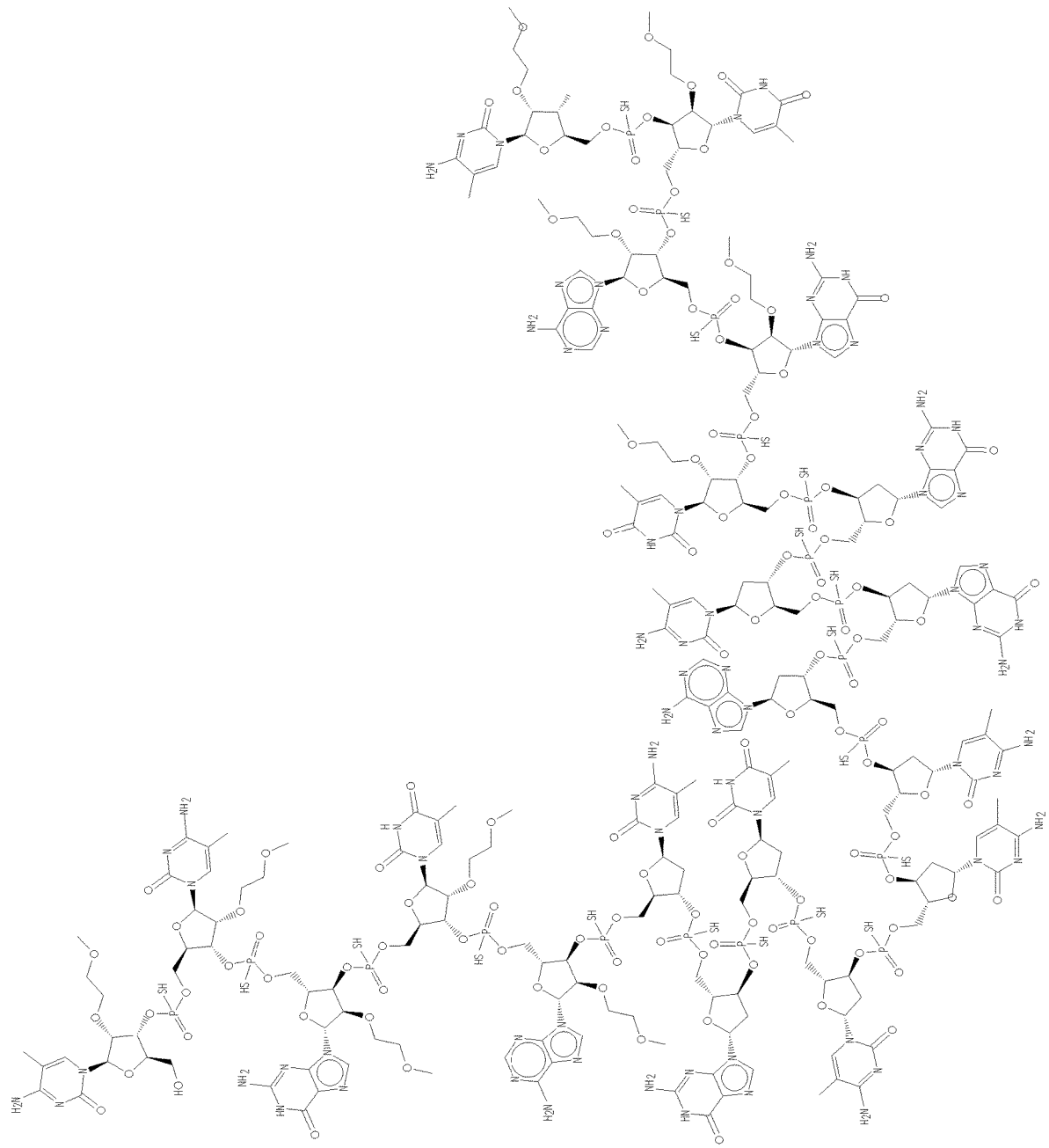

Provided herein are antisense oligonucleotides targeting microtubule-associated protein tau (MAPT), compositions comprising the antisense oligonucleotides, and methods for decreasing tau expression using these antisense oligonucleotides. The compositions and methods provided herein are useful in treating tau-associated diseases.

Definitions

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely examples and that equivalents of such are known in the art.

The term "2'-modification" refers to substitution of H or OH at the 2'-position of the furanose ring of a nucleoside or nucleotide with another group.

As used herein. "2'-O-methoxyethyl," "2'-MOE," or "2'-OCH2CH2-OCH3" refers to an O-methoxyethyl modification of the 2' position of a furanose ring. A 2'-O-methoxyethyl modified sugar is a modified sugar. A "2'-MOE nucleoside/nucleotide" or "2'-O-methoxyethyl nucleoside/nucleotide" refers to a nucleoside/nucleotide comprising a 2'-MOE modified sugar moiety.

A "5-methylcytosine" refers to a cytosine modified with a methyl group attached to the 5' position.

The term "antisense oligonucleotide" as used herein refers to a single-stranded oligonucleotide having a nucleobase sequence that is complementary to a corresponding segment of a target nucleic acid, e.g., a target genomic sequence, pre-mRNA, or mRNA molecule. In some embodiments, an antisense oligonucleotide is 12 to 30 nucleobases in length.

The term "complementarity" or "complementary" refers to the capacity of base pairing between the nucleobases of a first nucleic acid strand and the nucleobases of a second nucleic acid strand, mediated by hydrogen binding (e.g., Watson-Crick, Hoogsteen or reversed Hoogsteen hydrogen bonding) between corresponding nucleobases. For example, in DNA, adenine (A) is complementary to thymine (T); and guanosine (G) is complementary to cytosine (C). For example, in RNA, adenine (A) is complementary to uracil (U); and guanosine (G) is complementary to cytosine (C). In certain embodiments, complementary nucleobase means a nucleobase of an antisense oligonucleotide that is capable of base pairing with a nucleobase of its target nucleic acid. For example, if a nucleobase at a certain position of an antisense oligonucleotide is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

An "effective amount" refers to an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A "therapeutically effective amount" of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but are not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

As used herein, the term "gapmer" refers to a chimeric antisense oligonucleotide comprising a central gap segment consisting of contiguous 2'-deoxyribonucleotides, which is capable of activating RNAse H, flanked by two wing segments on the 5' and 3' ends, each comprising one or more modified nucleotides, which confer increased resistance to nuclease degradation.

The term "hybridization" refers to the base pairing of complementary nucleic acid strands and formation of a duplex structure. Hybridization can occur between fully complementary nucleic acid strands or between "substantially complementary" nucleic acid strands that contain minor regions of mismatch. While not limited to a particular mechanism, the most common mechanism of pairing involves hydrogen bonding, which may be Watson-Crick, Hoogsteen or reversed Hoogsteen hydrogen bonding, between complementary nucleobases of the nucleic acid strands. For example, adenine and thymine are complementary nucleobases which pair through the formation of hydrogen bonds. Hybridization can occur under varying stringent circumstances. As used herein, hybridization refers to base pairing of complementary nucleic acid strands and formation of a duplex structure at least under a relatively low stringency condition, for example, hybridization in 2×SSC (0.3 M sodium chloride, 0.03 M sodium citrate), 0.1% SDS at 37° C., followed by washing in solution containing 4×SSC, 0.1% SDS can be used at 37° C., with a final wash in 1×SSC at 45° C.

The term "inhibiting" or "inhibition" refers to a reduction or blockade of the expression or activity of a target nucleic acid or protein and does not necessarily indicate a total elimination of expression or activity of the target.

The term "internucleoside linkage" refers to the chemical bond between nucleosides.

The term "knockdown" or "expression knockdown" refers to reduced mRNA or protein expression of a gene after treatment of a reagent, e.g., an antisense oligonucleotide. Expression knockdown can occur during transcription. mRNA splicing, or translation.

The term "mismatch" refers to the case where a nucleobase of a first nucleic acid strand is not complementary to the corresponding nucleobase of a second nucleic acid strand.

The term "nucleobase sequence" refers to the order of contiguous nucleobases independent of any sugar, linkage, and/or nucleobase modification.

The term "oligonucleotide" refers to a polymer of linked deoxyribonucleotides (DNA) and/or ribonucleotides (RNA), each of which is modified or unmodified. Unless specifically limited, the term encompasses nucleic acids containing known analogues of natural nucleotides that have similar binding properties as the natural nucleic acid, and nucleic acids having alternative internucleoside linkages other than phosphodiester linkages.

The term "phosphorothioate linkage" refers to a linkage between nucleosides where the phosphodiester bond is modified by replacing one of the non-bridging oxygen atoms with a sulfur atom.

The term "sense strand" refers to the coding strand, plus strand, or non-template strand of the DNA molecule which consists of a double stranded structure. The coding strand has the same sequence as the mRNA sequence except that Thymine (T) in DNA is replaced by Uracil (U) in RNA. An "antisense strand" refers to the non-coding strand or template strand of the DNA molecule, which acts as a template for synthesis of mRNA. Therefore, the sequence of antisense strand is complementary to the sequence of sense strand and mRNA (U in RNA in place of T).

As used herein, the term "steric blocker" refers to an antisense oligonucleotide that hybridizes with a target nucleic acid (e.g., a target genomic sequence, pre-mRNA, or mRNA molecule), and interferes with the transcription, splicing, and/or translation of the target nucleic acid without activating RNAse H.

As used herein, "targeting" or "targeted" refers to design and selection of an antisense oligonucleotide that can specifically hybridize to a target nucleic acid, e.g., a target genomic sequence, pre-mRNA, or mRNA molecule, or a fragment or variant thereof, and modulate the transcription, splicing, and/or translation of the target nucleic acid.

As used herein, "tau" (also known as "microtubule-associated protein tau", MAPT, MSTD; PPND; DDPAC; MAPTL; MTBT1; MTBT2; FTDP-17; PPP1R103) refers to a microtubule-associated protein encoded by the gene MAPT. The human MAPT gene is mapped to chromosomal location 17q21.1, and the genomic sequence of human MAPT gene can be found in GenBank at NG_007398.1 (SEQ ID NO: 304). The MAPT intron and exon sequences and branch points can be determined based on Ensembl genomes database website using Transcript: MAPT-203 ENST00000344290. Due to complicated alternative splicing, eight tau isoforms are present in the human. The term "tau" is used to refer collectively to all isoforms of tau. The protein and mRNA sequences for the longest human tau isoform are:

```
Homo sapiens microtubule-associated protein tau (MAPT), transcript
variant 6, mRNA (NM_0011230663)
                                                          (SEQ ID NO: 305)
    1 agacggccga gcggcagggc gctcgcgcgc gcccactagt ggccagagga gaaggctccc 61 gcggaggccg cgctgcccgc cccctcccct ggggaggctc gcgttcccgc tgctcgcgcc 121 tgcgccgccc gccggcctca ggaacgcgcc ctcttcgccg gcgcgcgccc tcgcagtcac 181 cgccacccac cagctccggc accaacagca gcgccgctgc caccgcccac cttctgccgc 241 cgccaccaca gccaccttct cctcctccgc tgtcctctcc cgtcctcgcc tctgtcgact 301 atcaggtgaa ctttgaacca ggatggctga gccccgccag gagttcgaag tgatggaaga 361 tcacgctggg acgtacgggt tggggacag gaaagatcag gggggctaca ccatgcacca 421 agaccaagag ggtgacacgg acgctggcct gaaagaatct cccctgcaga cccccactga 481 ggacggatct gaggaaccgg gctctgaaac ctctgatgct aagagcactc caacagcgga 541 agatgtgaca gcacccttag tggatgaggg agctcccggc aagcaggctg ccgcgcagcc 601 ccacacggag atcccagaag gaaccacagc tgaagaagca ggcattggag acacccccag 661 cctggaagac gaagctgcta gtcacgtgac ccaagagcct gaaaatggta aggtggtcca 721 ggaaggcttc ctccgagagc caggcccccc aggtctgagc caccagctca tgtccggcat 781 gcctgggact cccctcctgc ctgagggcc cagagaggc acacgccaac cttcggggac 841 aggacctgag gacacagagg gcggccgcca cgcccctgag ctgctcaagc accagcttct 901 aggagacctg caccaggagg ggccgccact gaaggggca ggggcaaag agaggccggg 961 gagcaaggag gagatggatg aagaccgcga cgtcgatgag tcctcccccc aagactcccc 1021 tccctccaag gcctccccag cccaagatgg gcggcctccc cagacagccg ccagagaagc 1081 caccagcatc ccaggcttcc cagcggaggg tgccatcccc ctccctgtgg atttcctctc 1141 caaagtttcc acagagatcc cagcctcaga gcccgacggg cccagtgtag ggcgggccaa 1201 agggcaggat gcccccctgg agttcacgtt tcacgtagaa atcacaccca acgtacagaa 1261 ggagcaggcg cactcggagg agcatttggg aagggctgca tttccagggg cccctggaga 1321 ggggccagag acccggggcc cctctttggg agaggacaca aaagaggctg accttccaga 1381 gccctctgaa aagcagcctg ctgctgctcc gcggggaag cccgtcagcc gggtccctca 1441 actcaaagct cgcatgatca gtaaaagcaa agacgggact ggaagcgatg acaaaaaagc 1501 caagacatcc acacgttcct ctgctaaaac cttgaaaaat aggccttgcc ttagccccaa 1561 acaccccact cctggtaact cagaccctct gatccaaccc tccaaccctg ctatgtgccc 1621 agagccacct tcctctccta aatacgtctc ttctgtcact tcccgaactg gcagttctgg 1681 agcaaaggag atgaaactca aggggctga tggtaaaacg aagatcgcca caccgcgggg 1741 agcagcccct ccaggccaga agggccaggc caacgccacc aggattccag caaaaacccc
```

-continued

```
1801  gcccgctcca aagacaccac ccagctctgc gactaagcaa gtccagagaa gaccacccc
1861  tgcagggccc agatctgaga gaggtgaacc tccaaaatca ggggatcgca gcggctacag
1921  cagccccggc tccccaggca ctcccggcag ccgctcccgc accccgtccc ttccaacccc
1981  acccacccgg gagcccaaga aggtggcagt ggtccgtact ccacccaagt cgccgtcttc
2041  cgccaagagc cgcctgcaga cagcccccgt gcccatgcca gacctgaaga atgtcaagtc
2101  caagatcggc tccactgaga acctgaagca ccagccggga ggcgggaagg tgcagataat
2161  taataagaag ctggatctta gcaacgtcca gtccaagtgt ggctcaaagg ataatatcaa
2221  acacgtcccg ggaggcggca gtgtgcaaat agtctacaaa ccagttgacc tgagcaaggt
2281  gacctccaag tgtggctcat taggcaacat ccatcataaa ccaggaggtg gccaggtgga
2341  agtaaaatct gagaagctta acttcaagga cagagtccag tcgaagattg ggtccctgga
2401  caatatcacc cacgtccctg gcggaggaaa taaaaagatt gaaacccaca agctgacctt
2461  ccgcgagaac gccaaagcca agacagacca cggggcgag atcgtataca agtcgccagt
2521  ggtgtctggg gacacgtctc cacggcatct cagcaatgtc tcctccaccg gcagcatcga
2581  catggtagac tcgccccagc tcgccacgct agctgacgag gtgtctgcct ccctggccaa
2641  gcagggtttg tgatcaggcc cctggggcgg tcaataattg tggagaggag agaatgagag
2701  agtgtggaaa aaaaagaat aatgacccag cccccgcccct ctgcccccag ctgctcctcg
2761  cagttcggtt aattggttaa tcacttaacc tgcttttgtc actcggcttt ggctcgggac
2821  ttcaaaatca gtgatgggag taagagcaaa tttcatcttt ccaaattgat gggtaggcta
2881  gtaataaat atttaaaaaa aaacattcaa aaacatggcc acatccaaca tttcctcagg
2941  caattccttt tgattctttt ttcttccccc tccatgtaga gagggagaa agagaggctc
3001  tgaaagctgc ttctggggga tttcaaggga ctgggggtgc caaccacctc tggccctgtt
3061  gtggggtgt cacagaggca gtggcagcaa caaaggattt gaaacttggt gtgttcgtgg
3121  agccacaggc agacgatgtc aaccttgtgt gagtgtgacg ggggttgggg tggggcggga
3181  ggccacgggg gaggccgagg caggggctgg gcagagggga gaggaagcac aagaagtggg
3241  agtgggagag gaagccacgt gctggagagt agacatcccc ctccttgccg ctgggagagc
3301  caaggcctat gccacctgca gcgtctgagc ggccgcctgt ccttggtggc cgggggtggg
3361  ggcctgctgt gggtcagtgt gccaccctct gcagggcagc ctgtgggaga agggacagcg
3421  ggtaaaaaga gaaggcaagc tggcaggagg gtggcacttc gtggatgacc tccttagaaa
3481  agactgacct tgatgtcttg agagcgctgg cctcttcctc cctccctgca gggtagggg
3541  cctgagttga ggggcttccc tctgctccac agaaaccctg ttttattgag ttctgaaggt
3601  tggaactgct gccatgattt tggccacttt gcagacctgg gactttaggg ctaaccagtt
3661  ctctttgtaa ggacttgtgc ctcttgggag acgtccaccc gtttccaagc ctgggccact
3721  ggcatctctg gagtgtgtgg gagtctggga ggcaggtccc gagcccctg tccttcccac
3781  ggccactgca gtcaccccgt ctgcgccgct gtgctgttgt ctgccgtgag agcccaatca
3841  ctgcctatac ccctcatcac acgtcacaat gtcccgaatt cccagcctca ccaccccttc
3901  tcagtaatga ccctggttgg ttgcaggagg tacctactcc atactgaggg tgaaattaag
3961  ggaaggcaaa gtccaggcac aagaatggga ccccagcctc tcactctcag ttccactcat
4021  ccaactggga ccctcaccac gaatctcatg atctgattcg gttccctgtc tcctcctccc
4081  gtcacagatg tgagccaagg cactgctcag ctgtgaccct aggtgtttct gccttgttga
4141  catggagaga gccctttccc ctgagaaggc ctggccccctt cctgtgctga gcccacagca
```

-continued

```
4201 gcagactgga tatcttggtt atcagcggta gcaccaggat ggaagggcaa ggcacccagg
4261 gcaggccac agtcccgctg tcccccactt gcaccctagc ttgtagctgc caacctccca
4321 gacagcccag cccgctgctc agctccacat gcatagtatc aaccctccac acccgacaaa
4381 ggggaacaca ccccttgga aatggttctt ttcccccagt cccagctgga agccatgctg
4441 tctgttctgc tggagcagct gaacatatac atagatgttg ccctgccctc ccatctgca
4501 ccctgttgag ttgtagttgg atttgtctgt ttatgcttgg attcaccaga gtgactatga
4561 tagtgaaaag aaaaaaaaaa aaaaaaaagg acacatgtat cttaaaatgc ttgtaaagag
4621 gtttctaacc caccctcacg aggtgtctct caccccaca ctgggactcg tgtggcctgt
4681 gtggtgccac cctgctgggg cctcccaagt tttgaaaggc tttcctcagc acctgggacc
4741 caacagagac cagcttctag cagctaagga ggccgttcag ctgtgacgaa ggcctgaagc
4801 acaggattag gactgaagcg atgatgtccc cttccctact tccccttggg gctccctgtg
4861 tcagggcaca gactaggtct tgtggctggt ctggcttgcg gcgcgaggat ggttctctct
4921 ggtcatagcc cgaagtctca tggcagtccc aaaggaggct tacaactcct gcatcacaag
4981 aaaaaggaag ccactgccag ctggggggat ctgcagctcc cagaagctcc gtgagcctca
5041 gccacccctc agactgggtt cctctccaag ctcgccctct ggagggcag cgcagcctcc
5101 caccaaggc cctgcgacca cagcagggat tgggatgaat tgcctgtcct ggatctgctc
5161 tagaggccca agctgcctgc ctgaggaagg atgacttgac aagtcaggag acactgttcc
5221 caaagccttg accagagcac ctcagcccgc tgaccttgca caaactccat ctgctgccat
5281 gagaaaggg aagccgcctt tgcaaaacat tgctgcctaa agaaactcag cagcctcagg
5341 cccaattcta ccacttctgg tttgggtaca gttaaaggca accctgaggg acttggcagt
5401 agaaatccag ggcctcccct ggggctggca gcttcgtgtg cagctagagc tttacctgaa
5461 aggaagtctc tggacccaga actctccacc aagagcctcc ctgccgttcg ctgagtccca
5521 gcaattctcc taagttgaag ggatctgaga aggagaagga atgtggggt agatttggtg
5581 gtggttagag atatgccccc ctcattactg ccaacagtat cggctgcatt tcttcacgca
5641 cctcggttcc tcttcctgaa gttcttgtgc cctgctcttc agcaccatgg gccttcttat
5701 acggaaggct ctgggatctc cccttgtgg acaggctct tggggccagc ctaagatcat
5761 ggtttagggt gatcagtgct ggcagataaa ttgaaaaggc acgctggctt tgatcttaa
5821 atgaggacaa tcccccagg gctgggcact cctccctcc cctcacttct cccacctgca
5881 gagccagtgt ccttgggtgg gctagatagg atatactgta tgccggctcc ttcaagctgc
5941 tgactcactt tatcaatagt tccatttaaa ttgacttcag tggtgagact gtatcctgtt
6001 tgctattgct tgttgtgcta tgggggagg ggaggaat gtgtaagata gttaacatgg
6061 gcaaagggag atcttgggt gcagcactta aactgcctcg taacccttt catgatttca
6121 accacatttg ctagagggag ggagcagcca cggagttaga ggcccttggg gtttctcttt
6181 tccactgaca ggctttccca ggcagctggc tagttcattc cctccccagc caggtgcagg
6241 cgtaggaata tggacatctg gttgctttgg cctgctgccc tctttcaggg gtcctaagcc
6301 cacaatcatg cctccctaag accttggcat ccttccctct aagccgttgg cacctctgtg
6361 ccacctctca cactggctcc agacacacag cctgtgcttt tggagctgag atcactcgct
6421 tcacccacct catctttgtt ctccaagtaa agccacgagg tcggggcgag ggcagaggtg
6481 atcacctgcg tgtcccatct acagacctgc agcttcataa aacttctgat ttctcttcag
6541 cttgaaaag ggttaccctg gcactggcc tagagcctca cctcctaata gacttagccc
6601 ctttgagtag ccatgttgag caggactatt tctggcactt gcaaatccca tgatacttct
```

```
6661  ggtaattagt agggtggggg gagggacatg aaatcatatt agcttagctt tctgtctgtg 6721  aatgtctata taatgtattg tgttgattaa caaatgattt acactaactg ttgctgtaaa 6781  agtgaatttg gaaataaagt tattactctg attaaa
```

*Homo sapiens* microtubule-associated protein tau isoform 6 (NP_001116538.2)
(SEQ ID NO: 306)

```
MAEPRQEFEV MEDHAGTYGL GDRKDQGGYT MHQDQEGDTD

AGLKESPLQT PTEDGSEEPG SETSDAKSTP TAEDVTAPLV DEGAPGKQAA

AQPHTEIPEG TTAEEAGIGD TPSLEDEAAG HVTQEPESGK VVQEGFLREP

GPPGLSHQLM SGMPGAPLLP EGPREATRQP SGTGPEDTEG GRHAPELLKH

QLLGDLHQEG PPLKGAGGKE RPGSKEEVDE DRDVDESSPQ DSPPSKASPA

QDGRPPQTAA REATSIPGFP AEGAIPLPVD FLSKVSTEIP ASEPDGPSVG

RAKGQDAPLE FTFHVEITPN VQKEQAHSEE HLGRAAFPGA PGEGPEARGP

SLGEDTKEAD LPEPSEKQPA AAPRGKPVSR VPQLKARMVS KSKDGTGSDD

KKAKTSTRSS AKTLKNRPCL SPKIHTPGSS DPLIQPSSPA VCPEPPSSPK

YVSSVTSRTG SSGAKEMKLK GADGKTKIAT PRGAAPPGQK GQANATRIPA

KTPPAPKTPP SSATKQVQRR PPPAGPRSER GEPPKSGDRS GYSSPGSPGT

PGSRSRTPSL PTPPTREPKK VAVVRTPPKS PSSAKSRLQT APVPMPDLKN

VKSKIGSTEN LKHQPGGGKV QIINKKIDLS NVQSKCGSKD NIKHVPGGGS

VQIVYKPVDL SKVTSKCGSL GNIHHKPGGG QVEVKSEKLD FKDRVQSKIG

SIDNITHVPG GONKKIETHK LTFRENAKAK IDHGAFIVYK SPVVSGDTSP

RHLSNVSSIG SIDMVDSPQL ATLADEVSAS LAKQGL
```

The mRNA and protein sequences of the other human tau isoforms can be found in GenBank with the following Accession Nos:
  tau isoform 1: NM_016835.4 (mRNA)→NP_058519.3 (protein):
  tau isoform 2: NM_005910.5 (mRNA)→NP_005901.2 (protein):
  tau isoform 3: NM_016834.4 (mRNA)→NP_058518.1 (protein);
  tau isoform 4: NM_016841.4 (mRNA)→NP_058525.1 (protein):
  tau isoform 5: NM_001123067.3 (mRNA)→NP_001116539.1 (protein);
  tau isoform 7: NM_001203251.1 (mRNA)→NP_001190180.1 (protein);
  tau isoform 8: NM_001203252.1 (mRNA)→NP_001190181.1 (protein).

As used herein, human tau protein also encompasses proteins that have over its full length at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%6, 95%, 96%, 97%, 98%6, 99% or 100% sequence identity with any of the tau isoforms. The sequences of murine, cyno, and other animal tau proteins are known in the art.

The term "tau associated disease" includes, but is not limited to, a disease associated with abnormal tau protein expression, secretion, phosphorylation, cleavage, and/or aggregation. Tau-associated diseases include but are not limited to Alzheimer's disease (AD), amyotrophic lateral sclerosis/parkinsonism-dementia complex (ALS-PDC), argyrophilic grain dementia (AGD). British type amyloid angiopathy, cerebral amyloid angiopathy, chronic traumatic encephalopathy (CTE), corticobasal degeneration (CBD), Creutzfeldt-Jakob disease (CJD), dementia pugilistica, diffuse neurofibrillary tangles with calcification, Down's syndrome, Dravet's Syndrome, epilepsy, frontotemporal dementia (FTD), frontotemporal dementia with parkinsonism linked to chromosome 17 (FTDP-17), frontotemporal lobar degeneration, ganglioglioma, gangliocytoma, Gerstmann-Straussler-Scheinker disease, Hallervorden-Spatz disease, Huntington's disease, inclusion body myositis, lead encephalopathy, Lytico-Bodig disease, meningioangiomatosis, multiple system atrophy, myotonic dystrophy, Niemann-Pick disease type C (NP-C), non-Guamanian motor neuron disease with neurofibrillary tangles, Pick's disease (PiD), postencephalitic parkinsonism, prion protein cerebral amyloid angiopathy, progressive subcortical gliosis, progressive supranuclear palsy (PSP), subacute sclerosing panencephalitis, tangle only dementia. Tangle-predominant dementia, multi-infarct dementia, ischemic stroke, and tuberous sclerosis.

The term "homology" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit: e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. Percentage of "sequence identity" can be determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. The percentage can be calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence.

The term "isolated" refers to altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "treat" or "treatment" refers to both therapeutic treatment and prophylactic or preventive measures, wherein the object is to prevent or slow down an undesired physiological change or disorder. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The term "subject" refers to an animal, human or non-human, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

Antisense Oligonucleoddes

Antisense oligonucleotides (ASOs) are powerful and versatile agents utilized in a growing number of applications including RNA reduction, translation arrest, miRNA inhibition, splicing modulation, and polyadenylation site selection. An antisense oligonucleotide binds a target nucleic acid when a sufficient number of nucleobases of the antisense oligonucleotide can form hydrogen bond with the corresponding nucleobases of the target nucleic acid, and modulates the transcription and/or translation of the target nucleic acid. Thus, the nucleobase sequence of an antisense oligonucleotide is complementary to the nucleobase sequence of a target nucleic acid, e.g., a target genomic sequence, pre-mRNA, or mRNA molecule. Hybridization occurs when hydrogen bonding (e.g., Watson-Crick, Hoogsteen or reversed Hoogsteen hydrogen bonding) forms between the complementary nucleobases of the antisense oligonucleotide and target nucleic acid. Non-complementary nucleobases between an antisense oligonucleotide and a target nucleic acid may be tolerated provided that the antisense oligonucleotide remains able to specifically hybridize to a target nucleic acid.

ASOs can be designed to decrease the expression of a target protein through either RNase H-dependent or RNase H-independent manners (see Watts J K, et al., J Pathol. 2012 January; 226(2): 365-379). When an ASO comprising a contiguous stretch of DNA hybridizes with a target RNA, the DNA-RNA heteroduplex recruit RNase H, which cleaves the target RNA in the duplex and promotes subsequent degradation of the RNA fragments by cellular nucleases. ASOs can also decrease target expression independent of RNAse H by sterically blocking pre-mRNA processing and/or translation of mRNA into protein.

Provided herein are antisense oligonucleotides targeting microtubule-associated protein tau (MAPT). In some embodiments, the antisense oligonucleotides provided herein have a nucleobase sequence complementary to a segment of MAPT genomic DNA, pre-mRNA, or mRNA, with 1, 2, 3, 4, or 5 mismatches. No mismatch is counted between an oligonucleotide and the corresponding target nucleic acid if complete base-pairing occurs (e.g., pairing between A and T, and between C and G). A mismatch occurs when a nucleobase of a first nucleic acid is not capable of pairing with the corresponding nucleobase of a second nucleic acid when the two sequences are maximally aligned. For example, if a position in a first sequence has a nucleobase A, and the corresponding position on the second sequence has a nucleobase (e.g., C or G) that cannot pair with A, it constitutes a mismatch. A mismatch is also counted if a position in one sequence has a nucleobase, and the corresponding position on the other sequence has no nucleobase. A modification to the sugar moiety of a nucleotide or internucleoside linkage is not considered a mismatch. Thus, if one sequence comprises a G, and the corresponding nucleobase of a second sequence comprises a modified C (e.g., 5-methylcytosine), no mismatch would be counted.

In the context of a stretch of nucleic acid, the antisense oligonucleotides provided herein are complementary to a segment of MAPT genomic DNA, pre-mRNA, or mRNA, at least, 70%, 80%, 85%, 86%, 87%, 88%, 89%, 90%, 91%, 92%, 93%, 94%, 95%, 96%%, 97%, 98%, 99%, or 1000/% over the entire length of the segment. Percent complementarity of an antisense oligonucleotide with a target nucleic acid can be determined using routine methods, for example, BLAST programs (basic local alignment search tools) or PowerBLAST programs known in the art (Altschul et al., J. Mol. Biol., 1990, 215, 403 410; Zhang and Madden, Genome Res., 1997, 7, 649 656). In some embodiments, the antisense oligonucleotides provided herein have a nucleobase sequence 100% complementary (i.e., fully complementary) to a segment of MAPT genomic DNA, pre-mRNA, or mRNA. As used herein. "fully complementary" or "100% complementary" refers to each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound.

In some embodiments, antisense oligonucleotides provided herein comprise a nucleobase sequence that is complementary to at least 12 contiguous nucleobases (e.g., 12, 13, 14, 15, 16, 17, or 18 contiguous nucleobases) of any sequence provided in Table 1, with 1, 2, or 3 mismatches. In some embodiments, antisense oligonucleotides provided herein comprise a nucleobase sequence that is 100% complementary to at least 12 contiguous nucleobases (e.g., 12, 13, 14, 15, 16, 17, or 18 contiguous nucleobases) of any sequence provided in Table 1.

The antisense compounds provided herein may also have a defined percent identity to a particular nucleotide sequence, SEQ ID NO, or a portion thereof. As used herein, an antisense oligonucleotide is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense oligonucleotides described herein as well as oligonucleotides having non-identical bases relative to the antisense oligonucleotides provided herein also are contemplated. The non-identical bases may be adjacent to each other or dispersed throughout the antisense oligonucleotides. Percent sequence identity of an antisense oligonucleotide can be calculated according to the number of bases that have identical base pairing relative to the sequence to which it is being compared. Percent sequence identity, can be determined using routine methods, for example, BLAST programs (basic local alignment search tools) or PowerBLAST programs known in the art (Altschul et al., J. Mol. Biol., 1990, 215, 403 410; Zhang and Madden. Genome Res., 1997, 7, 649 656); or by the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In some embodiments, provided herein are antisense oligonucleotides comprising a nucleobase sequence that has at least 70% (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any of the nucleobase sequences provided in any of Tables 2-17, wherein C of any of the nucleobase sequences is either cytosine or 5-methylcytosine, and wherein at least one nucleotide of the oligonucleotide has a 2'-modification. In some embodiments, provided herein are antisense oligonucleotides comprising a nucleobase sequence that has at least 90% (e.g., 90%, 91%, 92%, 93%6, 94%, 95%, 96%, 97%, 98%, 99%, or 100%) sequence identity to any of the nucleobase sequences provided in any of Tables 2-17. In some embodiments, antisense oligonucleotides targeting MAPT comprise any of the nucleobase sequences provided in any of Tables 2-17. In some embodiments, antisense oligonucleotides targeting MAPT consist of any of the nucleobase sequences provided in any of Tables 2-17.

In some embodiments, the antisense oligonucleotides provided herein are 12 to 30 nucleobases in length. For example, an antisense oligonucleotide targeting MAPT can comprise 12, 13, 14, 15, 16, 17, 18, 19, 20, 21, 22, 23, 24, 25, 26, 27, 28, 29, or 30 nucleobases. In some embodiments, the antisense oligonucleotides targeting MAPT are 12 to 25 nucleobases in length. For example, an antisense oligonucleotide targeting MAPT can comprise 12, 13, 14, 15, 16, 17, 18, 19, 20, 21, 22, 23, 24, or 25 nucleobases. In some embodiments, the antisense oligonucleotides targeting MAPT are 15 to 20 nucleobases in length. For example, an antisense oligonucleotide targeting MAPT can comprise 15, 16, 17, 18, 19, or 20 nucleobases. In some embodiments, the antisense oligonucleotides targeting MAPT comprise 17 nucleobases. It is possible to increase or decrease the length of an antisense oligonucleotide, and/or introduce mismatch bases (e.g., 1, 2, 3, 4, or 5 mismatches) in an antisense oligonucleotide without eliminating its activity.

Chemical Modification of Antisense Oligonucleotides

Oligonucleotides consist of repeating nucleotide units that are linked together by internucleoside phosphodiester bonds. Each nucleotide is composed of a nucleoside, which comprises a nucleobase linked to a sugar moiety, and one or more phosphate groups covalently linked to the sugar moiety. The phosphodiester bonds are made up of a sugar residue (either ribose for RNA or deoxyribose for DNA, collectively furanose) linked via a glycosidic bond to a purine (guanine and/or adenine) and/or pyrimidine base (thymine and cytosine for DNA; and uracil and cytosine for RNA).

Antisense oligonucleotides provided herein can contain one or more modified nucleotide subunits and/or internucleoside linkages. Chemical modifications to oligonucleotides encompass changes to internucleoside linkages, sugar moieties, nucleobases, and/or backbones. Modifications can improve stability, efficacy, and/or reduce immunogenicity of the antisense oligonucleotides. For example, oligonucleotides can be modified to have increased resistance to nucleases, enhanced binding affinity for nucleic acid target, enhanced cellular uptake, and/or increased inhibitory activity when compared to the unmodified oligonucleotides.

In some embodiments, antisense oligonucleotides provided herein include naturally occurring phosphodiester internucleoside linkages. The phosphodiester linkages can be modified to other phosphorous-containing linkages such as phosphorothioate, phosphotriester, methylphosphonate, or phosphoramidate linkages, or non-phosphorous-containing linkages. In some embodiments, antisense oligonucleotides provided herein include one or more modified internucleoside linkages. In some embodiments, antisense oligonucleotides provided herein include phosphorothioate linkages. In some embodiments, each internucleoside linkage of an antisense oligonucleotide is a phosphorothioate internucleoside linkage.

In some embodiments, antisense oligonucleotides provided herein include chemically modified sugar moieties. For example, the antisense oligonucleotides can include 2' modification on the furanose ring, bridging of non-geminal ring atoms to form bicyclic nucleic acids (BNA), replacement of the sugar ring oxygen atom with other atoms, or combinations thereof. In some embodiments, each nucleotide of an antisense oligonucleotide has a 2'-modified furanose ring. Exemplary 2'-modification include 2'-fluoro, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-

DMAEOE), and 2'-O—N-methylacetamido (2'-O-NMA). In some embodiments, each nucleotide of an antisense oligonucleotide has 2'-O-MOE modification to the sugar moiety.

In some embodiments, the antisense oligonucleotides provided herein can include substitution of a nucleotide at a given position with a modified version of the same nucleotide. For example, a nucleotide (A, G, C or T) can be replaced by the corresponding hypoxanthine, xanthine, 4-acetylcytosine, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, beta-D-mannosylqueosine, 2-methylthio-N6-isopentenyladenine, wybutoxosine, queosine, 2-thiocytosine, or 2,6-diaminopurine.

In some embodiments, the antisense oligonucleotides provided herein include chemically modified oligonucleotides that reduce the immunogenicity of oligonucleotides. For example, oligonucleotides containing 5-methylcytosine or 2'-O-MOE modifications have been shown to exhibit decreased immune stimulation in mice (Henry S. et al., J Pharmacol Exp Ther. 2000 February; 292(2):468-79). In some embodiments, antisense oligonucleotides provided herein include 5-methylcytosines instead of cytosines. In some embodiments, antisense oligonucleotides provided herein include 2'-O-MOE modifications. In some embodiments, antisense oligonucleotides provided herein include 5-methylcytosines and 2' MOE modifications.

In some embodiments, the antisense oligonucleotides targeting MAPT provided herein include a C6 linker at the 3' end with the following structure:

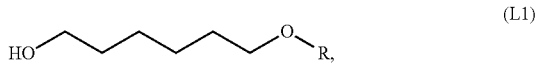

(L1)

which is attached to the 3' end of the oligonucleotide via a phosphate bridge, wherein R=PO2-O-oligonucleotide (for phosphodiester internucleoside linkages) or R=POS-O-oligonucleotide (for phosphorothioate internucleoside linkages). Such a 3' C6 linker can block 3'-exonuclease attack and therefore enhance the stability and duration of effect of the antisense oligonucleotides (see WO 2005/021749 for similar strategy applied to siRNA). In some cases, the 3' C6 linker can also facilitate synthesis and/or purification of the antisense oligonucleotides. In some embodiments, the antisense oligonucleotides targeting MAPT can have any of the following structures:

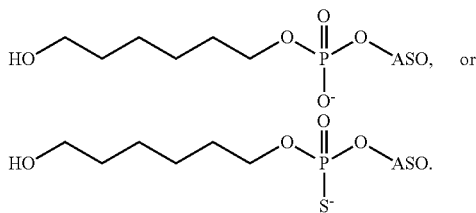

In some embodiments, antisense oligonucleotides provided herein can include an alternative backbone, for example, morpholino, locked nucleic acid (LNA), unlocked nucleic acid (UNA), threose nucleic acid (TNA), glycol nucleic acid (GNA), and/or peptide nucleic acid (PNA). In some embodiments, antisense oligonucleotides provided herein can include bicyclic nucleoside (BNA) comprising a bridge connecting two carbon atoms of the sugar ring. For example, such BNA can include "constrained ethyl" (or "cEt"), comprising a 4'-CH(CH3)-O-2' bridge connecting the 4'-carbon and the 2'-carbon of the sugar moiety. In some embodiments, antisense oligonucleotides provided herein can include locked nucleic acid (LNA) comprising a bridge connecting two carbon atoms between the 4' and 2' position of the nucleoside sugar unit. Such LNA can include α-L-methyleneoxy (4'-CH$_2$—O-2') LNA, β-D-methyleneoxy (4'-CH$_2$—O-2') LNA, ethyleneoxy (4'-(CH$_2$)$_2$—O-2') LNA, aminooxy (4'-CH$_2$—O—N(R)-2') LNA, oxyamino (4'-CH$_2$—N(R)—O-2') LNA, or any other LNA described in U.S. Pat. Nos. 7,053,207; 6,268,490; 6,770,748; 6,794,499; 7,034,133; 6,525,191; 7,696,345; 7,569,575; 7,314,923; 7,217,805; 7,084,125; or 6,670,461; Patent publication Nos. WO 98/39352 or WO 99/14226. Other suitable LNA include the LNAs described in Braasch et al., Chem. Biol. 8: 1-7, 2001; Elayadi et al., Curr. Opinion Invens. Drugs 2: 558-561, 2001; Frieden et al., Nucleic Acids Research, 21: 6365-6372, 2003: Koshkin et al., Tetrahedron, 54: 3607-3630, 1998; Morita et al., Bioorganic Medicinal Chemistry, 11: 2211-2226, 2003; Orum et al., Curr. Opinion Mol. Ther. 3; 239-243, 2001; Singh et al., Chem. Commun. 4: 455-456, 1998; Singh et al., J. Org. Chem., 63; 10035-10039, 1998; or Wahlestedt et al., PNAS 97; 5633-5638, 2000.

Steric Blockers

An antisense oligonucleotide can bind a target nucleic acid and sterically block the access of DNA or RNA binding proteins, transcription factors, splicing factors, ribosome, and/or the translation machinery to the target nucleic acid, and thus decrease the target expression, without activating RNAse H. For example, such steric blockers can reduce the expression of a target protein by hybridizing to sequences surrounding the start codon of the target, blocking intronic branch point sequences, targeting splice sites, bracketing intronic and/or exonic sequences, or targeting regulatory sequences such as exon splicing enhancers. Steric blockers can be designed based on previously determined or predicted intron-exon boundaries and gene structure, and a panel of different antisense oligonucleotides can be generated for blocking the same site. BLAST analyses can be performed for each ASO to minimize off-target hybridization.

Steric blockers can achieve mRNA reduction by exploiting endogenous cellular surveillance pathways that recognize and degrade aberrant mRNAs. One such pathway is nonsense-mediated mRNA decay (NMD), which modulates gene expression and prevents producing potentially toxic proteins from mRNAs. Defects in pre-mRNA processing can result in protein loss-of-function when a premature termination codon (PTC) is introduced and disrupts the open reading frame. Such PTC-containing mRNA can be a substrate for NMD, which involves communication between the translating ribosome and components of the exon junction complex, including the essential NMD factor UPF1, to degrade the RNA by endonuclease and exonuclease activity. ASOs can be rationally designed to cause target mRNA reduction by directing the target mRNA to the NMD pathway. This can be achieved by designing the sequences of steric blockers to be complementary to specific coding exons, intron-exon junctions, or other sequences necessary for proper pre-mRNA processing, to introduce exon skipping, frameshifting, and/or introducing PTC.

In some embodiments, the antisense oligonucleotides targeting MAPT provided herein are steric blockers, e.g., oligonucleotides comprising a nucleobase sequence that has at least 70% (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to any of the nucleobase sequences provided in any of Tables 2-8. In some embodiments, the antisense oligonucleotides targeting MAPT provided herein are steric blockers that comprise any of the nucleobase sequences provided in any of Tables 2-8. In some embodiments, the antisense oligonucleotides targeting MAPT provided herein are steric blockers that consist of any of the nucleobase sequences provided in any of Tables 2-8. As detailed in the examples below, the steric blockers were designed to target tau constitutive exons (e.g., exons 1, 4, 5, 7, 9, 11, 12, 13), sequences bracketing the start codon of MAPT, splice acceptors and donors, splicing branch points, polypyrimidine track-related sequences, or splicing enhancer or inhibitor sequences. Targeting the start codon and exon 1 would potentially block initiation of translation. ASOs that interfere with splicing and/or induce exon skipping would result in frameshifting and/or introducing a downstream premature stop codon, leading to reduction of MAPT mRNA and/or tau protein.

Chemical modifications can be incorporated into steric blockers to improve their stability, efficacy, and/or cellular uptake. Steric blockers can have chemical modification at each nucleotide position or at some selected positions. For example, incorporation of 2'-modification of the sugar ring (such as 2'-O-methoxyethyl, MOE), inclusion of locked nucleic acid (LNA) and/or backbone modifications (such as phosphorothioate) can decrease nuclease degradation and/or increase binding affinity of the antisense oligonucleotides. Besides sugar and/or backbone modifications, steric blockers can be made from oligomers that are quite different from DNA or RNA. Peptide nucleic acid (PNAs) is an oligonucleotide mimic whose nucleobases are linked by amide bonds. Because the amide backbone is uncharged, binding is characterized by high rates of association and high affinity (see Bentin T, Biochemistry. 1996; 35:8863-8869; Smulevitch S V, Nat Biotech. 1996; 14:1700-1704). Phosphorodiamidate morpholino oligomers (commonly called PMOs or "morpholinos") are another uncharged DNA analogue. PMOs do not bind complementary targets with the high affinities that characterize PNA binding, but have proven to be effective agents inside cells (see Summerton J, Antisense Nucleic Acid Drug Dev. 1997; 7:187-195; Corey D R, Genome Biol. 2001; 2:REVIEWS 1015).

In some embodiments, the antisense oligonucleotides targeting MAPT provided herein are steric blockers comprising 2'-modified nucleotides. The 2'-modification can be selected from the group consisting of 2'-fluoro, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In some embodiments, the antisense oligonucleotides targeting MAPT provided herein are steric blockers that have 2'-O-MOE modification at each nucleotide subunit.

In some embodiments, the antisense oligonucleotides targeting MAPT provided herein are steric blockers that have internucleoside phosphodiester or phosphorothioate linkages.

In some embodiments, the antisense oligonucleotides targeting MAPT provided herein are steric blockers that contain backbone modifications that hinder RNase H binding. Such steric blockers can include modified internucleoside linkages, e.g., methyl phosphonate linkage, methyl phosphonothioate linkage, phosphoromorpholidate linkage, phosphoropiperazidate linkage or phosphoramidite linkage. In some embodiments, every other one of the internucleoside linkagea may contain a modified phosphate with a 2' lower alkyl moiety (e.g., C1-C4, linear or branched, saturated or unsaturated alkyl, such as methyl, ethyl, ethenyl, propyl, 1-propenyl, 2-propenyl, and isopropyl) or a combination thereof. In some embodiments, the antisense oligonucleotides targeting MAPT provided herein are steric blockers that include one or more modified internucleoside linkages described in U.S. Pat. No. 5,149,797.

In some embodiments, the steric blockers targeting MAPT provided herein include a C6 linker at the 3 end with the following structure:

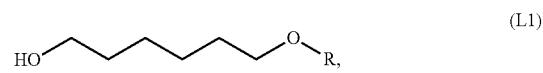

(L1)

which is attached to the 3' end of the oligonucleotide via a phosphate bridge, wherein R=PO2-O-oligonucleotide (for phosphodiester internucleoside linkages) or R=POS-O-oligonucleotide (for phosphorothioate internucleoside linkages). Accordingly, the steric blockers targeting MAPT with phosphodiester internucleoside linkages can have the following structure:

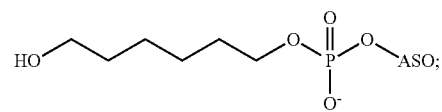

and the steric blockers targeting MAPT with phosphorothioate internucleoside linkages can have the following structure:

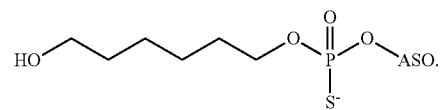

Gapmers

Antisense oligonucleotides comprising a contiguous stretch of DNA can recruit cellular endonuclease RNase H to the target RNA:DNA heteroduplex and cleave the target RNA in the RNA:DNA duplex. Gapmers are chimeric antisense compounds. Chimeric antisense compounds typically contain at least one region modified so as to confer increased resistance to nuclease degradation, increased cellular uptake, increased binding affinity for the target nucleic acid, and/or increased inhibitory activity, and a second region having nucleotides that are chemically different from the nucleotides of the first region.

Gapmers have a central gap segment consisting of a stretch of contiguous 2'-deoxyribonucleotides, positioned between two wing segments consisting of modified nucleotides on the 5' and 3' ends. The gap segment serves as the substrate for endonuclease RNAse H cleavage, while the wing segments with modified nucleotides confer increased resistance to other nuclease degradation. The wing-gap-wing segment can be described as "X-Y-Z," where "X" represents the length of the 5' wing, "Y" represents the length of the gap, and "Z" represents the length of the 3' wing. "X" and "Z" may comprise uniform, variant, or alternating sugar moieties.

In some embodiments, the central gap segment of a gapmer consists of at least five (e.g., 5, 6, 7, 8, 9, 10, 11, 12) contiguous 2'-deoxyribonucleotides; and the 5' and 3' wing segments comprise one or more 2'-modified nucleotides. It has been reported that a chimeric oligonucleotide comprising a stretch of up to four contiguous 2'-deoxyribonucleotides does not activate RNAse H. See U.S. Pat. No. 9,157,081. In some embodiments, the antisense oligonucleotides targeting MAPT provided herein are gapmers comprising at least seven (e.g., 7, 8, 9, 10, 11, 12) contiguous 2'-deoxyribonucleotides. In some embodiments, the antisense oligonucleotides targeting MAPT provided herein are gapmers comprising ten contiguous 2'-deoxyribonucleotides. The 2'-modification can be selected from the group consisting of 2'-fluoro, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

In some embodiments, the gapmers targeting MAPT are 5-10-5 gapmers that are 20 nucleosides in length, wherein the central gap segment comprises ten 2'-deoxynucleosides and is flanked by 5' and 3' wing segments each comprising five nucleosides each with a 2'-modification. Other suitable gapmers include, but are not limited to 5-9-5 gapmers, 5-8-5 gapmers, 4-8-6 gapmers, 6-8-4 gapmers, or 5-7-6 gapmers.

In some embodiments, the antisense oligonucleotides targeting MAPT provided herein are gapmers, e.g., oligonucleotides comprising a nucleobase sequence that has at least 70% (e.g., 70%, 75%, 80%, 81%, 82%, 83%, 84%, 85%, 86%, 87%, 88%, 89%, 90%, 91%, 92%/0, 93%, 94%, 95%, 96%, 97%, 98%, 99%, or 100%/0) sequence identity to any of the nucleobase sequences provided in any of Tables 9-15 and 17. In some embodiments, the antisense oligonucleotides targeting MAPT provided herein are gapmers that comprise any of the nucleobase sequences provided in any of Tables 9-15 and 17. In some embodiments, the antisense oligonucleotides targeting MAPT provided herein are gapmers that consist of any of the nucleobase sequences provided in any of Tables 9-15 and 17. As detailed in the examples below, the gapmers were designed to target sequences surrounding the start codon, exon 1, or 3' untranslated region (UTR) of MAPT transcript. In some embodiments, the gapmers were designed to target 3' UTR In some embodiments, the antisense oligonucleotides targeting MAPT provided herein are 5-10-5 gapmers that comprise any of the nucleobase sequences provided in any of Tables 9-15 and 17, wherein the first to fifth nucleotides each comprise a 2'-O-MOE modified nucleoside, wherein the sixth to fifteenth nucleotides each comprise a 2'-deoxynucleoside, and wherein the sixteenth to twentieth nucleotides each comprise a 2'-O-MOE modified nucleoside.

MAPT Genomic Sequences Targeted by Antisense Oligonucleotides

In some embodiments, antisense oligonucleotides are designed to target a particular region of MAPT genomic sequence (GenBank Accession No. NG_007398.1: SEQ ID NO: 304) or a region of the corresponding tau mRNA or transcript (SEQ ID NO: 306). The MAPT intron and exon sequences and branch points were determined based on Ensembl genomes database website using Transcript: MAPT-203 ENST00000344290. Screening of exons, introns, and intron/exon junctions of human MAPT gene revealed that targeting some regions in MAPT gene or transcript by antisense oligonucleotides is more effective to reduce tau expression than targeting other regions. For example, Table 1 lists sequences of some preferred regions in MAPT gene or transcript that can be targeted by antisense oligonucleotides.

In some embodiments, antisense oligonucleotides provided herein comprise a nucleobase sequence that is complementary to at least 12 contiguous nucleobases (e.g., 12, 13, 14, 15, 16, 17, or 18 contiguous nucleobases) of any one of SEQ ID NOs: 487-506, with 1, 2, or 3 mismatches. In some embodiments, antisense oligonucleotides provided herein comprise a nucleobase sequence that is 100% complementary to at least 12 contiguous nucleobases (e.g., 12, 13, 14, 15, 16, 17, or 18 contiguous nucleobases) of any one of SEQ ID NOs: 487-506.

TABLE 1

Selected MAPT genomic, mRNA or premRNA sequences targeted by tau antisense oligonucleotides

| Selected MAPT genomic sequences (antisense strand) targeted by tau ASO | SEQ ID NO | Location | Corresponding MAPT mRNA or pre-mRNA sequence targeted by tau ASO |
|---|---|---|---|
| ACGCTGGCCTGAAAGGTTAGTGGAC | 292 | Intron/exon 1 junction | GUCCACUAACCUUUCAGGCCAGCGU (SEQ ID NO: 503) |
| AAAAGCCAAGGTAAGCTGACGATGC | 293 | Intron/exon 5 junction | GCAUCGUCAGCUUACCUUGGCUUUU (SEQ ID NO: 504) |
| TTTTATATTTTATCAGCTCGCATGG | 294 | Intron/exon 5 junction | CCAUGCGAGCUGAUAAAAUAUAAAA (SEQ ID NO: 505) |
| ACCCACAAGCTGACCTTCCG | 295 | Exon 13 | CGGAAGGUCAGCUUGUGGGU (SEQ ID NO: 487) |
| ACCAGCTGAAGAAGCAGGCATTGGAGACAC | 296 | Exon 4 | GUGUCUCCAAUGCCUGCUUCUUCAGCUGGU (SEQ ID NO: 488) |

TABLE 1-continued

Selected MAPT genomic, mRNA or premRNA sequences targeted by tau antisense oligonucleotides

| Selected MAPT genomic sequences (antisense strand) targeted by tau ASO | SEQ ID NO | Location | Corresponding MAPT mRNA or pre-mRNA sequence targeted by tau ASO |
|---|---|---|---|
| CTCTCATCTCCAGGTGCAAATAGTC | 297 | Intron/exon II junction | GACUAUUUGCACCUGGAGAUGAGAG (SEQ ID NO: 506) |
| ATAGTCTACAAACCAGTTGA | 298 | Exon 11 | UCAACUGGUUUGUAGACUAU (SEQ ID NO: 489) |
| ATTAGGCAACATCCATCATA | 299 | Exon 11 | UAUGAUGGAUGUUGCCUAAU (SEQ ID NO: 490) |
| GAACCAGGATGGCTGAGCCC | 300 | Exon 1 | GGGCUCAGCCAUCCUGGUUC (SEQ ID NO: 491) |
| CGTCCCTGGCGGAGGAAA | 301 | Exon 12 | UUUCCUCCGCCAGGGACG (SEQ ID NO: 492) |
| TGGTCAGTAAAAGCAAAGAC | 302 | Exon 5 | GUCUUUGCUUUUACUGACCA (SEQ ID NO: 493) |
| CTGGAAGCGATGACAAAAAA | 303 | Exon 5 | UUUUUUGUCAUCGCUUCCAG (SEQ ID NO: 494) |
| CCTTGCTCAGGTCAACTGGT | 479 | Exon 12 | ACCAGUUGACCUGAGCAAGG (SEQ ID NO: 495) |
| GGTTGACATCGTCTGCCTGT | 480 | 3'UTR | ACAGGCAGACGAUGUCAACC (SEQ ID NO: 496) |
| GTCCCACTCTTGTGCCTGGA | 481 | 3'UTR | UCCAGGCACAAGAGUGGGAC (SEQ ID NO: 497) |
| GACATCGTCTGCCTGTGGCT | 482 | 3'UTR | AGCCACAGGCAGACGAUGUC (SEQ ID NO: 498) |
| CCCACTCTTGTGCCTGGACT | 483 | 3'UTR | AGUCCAGGCACAAGAGUGGG (SEQ ID NO: 499) |
| GTCCCAGGTCTGCAAAGTGG | 484 | 3'UTR | CCACUUUGCAGACCUGGGAC (SEQ ID NO: 500) |
| GTCTGCCTGTGGCTCCACGA | 485 | 3'UTR | UCGUGGACrCCACAGGCAGAC (SEQ ID NO: 501) |
| AGTCACTCTGGTGAATCCAA | 486 | 3'UTR | UUGGAUUCACCAGAGUGACU (SEQ ID NO: 502) |

Antisense Oligonucleotide Conjugates

Conjugation of antisense oligonucleotides with another moiety can improve the activity, cellular uptake, and/or tissue distribution of the antisense oligonucleotides. For example, antisense oligonucleotides can be covalently linked to one or more diagnostic compound, reporter group, cross-linking agent, nuclease-resistance conferring moiety, lipophilic molecule, cholesterol, lipid, lectin, linker, steroid, uvaol, hecigenin, diosgenin, terpene, triterpene, sarsasapogenin, Friedelin, epifriedelanol-derivatized lithocholic acid, vitamin, biotin, carbohydrate, dextran, dye, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, transferrin, coumarins, phenazine, folate, phenanthridine, anthraquinone, acridine, fluoresceins, and/or rhodamines.

In some embodiments, the antisense oligonucleotides provided herein are attached to a linker molecule. In some embodiments, the antisense oligonucleotides provided herein are linked to lipid or cholesterol. In some embodiments, the antisense oligonucleotides are linked to neutral liposomes (NL) or lipid nanoparticles (LNP). LNPs are self-assembling cationic lipid based systems, which can comprise, for example, a neutral lipid (the liposome base); a cationic lipid (for oligonucleotide loading); cholesterol (for stabilizing the liposomes); and PEG-lipid (for stabilizing the formulation, charge shielding and extended circulation in the bloodstream). Neutral liposomes (NL) are non-cationic lipid based particles.

In some embodiments, the antisense oligonucleotides provided herein are linked to a fatty acid, e.g., an omega-3 fatty acid or omega-6 fatty acid. Suitable omega-3 fatty acids include, e.g., alpha-linolenic acid (ALA), docosahexaenoic acid (DHA), eicosapentaenoic acid (EPA), docosapentaenoic acid (DPA), eicosatetraenoic acid (ETA), eicosatrienoic acid (ETE), eicosapentaenoic acid (EPA), hexadecatrienoic acid (HTA), heneicosapentaenoic acid (HPA), stearidonic acid (SDA), tetracosapentaenoic acid, and tetracosahexaenoic acid.

Testing Antisense Oligonucleotide Activities

The activity of antisense oligonucleotides can be tested in vitro or in vivo. For in vitro testing, the ASOs can be introduced into cultured cells by transfection or electroporation. Following a period of treatment, MAPT (tau) expression level in the ASO-treated cells can be determined and compared to MAPT (tau) expression level in the untreated control cells.

MAPT expression level can be determined by any appropriate method, for example, by quantitation of MAPT mRNA level, by measuring the quantity of cDNA produced from reverse transcription of MAPT mRNA, or by determining the quantity of tau protein. These methods can be performed on a sample by sample basis or modified for high throughput analysis.

MAPT mRNA level can be detected and quantitated by a probe that specifically hybridizes to a segment of MAPT transcript, e.g., by Northern blot analysis. MAPT mRNA level can also be detected and quantitated by polymerase chain reaction (PCR), using a pair of primers that recognize MAPT transcript. General procedures for PCR are taught in MacPherson et al., PCR: A Practical Approach, (IRL Press at Oxford University Press (1991)). However, PCR conditions used for each application reaction are empirically determined. A number of parameters influence the success of a reaction, for example, annealing temperature and time, extension time, $Mg^{2+}$ and/or ATP concentration, pH, and the relative concentration of primers, templates, and/or deoxyribonucleotides. After amplification, the resulting DNA fragments can be detected by agarose gel electrophoresis followed by visualization with ethidium bromide staining and ultraviolet illumination.

In some embodiments, MAPT mRNA level can be detected and quantitated by quantitative real-time PCR, which monitors the amplification of target nucleic acid by simultaneously incorporating a detectable dye or reporter during the amplification step, using any commercially available real-time PCR system.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example, nick translation or end-labeling (e.g., with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

The activity of antisense oligonucleotides can also be assessed by measuring tau protein levels using the methods known in the art. For example, tau protein level can be quantitated by Western blot analysis (immunoblotting), enzyme-linked immunosorbent assay (ELISA), immunohistochemistry, immunoassays, immunoprecipitation, immunofluorescent assays, immunocytochemistry, fluorescence-activated cell sorting (FACS), radioimmunoassays, immunoradiometric assays, high-performance liquid chromatography (HPLC), mass spectrometry, confocal microscopy, enzymatic assays, or surface plasmon resonance (SPR).

The in vive activity of antisense oligonucleotides can also be tested in animal models. Testing can be performed in normal animals or in experimental disease animal models. Antisense oligonucleotides can be formulated in a pharmaceutically acceptable diluent and delivered via a suitable administration route. Following a period of treatment, tissue samples, e.g., brain tissue, cerebrospinal fluid (CSF), spinal cord, can be collected and tau expression level can be measured using any of the methods described above. Histological analysis can be performed to evaluate the brain structure and/or the presence of neurofibrillary tangles. Phenotypic changes of the treated animals such as improved cognition or mobility can also be monitored and evaluated.

Synthesis and Characterization of Oligonucleotides

Single-stranded oligonucleotides can be synthesized using any nucleic acid polymerization methods known in the art, for example, solid-phase synthesis by employing phosphoramidite methodology (S. L. Beaucage and R. P. Iyer, Tetrahedron, 1993, 49, 6123. S. L. Beaucage and R. P. Iyer, Tetrahedron, 1992, 48, 2223), H-phosphonate, phosphotriester chemistry, or enzymatic synthesis. Automated commercial synthesizers can be used, for example, synthesizers from BioAutomation (Irving, Tex.), or Applied Biosystems (Foster City, Calif.). In some embodiments, single-stranded oligonucleotides are generated using standard solid-phase phosphoramidite chemistry, such as described in Current Protocols in Nucleic Acid Chemistry, Beaucage, S. L. et al. (Edrs.), John Wiley & Sons, Inc., New York, N.Y., USA. Phosphorothioate linkages can be introduced using a sulfurizing reagent such as phenylacetyl disulfide or DDTT (((dimethylamino-methylidene)amino)-3H-1,2,4-dithiazaoline-3-thione). It is well known to use similar techniques and commercially available modified amidites and controlled-pore glass (CPG) products such as biotin, fluorescein, acridine or psoralin-modified amidites and/or CPG to synthesize modified oligonucleotides, or fluorescently labeled, biotin, or other conjugated oligonucleotides.

Control of the quality of the starting materials and products from each synthetic step is vital to minimize impurity levels in the final product. However, given the number of synthetic steps per coupling and the number of couplings, presence of impurities is inevitable. Purification methods can be used to exclude the unwanted impurities from the final oligonucleotide product. Commonly used purification techniques for single-stranded oligonucleotides include reverse-phase ion pair high performance liquid chromatography (RP-IP-HPLC), capillary gel electrophoresis (CGE), anion exchange HPLC (AX-HPLC), and size exclusion chromatography (SEC).

After purification, oligonucleotides can be analyzed by mass spectrometry and quantified by spectrophotometry at a wavelength of 260 nm.

Therapeutic Uses and Methods of Treatment

Provided herein are methods of decreasing tau expression level in a subject, e.g., a human, by administering to the subject a therapeutically effective amount of any of the antisense oligonucleotides described herein. In some embodiments, the antisense oligonucleotide can be administered to the subject through an intrathecal, intracranial, intranasal, intravenous, oral, or subcutaneous route. In some embodiments, such methods further include identifying and selecting a subject who is afflicted with or susceptible to a tau-associated disease.

The antisense oligonucleotides provided herein, or pharmaceutical compositions thereof, can be used to treat or prevent a tau-associated disease in a subject. In some embodiments, the invention provides the antisense oligonucleotides as described herein, or pharmaceutical compositions thereof, for use in the treatment or prevention of a tau-associated disease in a patient. In further embodiments, the invention provides use of the antisense oligonucleotides as described herein in the manufacture of a medicament for use in treatment or prevention of a tau-associated disease in a patient.

Tau-associated diseases include, but are not limited to, Alzheimer's disease (AD), amyotrophic lateral sclerosis/parkinsonism-dementia complex (ALS-PDC), argyrophilic grain dementia (AGD), British type amyloid angiopathy, cerebral amyloid angiopathy, chronic traumatic encephalopathy (CTE), corticobasal degeneration (CBD), Creutzfeldt-Jakob disease (CJD), dementia pugilistica, diffuse neurofibrillary tangles with calcification, Down's syndrome, Dravet's Syndrome, epilepsy, frontotemporal dementia (FTD), frontotemporal dementia with parkinsonism linked to chromosome 17 (FTDP-17), frontotemporal lobar degeneration, ganglioglioma, gangliocytoma, Gerstmann-Straussler-Scheinker disease, Hallervorden-Spatz disease, Huntington's disease, inclusion body myositis, lead encephalopathy, Lytico-Bodig disease, meningioangiomatosis, multiple system atrophy, myotonic dystrophy, Niemann-Pick disease type C (NP-C), non-Guamanian motor neuron disease with neurofibrillary tangles, Pick's disease (PiD), postencephalitic parkinsonism, prion protein cerebral amyloid angiopathy, progressive subcortical gliosis, progressive supranuclear palsy (PSP), subacute sclerosing panencephalitis, tangle only dementia. Tangle-predominant dementia, multi-infarct dementia, ischemic stroke, and tuberous sclerosis.

Combination Therapies

The various oligonucleotides described above can be used in combination with other treatment partners. Accordingly, the methods of treating a tau-associated disease described herein can further include administering a second agent to the subject in need of treatment. For example, antisense oligonucleotides targeting microtubule-associated protein tau (MAPT) can be used in combination with an antibody that specifically binds tau protein and/or an agent targeting amyloid beta (AP3), e.g., an antibody that binds AP3 or a beta-secretase (BACE) inhibitor. In some embodiments, antisense oligonucleotides targeting MAPT are used in combination with an antibody that specifically binds tau protein. In some embodiments, antisense oligonucleotides targeting MAPT are used in combination with a BACE inhibitor.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g., synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., an oligonucleotide of the present invention and a combination partner, are both administered to a patient simultaneously in the form of a single entity or dosage. The term "non-fixed combination" means that the therapeutic agents, e.g., an oligonucleotide of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agents.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g., synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

Sample Preparation

Tissue samples can be obtained from a subject treated with antisense oligonucleotide using any of the methods known in the art, e.g., by biopsy or surgery. For example, a sample comprising cerebrospinal fluid can be obtained by lumbar puncture, in which a fine needle attached to a syringe is inserted into the spinal canal in the lumbar area and a vacuum is created such that cerebrospinal fluid may be sucked through the needle and collected in the syringe. CT imaging, ultrasound, or an endoscope can be used to guide this type of procedure.

The sample may be flash frozen and stored at −80° C. for later use. The sample may also be fixed with a fixative, such as formaldehyde, paraformaldehyde, or acetic acid/ethanol. RNA or protein may be extracted from a fresh, frozen or fixed sample for analysis.

Pharmaceutical Compositions, Dosage, and Administration

Also provided herein are compositions, e.g., pharmaceutical compositions, comprising one or more antisense oligonucleotides provided herein. Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Pharmaceutical compositions are typically formulated to be compatible with its intended route of administration. Examples of routes of administration include intrathecal, intracranial, intranasal, intravenous, oral, or subcutaneous administration.

In some embodiments, the antisense oligonucleotide described herein can be conjugated with an antibody capable of crossing blood-brain barrier (e.g., an antibody that binds transferrin receptor, insulin, leptin, or insulin-like growth factor 1) and be delivered intravenously (Evers et al., Advanced Drug Delivery Reviews 87 (2015): 90-103).

Methods of formulating suitable pharmaceutical compositions are known in the art, see, e.g., Remington: The Science and Practice of Pharmacy. 21st ed., 2005; and the books in the series Drugs and the Pharmaceutical Sciences: a Series of Textbooks and Monographs (Dekker, N.Y.). For example, solutions or suspensions used for parenteral, intradermal, intrathecal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders, for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798. Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the therapeutic compounds are prepared with carriers that will protect the therapeutic compounds against rapid elimination from the body, such as a controlled release formulation, including implants and microencapsulated delivery systems.

The pharmaceutical compositions can be included in a container, pack, or dispenser together with instructions for administration.

In non-limiting examples, the pharmaceutical composition containing at least one pharmaceutical agent is formulated as a liquid (e.g., a thermosetting liquid), as a component of a solid (e.g., a powder or a biodegradable biocompatible polymer (e.g., a cationic biodegradable biocompatible polymer)), or as a component of a gel (e.g., a biodegradable biocompatible polymer). In some embodiments, the at least composition containing at least one pharmaceutical agent is formulated as a gel selected from the group of an alginate gel (e.g., sodium alginate), a cellulose-based gel (e.g., carboxymethyl cellulose or carboxyethyl cellulose), or a chitosan-based gel (e.g., chitosan glycerophosphate). Additional, non-limiting examples of drug-eluting polymers that can be used to formulate any of the pharmaceutical compositions described herein include, carrageenan, carboxymethylcellulose, hydroxypropylcellulose, dextran in combination with polyvinyl alcohol, dextran in combination with polyacrylic acid, polygalacturonic acid, galacturonic polysaccharide, polysalactic acid, polyglycolic acid, tamarind gum, xanthum gum, cellulose gum, guar gum (carboxymethyl guar), pectin, polyacrylic acid, polymethacrylic acid, N-isopropylpolyacrylomide, polyoxyethylene, polyoxypropylene, pluronic acid, polylactic acid, cyclodextrin, cycloamylose, resilin, polybutadiene, N-(2-Hydroxypropyl)methacrylamide (HP MA) copolymer, maleic anhydrate-alkyl vinyl ether, polydepsipeptide, polyhydroxybutyrate, polycaprolactone, polydioxanone, polyethylene glycol, polyorganophosphazene, polyortho ester, polyvinylpyrrolidone, polylactic-co-glycolic acid (PLGA), polyanhydrides, polysilamine, poly N-vinyl caprolactam, and gellan.

In some embodiments, delivery of antisense oligonucleotide to a target tissue can be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacal 2002; 54(1): 3-27).

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but are not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population), and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, the antisense oligonucleotide described herein is dissolved in sterile water, saline (e.g., phosphate-buffered saline), or cerebrospinal fluid (CSF) for administration. In some embodiments, the antisense oligonucleotide described herein is administered intrathecally, e.g., by bolus injection at the L3 or L4 disk space or by infusion using an intrathecal pump.

In some embodiments, about 0.001-1000 mg (e.g., about 0.1-8) mg, about 1-600 mg, about 10-500 mg, about 50-450 mg, about 80-300 mg, about 100-200 mg) of the antisense oligonucleotide described herein is administered to a subject in need thereof.

Kits

Also provided are kits including one or more antisense oligonucleotides described above and instructions for use. Instructions for use can include instructions for diagnosis or treatment of a tau-associated disease. Kits as provided herein can be used in accordance with any of the methods described herein. Those skilled in the art will be aware of other suitable uses for kits provided herein, and will be able to employ the kits for such uses. Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

One skilled in the art will recognize many methods and materials similar or equivalent to those described herein, which could be used in the practice of the present invention. Indeed, the present invention is in no way limited to the methods and materials described.

Examples

The invention is further described in the following examples, which do not limit the scope of the invention described in the claims.

Example 1: General Materials and Methods

Synthesis and Purification of the Antisense Oligonucleotides

Modified antisense oligonucleotides described in this invention were prepared using standard phosphoramidite chemistry on Mermade192 Synthesizer (BioAutomation) for in vitro use and on Mermade 12 (BioAutomation) for in vivo purpose. Phosphoramidites were dissolved in acetonitrile at 0.15 M concentration (0.08M on Mermade192); coupling was made by activation of phosphoramidites by a 0.5M solution of 5-Ethlythiotetrazole in acetonitrile (0.25M on Mermade192). Coupling time was usually between 3-4 minutes. Sulfurization was made by using a 0.2 M solution of Phenylacetyl Disulfide for five minutes. Oxidation was made by a 0.02 M iodine solution in Pyridine (20%)/Water (9.5%)/Tetrahydrofuran (70.5%) for two minutes. A Capping was made using standard capping reagents. Oligonucleotide growing chains were detritylated for the next coupling by 3% dichloroacetic acid in toluene. After completion of the sequences the support-bound compounds were cleaved and deprotected by liquid ammonium hydroxide at 65° C. for 2 hours. The obtained crude solutions were directly purified by HPLC (Akta Explorer). The purified fractions were analyzed by mass spectrometry and quantified by UV according to their extinction coefficient at 260 nM. The pulled fractions are desalted and lyophilized to dryness.

In Vitro Testing of the Antisense Oligonucleotides

The antisense oligonucleotides were tested in vitro in various cell lines, including, but are not limited to, human cell lines such as Huh7 cells, Hela cells, and SH-SY5Y cells, and COS1 green monkey cell lines. Cells were obtained from commercial vendors (e.g., American Type Culture Collection (ATCC), Manassas, Va.), and cultured according to the vendors' instructions.

Antisense oligonucleotides were also tested in human neurons derived from human embryonic stem cells (hESCs), which were obtained from WiCell Research Institute, Inc., located in Madison, Wis., USA. hESC were converted into functional neuronal cells by forced expression of neurogenin-2 (Ngn2), a neuronal lineage-specific transcription factor. Ngn2 construct was delivered into hESCs by using lentiviral delivery for constitutive expression of rtTA and tetracycline-inducible expression of exogenous proteins driven by a tetO promoter. Samples are in compliance with the Guidelines for human Embryonic Stem Cell Research established by the National Council Institute of Medicine of the National Academies ("NAS Guidelines) and the Office for Human Research Protections. Department of Health and Human Services ("DHHS") regulations for the protection of human subjects (45 CFR Part1Q).

The antisense oligonucleotides were introduced into cultured cells by either transfection or nucleofection, when the cells reached approximately 60-80% confluency in culture. For transfection, the antisense oligonucleotides were mixed with OptiFect™ Transfection Reagent (Life Tech Cat #12579-017) in the appropriate cell culture media to achieve the desired antisense oligonucleotide concentration and an OptiFect™ concentration ranging from 2 to 12 ug/mL per 100 nM antisense oligonucleotide. For nucleofection, the antisense oligonucleotides were introduced into neuroblastoma SH-SY5Y cells with the Amaxa Nucleofector-II device (Lonza, Walkersville, Md.). To test ASO efficacy, nucleofection was carried out in 96-well plates. Nucleofector solution SF was selected based on high viability and efficient transfection after preliminary experiments. On the day of nucleofection, 60-80% confluent cultures were trypsinized, and cells plated in each well. hESC derived human neurons were treated by adding 1 or 10 uM antisense oligonucleotides into the medium to be uptaken through passive uptake.

Cells were harvested 24-72 hours after antisense oligonucleotide treatment, at which time tau mRNA or protein were isolated and measured using methods known in the art and as described herein. In general, when treatments were performed in multiple replicates, the data were presented as the average of the replicate treatments. The concentration of antisense oligonucleotide used varied from cell line to cell line. Methods to determine the optimal antisense oligonucleotide concentration for a particular cell line are well known in the art. The antisense oligonucleotides were typically used at concentrations ranging from 1 nM to 1,000 nM when transfected with OptiFect; and at concentrations ranging from 25 nM to 20.000 nM when transfected using nucleofection.

Quantitation of MAPT (tau) mRNA level was accomplished by quantitative real-time PCR using the ViiA7 Real-Time PCR system (Life Technologies) according to the manufacturer's instructions. Prior to real-time PCR, the isolated RNA was subjected to a reverse transcription reaction, which produced complementary DNA (cDNA) that was then used as the substrate for the real-time PCR amplification. The reverse transcription and real-time PCR reactions were performed sequentially in the same sample wells. Fastlane cell multiplex kit (Qiagen Cat #216513) was used to lyse cells in the well and reverse transcribe mRNAs into cDNAs directly from cultured cells without RNA purification. The cDNAs were then used for tau expression analysis using quantitative real-time PCR. The tau mRNA levels determined by real time PCR were normalized using the expression level of a housekeeping gene whose expression level is constant in cells, such as human glyceraldehyde 3-phosphate dehydrogenase (GAPDH), human TATA-box binding Protein (TBP), or human hypoxanthine-guanine phosphoribosyltransferase (HPRT1).

TaqMan gene expression assays were performed for Real-Time Quantitative RT-PCR, following the protocol as described in the QuantiTect Multiplex RT-PCR Kit (Qiagen Cat #204643) using a duplex RT-PCR reaction. Taqman probes specific to Human MAPT (LifeTech AssayID #Hs00902194_m1: FAM-MGB), Human GAPDH (LifeTech AssayID #Hs02758991_g1: VIC-MGB), Human TBP (LifeTech Cat #4326322E) or Human HPRT1 (LifeTech Cat #4333768T) were used. Samples were run on ViiA7 Real-Time PCR system (Life Technologies) following recommended cycling conditions for duplex RT-PCR. All data were controlled for quantity of cDNA input and tau mRNA levels were normalizing to the levels of the endogenous reference gene. Tau and control gene were amplified in the same reaction with similar, high PCR efficiencies, enabling relative quantification by the $\Delta\Delta CT$ method. Results were presented as percent residual tau mRNA relative to control cells treated with PBS.

In Vivo Testing of the Antisense Oligonucleotides

Antisense oligonucleotides for MAPT were tested in vive by delivering the ASOs into the cerebrospinal fluid (CSF) of mice via intracerebral ventricular (ICV) administration. Mice were anesthetized with 5% isoflurane after which isoflurane content in oxygen/nitrous oxygen was reduced to 1.5-2% for maintenance throughout the surgical procedure. Rectal temperature was maintained at 36.9±1.0° C. with homeothermic heating blanked and rectal probe. Anesthetized mice were placed in stereotaxic apparatus and the skin of head was shaved and disinfected with povidone-iodine solution (Betadine). Before incision, mice were given buprenorphine (Temgesic, 0.03 mg/kg, 1 ml/kg, s.c.). Thereafter, incision was made to expose the skull for determination of brain coordinates for the injection. The injection (total volume 2 µl) was given by using 10 µl Hamilton syringe and 28 G needle with micro pump (Harvard Apparatus) into the right lateral ventricle for all animals at following coordinates: AP=+0.5 mm; ML=+1.0 mm; DV=−2.5 mm. Flow rate was 1 µl/min, and needle was left in place for 1 minute after infusion before withdrawn. The skin was closed and the mice were allowed to recover in single cages before returning them to home cage. Additional doses of buprenorphine (Temgesic, 0.03 mg/kg, 1 ml/kg, s.c.) were administered twice a day during the first 48 hours.

Animals were daily monitored by laboratory/animal technicians. The general condition of the animals and wound recovery were monitored; and body weight was measured daily. At the end-point, the animals were deeply anesthetized with sodium pentobarbital (60 mg/kg Mebunat, Orion Pharma, Finland). The mice were subjected to cisterna magna puncture and CSF (3-5 µL per mouse) was collected. Thereafter the mice were subjected to cardiac puncture and blood samples were collected. Approximately 0.4-0.5 mL blood was collected into 500 µL plastic lavender K2EDTA anticoagulant tubes, and centrifuged at 2000 g for 10 min at 4° C. and plasma aliquoted. Thereafter mice were decapitated and brains were collected and dissected into different brain regions such as cortex, hippocampus, and cerebellum. In addition, spinal cords were also collected.

Example 2: Inhibition of Human Tau Expression in Huh7 Cells by 18 mer 2'-O-MOE Steric Blockers Antisense oligonucleotide steric blockers were designed to target intron-exon junctions of constitutive exons in human Tau, the invariable exons present in all isoforms. Antisense oligonucleotide steric blockers were designed to induce exon skipping, either by hybridizing to intronic branch point sequences, targeting splice sites directly, bracketing intronic and exonic sequences, exon splicing enhancers sites. The steric blockers targeting MAPT were initially designed as 18 nucleosides in length with 2'-O-(2-methoxyethyl) (2'-O-MOE) ribose sugar modifications in all nucleosides, which act through steric hindrance and do not activate RNase H or RISC. The internucleoside linkages throughout are phosphodiester linkages. An unbiased screen was carried out for the 18-mer uniformly modified 2'-MOE ASOs with phosphodiester backbone. BLAST analyses were performed for each morpholino oligonucleotide sequence to avoid off-target hybridization.

The 18-mer 2'-O-MOE steric blockers targeting tau were tested in vitro for their activity on human Tau mRNA inhibition. Huh7 cells were plated at a density of 10,000 cells per well and transfected using OptiFect reagent (LifeTech Cat #12579-017) with 25 nM of the antisense oligonucleotide. After a treatment period of 48 hours, cDNA was directly prepared from cultured cells using the Fastlane cell multiplex kit (Qiagen Cat #216513). Tau mRNA levels were measured by quantitative real-time PCR in a duplex RT-PCR reaction using Taqman probes specific to Human MAPT (LifeTech AssayID #Hs00902194_m1: FAM-MGB) and Human TBP (TATA-box binding Protein) Endogenous Control (LifeTech Cat #4326322E). All data were controlled for quantity of cDNA input and tau mRNA levels were normalizing to the levels of the endogenous reference gene TBP. Tau and TBP control gene were amplified in the same reaction with similar, high PCR efficiencies, enabling relative quantification by the ΔΔCT method. Results are presented as percent residual Tau mRNA relative to control cells treated with PBS. Table 2 shows the activities of those 18-mer 2'-O-MOE steric blockers in Huh7 cells.

TABLE 2

Inhibition of tau mRNA by 18-mer 2'-O-MOE steric blockers in Huh7 cells.

| SEQ ID NO | ASO Sequence[1] | % Residual mRNA[2] |
|---|---|---|
| 1 | GTCCACTAACCTTTCAGG | 19.5 |
| 2 | GCATCGTCAGCTTACCTT | 27.7 |
| 3 | TATTTGCACCTGGAGATG | 38.4 |
| 4 | GACTATTTGCACCTGGAG | 40.8 |
| 5 | CATGCGAGCTGATAAAAT | 40.9 |
| 6 | ACCATGCGAGCTGATAAA | 41.3 |
| 7 | CCATGCGAGCTGATAAAA | 43.3 |
| 8 | CGTCAGCTTACCTTGGCT | 44.1 |
| 9 | TGACCATGCGAGCTGATA | 47.4 |
| 10 | ATGCGAGCTGATAAAATA | 52.1 |
| 11 | TTTGCACCTGGAGATGAG | 52.3 |
| 12 | TTGCACCTGGAGATGAGA | 52.4 |
| 13 | ATTTGCACCTGGAGATGA | 61.9 |
| 14 | TCCACTAACCTTTCAGGC | 68.2 |
| 15 | GGTTCAATCTGCAAGAA | 68.8 |
| 16 | CCACTAACCTTTCAGGCC | 71.3 |
| 17 | CACTAACCTTTCAGGCCA | 72.9 |
| 18 | ACTAACCTTTCAGGCCAG | 76.7 |
| 19 | GCTCAGCCATCCTGGTTC | 77.3 |
| 20 | GTTTCAATCTGCAAGAAG | 80.4 |
| 21 | AGTTCACCTGGGGAAAGA | 85.8 |
| 22 | TTGGAGGTTCACCTGGGA | 85.9 |
| 23 | GGCTACCTGGTTTATGAT | 88.8 |
| 24 | AAAGTTCACCTGGGGAAA | 92.1 |
| 25 | GTTCACTGACCTTGGGTC | 96.8 |
| 26 | CAAAGTTCACCTGGGGAA | 98.4 |
| 27 | CAGCTTACCTTGGCTTTT | 99.8 |
| 28 | GGGCTACCTGGTTTATGA | 101.6 |
| 29 | TCTTCAGCTGGTGTATGT | 103.4 |
| 30 | TTCAAAGTTCACCTGGGG | 103.4 |
| 31 | CCCTTTACCTTTTTATTT | 104.7 |
| 32 | TGCTTCTTCAGCTGGTGT | 106.1 |
| 33 | TCAGCTTACCTTGGCTTT | 106.7 |
| 34 | CTGCTTCTTCAGCTGGTG | 107.9 |
| 35 | GGCCACCTCCTAGAACAC | 108.4 |

TABLE 2-continued

Inhibition of tau mRNA by 18-mer 2'-O-MOE steric blockers in Huh7 cells.

| SEQ ID NO | ASO Sequence[1] | % Residual mRNA[2] |
|---|---|---|
| 36 | TCTTACCAGAGCTGGGTG | 108.8 |
| 37 | AAGTTCACCTGGGGAAAG | 109.4 |
| 38 | GTCAGCTTACCTTGGCTT | 109.5 |
| 39 | GGGGCCTGATCACAAACC | 109.7 |
| 40 | AGGTTCACCTGGGAAGGA | 110.2 |
| 41 | GCTTACCTTGGCTTTTTT | 111.4 |
| 42 | TCAAAGTTCACCTGGGGA | 111.7 |
| 43 | CCACTCTCACCTTCCCGC | 112.8 |
| 44 | CCCCCTTTACCTTTTTAT | 113 |
| 45 | GAGGTTCACCTGGGAAGG | 113.3 |
| 46 | GTTCACCTGGGAAGGAAG | 113.6 |
| 47 | CACCTCCTAGAACACAAC | 114.1 |
| 48 | ACTCTCACCTTCCCGCCT | 114.5 |
| 49 | TTCAATCTGCAAGAAGAG | 114.6 |
| 50 | ACTGACCTTGGGTCACGT | 114.7 |
| 51 | TTTCAATCTGCAAGAAGA | 115.1 |
| 52 | TTCTTACCAGAGCTGGGT | 115.5 |
| 53 | CAGGGCTACCTGGTTTAT | 116.1 |
| 54 | GGGCCTGATCACAAACCC | 116.5 |
| 55 | AGGGCTACCTGGTTTATG | 117.2 |
| 56 | CCACCTCCTAGAACACAA | 117.6 |
| 57 | CACTGACCTTGGGTCACG | 118.4 |
| 58 | CCCCTTTACCTTTTTATT | 118.4 |
| 59 | TTCACTGACCTTGGGTCA | 118.6 |
| 60 | GGCCTGATCACAAACCCT | 119.6 |
| 61 | CACTCTCACCTTCCCGCC | 119.7 |
| 62 | CCTGGCCACCTCCTAGAA | 120.4 |
| 63 | CCTTTACCTTTTTATTTC | 120.6 |
| 64 | TCACTGACCTTGGGTCAC | 121.7 |
| 65 | GCCTGATCACAAACCCTG | 122 |
| 66 | CTTTACCTTTTTATTTCC | 122.5 |
| 67 | TTCTTCAGCTGGTGTATG | 124 |
| 68 | GCCACCTCCTAGAACACA | 126.5 |
| 69 | TCTCACCTTCCCGCCTCC | 127.4 |
| 70 | CTTCTTACCAGAGCTGGG | 129.8 |
| 71 | TTCTTCTTACCAGAGCTG | 131.2 |
| 72 | ATCAGCCCCTGTAAATG | 131.3 |

TABLE 2-continued

Inhibition of tau mRNA by 18-mer 2'-O-MOE steric blockers in Huh7 cells.

| SEQ ID NO | ASO Sequence[1] | % Residual mRNA[2] |
|---|---|---|
| 73 | GCTTCTTCAGCTGGTGTA | 133.9 |
| 74 | ACAGGGCTACCTGGTTTA | 134.3 |
| 75 | CTCAGCCATCCTGGTTCA | 134.4 |
| 76 | CAGCCCCTGTAAATGAA | 136.4 |
| 77 | GGGCTCAGCCATCCTGGT | 137.9 |
| 78 | TCTTCTTACCAGAGCTGG | 139 |
| 79 | CTCTCACCTTCCCGCCTC | 143.1 |
| 80 | TCAGCCCCTGTAAATGA | 145.9 |
| 81 | CTTCTTCAGCTGGTGTAT | 148 |
| 82 | GGTTCACCTGGGAAGGAA | 153.5 |
| 83 | CATCAGCCCCTGTAAAT | 156.4 |
| 84 | ACCATCAGCCCCTGTAA | 157.5 |

[1]Each nucleotide has a 2'-O-methoxyethyl (2'-O-MOE) modification; and the internucleoside linkages are phosphodiesters. Each oligonucleotide has a linker (L1) attached to the 3' end of the ASO via a phosphate bridge, and has the following structure:

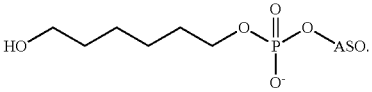

[2]% Residual mRNA is the level of tau mRNA in the Huh7 cells treated with a single dose of 25 nM of tan ASO for 48 hours as compared to the level of tau mRNA in control Huh7 cells treated with PBS. For example, 19.5% residual mRNA means the ASO of SEQ ID NO: 1 has 80.5% activity in decreasing tau mRNA level.

Example 3: Inhibition of Human Tau Expression in SH-SY5Y Cells by 18 mer 2'-O-MOE Steric Blockers Steric blockers that significantly decreased tau expression in Example 2 were selected and tested in human neuroblastoma SH-SY5Y cells. Cultured SH-SY5Y cells were nucleofected with 1,000 nM of a selected antisense oligonucleotide. After a treatment period of approximately 24 hours, cDNA was directly prepared from cultured cells using the Fastlane cell multiplex kit (Qiagen Cat #216513). Tau mRNA levels were measured by quantitative real-time PCR using a duplex RT-PCR reaction, Taqman probes specific to Human MAPT (LifeTech AssayID #Hs00902194_m1: FAM-MGB) and Human GAPDH (LifeTech AssayID #Hs02758991_g1: VIC-MGB) were used. All data were controlled for quantity of cDNA input and Tau mRNA levels were normalizing to the levels of the endogenous reference gene GAPDH. Tau and GAPDH control gene were amplified in the same reaction with similar, high PCR efficiencies, enabling relative quantification by the ΔΔCT method. Results are presented as percent residual Tau mRNA relative to control cells treated with PBS. Table 3 shows the activities of the selected 18-mer 2'-O-MOE steric blockers in SH-SY5Y cells.

TABLE 3

Inhibition of tau mRNA by 18mer 2'-O-MOE steric blockers in SH-SY5Y cells.

| ASO SEQ ID NO | % Residual mRNA[3] |
|---|---|
| 6 | 5.74 |
| 7 | 6.90 |
| 9 | 8.63 |
| 2 | 9.26 |
| 5 | 9.64 |
| 4 | 14.01 |
| 8 | 14.24 |
| 10 | 15.75 |
| 12 | 26.14 |
| 3 | 29.40 |
| 11 | 34.34 |
| 1 | 37.95 |

[3] % Residual mRNA is the level of tau mRNA in the SH-SY5Y cells treated with a single dose of 1,000 nM of tau ASO for 24 hours as compared to the level of tau mRNA in control cells treated with PBS.

Steric blockers that exhibited significant in vitro inhibition of tau mRNA were tested at different doses. Cultured SH-SY5Y cells were nucleofected with 0.125 nM, 0.25 nM, 0.5 nM, 1,000 nM, 2,000 nM, 4.000 nM and 8,000 nM of one selected antisense oligonucleotide. After a treatment period of approximately 24 hours, cDNA was directly prepared and tau mRNA levels were measured by quantitative real-time PCR as described above. Half maximal inhibitory concentration (IC50) was determined by constructing a dose-response curve and examining the effect of different concentrations of antisense oligonucleotides on reducing Tau mRNA. The IC50 values were calculated by determining the concentration needed to inhibit half of the maximum biological response of the compound and can be used as a measure of the potency of the antisense oligonucleotide. Table 4 shows the IC50 values of the selected 18-mer 2'-O-MOE steric blockers.

TABLE 4

IC50 of selected 18mer 2'-O-MOE steric blockers.

| ASO SEQ ID NO | IC50 (nM) |
|---|---|
| 7 | 65 |
| 5 | 88 |
| 6 | 103 |
| 2 | 200 |
| 4 | 288 |
| 10 | 290 |
| 12 | 430 |
| 3 | 490 |
| 11 | 560 |
| 1 | 590 |

Example 4: Inhibition of Human Tau Expression in SH-SY5Y Cells by 12-25 mer 2'-O-MOE Steric Blockers Steric blockers that significantly decreased tau expression in Examples 2 and 3 were selected and made to have different lengths from 12 to 25 nucleosides long. These 12-25 mer 2'-O-MOE steric blockers were tested in SH-SY5Y cells. Cultured SH-SY5Y cells were nucleofected with 2,000 nM of a selected antisense oligonucleotide. After a treatment period of approximately 24 hours, cDNA was directly prepared and Tau mRNA levels were measured as described above. Table 5 shows the activities of the 12-25 mer 2'-O-MOE steric blockers in SH-SY5Y cells.

TABLE 5

Inhibition of tau mRNA by 12-25mer 2'-O-MOE steric blockers in SH-SY5Y cells.

| SEQ ID NO | ASO Sequence[4] | % Residual mRNA[5] | Length of ASO | Tau exon targeted |
|---|---|---|---|---|
| 85 | GT$^m$C$^m$CA$^m$CTAA$^m$C$^m$CTTT$^m$CAGG$^m$C$^m$CGTGT$^m$C | 61.7 | 25 | 1 |
| 86 | GT$^m$C$^m$CA$^m$CTAA$^m$C$^m$CTTT$^m$CAGG$^m$C$^m$CGTGT | 61.6 | 24 | 1 |
| 87 | GT$^m$C$^m$CA$^m$CTAA$^m$C$^m$CTTT$^m$CAGG$^m$C$^m$CGTG | 74.7 | 23 | 1 |
| 88 | GT$^m$C$^m$CA$^m$CTAA$^m$C$^m$CTTT$^m$CAGG$^m$C$^m$CGT | 49.2 | 22 | 1 |
| 89 | GT$^m$C$^m$CA$^m$CTAA$^m$C$^m$CTTT$^m$CAGG$^m$C$^m$CG | 60.2 | 21 | 1 |
| 90 | GT$^m$C$^m$CA$^m$CTAA$^m$C$^m$CTTT$^m$CAGG$^m$C$^m$C | 60.6 | 20 | 1 |
| 91 | GT$^m$C$^m$CA$^m$CTAA$^m$C$^m$CTTT$^m$CAGG$^m$C | 67.8 | 19 | 1 |
| 92 | GT$^m$C$^m$CA$^m$CTAA$^m$C$^m$CTTT$^m$CAGG | 61.6 | 18 | 1 |
| 93 | GT$^m$C$^m$CA$^m$CTAA$^m$C$^m$CTTT$^m$CAG | 58.7 | 17 | 1 |
| 94 | GT$^m$C$^m$CA$^m$CTAA$^m$C$^m$CTTT$^m$CA | 65.4 | 16 | 1 |
| 95 | GT$^m$C$^m$CA$^m$CTAA$^m$C$^m$CTTT$^m$C | 64.2 | 15 | 1 |
| 96 | GT$^m$C$^m$CA$^m$CTAA$^m$C$^m$CTTT | 72.5 | 14 | 1 |
| 97 | GT$^m$C$^m$CA$^m$CTAA$^m$C$^m$CTT | 75.3 | 13 | 1 |
| 98 | GT$^m$C$^m$CA$^m$CTAA$^m$C$^m$CT | 87.1 | 12 | 1 |
| 99 | G$^m$CAT$^m$CGT$^m$CAG$^m$CTTA$^m$C$^m$CTTGG$^m$CTTTT | 35.4 | 25 | 5 |
| 100 | G$^m$CAT$^m$CGT$^m$CAG$^m$CTTA$^m$C$^m$CTTGG$^m$CTTT | 35.3 | 24 | 5 |

TABLE 5-continued

Inhibition of tau mRNA by 12-25mer 2'-O-MOE steric blockers in SH-SY5Y cells.

| SEQ ID NO | ASO Sequence[4] | % Residual mRNA[5] | Length of ASO | Tau exon targeted |
|---|---|---|---|---|
| 101 | G^mCAT^mCGT^mCAG^mCTTA^mC^mCTTGG^mCTT | 37.8 | 23 | 5 |
| 102 | G^mCAT^mCGT^mCAG^mCTTA^mC^mCTTGG^mCT | 38.7 | 22 | 5 |
| 103 | G^mCAT^mCGT^mCAG^mCTTA^mC^mCTTGG^mC | 50.2 | 21 | 5 |
| 104 | G^mCAT^mCGT^mCAG^mCTTA^mC^mCTTGG | 49.5 | 20 | 5 |
| 105 | G^mCAT^mCGT^mCAG^mCTTA^mC^mCTTG | 42.2 | 19 | 5 |
| 106 | G^mCAT^mCGT^mCAG^mCTTA^mC^mCTT | 25.2 | 18 | 5 |
| 107 | G^mCAT^mCGT^mCAG^mCTTA^mC^mCT | 15.0 | 17 | 5 |
| 108 | G^mCAT^mCGT^mCAG^mCTTA^mC^mC | 10.6 | 16 | 5 |
| 109 | G^mCAT^mCGT^mCAG^mCTTA^mC | 14.4 | 15 | 5 |
| 110 | G^mCAT^mCGT^mCAG^mCTTA | 11.9 | 14 | 5 |
| 111 | G^mCAT^mCGT^mCAG^mCTT | 19.6 | 13 | 5 |
| 112 | G^mCAT^mCGT^mCAG^mCT | 33.8 | 12 | 5 |
| 113 | GA^mCTATTTG^mCA^mC^mCTGGAGATGAGAG | 39.7 | 25 | 11 |
| 114 | GA^mCTATTTG^mCA^mC^mCTGGAGATGAGA | 41.1 | 24 | 11 |
| 115 | GA^mCTATTTG^mCA^mC^mCTGGAGATGAG | 45.7 | 23 | 11 |
| 116 | GA^mCTATTTG^mCA^mC^mCTGGAGATGA | 54.2 | 22 | 11 |
| 117 | GA^mCTATTTG^mCA^mC^mCTGGAGATG | 53.2 | 21 | 11 |
| 118 | GA^mCTATTTG^mCA^mC^mCTGGAGAT | 63.6 | 20 | 11 |
| 119 | GA^mCTATTTG^mCA^mC^mCTGGAGA | 50.6 | 19 | 11 |
| 120 | GA^mCTATTTG^mCA^mC^mCTGGAG | 51.0 | 18 | 11 |
| 121 | GA^mCTATTTG^mCA^mC^mCTGGA | 38.4 | 17 | 11 |
| 122 | GA^mCTATTTG^mCA^mC^mCTGG | 41.2 | 16 | 11 |
| 123 | GA^mCTATTTG^mCA^mC^mCTG | 45.6 | 15 | 11 |
| 124 | GA^mCTATTTG^mCA^mC^mCT | 46.8 | 14 | 11 |
| 125 | GA^mCTATTTG^mCA^mC^mC | 47.5 | 13 | 11 |
| 126 | GA^mCTATTTG^mCA^mC | 56.2 | 12 | 11 |
| 127 | ^mC^mCATG^mCGAG^mCTGATAAAATATAAAA | 20.0 | 25 | 5 |
| 128 | ^mC^mCATG^mCGAG^mCTGATAAAATATAAA | 14.7 | 24 | 5 |
| 129 | ^mC^mCATG^mCGAG^mCTGATAAAATATAA | 24.9 | 23 | 5 |
| 130 | ^mC^mCATG^mCGAG^mCTGATAAAATATA | 20.3 | 22 | 5 |
| 131 | ^mC^mCATG^mCGAG^mCTGATAAAATAT | 24.3 | 21 | 5 |
| 132 | ^mC^mCATG^mCGAG^mCTGATAAAATA | 27.2 | 20 | 5 |
| 133 | ^mC^mCATG^mCGAG^mCTGATAAAAT | 23.7 | 19 | 5 |
| 134 | ^mC^mCATG^mCGAG^mCTGATAAAA | 24.0 | 18 | 5 |
| 135 | ^mC^mCATG^mCGAG^mCTGATAAA | 19.8 | 17 | 5 |
| 136 | ^mC^mCATG^mCGAG^mCTGATAA | 17.9 | 16 | 5 |
| 137 | ^mC^mCATG^mCGAG^mCTGATA | 23.9 | 15 | 5 |

TABLE 5-continued

Inhibition of tau mRNA by 12-25mer 2'-O-MOE steric blockers in SH-SY5Y cells.

| SEQ ID NO | ASO Sequence[4] | % Residual mRNA[5] | Length of ASO | Tau exon targeted |
|---|---|---|---|---|
| 138 | $^mC^m$CATG$^m$CGAG$^m$CTGAT | 87.6 | 14 | 5 |
| 139 | $^mC^m$CATG$^m$CGAG$^m$CTGA | 24.6 | 13 | 5 |
| 140 | $^mC^m$CATG$^m$CGAG$^m$CTG | 23.1 | 12 | 5 |

[4]Each nucleotide has a 2'-O-methoxyethyl (2'-O-MOE) modification; and $^m$C stands for 5-methylcytosine. The internucleoside linkages are phosphodiesters. Each oligonucleotide has a linker (L1) attached to the 3' end of the ASO via a phosphate bridge, and has the following structure:

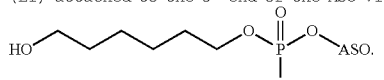

[5]% Residual mRNA is the level of tau mRNA in the SH-SY5Y cells treated with a single dose of 2,000 nM of tau ASO for 24 hours as compared to the level of tau mRNA in control cells treated with PBS.

The IC50 values of selected 12-25 mer 2'-O-MOE steric blockers with phosphodiester internucleoside linkages were determined as described above, and shown in Table 6.

A number of 12-25 mer 2'-O-MOE steric blockers with phosphorothioate internucleoside linkages were synthesized and the IC50 values of some of those steric blockers were shown in Table 7.

TABLE 6

$IC_{50}$ of selected 12-25mers 2'-O-MOE steric blockers with phosphodiester internucleoside linkages.

| ASO SEQ ID NO | $IC_{50}$ (nM) | Length of ASO |
|---|---|---|
| 103 | 2728 | 21 |
| 105 | 860 | 19 |
| 106 | 1793 | 18 |
| 107 | 838 | 17 |
| 108 | 791 | 16 |
| 109 | 512 | 15 |
| 110 | 728 | 14 |
| 131 | 682 | 21 |
| 133 | 1074 | 19 |
| 134 | 1482 | 18 |
| 135 | 574 | 17 |
| 136 | 544 | 16 |
| 137 | 555 | 15 |
| 138 | 1153 | 14 |
| 117 | 25610 | 21 |
| 120 | 4702 | 18 |
| 121 | 1002 | 17 |
| 122 | 1851 | 16 |
| 123 | 1870 | 15 |
| 124 | 2970 | 14 |

TABLE 7

$IC_{50}$ of selected 12-25mers 2'-O-MOE steric blockers with phosphorothioate internucleoside linkages.

| SEQ ID NO | ASO sequence[5] | IC50 (nM) | Length of ASO |
|---|---|---|---|
| 108 | G$^m$CAT$^m$CGT$^m$CAG$^m$CTTA$^mC^m$C | 193 | 16 |
| 111 | G$^m$CAT$^m$CGT$^m$CAG$^m$CTT | 353 | 13 |
| 109 | G$^m$CAT$^m$CGT$^m$CAG$^m$CTTA$^m$C | 426 | 15 |
| 107 | G$^m$CAT$^m$CGT$^m$CAG$^m$CTTA$^mC^m$CT | 579 | 17 |
| 140 | $^mC^m$CATG$^m$CGAG$^m$CTG | 877 | 17 |
| 139 | $^mC^m$CATG$^m$CGAG$^m$CTGA | 930 | 13 |
| 135 | $^mC^m$CATG$^m$CGAG$^m$CTGATAAA | 1201 | 17 |
| 134 | $^mC^m$CATG$^m$CGAG$^m$CTGATAAAA | 1398 | 18 |

[5]Each nucleotide has a 2'-O-methoxyethyl (2'-O-MOE) modification; and $^m$C stands for 5-methylcytosine. The internucleoside linkages are phosphorothioate. Each oligonucleotide has a linker (L1) attached to the 3' end of the ASO via a phosphate bridge, and has the following structure:

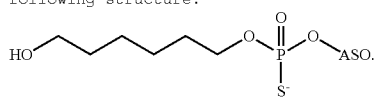

Example 5: Inhibition of Human Tau Expression in SH-SY5Y Cells by 17 mer 2'-O-MOE Steric Blockers 2'-MOE steric blockers that are 17 nucleosides in length were designed to target constitutive exons in human Tau. Those 17 mer 2'-O-MOE steric blockers were tested in SH-SY5Y cells. Cultured SH-SY5Y cells were nucleofected with 2,000 nM of a selected antisense oligonucleotide. After a treatment period of approximately 24 hours, cDNA was directly prepared and tau mRNA levels were measured as described above. Table 8 shows the activities of the 17 mer 2'-O-MOE steric blockers in SH-SY5Y cells.

TABLE 8

Inhibition of tau mRNA by 17mer MOE steric blockers in SH-SY5Y cells

| SEQ ID NO | ASO Sequence[6] | % Residual mRNA[7] | Tau Exon Targeted |
|---|---|---|---|
| 141 | AG$^m$C$^m$CAT$^m$C$^m$CTGGT$^m$CAAA | 131.7 | 1 |
| 142 | $^m$CAG$^m$C$^m$CAT$^m$C$^m$CTGGTTCAA | 173.6 | 1 |
| 143 | T$^m$CAG$^m$C$^m$CAT$^m$C$^m$CTGGTT$^m$CA | 148.3 | 1 |
| 144 | $^m$CT$^m$CAG$^m$C$^m$CAT$^m$C$^m$CTGGTT$^m$C | 127.7 | 1 |
| 145 | GG$^m$C$^m$CAG$^m$CGT$^m$C$^m$CGTGT$^m$CA | 115.9 | 1 |
| 146 | G$^m$C$^m$CAG$^m$CGT$^m$C$^m$CGTGT$^m$CA$^m$C | 103.6 | 1 |
| 147 | $^m$C$^m$CAG$^m$CGT$^m$C$^m$CGTGT$^m$CA$^m$C$^m$C | 96.5 | 1 |
| 148 | $^m$CAG$^m$CGT$^m$C$^m$CGTGT$^m$CA$^m$C$^m$C$^m$C | 121.9 | 1 |
| 149 | GT$^m$CT$^m$C$^m$CAATG$^m$C$^m$CTG$^m$CTT | 125.7 | 4 |
| 150 | TGT$^m$CT$^m$C$^m$CAATG$^m$C$^m$CTG$^m$CT | 120.5 | 4 |
| 151 | GTGT$^m$CT$^m$C$^m$CAATG$^m$C$^m$CTG$^m$C | 43.5 | 4 |
| 152 | GGTGT$^m$CT$^m$C$^m$CAATG$^m$C$^m$CTG | 114.1 | 4 |
| 153 | T$^m$CA$^m$CGTGA$^m$C$^m$CAG$^m$CAG$^m$CT | 105.1 | 4 |
| 154 | $^m$CA$^m$CGTGA$^m$C$^m$CAG$^m$CAG$^m$CTT | 109.1 | 4 |
| 155 | A$^m$CGTGA$^m$C$^m$CAG$^m$CAG$^m$CTT$^m$C | 114.6 | 4 |
| 156 | $^m$CGAAG$^m$CTG$^m$CTGGT$^m$CA$^m$CG | 135.5 | 4 |
| 157 | TTG$^m$CTTTTA$^m$CTGA$^m$C$^m$CA | 18.9 | 5 |
| 158 | $^m$CTTTG$^m$CTTTTA$^m$CTGA$^m$C$^m$C | 6.8 | 5 |
| 159 | T$^m$CTTTG$^m$CTTTTA$^m$CTGA$^m$C | 14.2 | 5 |
| 160 | GT$^m$CTTTG$^m$CTTTTA$^m$CTGA | 68.2 | 5 |
| 161 | TTTTTTGT$^m$CATCG$^m$CTT$^m$C | 18.5 | 5 |
| 162 | TTTTTGT$^m$CATCG$^m$CTT$^m$C$^m$C | 20.0 | 5 |
| 163 | TTTTGT$^m$CATCG$^m$CTT$^m$C$^m$CA | 24.4 | 5 |
| 164 | TTTGT$^m$CATCG$^m$CTT$^m$C$^m$CAG | 30.5 | 5 |
| 165 | AT$^m$CTT$^m$CGTTTTA$^m$C$^m$CAT$^m$C | 110.1 | 7 |
| 166 | GAT$^m$CTT$^m$CGTTTTA$^m$C$^m$CAT | 111.2 | 7 |
| 167 | $^m$CGAT$^m$CTT$^m$CGTTTTA$^m$C$^m$CA | 108.4 | 7 |
| 168 | G$^m$CGAT$^m$CTT$^m$CGTTTTA$^m$C$^m$C | 131.1 | 7 |
| 169 | TGGGTGGTGT$^m$CTTTGGA | 104.6 | 7 |
| 170 | GGGTGGTGT$^m$CTTTGGAG | 101.6 | 7 |
| 171 | GGTGGTGT$^m$CTTTGGAG$^m$C | 105.3 | 7 |
| 172 | GTGGTGT$^m$CTTTGGAG$^m$CG | 107.4 | 7 |
| 173 | AT$^m$C$^m$C$^m$C$^m$CTGATTTTGGAG | 130.3 | 9 |

TABLE 8-continued

Inhibition of tau mRNA by 17mer MOE steric blockers in SH-SY5Y cells

| SEQ ID NO | ASO Sequence[6] | % Residual mRNA[7] | Tau Exon Targeted |
|---|---|---|---|
| 174 | GAT^mC^mC^mCCTGATTTTGGA | 117.8 | 9 |
| 175 | ^mCGAT^mC^mC^mCCTGATTTTGG | 99.7 | 9 |
| 176 | G^mCGAT^mC^mC^mCCTGATTTTG | 116.1 | 9 |
| 177 | G^mC^mCT^mC^mC^mCGG^mCCTGGTG^mCT | 129.8 | 9 |
| 178 | ^mC^mCT^mC^mC^mCGG^mCCTGGTG^mCTT | 135.7 | 9 |
| 179 | ^mCT^mC^mC^mCGG^mCCTGGTG^mCTT^mC | 133.8 | 9 |
| 180 | T^mC^mC^mCGG^mCCTGGTG^mCTT^mCA | 153.5 | 9 |
| 181 | A^mCTGGTTTGTAGA^mCTAT | 32.6 | 11 |
| 182 | AA^mCTGGTTTGTAGA^mCTA | 51.5 | 11 |
| 183 | ^mCAA^mCTGGTTTGTAGA^mCT | 29.4 | 11 |
| 184 | T^mCAA^mCTGGTTTGTAGA^mC | 28.2 | 11 |
| 185 | TATGATGGATGTTG^mC^mCT | 41.7 | 11 |
| 186 | ATGATGGATGTTG^mC^mCTA | 46.4 | 11 |
| 187 | TGATGGATGTTG^mC^mCTAA | 40.9 | 11 |
| 188 | GATGGATGTTG^mC^mCTAAT | 53.6 | 11 |
| 189 | TTTTA^mCTT^mC^mCA^mC^mCTGG^mC | 130.4 | 17 |
| 190 | ATTTTA^mCTT^mC^mCA^mC^mCTGG | 111.2 | 17 |
| 191 | GATTTTA^mCTT^mC^mCA^mC^mCTG | 119.6 | 12 |
| 192 | AGATTTTA^mCTT^mC^mCA^mC^mCT | 123.1 | 12 |
| 193 | ATTT^mC^mCT^mC^mCG^mC^mCAGGGA | 78.0 | 12 |
| 194 | TTT^mC^mCT^mC^mCG^mC^mCAGGGA^mC | 76.1 | 17 |
| 195 | TT^mC^mCT^mC^mCG^mC^mCAGGGA^mCG | 71.5 | 12 |
| 196 | T^mC^mCT^mC^mCG^mC^mCAGGGA^mCGT | 89.0 | 12 |
| 197 | AAGGT^mCAG^mCCTTGTGGGT | 62.1 | 13 |
| 198 | GAAGGT^mCAG^mCCTTGTGGG | 49.9 | 13 |
| 199 | GGAAGGT^mCAG^mCCTTGTGG | 59.3 | 13 |
| 200 | ^mCGGAAGGT^mCAG^mCCTTGTG | 51.9 | 13 |
| 201 | A^mC^mC^mCTG^mCTTGG^mC^mCAGGG | 116.5 | 13 |
| 202 | ^mC^mC^mCTG^mCTTGG^mC^mCAGGGA | 106.1 | 13 |
| 203 | ^mC^mCTG^mCTTGG^mC^mCAGGGAG | 105.3 | 13 |
| 204 | ^mCTG^mCTTGG^mC^mCAGGGAGG | 133.6 | 13 |

[6]Each nucleotide has a 2'-O-MOE modification; and ^mC stands for 5-methylcytosine. The internucleoside linkages are phosphodiesters. Each oligonucleotide has a linker (L1) attached to the 3' end of the ASO via a phosphate bridge, and has the following structure:

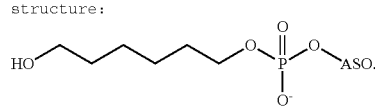

[7]% Residual mRNA is the level of tau mRNA in the SH-SY5Y cells treated with a single dose of 2,000 nM of tau ASO for 24 hours as compared to the level of tau mRNA in control cells treated with PBS.

Example 6: Inhibition of Human Tau Expression in Huh7 Cells by 5-10-5 Gapmers Antisense oligonucleotides sequences were designed to be complementary to the shortest Tau isoform, transcript variant 4. mRNA (GenBank: NM_016841.4). BLAST analyses were performed for each oligonucleotide sequence to avoid off-target hybridization. Newly designed modified chimeric antisense oligonucleotides were designed as 5-10-5 gapmers that are 20 nucleosides in length, wherein the central gap segment comprises ten 2'-deoxynucleosides and is flanked by wing segments on the 5' direction and the 3' direction comprising five nucleosides each with a 2'-O-MOE ribose sugar modification. The internucleoside linkages throughout each gapmer are phosphorothioate (P=S) linkages.

The gapmers targeting tau were tested for inhibiting human Tau mRNA expression in vitro. Huh7 cells were plated at a density of 10,000 cells per well and transfected using OptiFect reagent (LifeTech Cat #12579-017) with 25 nM of the antisense oligonucleotide. After a treatment period of 48 hours, cDNA was directly prepared from cultured cells using the Fastlane cell multiplex kit (Qiagen Cat #216513). Tau mRNA levels were measured by quantitative real-time PCR in a duplex RT-PCR reaction using Taqman probes specific to Human MAPT (LifeTech AssayID #Hs00902194_m1: FAM-MGB) and Human TBP (TATA-box binding Protein) Endogenous Control (LifeTech Cat #4326322E). All data were controlled for quantity of cDNA input and Tau mRNA levels were normalizing to the levels of the endogenous reference gene TBP. Tau and TBP control gene were amplified in the same reaction with similar, high PCR efficiencies, enabling relative quantification by the ΔΔCT method. Results are presented as percent residual Tau mRNA relative to control cells treated with PBS. Table 9 shows the activities of the gapmers in Huh7 cells.

TABLE 9

Inhibition of Tau mRNA by 5-10-5 MOE gapmers i Huh7 cells

| SEQ ID NO | ASO Sequence[8] | % Residual mRNA[9] |
|---|---|---|
| 205 | C*C*G*T*A*CGTCCCAGCGT*G*A*T*C* | 72.5 |
| 206 | G*G*C*T*C*AGCCATCCTGG*T*T*C*A* | 26.4 |
| 207 | C*C*C*G*T*ACGTCCCAGCG*T*G*A*T* | 29 |
| 208 | G*G*T*T*G*ACATCGTCTGC*C*T*G*T* | 29.1 |
| 209 | G*G*G*C*T*CAGCCATCCTG*G*T*T*C* | 30.1 |
| 210 | G*G*C*C*A*GCGTCCGTGTC*A*C*C*C* | 32.8 |
| 211 | G*G*C*T*C*TCCCAGCGGCA*A*G*G*A* | 32.8 |
| 212 | C*C*C*T*C*TTGGTCTTGGT*G*C*A*T* | 33.2 |
| 213 | C*G*G*G*A*CCTGCCTCCCA*G*A*C*C* | 33.6 |
| 214 | G*C*T*G*G*TCTCTGTTGGG*T*C*C*C* | 34.5 |
| 215 | G*G*G*C*T*CTCTCCATGTC*A*A*C*A* | 34.6 |
| 216 | G*G*T*C*T*CTGTTGGGFCC*C*A*G*G* | 34.9 |
| 217 | G*G*G*A*C*CTGCCTCCCAG*A*C*C*C* | 35.2 |
| 218 | C*C*C*A*A*CCCGTACGTCC*C*A*G*C* | 37.4 |
| 219 | G*C*T*T*C*GTCTTCCAGGC*T*G*G*G* | 39 |
| 220 | C*C*G*T*G*TCACCCTCTTG*G*T*C*T* | 40.8 |
| 221 | C*T*T*G*G*CTCTCCCAGCG*G*C*A*A* | 40.8 |
| 222 | C*G*G*C*C*TCCTTAGCTGC*T*A*G*A* | 41.7 |
| 223 | C*A*G*C*G*TCCGTGTCACC*C*T*C*T* | 42.8 |
| 224 | G*C*T*C*A*GCCATCCTGGT*T*C*A*A* | 42.9 |
| 225 | C*C*T*G*G*ACTTTGCCTTC*C*C*T*T* | 43.5 |
| 226 | G*T*C*C*C*ACTCTTGTGCC*T*G*G*A* | 44.1 |
| 227 | A*C*C*T*G*GCCACCTCCTG*G*T*T*T* | 45 |
| 228 | T*T*G*G*C*TTTGGCGTTCT*C*G*C*G* | 45.1 |
| 229 | C*G*C*T*T*CCAGTCCCGTC*T*T*T*G* | 46.4 |
| 230 | G*G*T*G*A*TCACCTCTGCC*C*T'T*G* | 46.4 |
| 231 | G*G*T*A*C*CTCCTGCAACC*A*A*C*C* | 47.7 |
| 232 | C*A*C*G*T*GGCTTCCTCTC*C*C*A*C* | 49.4 |
| 233 | G*C*G*T*C*CGTGTCACCCT*C*T*T*G* | 50.6 |
| 234 | C*A*C*C*C*TCTTGGTCTTG*G*T*G*C* | 52.3 |
| 235 | G*T*C*C*C*AGCGTGATCTT*C*C*A*T* | 52.5 |
| 236 | G*C*C*A*G*CACTGATCACC*C*T*A*A* | 53.1 |
| 237 | T*G*G*T*C*TCTGTTGGGTC*C*C*A*G | 53.6 |
| 238 | C*C*G*C*C*TCCCGGCTGGT*G*C*T*T* | 55.6 |
| 239 | G*G*C*C*A*CACGAGTCCCA*G*T*G*T* | 58.2 |
| 240 | G*T*C*C*C*TCAGGGTTGCC*T*T*T*A* | 58.5 |
| 241 | G*G*A*C*C*ACTGCCACCTT*C*T*T*G* | 58.8 |
| 242 | C*A*C*C*T*GGCCACCTCCT*G*G*T*T* | 58.9 |
| 243 | C*C*C*G*C*CTCCCGGCTGG*T*G*C*T* | 59.7 |
| 244 | G*G*T*G*C*CTTGCCCTTCC*A*T*C*C* | 60.3 |
| 245 | C*C*C*G*T*CACACTCACAC*A*A*G*G* | 61.1 |
| 246 | C*C*C*A*A*TCCCTGCTGTG*G*T*C*G* | 61.4 |
| 247 | G*G*G*T*C*CCACTCTTGTG*C*C*T*G* | 62.9 |
| 248 | G*C*T*T*C*CAGTCCCGTCT*T*T*G*C* | 63 |
| 249 | C*C*C*T*T*CTCCCACAGGC*T*G*C*C* | 63.1 |
| 250 | C*T*G*G*T*GCCACCACTGA*C*A*A*C* | 63.2 |
| 251 | G*C*C*A*C*TGCCTCTGIGA*C*A*C*C* | 63.3 |
| 252 | G*T*G*C*C*ACCACTGACAA*C*C*A*A* | 63.5 |
| 253 | C*T*T*G*C*CCTTCCATCCT*G*G*T*G* | 63.7 |
| 254 | G*C*C*T*G*GACTTTGCCTT*C*T*C*T* | 64.3 |

TABLE 9-continued

Inhibition of Tau mRNA by 5-10-5 MOE gapmers i Huh7 cells

| SEQ ID NO | ASO Sequence[8] | % Residual mRNA[9] |
|---|---|---|
| 255 | G*C*C*T*C*TAACTCCGTGG*C*T*G*C* | 65.1 |
| 256 | G*A*T*C*C*CAGAGCCTTCC*G*T*A*T* | 66.3 |
| 257 | C*A*T*C*C*TCGCGCCGCAA*G*C*C*A* | 66.7 |
| 258 | G*C*C*T*C*CCGGCTGGTGC*T*T*C*A* | 66.8 |
| 259 | G*T*G*C*C*TGGACTTTGCC*T*T*C*C* | 67.1 |
| 260 | C*T*G*C*C*ACTGCCTCTGT*G*A*C*A* | 69.7 |
| 261 | C*C*T*G*G*CCACCTCCTGG*T*T*T*A* | 70.3 |
| 262 | G*G*G*T*G*CCTTGCCCTTC*C*A*T*C* | 71.1 |
| 263 | C*C*A*C*T*CCCACTTCTTG*T*G*C*T* | 71.8 |
| 264 | G*T*G*C*T*TCAGGCCTTCG*T*C*A*C* | 74.6 |
| 265 | C*T*G*[m]C*C*AGCTTGCCTTC*T*C*T*T* | 75.9 |
| 266 | C*T*C*C*C*GGCTGGTGCTT*C*A*G*G* | 76.2 |
| 267 | C*G*C*C*T*CCCGGCTGGFG*C*T*T*C* | 78 |
| 268 | C*T*G*G*C*CACCTCCTGGT*T*T*A*T* | 78.7 |
| 269 | G*G*C*C*A*CCTCCTGGTTT*A*T*G*A* | 79.1 |
| 270 | C*C*A*T*T*CTGGTGCCACC*A*C*T*G* | 82.9 |
| 271 | C*C*T*G*C*CAGCTTGCCTT*C*T*C*T* | 83.7 |
| 272 | A*A*T*C*C*CTGCTGTGGTC*G*C*A*G* | 83.7 |
| 273 | G*C*C*A*C*CACTGACAACC*A*A*G*A* | 84.1 |
| 274 | C*T*T*G*T*CGGCCATGAT*A*T*A*G* | 87.7 |
| 275 | T*A*A*G*C*AGTGGGTTCTC*T*A*G*T* | 88 |
| 276 | C*C*T*C*C*CGGCTGGTGCT*T*C*A*G* | 88.8 |
| 277 | C*T*C*C*T*GCCAGCTTGCC*T*T*C*T* | 92.2 |
| 278 | C*T*T*C*T*CCTCCGGCCAC*T*A*G*T* | 93.6 |
| 279 | C*T*C*C*T*CCGGCCACTAG*T*G*G*G* | 94.2 |
| 280 | C*C*T*T*C*TCCTCCGGCCA*C*T*A*G* | 94.9 |
| 281 | G*A*G*C*C*TTCTCCTCCGG*C*C*A*C* | 105.7 |
| 282 | G*C*C*T*T*CTCCTCCGGCC*A*C*T*A* | 112.5 |
| 283 | C*C*T*T*A*CCTGCTAGCTG*G*C*G*T* | 128.7 |

[8]The nucleotides with* have a 2'-O-MOE modification; the nucleotides without * are 2'-deoxynucleosides. The inter-nucleoside linkages are phosphorothioate.
[9]%Residual mRNA is the level of tau mRNA in the Huh7 cells treated with a single dose of 25 nM of tau ASO for 48 hours as compared to the level of tau mRNA in control Huh7 cells treated with PBS.

Example 7: Inhibition of Human Tau Expression in SH-SY5Y Cells by 5-10-5 Gapmers Gapmers that significantly decreased Tau mRNA expression in Example 6 were selected and tested in SH-SY5Y cells. Cultured SH-SY5Y cells were nucleofected with 2,000 nM antisense oligonucleotide. After a treatment period of approximately 24 hours, cDNA was directly prepared from cultured cells using the Fastlane cell multiplex kit (Qiagen Cat #216513). Tau mRNA levels were measured by quantitative real-time PCR using a duplex RT-PCR reaction, Taqman probes specific to Human MAPT (LifeTech AssayID #Hs00902194_m1: FAM-MGB) and Human GAPDH (LifeTech AssayID #Hs02758991_g1: VIC-MGB) were used. All data were controlled for quantity of cDNA input and Tau mRNA levels were normalizing to the levels of the endogenous reference gene GAPDH. Tau and GAPDH control gene were amplified in the same reaction with similar, high PCR efficiencies, enabling relative quantification by the ΔΔCT method. Results are presented as percent residual Tau mRNA relative to control cells treated with PBS. Table 10 shows the activities of selected 5-10-5 gapmers in SH-SY5Y cells. The IC50 values of selected 5-10-5 gapmers with 5-methylcytosines were determined in SH-SY5Y cells as described above, and shown in Table 11.

TABLE 10

Inhibition of Tau mRNA by 5-10-5 gapmers in SH-SY5Y cells

| ASO SEQ ID NO | % Residual mRNA[10] |
|---|---|
| 204 | 3.0 |
| 205 | 7.6 |
| 202 | 10.7 |
| 203 | 15.3 |
| 208 | 19.2 |
| 207 | 24.6 |
| 209 | 34.3 |
| 210 | 46.9 |
| 206 | 51.4 |
| 211 | 62.1 |
| 201 | 83.2 |

[10]% Residual mRNA is the level of tau mRNA in the SH-SY5Y cells treated with a single dose of 2,000 nM of tau ASO for 24 hours as compared to the level of tau mRNA in control cells treated with PBS.

TABLE 11

IC50 of selected 5-10-5 gapmers with 5-methylcytosine in SH-SY5Y cells

| SEQ ID NO | ASO Sequence[11] | IC$_{50}$ (nM) |
|---|---|---|
| 284 | [m]C*[m]C*G*T*A*[m]CGT[m]C[m]C[m]CAG[m]CGT*G*A*T*[m]C* | 331 |
| 285 | G*G*T*T*G*A[m]CAT[m]CGT[m]CTG[m]C*[m]C*T*G*T* | 170 |

TABLE 11-continued

IC50 of selected 5-10-5 gapmers with 5-methylcytosine in SH-SY5Y cells

| SEQ ID NO | ASO Sequence[11] | $IC_{50}$ (nM) |
|---|---|---|
| 286 | G*G*G*$^m$C*T*$^m$CAG$^m$C$^m$CAT$^m$C$^m$CTG*G*T*T*$^m$C* | 268 |
| 287 | G*G*$^m$C*T*$^m$C*T$^m$C$^m$C$^m$CAG$^m$CGG$^m$CA*A*G*G*A* | 78 |
| 288 | $^m$C*$^m$C*$^m$C*T*$^m$C*TTGGT$^m$CTTGGT*G*$^m$C*A*T* | 366 |
| 289 | G*$^m$C*T*G*G*T$^m$CT$^m$cTGTTGGG*T*$^m$C*$^m$C*$^m$C* | 133 |
| 290 | G*T*$^m$C*$^m$C*$^m$C*A$^m$CT$^m$CTTGTG$^m$C$^m$C*T*G*G*A* | 458 |
| 791 | G*G*G*$^m$C*T*$^m$CT$^m$CT$^m$C$^m$CATGT$^m$C*A*A*$^m$C*A* | 118 |

[11]The nucleotides with * have a 2'-O-MOE modification; the nucleotides without * are 2'-deoxynucleosides; and $^m$C stands for 5-methylcytosine. The internucleoside linkages are phosphorothioate.

Example 8: Characterization of Antisense Oligonucleotide Targeting MAPT

Figure 1A:
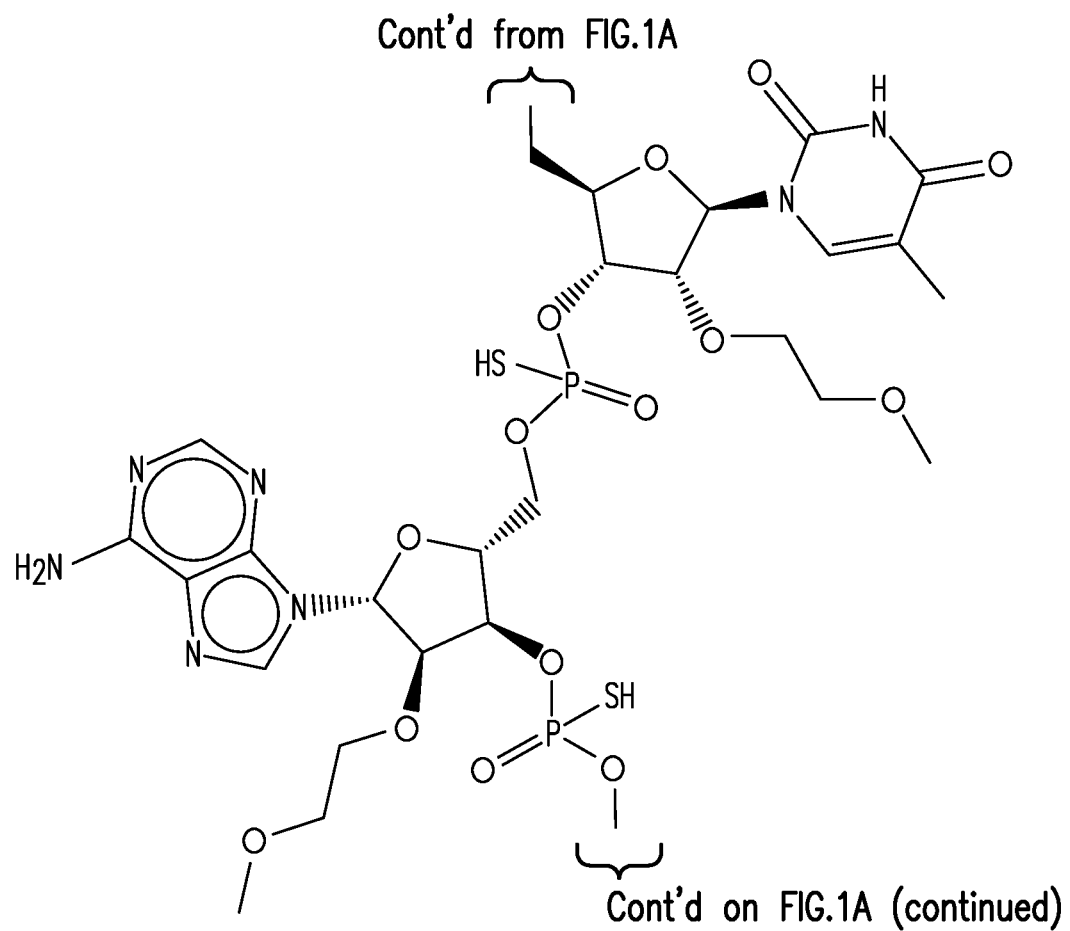
Figure 1A:
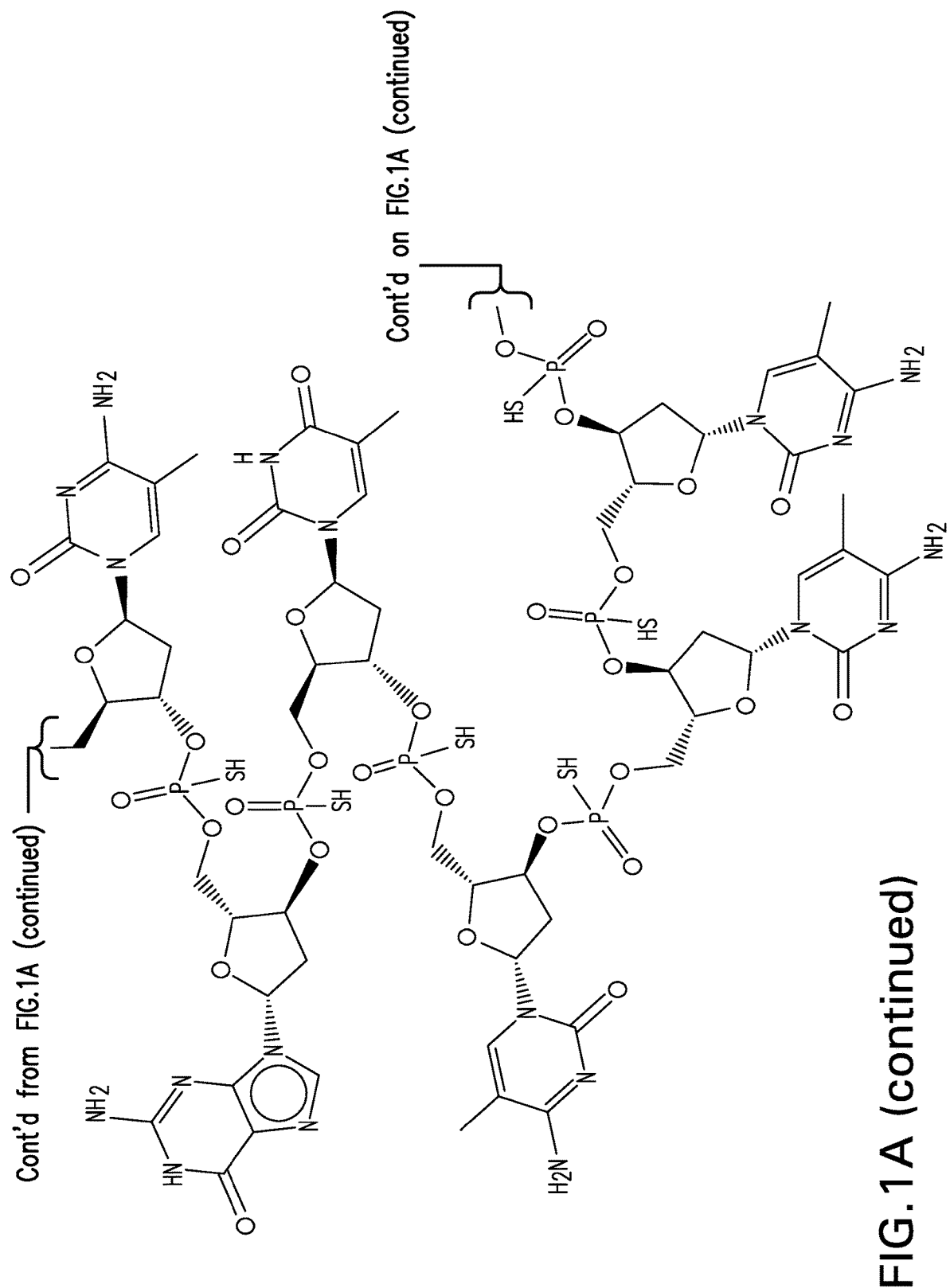
Figure 1A:
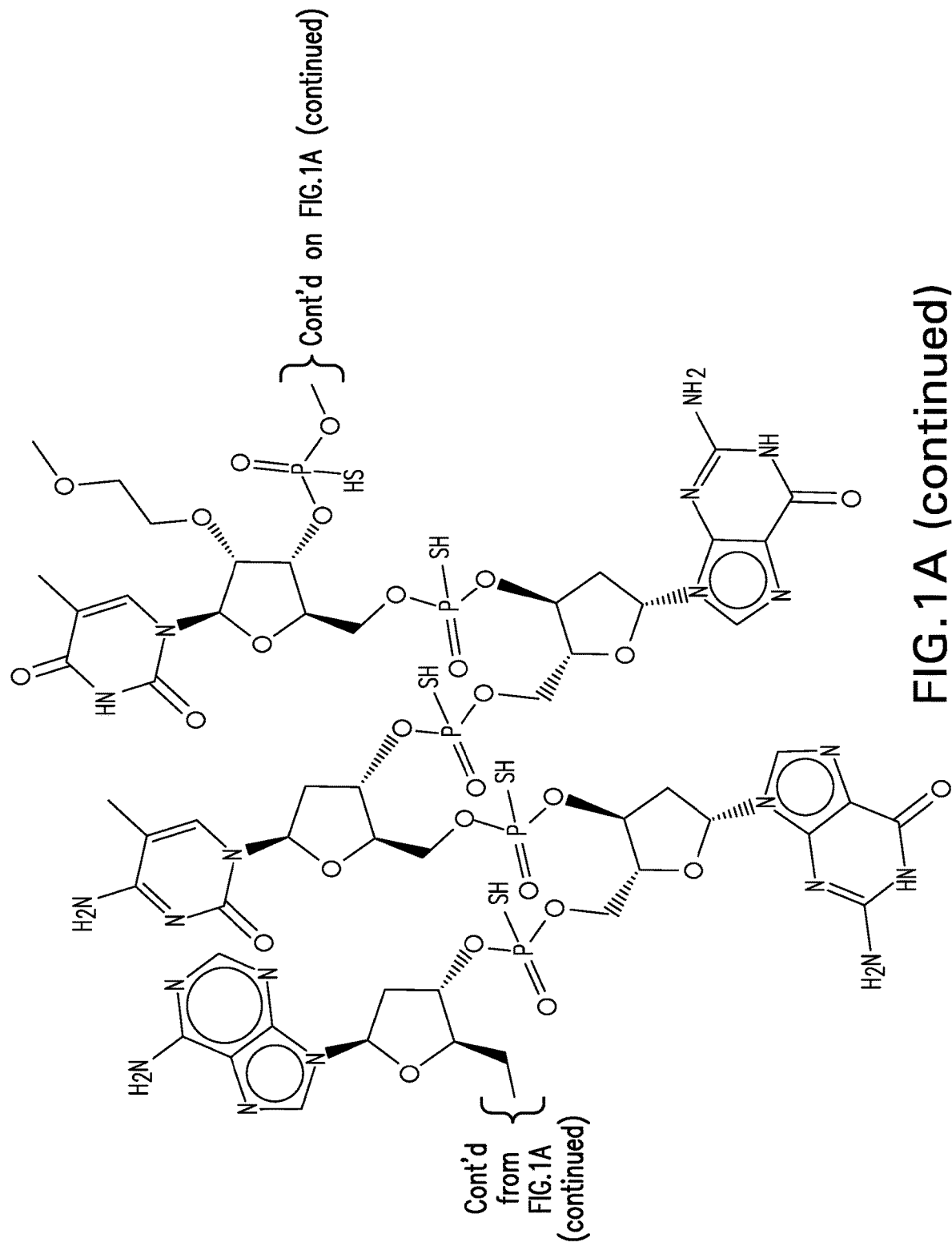
Figure 1A:
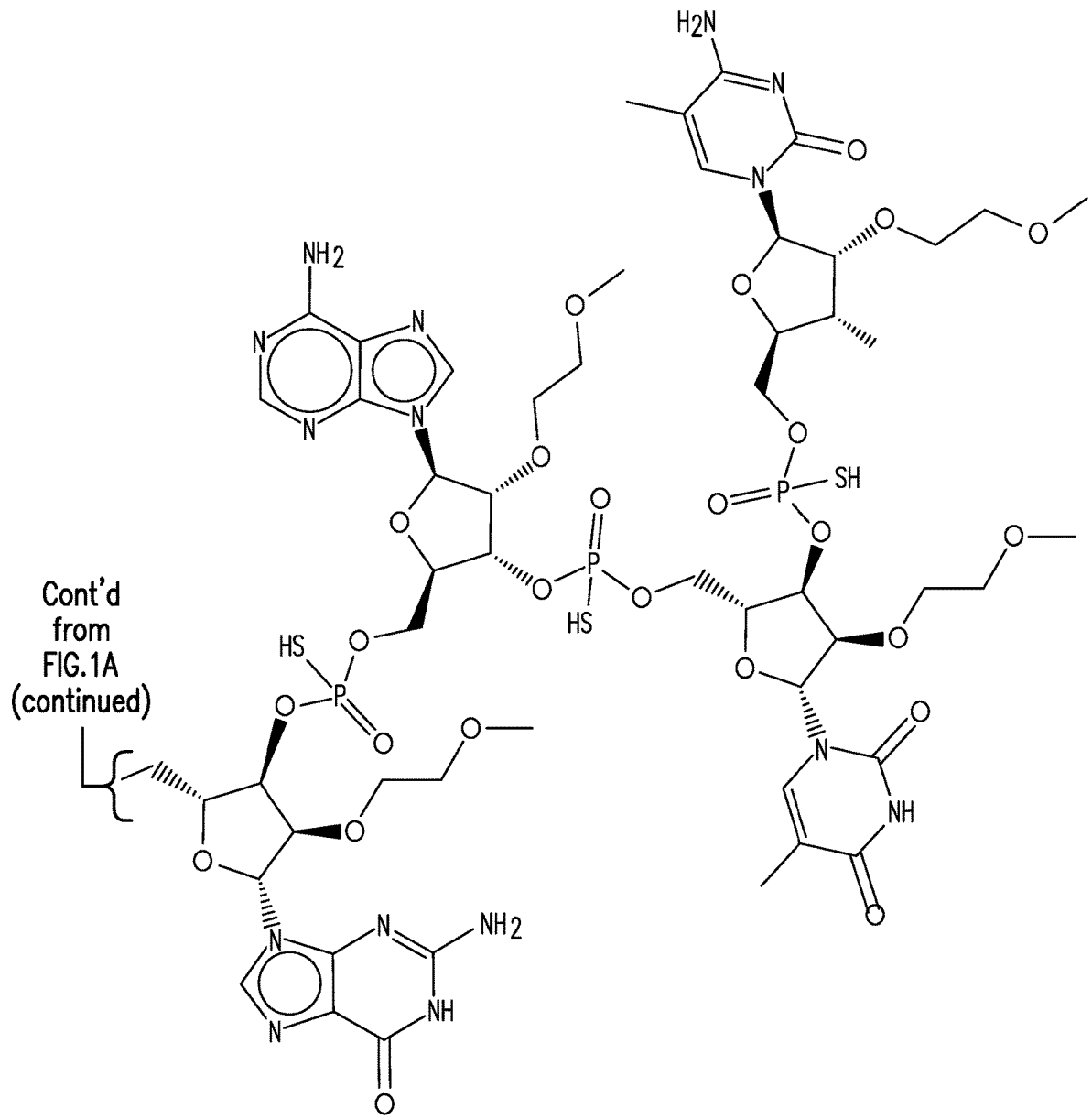
Figures 1, 1A:
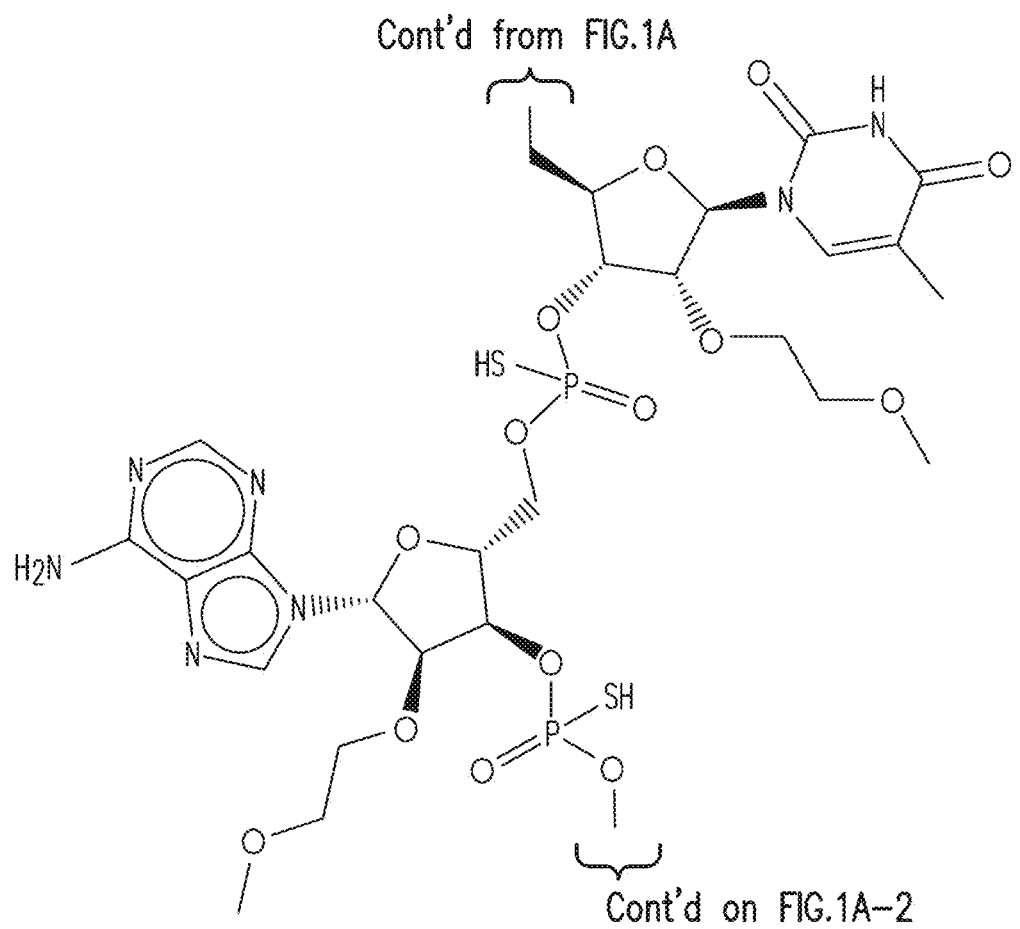
Figures 1, 1A, 2:
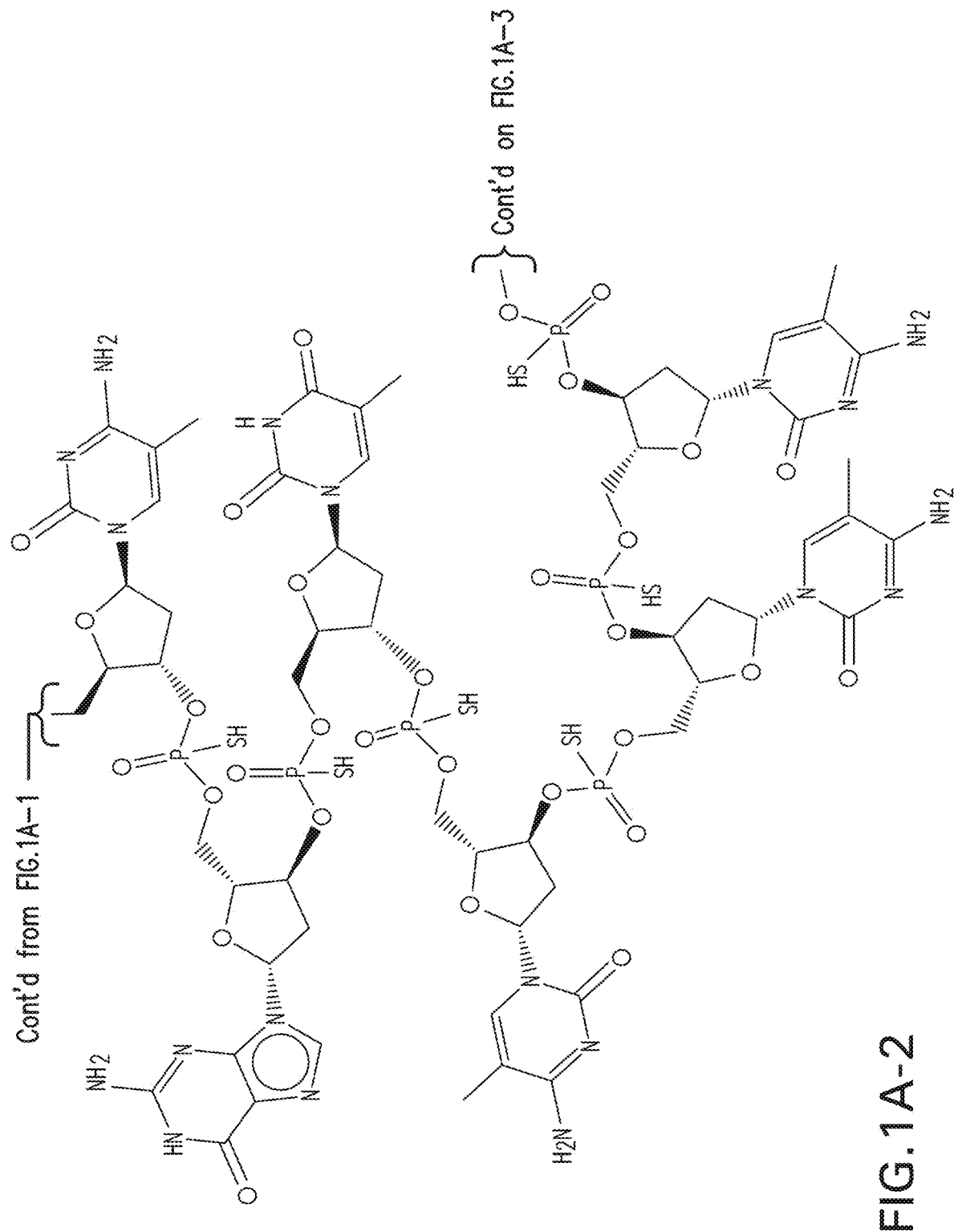

Antisense oligonucleotides targeting MAPT were characterized by using Thermo Scientific high-throughput liquid chromatography-mass spectrometry (LC-MS) instrument. This method was used to confirm the expected masses of antisense oligonucleotide (ASO) and provide information about sample purity and the identification of major components present. For example, the antisense oligonucleotide comprising SEQ ID NO: 284 has the structure shown in FIG. 1A and the formula of C230H321N72O120P19S19. Thus, the expected molecular weight for ASO comprising SEQ ID NO: 284 is about 7212.3 Da. FIG. 1B shows the peak mass for ASO comprising SEQ ID NO: 284 as measured by LC-MS is 7214.3 Da. FIG. 1C shows the deconvolution peak report of LC-MS for ASO comprising SEQ ID NO: 284.

Figures 1, 1A, 2, 3:
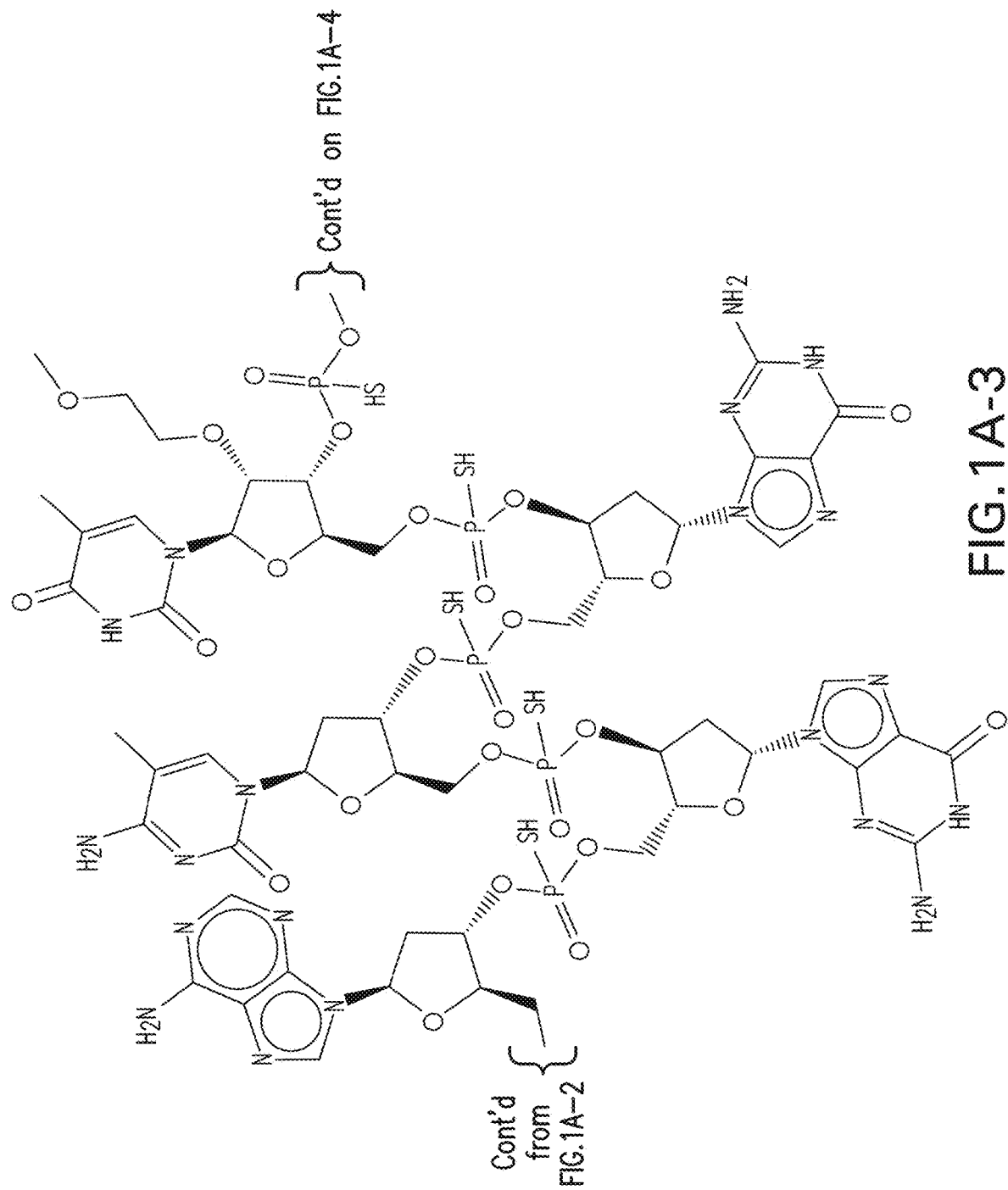
Figures 1, 1A, 2, 3, 4:
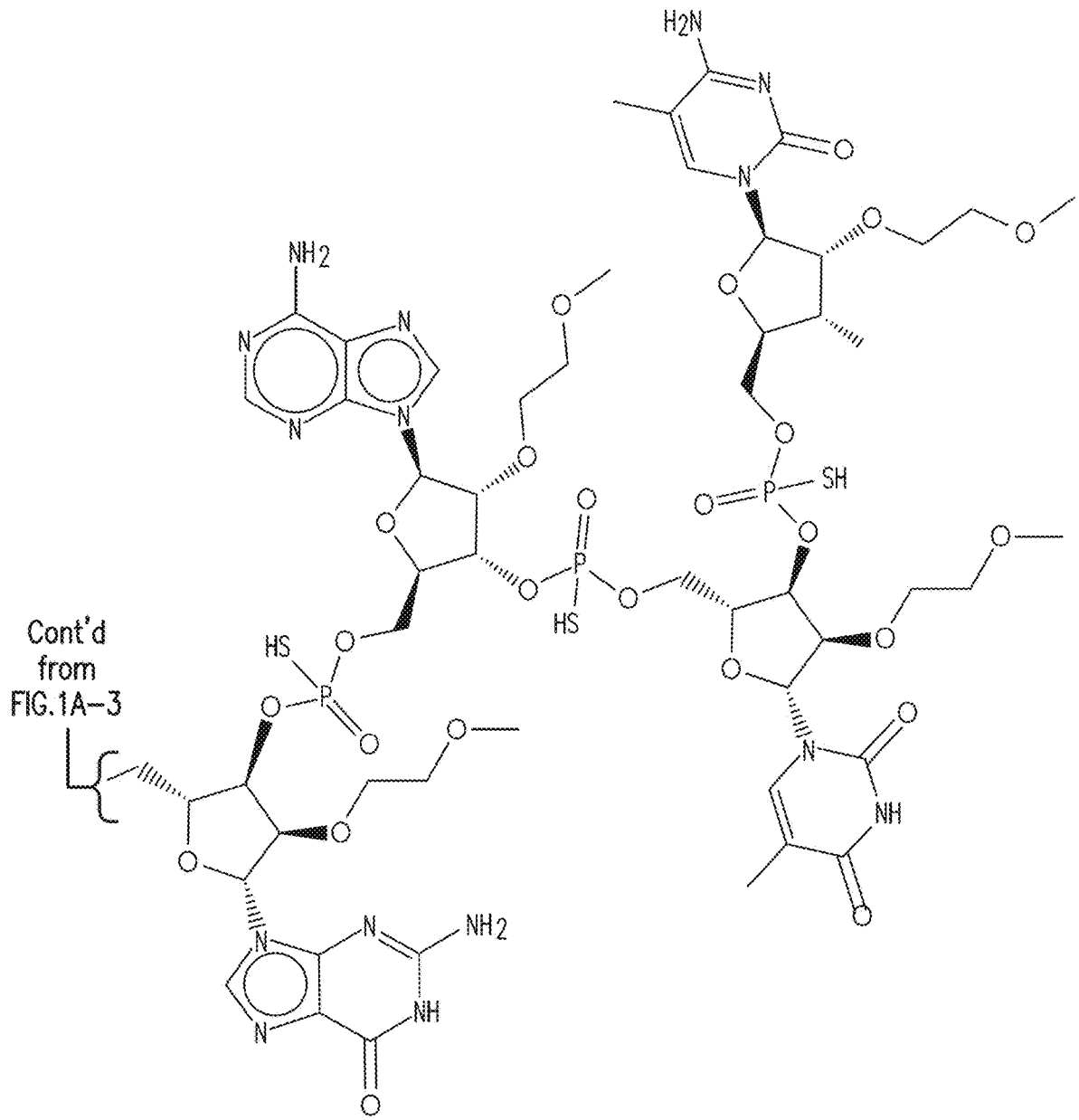
Figures 1D, 1E:
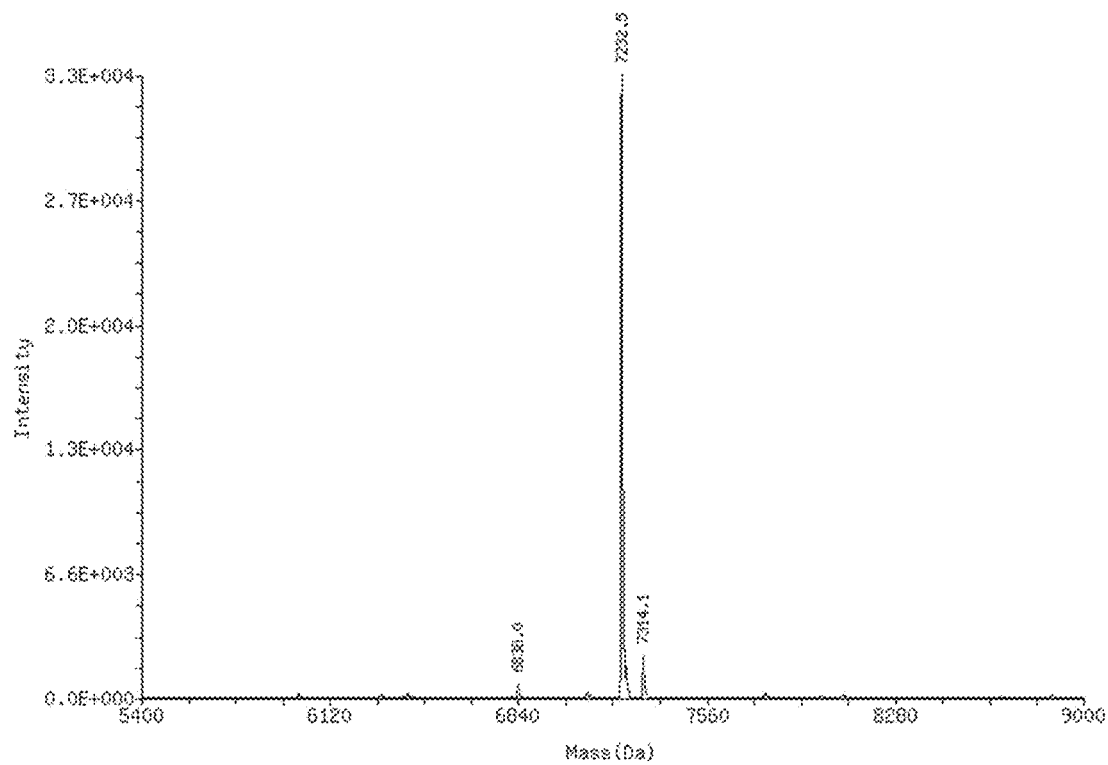

The antisense oligonucleotide comprising SEQ ID NO: 285 has the formula of C230 N69 O124 P19 S19 H318, with an estimated molecular weight of 7231.11 Da. FIG. 1D shows the peak mass for ASO comprising SEQ ID NO: 285 as measured by LC-MS is 7232.5. FIG. 1E shows the deconvolution peak report of LC-MS for ASO comprising SEQ ID NO: 285.

Example 9: In Vivo Testing of Gapmers Targeting MAPT

Generation of Human Tau (hTau) Transgenic Mice

Figure 2A:
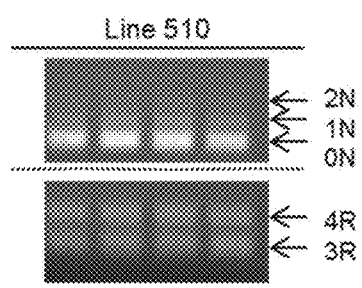
FIGS. 2A-2E show the expression level of human tau mRNA and protein in a representative hTau BAC transgenic mouse line before and after antisense oligonucleotide treatment.
Figure 2B:
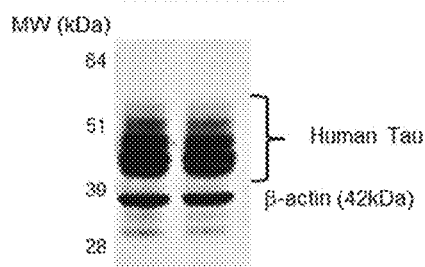
Figure 2C:
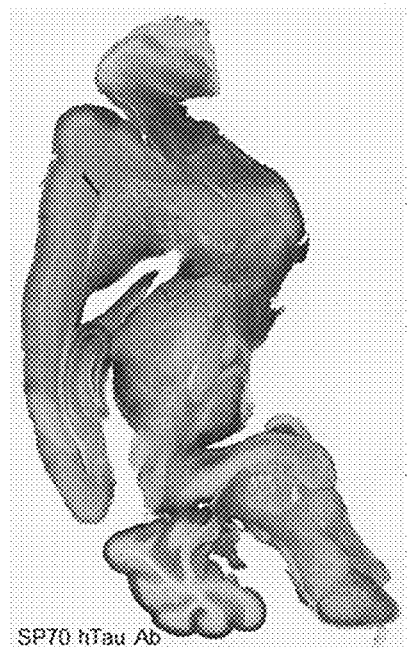

The BAC vectors (pBACe3.6) containing the human tau gene MAPT was obtained from Life technologies human genomic libraries. Three vectors predicted to contain all regulatory regions of MAPT gene were screened. Human genomic DNA were subjected to standard PCR to test for the presence of each exon, primers spanning introns of the human tau gene and regulatory regions were also used to determine the sequence of the clones. Comparison to human DNA showed that one clone (RP11 669E14) was intact for the all portions of the tau gene. This BAC vector was used to generate hTau BAC transgenic mice. The purified DNA was injected into fertilized embryos of C57BL/6 mice. Tail DNA from founder pups was digested with restriction enzymes and hybridized with exon specific probes, using similarly digested human DNA as a control to test for transgene integrity. Positive founder pups were expanded. Several hTau BAC transgenic lines were generated and one line showed human MAPT mRNA and protein expression (FIGS. 2A-2C). This line expressed all six human brain transcripts and protein isoforms found in the human brain (FIGS. 2A-2C). Heterozygote hTau BAC transgenic mice carry one copy of the transgene and the levels of RNA and human tau expression are comparable to the endogenous murine Tau expression.

In Vivo Knockdown of Human Tau by Antisense Oligonucleotides

Selected antisense oligonucleotides were tested in vivo. Groups of five hTau BAC transgenic mice were administered with 1, 10, 50, 200, or 400 ug of a selected antisense oligonucleotide by intracerebroventricular (ICV) bolus injection, or left untreated as a group of control mice. All procedures were performed under isoflourane anesthesia and in accordance with IACUC regulations. For ICV bolus injections, the antisense oligonucleotide was injected into the right lateral ventricle of hTau BAC transgenic mice. Two or four microliters of a PBS solution containing 100 ug/ul of oligonucleotide were injected. Tissues were collected immediately after, 1 hour, 4 hours, 24 hours, 2 weeks, 4 weeks, 12 weeks or 24 weeks after oligonucleotide administration. RNA was extracted from hippocampus or cortex and examined for human tau mRNA expression by real-time PCR analysis. Human tau mRNA levels were measured as described above. Results were calculated as percent inhibition of human tau mRNA expression normalized to GAPDH levels compared to the control untreated mice. Protein was extracted from hippocampus or cortex and examined for human tau protein expression level by ELISA and normalized to total protein level.

The in vivo activity of 5-10-5 gapmers comprising SEQ ID NO: 284 or SEQ ID NO: 285 were tested using the methods described above. As shown in Table 12, both antisense oligonucleotides significantly inhibited human tau mRNA expression in cortex and hippocampus 2 weeks after a single ICV injection of antisense oligonucleotides. The knockdown of human tau mRNA was approximately 65% in both cortex and hippocampus for the gapmer comprising SEQ ID NO: 285. The knockdown of human tau mRNA was approximately 42% in both cortex and hippocampus for the gapmer comprising SEQ ID NO: 284. For tau protein level after 2 weeks of ASO treatment, the gapmer comprising SEQ ID NO: 285 knocked down about 50% of tau protein expression in cortex; and the gapmer comprising SEQ ID NO: 284 knocked down about 36% of the tau protein expression in cortex. We did not observe a significant reduction of tau protein level in hippocampus after 2 weeks of ASO treatment.

TABLE 12

Inhibition of Tau mRNA and protein expression by 5-10-5 MOE gapmers in vivo

| ASO SEQ ID NO | % Residual tau mRNA two weeks after ASO treatment[12] | | % Residual tau protein two weeks after ASO treatment[13] | |
|---|---|---|---|---|
| | Cortex | Hippocampus | Cortex | Hippocampus |
| 285 | 35.26 | 33.55 | 50.8 | 91.1 |
| 284 | 58.8 | 56.77 | 64 | 100 |

[12]% Residual tau mRNA is the level of tau mRNA in the indicated brain tissue of hTau BAC transgenic mice two weeks after a single ICV injection of the indicated ASO, as compared to the level of tau mRNA in the corresponding brain tissue of the control htau BAC transgenic mice that were not treated with ASO.
[13]% Residual tau protein is the level of tau protein in the indicated brain tissue of hTau BAC transgenic mice two weeks after a single ICV injection of the indicated ASO, as compared to the level of tau protein in the corresponding brain tissue of the control hTau BAC transgenic mice that were not treated with ASO.

Figure 2D:
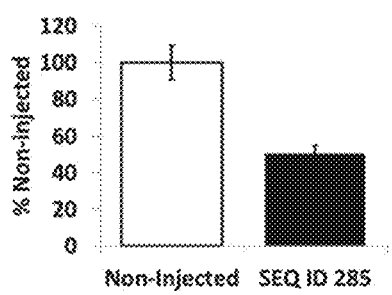
Figure 2E:
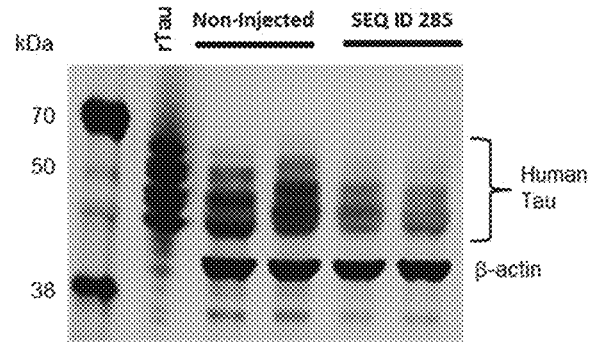
Figure 3:
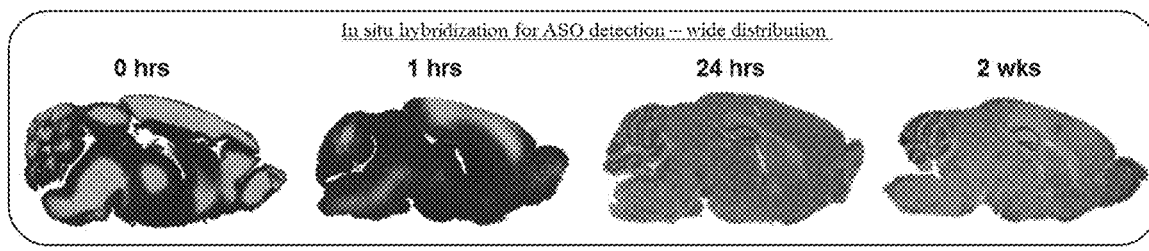

Tau mRNA and protein level were also tested 4 weeks after the single ICV injection of the gapmers. The antisense oligonucleotides comprising SEQ ID NO: 285 significantly inhibited human tau mRNA (FIG. 2D) and protein (FIG. 2E) expression in brain. The knockdown of human tau mRNA was approximately 60% in both cortex and hippocampus for the gapmer comprising SEQ ID NO: 285 (FIG. 2D and data unshown). Western blot analysis showed that the gapmer comprising SEQ ID NO: 285 knocked down human tau protein level by approximately 50% in the hippocampus 4 weeks post treatment (FIG. 2E).

To detect the brain distribution of the antisense oligonucleotides in the brain of hTau BAC transgenic mice, in situ hybridization experiments were performed using a double digoxigenin (DIG) labeled Locked Nucleic Acid (LNA™, Exiqon) probe. Double-DIG LNA probes complementary to target antisense oligonucleotides were hybrizied overnight. The pobes were then detected using a sheep anti-DIG alkaline phosphatase conjugated antibody (Roche Diagnostics, Cat. #11093274910) and the colorimetric reaction of Nitro Blue Tetrazolium conjungated with the alkaline phosphatase substrate 5-Bromo-4-Chloro-3-Indolyl Phosphate (BCIP). The brain distribution of the antisense oligonucleotide of SEQ ID NO: 285 in a representative experiment was shown in FIG. 3, which shows initial diffusion of the ASO from the ventricles to the mouse brain parenchyma and the distribution signal does not change between 24 hrs and 2 weeks. (FIG. 3). The antisense oligonucleotide is stable in the brain even after 4 weeks (data unshown).

Figure 4A:
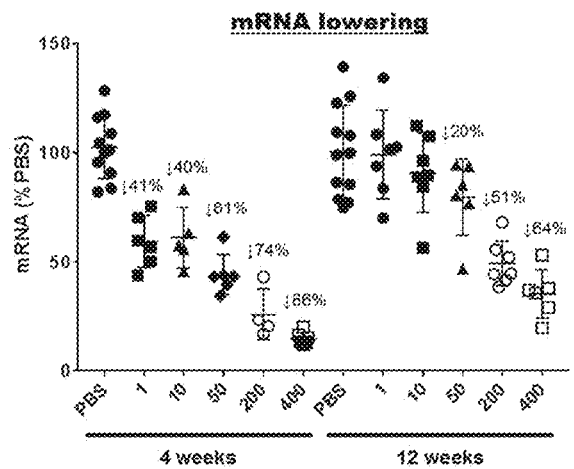
FIGS. 4A and 4B are dot plots showing dose-dependent inhibition of human tau mRNA (FIG. 4A) and protein (FIG. 4B) expression in hTau BAC transgenic mouse at 4 weeks or 12 weeks after a single ICV injection of 1, 10, 50, 200, or 400 ug of the antisense oligonucleotide of SEQ ID NO: 285.
Figure 4B:
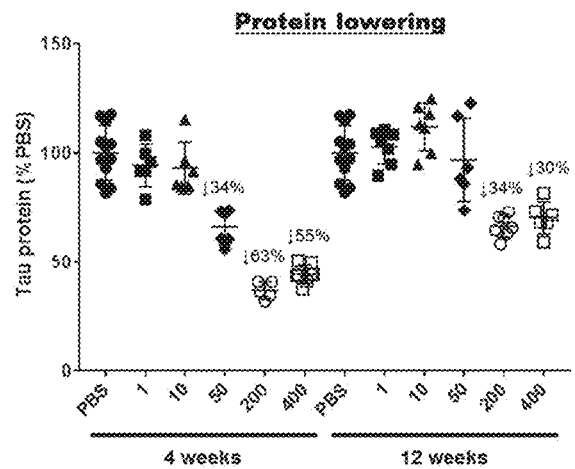

Dose-dependent inhibition of human tau mRNA (FIG. 4A) and protein (FIG. 4B) expression in hTau BAC transgenic mouse by the antisense oligonucleotide of SEQ ID NO: 285 was observed (FIGS. 4A and 4B).

Figure 5A:
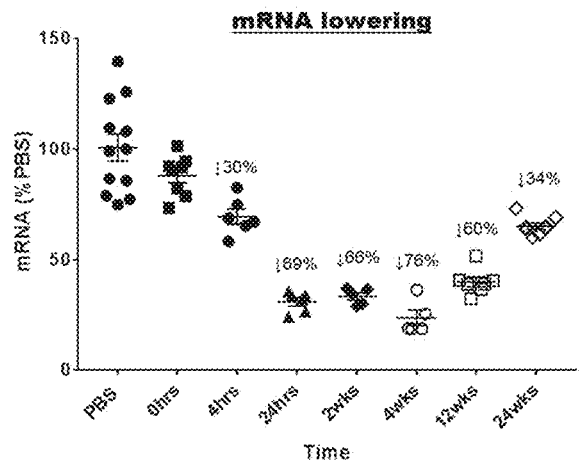
FIGS. 5A and 5B are dot plots showing the time course of human tau mRNA (FIG. 5A) and protein (FIG. 5B) expression level in hTau BAC transgenic mouse after a single ICV injection of 200 ug of the antisense oligonucleotide of SEQ ID NO: 285.
Figure 5B:
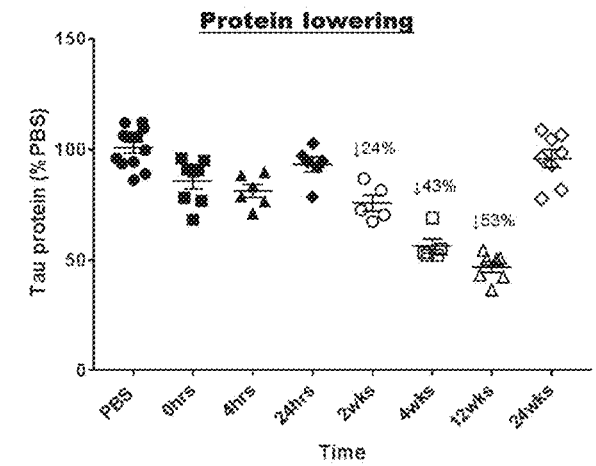

The time course of human tau mRNA (FIG. 5A) and protein (FIG. 5B) expression level in hTau BAC transgenic mouse after a single ICV injection of 200 ug of the antisense oligonucleotide of SEQ ID NO: 285 showed sustained inhibition of tau mRNA and protein expression up to 12 weeks by the antisense oligonucleotide of SEQ ID NO: 285 (FIGS. 5A and 5B).

Example 10: Inhibition of Human Tau Expression in Huh7 and SH-SY5Y Cells by Additional 5-10-5 Gapmers with 5-Methylcytosine Additional gapmers sequences with 5-methylcytosine targeting tau were tested for inhibiting human Tau mRNA expression in vitro Huh7 and SH-SY5Y cells as described above. Results are presented as percent residual Tau mRNA relative to control cells treated with PBS. Table 13 shows the activities of additional screened sequences of 5-10-5 gapmers in Huh7 and SH-SY5Y cells.

TABLE 13

Inhibition of Tau mRNA by 5-10-5 MOE gapmers in Huh7 and SH-SY5Y cells

| SEQ ID NO | ASO Sequence[14] | % Residual mRNA in SHSY5Y cells[15] | % Residual mRNA in HUH7 cells[16] |
|---|---|---|---|
| 307 | G*$^m$C*$^m$C*$^m$C*T*T*T$^m$CTGG$^m$C$^m$CTGGA*G*G*G*G* | 66.8 | 34.7 |
| 308 | T*G*G*$^m$C*$^m$C*CTT$^m$CTGG*$^m$C$^m$CTG*G*A*G*G* | 57.7 | 41.1 |
| 309 | G*$^m$C*T*G*G*TG$^m$CTT$^m$CAGGTT*$^m$C*T*$^m$C*A* | 60.4 | 42.7 |
| 310 | T*$^m$C*A*G*G*T$^m$CAA$^m$CTGGTTT*G*T*A*G* | 30.5 | 37.3 |
| 311 | T*G*$^m$C*T*$^m$C*AGGT$^m$CAA$^m$CTGG*T*T*T*G* | 42.6 | 35.5 |
| 312 | T*T*G*$^m$C*T*$^m$CAGGT$^m$CAA$^m$CTG*G*T*T*T* | 44.9 | 44.7 |
| 313 | $^m$C*$^m$C*T*T*G*$^m$CT$^m$CAGGT$^m$CAA$^m$C*T*G*G*T | 10.3 | 20.9 |
| 314 | $^m$C*$^m$C*$^m$C*T*$^m$C*TT$^m$CTA$^m$CATGGA*G*G*G*G* | 67.7 | 51.3 |
| 315 | T*T*$^m$C*T*$^m$C*$^m$C*$^m$CT$^m$CTT$^m$CTA$^m$CA*T*G*G*A* | 76.7 | 95.1 |
| 316 | $^m$C*T*T*$^m$C*T*$^m$C*$^m$C*$^m$CT$^m$CTT$^m$CTA$^m$C*A*T*G*G* | 68.2 | 77.6 |
| 317 | $^m$C*$^m$C*T*T*$^m$C*T$^m$C*$^m$C*$^m$CT$^m$CTT$^m$CTA*$^m$C*A*T*G* | 50.4 | 72.3 |
| 318 | $^m$C*A**A*A*T*$^m$C$^m$CTTTGTTG$^m$CT*G*$^m$C*$^m$C*A* | 33.6 | 54.4 |
| 319 | T*$^m$C*A*A*A*T$^m$C$^m$CTTTGTTG$^m$C*T*G*$^m$C*$^m$C* | 28.5 | 44.5 |
| 320 | T*G*G*$^m$C*T*$^m$C$^m$CA$^m$CGAA$^m$CA$^m$CA*$^m$C*$^m$C*A*A* | 24.2 | 55.1 |

TABLE 13-continued

Inhibition of Tau mRNA by 5-10-5 MOE gapmers in Huh7 and SH-SY5Y cells

| SEQ ID NO | ASO Sequence[14] | % Residual mRNA in SHSY5Y cells[15] | % Residual mRNA in HUH7 cells[16] |
|---|---|---|---|
| 321 | G*T*G*G*$^m$C*T$^m$C$^m$CA$^m$CGAA$^m$CA$^m$C*A*$^m$C*$^m$C*A* | 22.9 | 51.6 |
| 322 | T*G*T*G*G*$^m$CT$^m$C$^m$CA$^m$CGAA$^m$CA*$^m$C*A*$^m$C*$^m$C* | 25.4 | 62.4 |
| 323 | $^m$C*T*G*T*G*G*$^m$CT$^m$C$^m$CA$^m$CGAA*$^m$C*A*$^m$C*A*$^m$C* | 31.1 | 49.2 |
| 324 | $^m$C*$^m$C*T*G*T*GG*$^m$CT$^m$CACA$^m$CGAA*$^m$C*A*$^m$C*A* | 34.8 | 56.7 |
| 325 | G*$^m$C*$^m$C*T*G*TGG$^m$CT$^m$C$^m$CA$^m$CGA*A*$^m$C*A*$^m$C* | 31.4 | 51.3 |
| 326 | T*G*$^m$C*$^m$C*T*GTGG$^m$CT$^m$C$^m$CA$^m$CG*A*A*$^m$C*A* | 24.2 | 50.2 |
| 327 | $^m$C*T*G*$^m$C*$^m$C*TGTGG$^m$CT$^m$C$^m$CA$^m$C*G*A*A*$^m$C* | 18.9 | 56.7 |
| 328 | T*$^m$C*T*G*$^m$C*$^m$CTGTGG*$^m$CT*$^m$C*CA*$^m$C*G*A*A* | 25.0 | 43.7 |
| 329 | G*T*$^m$C*T*G*$^m$C$^m$CTGTGG$^m$CT$^m$C*$^m$C*A*$^m$C*G*A* | 10.1 | 35.5 |
| 330 | $^m$C*G*T*$^m$C*T*G$^m$*C$^m$CTGTGG$^m$CT$^m$C*$^m$C*A*$^m$C*G* | 12.6 | 37.9 |
| 331 | T*$^m$C*G*T*$^m$C*TG$^m$C$^m$CTGTGG$^m$CT*$^m$C*$^m$C*A*$^m$C* | 9.1 | 44.6 |
| 332 | A*T*$^m$C*G*T*$^m$CTG$^m$C$^m$CTGTGG*$^m$C*T*$^m$C*$^m$C*A* | 18.8 | 55.4 |
| 333 | $^m$C*A*T*$^m$C*G*T*$^m$CTG*$^m$C$^m$CTGTGG*$^m$*C*T*$^m$C*$^m$C* | 17.1 | 62.3 |
| 334 | A*$^m$C*A*T*$^m$C*GT*$^m$CTG*$^m$C$^m$CTGTG*G*$^m$C*T*$^m$C* | 14.3 | 57.7 |
| 335 | G*A*$^m$C*A*T*$^m$CGT*$^m$CTG*$^m$C$^m$CTGT*G*G*$^m$C*T* | 11.7 | 33.5 |
| 336 | T*G*A*$^m$C*A*T$^m$CGT*$^m$CTG*$^m$C$^m$CTG*T*G*G*$^m$C* | 15.2 | 38.4 |
| 337 | T*T*G*A*$^m$C*AT$^m$CGT$^m$CT*$^m$C$^m$CT*G*T*G*G* | 26.2 | 43.3 |
| 338 | G*T*T*G*A*$^m$CAT$^m$CGT$^m$CTG*$^m$C$^m$C*T*G*T*G* | 18.0 | 44.5 |
| 285 | G*G*T*T*G*A$^m$CAT$^m$CGT$^m$CTG*$^m$C*$^m$C*T*G*T* | 17.2 | 42.7 |
| 339 | A*G*G*T*T*GA$^m$CAT$^m$CGT$^m$CTG*$^m$C*$^m$C*T*G* | 23.4 | 48.9 |
| 340 | A*A*G*G*T*TGA$^m$CAT$^m$CGT$^m$CT*G*$^m$C*$^m$C*T* | 17.2 | 38.6 |
| 341 | $^m$C*A*A*G*G*TTGA$^m$CAT$^m$CGT*$^m$C*T*G*$^m$C*$^m$C* | 25.7 | 47.4 |
| 342 | A*$^m$MC*A*A*G*GTTGA$^m$CAT$^m$CGT*$^m$C*T*G*$^m$C* | 24.3 | 43.0 |
| 343 | $^m$C*A*$^m$C*A*A*GGTTGA$^m$CAT$^m$CG*T*$^m$C*T*G* | 28.9 | 52.9 |
| 344 | A*$^m$C*A*$^m$C*A*AGGTTGA$^m$CAT*$^m$C*G*T*$^m$C*T* | 23.0 | 51.4 |
| 345 | $^m$C*A*$^m$C*A*$^m$C*AAGGTTGA$^m$CAT*$^m$C*G*T*$^m$C* | 33.5 | 78.2 |
| 346 | T*$^m$C*A*$^m$C*A*$^m$CAAGGTTGA*$^m$CA*T*$^m$C*G*T* | 44.4 | 60.4 |
| 347 | $^m$C*T*$^m$C*A*$^m$C*A$^m$CAAGGTGA$^m$C*A*T*$^m$C*G* | 35.4 | 67.6 |
| 348 | A*$^m$C*T*$^m$C*A*$^m$CA$^m$CAAGGTGA*$^m$C*A*T*$^m$C* | 61.9 | 66.1 |
| 349 | $^m$C*A*$^m$C*T*$^m$C*A$^m$CA$^m$CAAGGTTG*A*$^m$C*A*T* | 67.3 | 72.0 |
| 350 | A*$^m$C*A*$^m$C*T*$^m$CA$^m$CA$^m$CAAGGTT*G*A*$^m$C*A* | 64.0 | 72.7 |
| 351 | $^m$C*A*$^m$C*A*$^m$C*T$^m$CA$^m$CA$^m$CAAGGT*T*G*A*$^m$C* | 46.3 | 64.8 |
| 352 | T*$^m$C*A*$^m$C*A*$^m$CT$^m$CA$^m$CA$^m$CAAGG*T*T*G*A* | 55.9 | 73.2 |
| 353 | G*T*$^m$C*A*$^m$C*A$^m$CT$^m$CA$^m$CA$^m$CAAG*G*T*T*G* | 31.9 | 53.3 |
| 354 | $^m$C*G*T*$^m$C*A*$^m$CA$^m$CT$^m$CA$^m$CA$^m$CAA*G*G*T*T* | 29.1 | 57.6 |
| 355 | $^m$C*$^m$C*G*T*$^m$C*A$^m$CA$^m$CT$^m$CA$^m$CA$^m$CA*A*G*G*T* | 33.5 | 57.7 |

TABLE 13-continued

Inhibition of Tau mRNA by 5-10-5 MOE gapmers in Huh7 and SH-SY5Y cells

| SEQ ID NO | ASO Sequence[14] | % Residual mRNA in SHSY5Y cells[15] | % Residual mRNA in HUH7 cells[16] |
|---|---|---|---|
| 356 | $^mC*^mC*^mC*^mC*G*T^mCA^mCA^mCT^mCA^mCA*^mC*A*A*G*$ | 33.3 | 70.1 |
| 357 | $^mC*^mC*^mC*T*T*^mCT^mC^mCA^mCAGG^mC*T*G*^mC*^mC*$ | 40.3 | 65.4 |
| 358 | $^mC*A*T*^mC*A*AGGT^mCAGT^mCTT*T*T*MC*T*$ | 43.5 | 61.8 |
| 359 | $^mC*^mC*A*A*^mC*^mCTT^mCAGAA^mCT*^mC*A*A*T*A*$ | 30.7 | 71.0 |
| 360 | $T*^mC*^mC*A*A*^mC^mCTT^mCAGAA^mCT*^mC*A*A*T*$ | 30.7 | 77.6 |
| 361 | $T*T*^mC*^mC*A*A^mC^mCTT^mCAGAA*^mC*T*^mC*A*A*$ | 29.7 | 66.5 |
| 362 | $G*T*T*^mC*^mC*AA^mC^mCTT^mCAGAA*^mC*T*^mC*A*$ | 22.9 | 72.7 |
| 363 | $A*G*T*T*^mC*^mCAA^mC^mCTT^mCAGA*A*^mC*T*^mC*$ | 47.6 | 66.5 |
| 364 | $^mC*A*G*T*T*^mC^mCAA^mC^mCTT^mCAG*A*A*^mC*T*$ | 63.6 | 70.0 |
| 365 | $G*^mC*A*G*T*T*^mC^mCAA^mC^mCTT^mCA*G*A*A*^mC*$ | 28.6 | 47.6 |
| 366 | $G*T*^mC*^mC*^mC*AGGT^mCTG^mCAAA*G*T*G*G*$ | 18.1 | 41.7 |
| 367 | $A*A*G*T*^mC*^mC*CAGGT^mCTG^mCA*A*A*G*T*$ | 48.5 | 68.1 |
| 368 | $A*A*A*G*T*^mC*^mC*CAGGT^mCTG^mC*A*A*A*G*$ | 53.0 | 73.7 |
| 369 | $G*G*^mC*A*^mC*AAGT^mC^mCTTA^mCA*A*A*G*A*$ | 43.7 | 80.9 |
| 370 | $A*G*G*^mC*A*^mCAAGT^mC^mCTTA*^mC*A*A*A*G*$ | 41.8 | 76.8 |
| 371 | $T*^mC*A*^mC*^mC*^mCT^mCAGTATGGA*G*T*A*G*$ | 35.8 | 67.9 |
| 372 | $T*T*^mC*A*^mC*^mC*CT^mCAGTATGG*A*G*T*A*$ | 35.7 | 58.3 |
| 373 | $T*T*T*^mC*A*^mC^mC*CT^mCAGTATG*G*A*G*T*$ | 33.9 | 65.5 |
| 374 | $A*T*T*T*^mC*A^mC^mC*CT^mCAGTAT*G*G*A*G*$ | 51.1 | 54.0 |
| 375 | $A*A*T*T*T*^mCA^mC^mC^mCT^mCAGTA*T*G*G*A*$ | 86.4 | 67.7 |
| 376 | $^mC*^mC*T*T*A*ATTT^mCA^mC^mC^mCT*^mC*A*G*T*A*$ | 35.6 | 72.8 |
| 377 | $^mC*^mC*^mC*T*T*AATTT^mCA^mC^mC^mCT*^mC*A*G*T*$ | 32.4 | 60.4 |
| 378 | $T*^mC*^mC*^mC*T*TAATTT^mCA^mC^mC^mC*T*^mC*A*G*$ | 26.7 | 71.7 |
| 379 | $T*T*^mC*^mC*^mC*^mCTTAATTT^mCA^mC^mC*^mC*T*^mC*A*$ | 20.4 | 73.9 |
| 380 | $^mC*T*T*^mC*^mC*^mC*^mCTTAATTT^mCA^mC*^mC*^mC*T*^mC*$ | 28.1 | 86.4 |
| 381 | $A*^mC*T*^mC*T*TGTG^mC^mCTGGA^mC*T*T*T*G*$ | 32.4 | 44.6 |
| 382 | $^mC*A*^mC*T*^mC*TTGTG^mC^mCTGGA*^mC*T*T*T*$ | 33.4 | 58.2 |
| 383 | $^mC*^mC*A*^mC*T*^mCTTGTG^mC^mCTGG*A*^mC*T*T*$ | 26.8 | 68.5 |
| 384 | $^mC*^mC*^mC*A*^mC*T*CTTGTG^mC^mCTG*G*A*^mC*T*$ | 16.5 | 43.4 |
| 385 | $T*^mC*^mC*^mC*A*^mCT*CTTGTG^mC^mCT*G*G*A*^mC*$ | 10.6 | 38.9 |
| 386 | $G*T*^mC*^mC*^mC*A*^mCT*CTTGTG^mC^mC*T*G*G*A*$ | 23.0 | 37.4 |
| 387 | $G*G*T*^mC*^mC*^mCA*CT*CTTGTG^mC*^mC*T*G*G*$ | 31.0 | 36.9 |
| 388 | $G*G*G*T*^mC*^mC*^mCA*CT*CTTGTG*^mC*^mC*T*G*$ | 45.9 | 47.5 |
| 389 | $G*T*G*^mC*^mC*^mCTGG^mCT^mCA^mCAT*^mC*T*G*T*$ | 42.8 | 81.7 |
| 390 | $A*G*T*G*^mC*^mC*^mCTGG^mCT^mCA^mCA*T*^mC*T*G*$ | 28.1 | 51.0 |
| 391 | $^mC*A*G*T*G*^mC*^mC*CTGG^mCT^mCA*^mC*A*T*^mC*T*$ | 49.1 | 85.8 |
| 392 | $G*^mC*A*G*T*G*^mC^mC*CTGG^mCT^mCA*^mC*A*T*^mC*$ | 34.4 | 65.8 |

TABLE 13-continued

Inhibition of Tau mRNA by 5-10-5 MOE gapmers in Huh7 and SH-SY5Y cells

| SEQ ID NO | ASO Sequence[14] | % Residual mRNA in SHSY5Y cells[15] | % Residual mRNA in HUH7 cells[16] |
|---|---|---|---|
| 393 | A*G*$^m$C*A*G*TG$^m$C$^m$C$^m$CTGG$^m$CT$^m$C*A*$^m$C*A*T* | 40.5 | 72.6 |
| 394 | T*G*A*G*$^m$C*AGTG$^m$C$^m$C$^m$CTGG*$^m$C*T*$^m$C*A*$^m$C* | 91.8 | 57.9 |
| 395 | G*$^m$C*A*T*G*G$^m$CTT$^m$C$^m$CAG$^m$CTG*G*G*G*A*$^m$C* | 38.5 | 60.3 |
| 396 | A*G*$^m$C*T*G**$^m$CT$^m$C$^m$CAG$^m$CAGAA*$^m$C*A*G*A* | 80.8 | 78.5 |
| 397 | T*A*T*A*T*GTT$^m$CAG$^m$CTG*$^m$CT*$^m$C*$^m$C*A*G* | 49.9 | 63.2 |
| 398 | G*T*A*T*A*TGTT$^m$CAG$^m$CTG*$^m$C*T*$^m$C*$^m$C*A* | 55.2 | 64.3 |
| 399 | T*G*T*A*T*ATGG$^m$CAG$^m$CTG*$^m$C*T*$^m$C*$^m$C* | 59.9 | 74.6 |
| 400 | G*$^m$C*A*G*G*G$^m$CAA$^m$CAT$^m$CTAT*G*T*A*T* | 58.3 | 73.2 |
| 401 | G*G*$^m$C*A*G*GG$^m$CAA$^m$CAT$^m$CTA*T*G*T*A* | 61.5 | 74.5 |
| 402 | G*G*G*$^m$C*A*GGG$^m$CAA$^m$CAT$^m$CT*A*T*G*T* | 48.1 | 68.0 |
| 403 | T*$^m$C*A*$^m$C*T*$^m$CTGGTGAAT$^m$C*$^m$C*A*A*G*$^m$C* | 21.9 | 54.5 |
| 404 | G*T*$^m$C*A*$^m$C*T*$^m$CTGGTGAAT$^m$C*$^m$C*A*A*G* | 13.8 | 61.3 |
| 405 | A*G*T*$^m$C*A*$^m$CT$^m$CTGGTGAAT*$^m$C*$^m$C*A*A* | 15.1 | 55.2 |
| 406 | T*A*G*T*$^m$C*A$^m$CT$^m$CTGGTGAA*T*$^m$C*$^m$C*A* | 36.7 | 70.9 |
| 407 | A*T*A*G*T*$^m$CA$^m$CT$^m$CTGGTGA*A*T*$^m$C*$^m$C* | 42.4 | 76.6 |
| 408 | $^m$C*A*T*A*G*T*$^m$CA$^m$CT$^m$CTGGTG*A*A*T*$^m$C* | 57.0 | 77.2 |
| 409 | T*$^m$C*A*T*A*GT$^m$CA$^m$CT$^m$CTGGT*G*A*A*T* | 45.8 | 65.5 |
| 410 | $^m$C*T*G*T*$^m$C*$^m$CTGTTGGGT*$^m$C*$^m$C*$^m$C*A* | 37.2 | 60.5 |
| 411 | A*T*$^m$C*$^m$C*T*GTG$^m$CTT$^m$CAGG$^m$C*$^m$C*T*T*$^m$C* | 31.2 | 66.6 |
| 412 | A*A*T*$^m$C*$^m$C*TGTG$^m$CTT$^m$CAGG*$^m$C*$^m$C*T*T* | 41.2 | 73.5 |
| 413 | $^m$C*T*A*A*T*$^m$C$^m$CTGTG$^m$CTT$^m$CA*G*G*$^m$C*$^m$C* | 38.7 | 65.1 |
| 414 | $^m$C*$^m$C*T*A*A*T$^m$C$^m$CTGTG$^m$CTT$^m$C*A*G*G*$^m$C* | 31.9 | 64.8 |
| 415 | T*$^m$C*$^m$C*T*A*AT$^m$C$^m$CTGTG$^m$CTT*$^m$C*A*G*G* | 45.9 | 73.6 |
| 416 | G*T*$^m$C*$^m$C*T*AAT$^m$C$^m$CTGTG$^m$CT*T*$^m$C*A*G* | 50.0 | 80.9 |
| 417 | A*G*T*$^m$C*$^m$C*TAAT$^m$C$^m$CTGTG$^m$C*T*T*$^m$C*A* | 51.9 | 77.1 |
| 418 | $^m$C*A*G*T*$^m$C*$^m$CTAAT$^m$C$^m$CTGTG*$^m$C*T*T*$^m$C* | 53.2 | 68.4 |
| 419 | T*$^m$C*A*G*T*$^m$C*$^m$CTAAT$^m$C$^m$CTGT*G*$^m$C*T*T* | 58.9 | 78.3 |
| 420 | T*T*$^m$C*A*G*T*$^m$C$^m$CTAAT$^m$C$^m$CTG*T*G*$^m$C*T* | 51.1 | 72.9 |
| 421 | $^m$C*T*T*$^m$C*A*GT$^m$C$^m$CTAAT$^m$C$^m$CT*G*T*G*$^m$C* | 49.4 | 69.1 |
| 422 | G*$^m$C*T*T*$^m$C*AGT$^m$C$^m$CTAAT$^m$C*$^m$C*T*G*T*G* | 39.5 | 56.8 |
| 423 | G*G*A*G*T*TGTAAG$^m$C$^m$CT$^m$C*$^m$C*T*T*T*G* | 61.8 | 66.4 |
| 424 | G*$^m$C*T*$^m$C*T*GGT$^m$CAAGG$^m$CTT*T*G*G*G* | 33.8 | 49.8 |
| 425 | T*G*$^m$C*T*$^m$C*TGGT$^m$CAAGG*$^m$CT*T*T*G*G* | 37.9 | 55.5 |
| 426 | G*T*G*$^m$C*T*$^m$CTGGT$^m$CAAGG*$^m$C*T*T*T*G* | 48.0 | 74.1 |
| 427 | G*T*G*$^m$C*T*$^m$CTGGT$^m$CAAGG*$^m$C*T*T*T* | 51.4 | 68.7 |
| 428 | T*G*A*G*G*TG$^m$CT$^m$CTGGT$^m$CA*A*G*G*$^m$C* | 38.0 | 72.9 |

TABLE 13-continued

Inhibition of Tau mRNA by 5-10-5 MOE gapmers in Huh7 and SH-SY5Y cells

| SEQ ID NO | ASO Sequence[14] | % Residual mRNA in SHSY5Y cells[15] | % Residual mRNA in HUH7 cells[16] |
|---|---|---|---|
| 429 | T*T*T*$^m$C*T*$^m$CATGG$^m$CAG$^m$CAG*A*T*G*G* | 87.5 | 84.7 |
| 430 | T*G*$^m$C*T*G*AGTTT$^m$CTTTAG*G*$^m$C*A*G* | 61.8 | 94.7 |
| 431 | $^m$C*T*G*$^m$C*T*GAGTTT$^m$CTTTA*G*G*$^m$C*A* | 51.5 | 61.1 |
| 432 | G*$^m$C*T*G*$^m$C*TGAGTTT$^m$CTTT*A*G*G*$^m$C* | 46.5 | 94.4 |
| 433 | G*G*$^m$C*T*G*$^m$CTGAGTTT$^m$CTT*T*A*G*G* | 61.8 | 80.4 |
| 434 | A*G*G*$^m$C*T*G$^m$CTGAGTTT$^m$CT*T*T*A*G* | 68.1 | 74.7 |
| 435 | G*A*G*G*$^m$C*TG$^m$CTGAGTTT$^m$C*T*T*T*A* | 52.3 | 83.7 |
| 436 | T*G*A*G*G*$^m$CTG$^m$CTGAGTTT*$^m$C*T*T*T* | 62.3 | 71.5 |
| 437 | $^m$C*T*G*$^m$C*$^m$C*AAGT$^m$C$^m$C$^m$CT*CAG*G*G*T*T* | 43.3 | 74.6 |
| 438 | A*$^m$C*T*G*$^m$C*$^m$CAAGT$^m$C$^m$C$^m$CT*CA*G*G*G*T* | 53.4 | 78.8 |
| 439 | T*A*$^m$C*T*G*$^m$C*$^m$CAAGT$^m$C$^m$C$^m$CT*$^m$C*A*G*G* | 34.5 | 74.9 |
| 440 | $^m$C*T*A*$^m$C*T*G*$^m$C*$^m$CAAGT$^m$C$^m$C$^m$CT*$^m$C*A*G*G* | 35.4 | 73.6 |
| 441 | T*$^m$C*T*A*$^m$C*TG*$^m$C*$^m$CAAGT$^m$C$^m$C$^m$C*T*$^m$C*A*G* | 65.7 | 84.0 |
| 442 | T*T*$^m$C*T*A*$^m$CTG$^m$C*$^m$CAAGT$^m$C$^m$C*$^m$C*T*$^m$C*A* | 47.9 | 93.1 |
| 443 | T*T*T*$^m$C*T*A*$^m$CTG$^m$C*$^m$CAAGT$^m$C*$^m$C*$^m$C*T*$^m$C* | 53.6 | 85.3 |
| 444 | A*T*T*T*$^m$C*TA$^m$CTG$^m$C*$^m$CAAGT*$^m$C*$^m$C*$^m$C*T* | 72.4 | 100.6 |
| 445 | G*A*T*T*T*$^m$CTA*$^m$CTG$^m$C*$^m$CAAG*T*$^m$C*$^m$C*$^m$C* | 68.6 | 79.7 |
| 446 | G*G*A*T*T*T*$^m$CTA$^m$CTG$^m$C*$^m$CAA*G*T*$^m$C*$^m$C* | 72.1 | 88.6 |
| 447 | T*G*G*A*T*TT$^m$CTA*$^m$CTG$^m$C*$^m$CA*A*G*T*$^m$C* | 65.7 | 79.7 |
| 448 | $^m$C*T*G*G*A*TTT$^m$CTA*$^m$CTG$^m$C*$^m$C*A*A*G*T* | 51.0 | 68.6 |
| 449 | A*T*$^m$C*T*T*AGG$^m$CTGG*$^m$C$^m$C$^m$C*$^m$C*A*A*G*A* | 43.6 | 74.1 |
| 450 | T*G*A*T*$^m$C*TTAGG$^m$CTGG*$^m$C$^m$C*$^m$C*$^m$C*A*A* | 38.8 | 70.0 |
| 451 | T*T*T*A*T*$^m$CTG*$^m$C*$^m$CAG*CA$^m$CT*G*A*T*$^m$C* | 51.0 | 76.2 |
| 452 | A*T*T*T*A*T*CTG$^m$C*$^m$CAG$^m$CA*$^m$C*T*G*A*T* | 55.2 | 77.7 |
| 453 | A*A*T*T*T*AT*CTG$^m$C*$^m$CAG*CA*$^m$C*T*G*A* | 68.1 | 71.1 |
| 454 | T*A*T*A*T*$^m$C*$^m$CTAT$^m$CTAG*$^m$C$^m$C*$^m$C*A*$^m$C*$^m$C* | 60.1 | 88.2 |
| 455 | G*T*A*T*A*T*$^m$C*$^m$CTAT$^m$CTAG*$^m$C*$^m$C*$^m$C*A*$^m$C* | 64.2 | 85.2 |
| 456 | A*G*T*A*T*AT$^m$C*$^m$CTAT$^m$CTAG*$^m$C*$^m$C*$^m$C*A* | 62.8 | 86.2 |
| 457 | A*A*$^m$C*$^m$C*$^m$C*$^m$CAAGGG*$^m$C$^m$CT$^m$CT*A*A*$^m$C*T* | 83.3 | 90.7 |
| 458 | G*$^m$C*A*A*$^m$C*$^m$CAGATGT$^m$C*$^m$CAT*A*T*T*$^m$C* | 50.9 | 87.2 |
| 459 | G*G*$^m$C*T*T*AGGA$^m$C$^m$C$^m$C*$^m$CTGA*A*A*G*A* | 59.8 | 71.1 |
| 460 | G*G*$^m$C*A*T*GATTGTGGG$^m$CT*T*A*G*G* | 32.3 | 51.6 |
| 461 | A*G*G*$^m$C*A*TGATTGTGGG*$^m$C*T*T*A*G* | 31.0 | 60.2 |
| 462 | G*T*A*A*$^m$C*$^m$C*CTTTT$^m$CAAAG*$^m$C*T*G*A* | 50.2 | 63.6 |
| 463 | G*G*T*A*A*$^m$C*$^m$C*CTTTT$^m$CAAA*G*$^m$C*T*G* | 27.1 | 51.9 |
| 464 | G*G*G*T*A*A*$^m$C*$^m$C*CTTTT$^m$CAA*A*G*$^m$C*T* | 45.6 | 64.5 |
| 465 | A*G*G*G*T*AA$^m$C*$^m$C*CTTTT$^m$CA*A*A*G*$^m$C*$^m$C* | 60.3 | 61.5 |

TABLE 13-continued

Inhibition of Tau mRNA by 5-10-5 MOE gapmers in Huh7 and SH-SY5Y cells

| SEQ ID NO | ASO Sequence[14] | % Residual mRNA in SHSY5Y cells[15] | % Residual mRNA in HUH7 cells[16] |
|---|---|---|---|
| 466 | $^m$C*A*G*G*TAA$^m$C$^m$C$^m$CTTTTMC*A*A*A*G* | 59.2 | 82.8 |
| 467 | $^m$C*$^m$C*A*G*G*GTAA$^m$C$^m$C$^m$CTTTT*$^m$C*A*A*A* | 48.5 | 57.9 |
| 468 | $^m$C*$^m$C*$^m$C*A*G*GGTAA$^m$C$^m$C$^m$CTTT*T*$^m$C*A*A* | 37.8 | 70.2 |
| 469 | G*$^m$C*$^m$C*$^m$C*A*GGGTAA$^m$C$^m$C$^m$CTT*T*T*$^m$C*A* | 31.9 | 58.2 |
| 470 | T*G*$^m$C*T*$^m$C*AA$^m$CATGG$^m$CAAA*$^m$C*T*$^m$C*A* | 42.1 | 70.5 |
| 471 | T*$^m$C*$^m$C*T*G*$^m$CTCAA$^m$CATGG*$^m$C*A*A*A*$^m$C* | 45.2 | 77.7 |
| 472 | G*T*$^m$C*$^m$C*T*G*$^m$CT$^m$CAA$^m$CATGG*$^m$C*A*A*A* | 42.9 | 64.0 |

[14]The nucleotides with * have a 2'-O-MOE modifications; the nucleotides without * are 2'-deoxynucleosides; and $^m$C stands for 5-methylcytosine. The internucleoside linkages are phosphorothioate.
[15]% Residual mRNA is the level of tau mRNA in the SH-SY5Y cells treated with a single does of 2,000 nM of tau ASO for 24 hours as compared to the level of tau mRNA in controls cells treated with PBS.
[16]% Residual mRNA is the level of tau mRNA in the Huh7 cells treated with a single does of 25 nM of tau ASO for 48 hours as compared to the level of tau mRNA in control cells treated with PBS.

Gapmers that significantly decreased Tau mRNA expression in Table 13 were selected and tested in SH-SY5Y cells. The IC50 values of selected 5-10-5 gapmers with 5-methylcytosines were determined in SH-SY5Y cells as described above, and shown in Table 14.

TABLE 14

IC50 of selected 5-10-5 gapmers with 5-methylcytosine in SH-SY5Y

| SEQ ID NO | ASO Sequence[17] | IC50 (nM) |
|---|---|---|
| 313 | $^m$C*$^m$C*T*T*G*A*$^m$CT$^m$CAGGT$^m$CAA$^m$C*T*G*G*T* | 1115 |
| 327 | $^m$C*T*G*$^m$C*$^m$C*TGTGG$^m$CT$^m$C$^m$CA$^m$C*G*A*A*$^m$C* | 844 |
| 329 | G*T*$^m$C*T*G*$^m$C$^m$CTGTGG$^m$CT$^m$C$^m$C*A*$^m$C*G*A* | 481 |
| 330 | $^m$C*G*T*$^m$C*T*G$^m$C$^m$CTGTGG$^m$CT$^m$C*$^m$C*A*$^m$C*G* | 555 |
| 331 | T*$^m$C*G*T*$^m$C*TG$^m$C$^m$CTGTGG$^m$CT*$^m$C*$^m$C*A*$^m$C* | 818 |
| 332 | A*T*$^m$C*G*T*$^m$CTG$^m$C$^m$CTGTGG$^m$C*T*$^m$C*$^m$C*A* | 918 |
| 333 | $^m$C*A*T*$^m$C*G*T$^m$CTG$^m$C$^m$CTGTGG*$^m$C*T*$^m$C*$^m$C* | 981 |
| 334 | A*$^m$C*A*T*$^m$C*GT$^m$CTG$^m$C$^m$CTGTG*G*$^m$C*T*$^m$C* | 608 |
| 335 | G*A*$^m$C*A*T*$^m$CGT$^m$CTG$^m$C$^m$CTGT*G*G*$^m$C*T* | 414 |
| 336 | T*G*A*$^m$C*A*T$^m$CGT$^m$CTGMC$^m$CTG*T*G*G*$^m$C* | 393 |
| 338 | G*T*T*G*A*$^m$CAT$^m$CGT$^m$CTG*$^m$C*$^m$C*T*G*T*G* | 588 |
| 340 | A*A*G*G*T*TGA$^m$CAT$^m$CGT$^m$CT*G*$^m$C*$^m$C*T* | 496 |
| 366 | G*T*$^m$C*$^m$C*$^m$C*AGGT$^m$CTG$^m$CAAA*G*T*G*G* | 793 |
| 384 | $^m$C*$^m$C*$^m$C*A*$^m$C*T$^m$CTTGTG$^m$C$^m$CTG*G*A*$^m$C*T* | 810 |
| 385 | T*$^m$C*$^m$C*$^m$C*A*$^m$CT$^m$CTTGTG$^m$C$^m$CT*G*G*A*$^m$C* | 954 |

TABLE 14-continued

IC50 of selected 5-10-5 gapmers with 5-methylcytosine in SH-SY5Y

| SEQ ID NO | ASO Sequence[17] | IC50 (nM) |
|---|---|---|
| 404 | G*T*$^m$C*A*$^m$C*T$^m$CTGGTGAAT$^m$C*$^m$C*A*A*G* | 12035 |
| 405 | A*G*T*$^m$C*A*$^m$CT$^m$CTGGTGAAT*$^m$C*$^m$CA*A* | 743 |
| 381 | A*$^m$C*T*$^m$C*T*TGTG$^m$C$^m$CTGGA$^m$C*T*T*T*G* | 2737 |

[17]The nucleotides with * have a 2'-O-MOE modification; the nucleotides without * are 2'-deoxynucleosides; and $^m$C stands for 5-methylcytosine. The internucleoside linkages are phosphorothioate.

Example 11: Inhibition of Monkey and Human Tau Expression by Antisense Oligonucleotides with 5-Methylcytosine Some gapmers that significantly decreased Tau mRNA expression were selected and tested in COS1 green monkey cells. Results are presented as percent residual Tau mRNA relative to control cells treated with PBS. Table 15 shows the activities of selected 5-10-5 gapmers in COS1 cells.

Some antisense oligonucleotides that significantly decreased Tau mRNA expression were selected and tested in human embryonic stem cell (hESC) derived neurons. Results are presented as percent residual Tau mRNA relative to control cells treated with PBS. Table 16 shows the activities of selected antisense oligonucleotides in human neurons.

TABLE 15

Inhibition of green monkey Tau mRNA by 5-10-5 MOE gapmers in Cos1 cells

| SEQ ID NO | ASO Sequence[18] | % Residual tau mRNA[19] |
|---|---|---|
| 285 | G*G*T*T*G*A$^m$CAT$^m$CGT$^m$CTG$^m$C*$^m$C*T*G*T* | 39 |
| 284 | $^m$C*$^m$C*G*T*A*$^m$CGT$^m$C$^m$C$^m$CAG$^m$CGT*G*A*T*$^m$C* | 61 |
| 473 | $^m$C*$^m$C*$^m$C*G*T*A$^m$CGT$^m$C$^m$C$^m$CAG$^m$CG*T*G*A*T* | 62 |
| 474 | G*G*$^m$C*$^m$C*A*G$^m$CGT$^m$C$^m$CGTGT$^m$C*A*$^m$C*$^m$C*$^m$C* | 64 |
| 386 | G*T*$^m$C*$^m$C*$^m$C*A$^m$CT$^m$CTTGTG$^m$C$^m$C*T*G*G*A* | 53 |
| 315 | G*A*$^m$C*A*T*$^m$CGT$^m$CTG$^m$C$^m$CTGT*G*G*$^m$C*T* | 39 |
| 384 | $^m$C*$^m$C*$^m$C*A*$^m$C*T$^m$CTTGTG$^m$C$^m$CTG*G*A*$^m$C*T* | 51 |
| 313 | $^m$C*$^m$C*T*T*G*$^m$CT$^m$CAGGT$^m$CAA$^m$C*T*G*G*T* | 37 |
| 366 | G*T*$^m$C*$^m$C*$^m$C*AGGT$^m$CTG$^m$CAAA*G*T*G*G* | 35 |
| 329 | A*G*T*$^m$C*A*$^m$CT$^m$CTGGTGAAT*$^m$C*$^m$C*A*A* | 34 |
| 405 | A*G*T*$^m$C*A*$^m$CT$^m$CTGGTGAAT*$^m$C*$^m$C*A*A* | 37 |

[18]The nucleosides with * have a 2'-O-MOE modification; the nucleosides without * are 2'-deoxynucleosides; and $^m$C stands for 5-methylcytosine. The internucleoside linkages are phosphorothioate.

[19]% Residual mRNA is the level of tau mRNA in the Cos1 cells treated with a single dose of 2,000 nM of tau ASP for 24 hours as compared to the level of tau mRNA in control cells treated with PBS.

TABLE 16

Inhibition of human Tau expression hESC derived neurons by selected Tau ASO

| SEQ ID NO | ASO Sequence[20] | % Residual mRNA[21] |
|---|---|---|
| 285 | G*G*T*T*G*A*$^m$CAT*$^m$CGT*$^m$CTG*$^m$C*$^m$C*$^m$C*T*G*T* | 9.8 |
| 475 | $^m$C*$^m$C*A*T*G*$^m$C*G*A*G*$^m$C*T*G*A*T*A*A*A* | 20.9 |
| 476 | G*$^m$C*A*T*$^m$C*G*T*$^m$C*A*G*$^m$C*T*T*A*$^m$C*$^m$C*T* | 40.0 |
| 477 | $^m$C*T*T*T*G*$^m$C*T*T*T*T*A*$^m$C*T*G*A*$^m$C*$^m$C* | 16.2 |
| 478 | T*$^m$C*A*A*$^m$C*T*G*G*T*T*T*G*T*A*G*A*$^m$C* | 34.9 |

[20]The nucleotides with * have a 2'-O-MOE modification; the nucleotides without * are 2'-deoxynucleosides; and $^m$C stands for 5-methylcytosine. The internucleoside linkages are phosphorothioate.
[21]%Residual mRNA is the level of tau mRNA in the hESC-deilved neurons treated with a single dose of 10 µM of tau ASO for 10 to 14 days as compared to the level of tau mRNA in control cells treated with PBS.

Example 12: In Vivo Testing of Gapmers Targeting MAPT

The in vivo activity of selected 5-10-5 gapmers were tested using the methods described in Example 9. As shown in Table 17, some antisense oligonucleotides significantly inhibited human tau mRNA and protein expression in cortex and hippocampus.

TABLE 17

Inhibition of Tau mRNA and protein expression by 5-10-5 MOE gapmers in vivo

| SEQ ID NO | Dose (ug) | Treatment Duration (weeks) | % Residual tau mRNA after ASO treatment[22] | | % Residual tau protein after ASO treatment[23] | |
|---|---|---|---|---|---|---|
| | | | Cortex | Hippocampus | Cortex | Hippocampus |
| 284 | 200 | 4 | 56 | 61 | 98 | 82 |
| 473 | 200 | 4 | 76 | 44 | 73 | 69 |
| 474 | 200 | 4 | 48 | 26 | 73 | 66 |
| 386 | 200 | 4 | 50 | 48 | 69 | 68 |
| 335 | 50 | 4 | N/T[24] | 76 | N/T | 103 |
| 384 | 50 | 4 | N/T | 65 | N/T | 111 |
| 313 | 50 | 4 | N/T | 98 | N/T | 144 |

[22]% Residual tau mRNA is the level of tau mRNA in the indicated brain tissue of hTau BAC transgenic mice four weeks after a single ICV injection of the indicated ASO, as compared to the level of tau mRNA in the corresponding brain tissue of the control hTau BAC transgenic mice that were not treated with ASO.
[23]% Residual tau protein is the level of tau protein in the indicated brain tissue of hTau BAC tnansgenic mice four weeks after a single ICV injection of the indicated ASO, as compared to the level of tau protein in the corresponding brain tissue of the control hTau BAC transgenic mice that were not treated with ASO.
[24]N/T means not tested.

Unless defined otherwise, the technical and scientific terms used herein have the same meaning as they usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

The invention claimed is:

1. An antisense oligonucleotide targeting microtubule-associated protein tau (MAPT) comprising a nucleobase sequence of:

GGTTGACATC GTCTGCCTGT (SEQ ID NO: 480)

wherein C in any of the nucleobase sequences is either cytosine or 5-methylcytosine, and wherein at least one nucleotide of the oligonucleotide has a 2'-modification, wherein at least one internucleoside linkage of the oligonucleotide is a phosphorothioate linkage; and wherein the oligonucleotide is capable of decreasing tau mRNA or protein expression level.

2. The antisense oligonucleotide of claim 1, wherein the oligonucleotide comprises at least five contiguous 2'-deoxynucleosides.

3. The antisense oligonucleotide of claim 1, wherein the oligonucleotide comprises at least seven contiguous 2'-deoxynucleosides.

4. The antisense oligonucleotide of claim 1, wherein the oligonucleotide comprises ten contiguous 2'-deoxynucleosides.

5. The antisense oligonucleotide of claim 1, wherein each C in the nucleobase sequences is 5-methylcytosine.

6. The antisense oligonucleotide of claim 1, wherein the 2'-modification is selected from the group consisting of 2'-fluoro, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

7. The antisense oligonucleotide of claim 1, wherein the 2'-modification is 2'-O-methoxyethyl (2'-O-MOE).

8. The antisense oligonucleotide of claim 1, wherein the first to fifth nucleotides of the nucleobase sequence each comprise a 2'-O-MOE modified nucleoside, wherein the sixth to fifteenth nucleotides of the nucleobase sequence each comprise a 2'-deoxynucleoside, and wherein the sixteenth to twentieth nucleotides of the nucleobase sequence each comprise a 2'-O-MOE modified nucleoside.

9. An antisense oligonucleotide comprising a nucleobase sequence selected from the group consisting of:

G*G*T*T*G*ACATCGTCTGC*C*T*G*T*(SEQ ID N0:208) and G*G*T*T*G*A$^m$CAT$^m$CGT$^m$CTG$^m$C*$^m$C*T*G*T*(SEQ ID NO: 285).

10. A composition comprising the antisense oligonucleotide of claim 1 or claim 9, and a pharmaceutically acceptable carrier.

* * * * *

SEQUENCE LISTING

<160> NUMBER OF SEQ ID NOS: 506

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gtccactaac ctttcagg                                           18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcatcgtcag cttaccctt                                          18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tatttgcacc tggagatg                                           18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gactatttgc acctggag                                           18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
catgcgagct gataaaat                                           18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
accatgcgag ctgataaa                                           18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccatgcgagc tgataaaa                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgtcagctta ccttggct                18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgaccatgcg agctgata                18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atgcgagctg ataaaata                18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tttgcacctg gagatgag                18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttgcacctgg agatgaga                18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atttgcacct ggagatga                                              18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tccactaacc tttcaggc                                              18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggtttcaatc tgcaagaa                                              18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccactaacct ttcaggcc                                              18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cactaacctt tcaggcca                                              18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
actaaccttt caggccag                                              18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

-continued gctcagccat cctggttc                                          18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtttcaatct gcaagaag                                          18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agttcacctg gggaaaga                                          18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttggaggttc acctggga                                          18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggctacctgg tttatgat                                          18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaagttcacc tggggaaa                                          18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gttcactgac cttgggtc                                                18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
caaagttcac ctgggaa                                                 18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cagcttacct tggcttt                                                 18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gggctacctg gtttatga                                                18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tcttcagctg gtgtatgt                                                18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttcaaagttc acctgggg                                                18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cccttaccct ttttattt                                                18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgcttcttca gctggtgt                                                  18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcagcttacc ttggcttt                                                  18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctgcttcttc agctggtg                                                  18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggccacctcc tagaacac                                                  18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcttaccaga gctgggtg                                                  18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aagttcacct ggggaaag                                                  18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtcagcttac cttggctt                                                 18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggggcctgat cacaaacc                                                 18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aggttcacct gggaagga                                                 18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gcttaccttg gctttttt                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcaaagttca cctgggga                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ccactctcac cttcccgc                                                 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44 cccccttttac cttttat                                                   18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gaggttcacc tgggaagg                                                   18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gttcacctgg gaaggaag                                                   18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cacctcctag aacacaac                                                   18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
actctcacct tcccgcct                                                   18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ttcaatctgc aagaagag                                                   18

<210> SEQ ID NO 50

<211> LENGTH: 18
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 50
actgaccttg ggtcacgt                                                 18

<210> SEQ ID NO 51
    <211> LENGTH: 18
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 51
tttcaatctg caagaaga                                                 18

<210> SEQ ID NO 52
    <211> LENGTH: 18
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 52
ttcttaccag agctgggt                                                 18

<210> SEQ ID NO 53
    <211> LENGTH: 18
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 53
cagggctacc tggtttat                                                 18

<210> SEQ ID NO 54
    <211> LENGTH: 18
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 54
gggcctgatc acaaaccc                                                 18

<210> SEQ ID NO 55
    <211> LENGTH: 18
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 55
agggctacct ggtttatg                                                 18

<210> SEQ ID NO 56
    <211> LENGTH: 18

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ccacctccta gaacacaa                                                    18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cactgacctt gggtcacg                                                    18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cccctttacc tttttatt                                                    18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ttcactgacc ttgggtca                                                    18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggcctgatca caaaccct                                                    18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cactctcacc ttcccgcc                                                    18

<210> SEQ ID NO 62
<211> LENGTH: 18
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 62
cctggccacc tcctagaa                                                     18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cctttacctt tttatttc                                                     18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tcactgacct tgggtcac                                                     18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gcctgatcac aaaccctg                                                     18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ctttaccttt ttatttcc                                                     18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ttcttcagct ggtgtatg                                                     18

<210> SEQ ID NO 68
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 68
gccacctcct agaacaca                                                     18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tctcaccttc ccgcctcc                                                     18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cttcttacca gagctggg                                                     18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ttcttcttac cagagctg                                                     18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
atcagccccc tgtaaatg                                                     18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gcttcttcag ctggtgta                                                     18

<210> SEQ ID NO 74
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 74
acagggctac ctggttta                                                    18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctcagccatc ctggttca                                                    18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cagccccctg taaatgaa                                                    18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gggctcagcc atcctggt                                                    18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tcttcttacc agagctgg                                                    18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ctctcacctt cccgcctc                                                    18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 80
tcagccccct gtaaatga                                               18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cttcttcagc tggtgtat                                               18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ggttcacctg ggaaggaa                                               18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
catcagcccc ctgtaaat                                               18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
accatcagcc ccctgtaa                                               18

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gtccactaac ctttcaggcc gtgtc                                       25

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gtccactaac ctttcaggcc gtgt                                          24

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gtccactaac ctttcaggcc gtg                                           23

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gtccactaac ctttcaggcc gt                                            22

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gtccactaac ctttcaggcc g                                             21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gtccactaac ctttcaggcc                                               20

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gtccactaac ctttcaggc                                                19

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 92
gtccactaac ctttcagg                                                   18

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gtccactaac ctttcag                                                    17

<210> SEQ ID NO 94
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gtccactaac ctttca                                                     16

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gtccactaac ctttc                                                      15

<210> SEQ ID NO 96
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gtccactaac cttt                                                       14

<210> SEQ ID NO 97
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtccactaac ctt                                                        13

<210> SEQ ID NO 98
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
```
gtccactaac ct 12

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcatcgtcag cttaccttgg ctttt 25

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gcatcgtcag cttaccttgg cttt 24

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gcatcgtcag cttaccttgg ctt 23

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gcatcgtcag cttaccttgg ct 22

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcatcgtcag cttaccttgg c 21

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104

```
gcatcgtcag cttaccttgg                                                20
```

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105

```
gcatcgtcag cttaccttg                                                 19
```

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106

```
gcatcgtcag cttacctt                                                  18
```

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107

```
gcatcgtcag cttacct                                                   17
```

<210> SEQ ID NO 108
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108

```
gcatcgtcag cttacc                                                    16
```

<210> SEQ ID NO 109
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109

```
gcatcgtcag cttac                                                     15
```

<210> SEQ ID NO 110
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110

```
gcatcgtcag ctta                                                      14
```

<210> SEQ ID NO 111
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gcatcgtcag ctt                                                          13

<210> SEQ ID NO 112
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gcatcgtcag ct                                                           12

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gactatttgc acctggagat gagag                                             25

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gactatttgc acctggagat gaga                                              24

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gactatttgc acctggagat gag                                               23

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gactatttgc acctggagat ga                                                22

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gactatttgc acctggagat g                                          21

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gactatttgc acctggagat                                            20

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gactatttgc acctggaga                                             19

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gactatttgc acctggag                                              18

<210> SEQ ID NO 121
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gactatttgc acctgga                                               17

<210> SEQ ID NO 122
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gactatttgc acctgg                                                16

```
<210> SEQ ID NO 123
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gactatttgc acctg                                                      15

<210> SEQ ID NO 124
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gactatttgc acct                                                       14

<210> SEQ ID NO 125
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gactatttgc acc                                                        13

<210> SEQ ID NO 126
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gactatttgc ac                                                         12

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ccatgcgagc tgataaaata taaaa                                           25

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ccatgcgagc tgataaaata taaa                                            24

<210> SEQ ID NO 129
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ccatgcgagc tgataaaata taa                                              23

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ccatgcgagc tgataaaata ta                                               22

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ccatgcgagc tgataaaata t                                                21

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ccatgcgagc tgataaaata                                                  20

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ccatgcgagc tgataaaat                                                   19

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ccatgcgagc tgataaaa                                                    18

<210> SEQ ID NO 135
<211> LENGTH: 17
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ccatgcgagc tgataaa                                                      17

<210> SEQ ID NO 136
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ccatgcgagc tgataa                                                       16

<210> SEQ ID NO 137
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ccatgcgagc tgata                                                        15

<210> SEQ ID NO 138
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ccatgcgagc tgat                                                         14

<210> SEQ ID NO 139
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ccatgcgagc tga                                                          13

<210> SEQ ID NO 140
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ccatgcgagc tg                                                           12

<210> SEQ ID NO 141
<211> LENGTH: 17
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 141
agccatcctg gttcaaa                                                     17

<210> SEQ ID NO 142
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cagccatcct ggttcaa                                                     17

<210> SEQ ID NO 143
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tcagccatcc tggttca                                                     17

<210> SEQ ID NO 144
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ctcagccatc ctggttc                                                     17

<210> SEQ ID NO 145
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ggccagcgtc cgtgtca                                                     17

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gccagcgtcc gtgtcac                                                     17

<210> SEQ ID NO 147
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 147
ccagcgtccg tgtcacc                                                        17

<210> SEQ ID NO 148
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
cagcgtccgt gtcaccc                                                        17

<210> SEQ ID NO 149
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gtctccaatg cctgctt                                                        17

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tgtctccaat gcctgct                                                        17

<210> SEQ ID NO 151
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gtgtctccaa tgcctgc                                                        17

<210> SEQ ID NO 152
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ggtgtctcca atgcctg                                                        17

<210> SEQ ID NO 153
<211> LENGTH: 17
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 153
tcacgtgacc agcagct                                                  17

<210> SEQ ID NO 154
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
cacgtgacca gcagctt                                                  17

<210> SEQ ID NO 155
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
acgtgaccag cagcttc                                                  17

<210> SEQ ID NO 156
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cgaagctgct ggtcacg                                                  17

<210> SEQ ID NO 157
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157 tttgcttttα ctgacca                                                  17

<210> SEQ ID NO 158
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ctttgctttt actgacc                                                  17

<210> SEQ ID NO 159
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 159
tctttgcttt tactgac                                                    17

<210> SEQ ID NO 160
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gtctttgctt ttactga                                                    17

<210> SEQ ID NO 161
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161 tttttgtca tcgcttc                                                     17

<210> SEQ ID NO 162
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tttttgtcat cgcttcc                                                    17

<210> SEQ ID NO 163
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ttttgtcatc gcttcca                                                    17

<210> SEQ ID NO 164
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tttgtcatcg cttccag                                                    17

<210> SEQ ID NO 165
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 165
atcttcgttt taccatc                                                17

<210> SEQ ID NO 166
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gatcttcgtt ttaccat                                                17

<210> SEQ ID NO 167
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cgatcttcgt tttacca                                                17

<210> SEQ ID NO 168
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gcgatcttcg ttttacc                                                17

<210> SEQ ID NO 169
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tgggtggtgt ctttgga                                                17

<210> SEQ ID NO 170
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gggtggtgtc tttggag                                                17

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 171
ggtggtgtct ttggagc                                                17

<210> SEQ ID NO 172
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gtggtgtctt tggagcg                                                17

<210> SEQ ID NO 173
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
atcccctgat tttggag                                                17

<210> SEQ ID NO 174
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gatcccctga ttttgga                                                17

<210> SEQ ID NO 175
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
cgatcccctg attttgg                                                17

<210> SEQ ID NO 176
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gcgatcccct gattttg                                                17

<210> SEQ ID NO 177
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gcctcccggc tggtgct                                                17

<210> SEQ ID NO 178
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
cctcccggct ggtgctt                                                17

<210> SEQ ID NO 179
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ctcccggctg gtgcttc                                                17

<210> SEQ ID NO 180
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
tcccggctgg tgcttca                                                17

<210> SEQ ID NO 181
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
actggtttgt agactat                                                17

<210> SEQ ID NO 182
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
aactggtttg tagacta                                                17

<210> SEQ ID NO 183
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
caactggttt gtagact					17

<210> SEQ ID NO 184
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tcaactggtt tgtagac					17

<210> SEQ ID NO 185
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tatgatggat gttgcct					17

<210> SEQ ID NO 186
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
atgatggatg ttgccta					17

<210> SEQ ID NO 187
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tgatggatgt tgcctaa					17

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gatggatgtt gcctaat					17

<210> SEQ ID NO 189
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ttttacttcc acctggc					17

```
<210> SEQ ID NO 190
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
attttacttc cacctgg                                                        17

<210> SEQ ID NO 191
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gattttactt ccacctg                                                        17

<210> SEQ ID NO 192
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
agattttact tccacct                                                        17

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
atttcctccg ccaggga                                                        17

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tttcctccgc cagggac                                                        17

<210> SEQ ID NO 195
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ttcctccgcc agggacg                                                        17
```

<210> SEQ ID NO 196
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tcctccgcca gggacgt                                                  17

<210> SEQ ID NO 197
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
aaggtcagct tgtgggt                                                  17

<210> SEQ ID NO 198
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gaaggtcagc ttgtggg                                                  17

<210> SEQ ID NO 199
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ggaaggtcag cttgtgg                                                  17

<210> SEQ ID NO 200
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
cggaaggtca gcttgtg                                                  17

<210> SEQ ID NO 201
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
accctgcttg gccaggg                                                  17

```
<210> SEQ ID NO 202
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ccctgcttgg ccaggga                                                          17

<210> SEQ ID NO 203
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
cctgcttggc cagggag                                                          17

<210> SEQ ID NO 204
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ctgcttggcc agggagg                                                          17

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ccgtacgtcc cagcgtgatc                                                       20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ggctcagcca tcctggttca                                                       20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
cccgtacgtc ccagcgtgat                                                       20

<210> SEQ ID NO 208
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ggttgacatc gtctgcctgt                                              20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gggctcagcc atcctggttc                                              20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ggccagcgtc cgtgtcaccc                                              20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ggctctccca gcggcaagga                                              20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ccctcttggt cttggtgcat                                              20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
cgggacctgc ctcccagacc                                              20

<210> SEQ ID NO 214
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
gctggtctct gttgggtccc                                              20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gggctctctc catgtcaaca                                              20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
ggtctctgtt gggtcccagg                                              20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gggacctgcc tcccagaccc                                              20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
cccaacccgt acgtcccagc                                              20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
gcttcgtctt ccaggctggg                                              20

<210> SEQ ID NO 220
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 220
ccgtgtcacc ctcttggtct                                              20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
cttggctctc ccagcggcaa                                              20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
cggcctcctt agctgctaga                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cagcgtccgt gtcaccctct                                              20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gctcagccat cctggttcaa                                              20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
cctggacttt gccttccctt                                              20

<210> SEQ ID NO 226
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 226
gtcccactct tgtgcctgga                                                20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
acctggccac ctcctggttt                                                20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ttggctttgg cgttctcgcg                                                20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
cgcttccagt cccgtctttg                                                20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ggtgatcacc tctgccctcg                                                20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggtacctcct gcaaccaacc                                                20

<210> SEQ ID NO 232
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 232
cacgtggctt cctctcccac                                                    20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gcgtccgtgt caccctcttg                                                    20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
caccctcttg gtcttggtgc                                                    20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gtcccagcgt gatcttccat                                                    20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gccagcactg atcaccctaa                                                    20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tggtctctgt tgggtcccag                                                    20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 238
ccgcctcccg gctggtgctt                                       20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ggccacacga gtcccagtgt                                       20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
gtccctcagg gttgccttta                                       20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ggaccactgc caccttcttg                                       20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
cacctggcca cctcctggtt                                       20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
cccgcctccc ggctggtgct                                       20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggtgccttgc ccttccatcc                                              20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
cccgtcacac tcacacaagg                                              20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
cccaatccct gctgtggtcg                                              20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gggtcccact cttgtgcctg                                              20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gcttccagtc ccgtctttgc                                              20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
cccttctccc acaggctgcc                                              20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 250
ctggtgccac cactgacaac                                                    20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gccactgcct ctgtgacacc                                                    20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
gtgccaccac tgacaaccaa                                                    20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
cttgcccttc catcctggtg                                                    20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gcctggactt tgccttccct                                                    20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
gcctctaact ccgtggctgc                                                    20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
```
gatcccagag ccttccgtat                                              20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
catcctcgcg ccgcaagcca                                              20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gcctcccggc tggtgcttca                                              20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gtgcctggac tttgccttcc                                              20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ctgccactgc ctctgtgaca                                              20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
cctggccacc tcctggttta                                              20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gggtgccttg cccttccatc                                               20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ccactcccac ttcttgtgct                                               20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gtgcttcagg ccttcgtcac                                               20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ctgccagctt gccttctctt                                               20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ctcccggctg gtgcttcagg                                               20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
cgcctcccgg ctggtgcttc                                               20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ctggccacct cctggtttat                                               20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ggccacctcc tggtttatga                                         20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ccatcctggt gccaccactg                                         20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
cctgccagct tgccttctct                                         20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
aatccctgct gtggtcgcag                                         20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gccaccactg acaaccaaga                                         20

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
cttgtcggcc atgatatag                                          19

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
taagcagtgg gttctctagt                                              20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
cctcccggct ggtgcttcag                                              20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ctcctgccag cttgccttct                                              20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
cttctcctcc ggccactagt                                              20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ctcctccggc cactagtggg                                              20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ccttctcctc cggccactag                                              20

-continued

```
<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
gagccttctc ctccggccac                                                  20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gccttctcct ccggccacta                                                  20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ccttacctgc tagctggcgt                                                  20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ccgtacgtcc cagcgtgatc                                                  20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: 2'-O-MOE modified nucleotide
<220> FEATURE:
<221> NAME/KEY: modified_base
<222> LOCATION: (7)..(7)
<223> OTHER INFORMATION: 5-methylcytosine
<220> FEATURE:
<221> NAME/KEY: modified_base
<222> LOCATION: (10)..(10)
<223> OTHER INFORMATION: 5-methylcytosine
<220> FEATURE:
<221> NAME/KEY: modified_base
<222> LOCATION: (13)..(13)
<223> OTHER INFORMATION: 5-methylcytosine
<220> FEATURE:
<221> NAME/KEY: modified_base
<222> LOCATION: (16)..(17)
<223> OTHER INFORMATION: 5-methylcytosine
```

```
<220> FEATURE:
<221> NAME/KEY: modified_base
<222> LOCATION: (16)..(20)
<223> OTHER INFORMATION: 2'-O-MOE modified nucleotide

<400> SEQUENCE: 285
ggttgacatc gtctgcctgt                                                  20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gggctcagcc atcctggttc                                                  20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ggctctccca gcggcaagga                                                  20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
ccctcttggt cttggtgcat                                                  20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gctggtctct gttgggtccc                                                  20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gtcccactct tgtgcctgga                                                  20

<210> SEQ ID NO 291
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 291
gggctctctc catgtcaaca                                                      20

<210> SEQ ID NO 292
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
acgctggcct gaaaggttag tggac                                                25

<210> SEQ ID NO 293
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
aaaagccaag gtaagctgac gatgc                                                25

<210> SEQ ID NO 294
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294 ttttatatttt tatcagctcg catgg                                               25

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
acccacaagc tgaccttccg                                                      20

<210> SEQ ID NO 296
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
accagctgaa gaagcaggca ttggagacac                                           30

<210> SEQ ID NO 297
<211> LENGTH: 25
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 297
ctctcatctc caggtgcaaa tagtc                                         25

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
atagtctaca aaccagttga                                               20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
attaggcaac atccatcata                                               20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gaaccaggat ggctgagccc                                               20

<210> SEQ ID NO 301
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
cgtccctggc ggaggaaa                                                 18

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
tggtcagtaa aagcaaagac                                               20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 303
ctggaagcga tgacaaaaaa          20

<210> SEQ ID NO 304
<211> LENGTH: 140924
<212> TYPE: DNA
<213> ORGANISM: Homo sapiens

<400> SEQUENCE: 304

| | | | | | |
|---|---|---|---|---|---|
| gggattacag | gcgtgagcca | ccacacccag | cccagaatgt | ttattagaat | gcacaattaa | 60 |
| taccagaggc | agtggggaag | gaaggactga | gcagaggagg | aagttgagtt | gtgattcaac | 120 |
| ccaacaactg | cctggctggc | atggggagct | ctggagttaa | atagggccat | cagactttcc | 180 |
| cagtgtgggg | ccaacatgac | tgggtcttta | taccccacc | tctgtcagtc | actcaacgtg | 240 |
| gtctccctgc | aacaaggtga | ctcttgcagc | cgagacaatc | cctgaaggga | cagaggctga | 300 |
| agcctgtctg | ccaacagcac | tcccagtggc | tggaacaagt | ccttccctat | aggggaatct | 360 |
| gggcggcaca | cctccatctc | catgtccatc | acatacgata | tcacagacat | ttaaatattt | 420 |
| tgataactgt | acataagagt | ttcctttata | atcttataga | tcttatttta | tgcatttgaa | 480 |
| aatattcttc | tgagacaggg | cttttatcat | attgccatag | ggtgccacga | tataaaaaag | 540 |
| gttaaatact | ctctgattca | gaagtatcca | atgatgactt | ctctctcatg | catttaattg | 600 |
| aaaatctggt | ttttctcctt | ctctgctagt | tctctacctc | tctccccacc | tcccacatca | 660 |
| tagcctattc | acatatgtct | gaatctcatg | atagacaagt | tcaggttctt | ttcccaggtt | 720 |
| cttttttacca | catccccca | ccccacata | aaagtatat | atggcacagc | ctaggttcca | 780 |
| cccaaatcct | ttctcctctt | cttcctgggc | ccacaactct | cctacataca | ttggtatacc | 840 |
| ttgcgcttag | ggatggccat | gtgactaagt | tctaacagtg | gaacatgatc | agatgccact | 900 |
| tccagcctct | aagacagcca | gtgtgtttcc | tccataagct | ccttctcttc | ctcccaactg | 960 |
| gagactctaa | atgatgaccc | tgcctcaagc | aagcaaacaa | caagtccctc | aggggtggtg | 1020 |
| taggctgcaa | atgaaggag | cttgagtccc | aaaccttcca | cggagaaggc | tggctaccaa | 1080 |
| cctggatcac | tcacccaaga | ctgctcgaag | agttggtttg | aaccattgtg | ttttggggtc | 1140 |
| tatttattac | aacagtttag | cttgctttgt | gaatagattt | agtggcagag | cctccaaatt | 1200 |
| ctatagatac | attgatctca | gtcctaaccg | catctggaac | accattaaat | aaaggaattg | 1260 |
| caaacccaga | gaaggtaatg | aatttgtcta | aggtcataca | agatggctag | gatcaggacc | 1320 |
| caactctcca | gttttctttc | ttctctgcta | ttctgccttc | tgtgatccta | cataagtggg | 1380 |
| catgattgta | taacatatgc | ggccatgaga | tttctctttc | agcaagagaa | agggacagga | 1440 |
| agaaagagag | ggaatgcatt | ttcttggcct | gaattagtgt | gagccattag | ttacctacat | 1500 |
| tgactaaatt | atctggaatg | aacattcaac | tctacatcac | atatagttaa | aatgacagat | 1560 |
| ctgcttaaga | ttgtttctag | catacgttat | ttcaatttag | gcaaatgtga | ccattcagtg | 1620 |
| tgagggggacc | atactgtcat | taggtccctg | tcagttctca | attatactgt | tatcttagag | 1680 |
| ggggaaaaat | gtgaaatttg | aatgtagacg | agtgttgatt | tgactgctac | agtttatttt | 1740 |
| acgtatagaa | ataaaataat | gtgtagcaaa | agcattatta | caaagatgat | aatgaaataa | 1800 |
| ctagtattta | taatagtata | atagtatagt | atttataata | gtatgatagt | ttaatgacta | 1860 |
| tttgtcagat | gttgtgtaag | aaactttata | cacacacaca | cacacacctc | atttaattcc | 1920 |
| tgtatcaatc | aggatacagg | acgctgtggt | aacaactcct | caaatctcgg | tggcttgcac | 1980 |

```
aacaaatgct tatttctttt ttttttttga caccaagtct tgctctgtaa caggctggag    2040
tgcaatggtg caatctcggc tcactgcagc ctctgcctcc tgggttcaag cgattctcct    2100
gcctcagtct ctcgagtagc tgggaacaca ggcacgcgcc accacatctg gctaattttt    2160 gtgatttttag tagagatggg atttcaccat gttgctcagg ctggccttga actcctgacc    2220
tcaagcgatc cacccacctc agcctcccaa agtgctggga ttacaggcat gagccactgc    2280
gcccagcccc aaatgtttat tcttgctcca tgtgacatgt acttcctcga ttttttcctt    2340
cctgagatct aagctgaagg aacagctctc tggagccacg ccattctggt ggcggaaagg    2400
aagagtaaaa gtggtagaac cttgcaatgc tcttgaagcg cctatttgga atgtctacat    2460
catgtaaatg gtaatggaca agtatgtata atccccacac caaaaaaagg ggacactatt    2520
ggggacaata accacatttc aatgctgcaa gacggatatt gactgcaccc ccttcccact    2580
ttcagaaaga agaagagtaa ttttgctgaa ctccttctag agactggaaa tgtcccttcc    2640
agttggggtg attagggaag ctttggtaa aatttgagct agagtttgaa ggttaggtag    2700
actactggtg ggtgaagaaa gaacaaggac ctttgtaggc aaaggaaaac ctcagaatta    2760
cagaggtgga aaaagagttc tagtcaagcc acttcagctg gctacagagt aggtgggaaa    2820
gaaaatggga ggacaagggc tcagatgatg gggggttggg gcattggggg gacacttgaa    2880
agctaaacta aggggttgaa cttaatttag gaggcagtta gaagctttta catattttg    2940 agcaagagag tgacataatt aaaatgatct gggccaggtg tggtggctca cacctgtaat    3000
cccagcactt tgggaggctg aggagcttgg gtcacctgag gtcaggagat cgagaccagc    3060
ctggccaaca tggtgaaatc ccgtcctact aaaaatacaa aaattagccg ggagtggtgg    3120
catatgcctg taatcccagt agctggggagg ctgagacagg aaaatcgctt gaacccggga    3180
aacaggttgc agtgagccga tcgtgcca ctgcactcca gcctgggcaa cagagcgaga    3240
ctccatctca aaaaacaaa acaaacacac acaaaaaacc aaaaataaat aaataaaatg    3300
atcacttctg aatactgatc taactagggg ttgcagggtg ggctgatata gggagaaact    3360
ggagagcaag gagatcacta aggtccctac atgtccagaa ccaagataga ggtcttgaac    3420
taggatggtg gcagttagaa caacaacaac aaaaagtcaa ttccaggctg agtgcagtgg    3480
ctcatgcttg taatcccaac gctttgggag gctgaggtgg gagttagaaa gcagcctggg    3540
caacactgca agacctcctc tctaaaaaaa aaaaaaaaaa aaagttagcc aggtgtggtg    3600
gtgcccacct gtagtcccag caactcagaa ggctgaggtg ggaagattgc ttgagcccca    3660
ggagttcaag cttgccgtga gctacgattg tgccactgca ctccagcctg agcaagacct    3720
tgtctccaaa aaaaggtcaa ttccactgac ttttctaagg tgtacaccat caaggggcag    3780
ctccatctcc aggccattgg ctcatgagac attctgtagt cagaaggcta gggcagattg    3840
ctttgagcaa gcccccatgg tggttctcac tcctacttct ttgggtatat gcccctctgt    3900
ttaaaaataa agttaatatg catttaaaaa aaaaaggag aaaaaggtca gttccagaaa    3960
ctgtgtgaat aaagcatttt acttgctttt tctattaatc tataacatat gttgattttt    4020
taaaaagaat ataagagcta tgcaaattgg agcttcaaga caacttccca tctccctagg    4080
aggagatggc tgccctaaac cccctacat agaaatcatc ccactgcttg gcttaaaact    4140
tgatgttggg gaaatgaaaa atccaagcta aggccgaagc ctgggccctg gcgaccagc    4200 agaatgagga ccactggtca gtttcaggct gaggtgcgtc ttccaggga caatctctag    4260 ctggccctta aacattcaga cttcaagctc tatttacagc ataaaggtgt ttcaaaagac    4320
```

```
gtgatacaaa taactgcaaa tgctctgcga tgtgttaagc actgtttgaa attcgtctaa    4380
tttaagattt ttttttctga cgtaacggtt agattcacgt ttcttttttt ttaagtacag    4440
ttctactgta ttgtaactga gttagcttgc tttaagccga tttgttaagg aaaggattca    4500
ccttggtcag taacaaaaaa ggtgggaaaa aagcaaggag aaaggaagca gcctggggga    4560
aagagacctt agccagggggg gcggtttcgg gactacgaag ggtcggggcg gacggactcg    4620
agggccggcc acgtggaagg ccgctcagga cttctgtagg agaggacacc gccccaggct    4680
gactgaaagt aaagggcagc ggacccagcg gcggagccac tggccttgcc ccgaccccgc    4740
atggcccgaa ggaggacacc cacccccaca acgacacaaa gactccaact acaggaggtg    4800
gagaaagcgc gtgcgccacg gaacgcgcgt gcgcgctgcg gtcagcgccg cggcctgagg    4860
cgtagcggga gggggaccgc gaaagggcag cgccgagagg aacgagccgg gagacgccgg    4920
acggccgagc ggcagggcgc tcgcgcgcgc ccactagtgg ccggaggaga aggctcccgc    4980
ggaggccgcg ctgcccgccc cctcccctgg ggaggctcgc gttcccgctg ctcgcgcctg    5040 cgccgccccgc cggcctcagg aacgcgccct cttcgccggc gcgcgccctc gcagtcaccg    5100
ccacccacca gctccggcac caacagcagc gccgctgcca ccgcccacct tctgccgccg    5160
ccaccacagc caccttctcc tcctccgctg tcctctcccg tcctcgcctc tgtcgactat    5220
caggtaagcg ccgcggctcc gaaatctgcc tcgccgtccg cctctgtgca cccctgcgcc    5280 gccgccctc gccctccctc tccgcagact ggggcttcgt gcgccgggca tcggtcgggg    5340
ccaccgcagg gcccctccct gcctcccctg ctcgggggct ggggccaggg cggcctggaa    5400
agggacctga gcaagggatg cacgcacgcg tgagtgcgcg cgtgtgtgtg tgctggaggg    5460
tcttcaccac cagattcgcg cagaccccag gtggaggctg tgccggcagg gtggggcgcg    5520
gcggcggtga cttgggggag ggggctgccc ttcactctcg actgcagcct tttgccgcaa    5580
tgggcgtgtg tgtgtgtgtg tgtgtgtgtg tgtgtgtgtg tgtgtgtgtg gaggggtccg    5640
ataacgaccc ccgaaaccga atctgaaatc cgctgtccct gccgctgttc gccatcagct    5700
ctaagaaaga cgtggatcgg gttctagaaa agatgactcc ctgcacgccc ctccctgcac    5760
ctcccgagca gtgattccga cagggccttc actgcccctg attttaggcg ggggccggcc    5820
ccctcccctt ttcctccttc agaaacccgt aggggacatt tgggggctgg gagaaatcga    5880
ggagatgggg aggggtccac gcgctgtcac tttagttgcc cttccccctg cgcacgcctg    5940
gcacagagac gcgagcagcg ccgtgcctga gaacagtgcg cggatcccac tgtgcacgct    6000
cgcaaaggca gggttcacct ggcctggcga tgtggacgga ctcggcggcc gctggtcccc    6060
gttcgcgggc acgcacagcc gcagccacgc acggatgggc gcgggctgc aggtgcatct    6120 cggggcggat ttcttttctca gcgctcggag cgcagggcgc ccggcgtgtg cgctcccctgc    6180 cggaggcgcg gggctggcgc gcagggctcg ccctcactg cggcagtggg tgtggaccct    6240
ggtgggcgag gaaggggggag gataggctgt gcctcctccc actcccgccc ccagcccccc    6300 ttttttccc cctcggaacg cgaggtgcca tcttttttcg gcgtgtcacg tctttacggt    6360
gccatgccaa accgggtggc cgggcttcat aggacagggc ggggcctggc attaaaggga    6420
gggggacaat cagcgctgaa atcttggcgt tttgctgctg cgggcgtgag cactgggggc    6480
gttcgcccag caccttcttc gggggctctt tgctttgtct gtagaggtta cgtgatctgc    6540
gctcccagcc ctggtttctg ctttttattc tgagggtgtt cagtcaacct ccccctacg    6600 cccatgcgcc tctctttcct ttttcgctcc tcatttccga gccattgtt ggatctcgag    6660 gcttgctggg ttcgatgaac tcgagtcaac cccccgaccc ccggcacgca tggaacgggc    6720
```

```
gtgaccgcgc gcagcctcgt ctcggagtct gccggcgccg ggaagcttct gaagggatgg    6780
gattcgagtc tccgtgcgcg ctgcgggcgg cggcagaggg atctcgcccc tccctacacc    6840
ccaagtgtcc tgagggccac gccacaccag gttgcccagc gagggacgct ggctacccat    6900
ccggggatgg gtggggagcc ctggcggggc ctctccggct ttacgccctg ttgcttcgcc    6960
tggccggaga atgtgaggaa ggggcataag gttactggtg cttcggccac acccatcttt    7020
ctgagcccac tggactgggc gcagaggggg gattgccatg gaaaccacag gtgtccggag    7080
aggggatctt ggggctggcc tcaccccttc cctgcggaga ttggggaccc tggggtaggg    7140
ggagccgcgc ccagtcggcc tcctggagga cacgggagga agccccgaac ccccgcgcct    7200
gaggctgttt ctgattggcc cctggaggcc gcagacacgc agataggcgg ccctgggtgt    7260
attttattta atatattatgtc cgtactgatt aatattattt atcttaaata aatttcaccc    7320
```



```
atttttatta atattatgtc cgtactgatt aatattattt atcttaaata aatttcaccc    7320
gtgtccaagt tcaccgcgcc cccaaaaccg agtctggggc ggcaggggga actcctggcc    7380
aacgaatcca tgcctcgccc tcctgtgatg aacctggtac gcacggtttt ctggttaatt    7440
ctatcgctga aaactggtgc ggggggcgca cttctgagac ggaagagcat ctaggagctg    7500
aatcctccac gcgggtcgcc caggttgatc tgaatttctg gggaatggct tggctgcccg    7560
cccgggacca ggccgaccct ccttgacggt ggcgtagagg gctggagcct gggtactgcg    7620
aggctcctcg catggctggg cccgccgcga ggggttgcag agcggctcag ggatcgattc    7680
aagcatcgtc tctcctccct cgcccccaga cagagctggg cgcggggttc cccttccaga    7740
tggagcgagg gtctcggggt ggccccggaa aaggggagcc cgcggccacg gctacgtatt    7800
gccatctcgc gagcagagat gtcacctcct gcctttggag gaaagggagc ccggtgggga    7860
tgagcgcatt tagcccaatg ctgggaacaa agcgcactcc gcgcttctgc gatttcgctc    7920
cattttgaaa tgtgttggcg cctttggtggg ccgctgcgg tgggcaaggc cggggcgct    7980
```

```
cattttgaaa tgtgttggcg ctttggtggg ccgctgcgcg tgggcaaggc cggggcgct     7980 gttaatggag gaacctcagg gggacggtcc ttcgtaggaa actctatcct ggctctgcgc    8040
gcgctttaag gaaatggctt ccctccagga cctcgaggga tgcagctttt gcgcggatga    8100
cggtggggtg ctgaaccagc cggtgcgcct ctggaaatgt ctgggcacgg atcctggggc    8160
catcgacgac tcctccccat tcccagcagg cgggagctct tacattccga gcgagtgacc    8220
cctctcaccc tctggcgctc acacacctgt aactccaaac ctccgtctca gaatggtcca    8280
ggctggaagg gatgatgggg gctccgacag cgactgccta gctcacccct ctgcgtgctc    8340
aggctccagg ctcagcagga ccaatttgag ttctatctga tcccccctcgg cccccttaact    8400 gacccatcct acaggagaca gggaaatgtc tttcctaccg cggttgattc tggggtgtca    8460
ttttgtgttt tgtgatggct gcttatattt actgtataag cattgtattt actgtataag    8520
cattgtatta taattactgt ataagctgct tatatttact gtaagcat ctccaaatcc    8580 tccctctacg taaacaaatt aatggataaa cagataagtg tatccctgc ccccacccct    8640 gctacgcagg tccggagtga ctcttgaagc tcatacattc cttggccaag tttgcttctc    8700
taacagatgt ttatatagca ataacctggc ttggctcttg ggttcacctt tggacgattt    8760
ggggaagggg cttgttggct ttgctgggtt ttggatgagt gacagtccat gactgttcct    8820 gctgaaggg cgtgactttt aagtggtttc taatatcagg cattgctcct ccgacaggaa    8880
caaaagaaat ggatactgcc cataaattgt tagaaaactt agaatcgctt tgattgagga    8940
aaggttagat ttattccggt tggaaaaagt ggccttccta ttaaacgtgc cctttgaccc    9000
tcatgccctt ggaggtcggt gccagcctgg agatgggata agattgtggt tttccttctg    9060
```

```
cctttttaac atctgttgtt acagtccatt tgttgaaaat ttaaagaaac tgttttattc   9120
cactttccct cagcatttat gtgtgtggtt tcagtagctc tgtggctata tgtacgaaca   9180
cgtgttattt ttccaattgg acatgtgata attttccaac tggaccttgc cttctattga   9240
tgtatttatt tagcatcttc cttactccct ccttgaaaaa gaatcactca aaaacaaata   9300
aaaacagccg tagggccta atacagtgct agacatacaa gaggtattcg gtccatacca    9360
aatggatttt atccatgaag gataaatggg gaaatacagt gggaagcagg tgggaaactg   9420
cgtttgactc tgctctttcc tccaccacca ctttcctcat caccgtgttc agagaccccc   9480
aaagccccct cacactccca gaaacacccc cctggccact cctaacttgc catgcccagg   9540
agttaggtgc ttccactagt gacatggagc tggcgtttgg ggggcacctc agcaggtgac   9600
gggaagagaa gaccccagcc tcaccagctg ggctgcagca gggagaggag tcctcatgtt   9660
ccagcaggga ctctcagctg ttttcctgta aaaccatggt tctcaactgg gggccactga   9720
gatgtctaga gagatgtttt tgttttcaca actcggggag ggtgctactg acatcttgtg   9780
ggtagaggcc aggaatgctg ttaaacatcc tacaaggaag gcacaggaca gtctcctaca   9840
tcaaaatatg acccagtccc aatgtcacca ctgctggggt tgacactggc actgctatct   9900
taattacatt cattgagtgt ctttttaggag gccctattct aagtgcttgc taagattatc   9960
tcatttaatc ctcacaacac ttccgctatg tagcaggtgc tgttattatc tccgtgatgg  10020
ggaaactgaa gcacagagag ggttagtaac ttgctaaagg tcacagagcc agtgggtggt  10080
ggagctggtt gcctgacact agttccctcc cctctcagcc acatgtgggt ttacttggcc  10140
attgtggact agtctgggaa cccagatatg atctataaca ttgacccagt agaatattga  10200
ttccaaaacc actgtctcac aaatgaattt ttacaagagt ctgtaatcgg agcatgaccc  10260
agaataaggt tagggagatg tggagttaaa gctctcaatt tcttatctgg ccccgacaca  10320
gagagcaagg catttcactc tacattggtg ctctgtttat aaaacaaaga gcaaatatct  10380
cttcctaagg tccttaaacc tcttccccca atccagggtt tctggactgc tctgccatat  10440
gacggggcag ctggtttgat tgacccaggg aaggctggaa atcaagactg ggggatcaag  10500
acgtagattc agtgtggcca aggtcaagtc tctgaggttt agggacatca gatccccagc  10560
ttaggttctg tacctcggca aggtgaaagc gttggcgccc actgatgagg cctgctctga  10620
gattgtgggt gtgggttgag ttgggtgggc ataggcaagt cctcttgtaa gaatcttttg  10680
gcaaagatgg gcctgggagg cttttctcac ttcctggggc ccaggctttg caataagtat  10740
tccattatac tgtggtacct tggggctacc tgagaatcct ctgtctcgcc cctgttgcct  10800
tgccaaagag tttgctgtcc aagaattcct ttcctgtctc caggtgccat gctcctgcca  10860
cctctgccag gttccctgcc tgcccagatg gctcccaact gagtgtgagg aggaatttga  10920
gacaggtttt gagctttctg ggttctccag ttaggaaact ttctgtaagc atgcagatag  10980
aatgggcttc agcaaaatac aaactcgaac aacttccatg tatagtccct taattttctt  11040
tgcttttttc atatttcatc aggctccatg ctgagcccaa tcaggaccc gatagaaatc    11100
caaacaccat gtcagcgagt ccccaagaaa tgcattttgt gccaaggcta ttcaaggaag  11160
gtttgggagc agctcaaggg cagacactgt taccctcccc caggtcccca gtgcaggca    11220
gtgttctgca tgtggaggca gtttggccta atggttaagg aggtaggctc tgatcgggcc  11280
tcctgggcac aaatcccagc tccctgctca ctgtgagacc taagccatat tgtttagctg  11340
cttggagagt ttttgtcat ccacaacttg gagtatgatg gtacctgtct cacgggttgc    11400
catggggttc acacaagcta acccggtact cactagggcc aagcacatag taactgctca  11460
```

```
gtaaatggca tcatcggcgg tgtcctgtgg atgagtgctt gtgattggct gaatgaccag   11520 agggggtctaa agatcctggt gatggaatca gttgtacaga taaattgtta cactgagtag   11580
ggatcaagat aggaaaagtc ggcaactacc cagctcccct gcaccaaact gggcagaagt   11640
ggatcctctg aaaattgcac acacccatgt ttaaatgtac acacagaact cttgccacag   11700
gcaagcggag atttgtcatc tgctgtccct gcctcatctt cttcctgaaa tccactccat   11760
gccaggaata aactgcatgc tctccaccag cccaaactga cctgccttcc cgccagccat   11820
cccgggcagg gtgacctggc ttagtacatc gggttcagag atctttccag tttactcgtt   11880
gaataaaaag tgagggctga tcgagaaagt aatggcagtc agggaaggcg aaggaggtaa   11940
agaagagatt ttacaaatga agtaattcaa cagagtgctg acattggtaa actggcaaac   12000
agatttcagg gtggttggtt gagagtagag tagaaaagga ttaaataaag caaacttgtg   12060
gtgtactgaa tcttaggaat tccatgtatc caataagtat agtcatttat gaattaataa   12120
attcggccta agaagccttc ttatcgctta aatcaagact aagtaacaat atatcagttt   12180
taaaaagtca ttatatcaga aaatcattta aatgatacac atagatttcc aagattttac   12240
tttaaccgaa actatataaa tgtgaatttg ttcacccatc ttttgacaca gggctcaggt   12300
cttctcttgg tgtctggatc agccagttga aatttcttgt ctgttttgcc tatgccacat   12360
taataatgca ctgtctgggt cctccgattt cagtttggat tttgggttta cattgtggag   12420
tcatctgaat gcagaatcct tcagggattt tacttttttt tttttttttc atggtcttta   12480
ccatcccatt tgatagtaaa tattactcac ctttatgaag tctttccaaa acattcaact   12540
aaattttctt aaaatcattg aatgatttga agagcttatt cctcagcact tttactccat   12600
cagcttgcac cttatttttt aatcttttt tgagacggag tctcgctcta tcgcccaggc   12660
ttaagtgcaa tggcgcgatc ttggctcact gcgacctcca cctcctgggt tcaagcaatt   12720
ccgcctcagc ctccgccgta gccgggacta caggtacaca ccataatgct cggctgattt   12780
ttgtattttt gtagggatgg ggtatcgcca tgttggccag gctggtcccg aacttctgac   12840
ccaagtgatc cacccacctc ggcctcccaa agtgctggga ttacaggtgt gagccaccgc   12900
gcccggccag cttgcacctt atttaggata tgtgattatt atagcaagtc tggtgtacat   12960
acaagatttt gaatgggcac agatgacctt tagtaagtgc ttggctgtga taagaggcag   13020
tcctgactgc agatcaggct gtgtggaccc cagccttgca tgtttacaga ccttcatgtc   13080
ttattcttac agggtatcag aagaacacct actggggaaa cttataaatt agtaaaaggt   13140
gggcattctc cccgcccatc ttctgtctgt ctgccaggac tagcacagca ctttgaagtc   13200
attcacatag aatcccaact taagagggta aaatcctcct caacagactg aaaataagtt   13260
taaattccct ttgctatatt aactcccctg aggaaagagt cttagatcaa tgtccaacac   13320
taaaaacagt tttaaatcag caagtgagaa ttaaatctga agcaattgat aataatgttt   13380
cattcattcc tctcctttgg ccccgtccac cctactgcta aatccaggca tcaaagagaa   13440
gagggacata attatctcta gtcccagctg ctggttttcc ttccagccta tggcccagtt   13500
ttctgtttta ctgagaaggc tggtgatgtt atcttgggat ctaagtctgc agtttcacca   13560
caaaaagtcc agggatgcac tttcatgctt gtgtcctcct ccctgggata gcaaggatat   13620
tagaagaccc ctggctctgt aattgcttgt catgtgctct acagacgcca cagaatgcca   13680
agaacgaagt gctgggaagg acaaattcat ggaaccgtgg acggtgctc ctcccccagc   13740 gtaaaggaca gctcctcctc ctgaattgga gccagcgttc taaatcatgt gtcaacagag   13800
```

```
ttgtcctgga tcggatccag ttctgccatt gatttgcagg tcatttcagt ggtacctgtt   13860
tccagttgtt cttaattgaa cagtggcacc aaactattgt cttgcctcat ccccctccca   13920
tggcctgtcc cccaaaaaga gacttcttgg gtaattaatc agggcaacat caggcagtct   13980
gggcgcggtg gctcacgcct gtaatcccag cactttggga ggccgaggcg ggcagatcat   14040
gaggttagga gattgagacc atcctggctt tgtgaaaccc cgtctctact aaaaatacaa   14100
aaaattagcc gggcgtggtg gcgggcgcct gtagtcccag ctactcgaga ggctgaggca   14160
ggggaatggc gtgaacccgg gaggtggagg ttgcagtgag ccgagatcgc accactgcac   14220
tctagcctgg gcgacagagc tagacttctt ctcaaaaaaa aaaaaaaaaa ggaatctctt   14280
tggttttata tattttttt tatatatata atatatatta aaatataata tatatattta    14340
tataatataa tatataaata tattatatat tatatatttt tatatattat atattatata   14400
tattatatat tatatattta tatatttata tattatatat atttatatat tatatattta   14460
tatatattat atatttatat ataatatata ttatatatta tatattatat attatatatt   14520
atatatttat atatattata tattatatat attatatatt atatatttat atattatata   14580
tttatatata ttatatatta tatattatat atttatatat tatatattta tatattatat   14640
atatttatat atattatata ttatatatta tatatgtata tattatatat gttatatatt   14700
atatatattt atatatataa tatattgtat atattatata tctaatatat tatatatatt   14760
atatatatta tatattataa tatatattat atattatata tattttttata tatataatat   14820 gtataatata taatatatat aaaaacatat ataatatata ttatatatta tatatatatt   14880
atatatatta tatatattaa atatatttta tatatattat atatattata tatattaaat   14940 atatttata tatattatat atatatacac atatatatat ataaatgagg ccaggctcgg    15000
tggctcacac ttgtaatccc agcactgtgg gaggatcact tgaagccagg agtctgagac   15060
tagcctgggc aacaaaacaa gatcctgtct ctacaaaagg aaactgtaaa aattagctgg   15120
gcatgatggc atgtgtctgt agccctagct acttgggagg ccgaagcagg aggatcgctt   15180
gagcccagga gttcaaggct acagtgagct atgattgtcc catagcactc cagcctgggt   15240
aacacagcaa ggccctgtct ctaaactttt ttttttaat tctatttata tttacatgta    15300
tttaaatgtg aatattcact acctatttgt tgcatgcctg catttttat actgggcttg    15360 ccaaaaaccc gaacagcttt ctactttgac aatgtatcag aatttaaatc agcaatatgt   15420
taataagcca agcaaaggtt atatatgcaa ataaaactgt tgtctataac ctcctgttac   15480 actgggcac agcaaaagtc atggtgtagt cgcatgtgaa cctgtccctt tcatagctgc     15540
tcattgccag gaaacatcag gaatagccat ttggaagagt catcagccct cccaccatcc   15600
gttttctgtc ttgtcttttc cctatgagca ggggaaattc cacgctggcc ccaatcccca   15660
gtgcagcggc tcagcctctg cctctgctgc tggtccccat gaggccagct tagaaacgga   15720
ggattttgca gaacatccct aaatccgctt gaataatgaa gtgatcattc ataaactcac   15780
ctgaacctta ttaaaaccta tttaatattt ttcctggata tcctataggg ataacttgc    15840 ctcctgggct tctctccacc gggttcagtt cttccttag tggtgaagtt cctcccttct    15900
tagcatctca actgtgcctg agaaaaggcc agtggcggct gcactctgtt ccctgtggag   15960
tgttaataaa gactgaataa attgaaataa atcccttca atgtcattaa gtgctataaa    16020
taatcatgaa ccaatgttcg atggctgatg agaaatgcaa gaaaaattt ttaatcagta    16080 ggattcataa gttgacaatc tgggccaagt taaaaaaaat aaaataaaa agacttttaa    16140 aaagatctta tcgtttgtta ccagtaagac tgaattccag aagcaagcta ctccctcatt   16200
```

-continued

```
tgtgggcccc tgttatcact ggctgcttag ggttgccaag ccctgaattc atttgtcaac    16260
taagagattt ttggccaaga ttaagatttc ccatgcctcc atatttccat ctgagaaatg    16320
gagattatac tgtcttcccc ctcagaatgg atgataatgt ggtctctctt ctgttcgcat    16380
agtcatagaa ctgaaataaa acaacttaag agaattcctt tgagcttctc agaagtgctg    16440
cagggctggg ggatgcctcc caggagccgc agtcaggtgc tgatctgaag tctttggtgg    16500
gctgacttta gcctgacctg aaatagtata gctgctgcca cctggctccc ttagcgtcag    16560
tcagacggtg cagctggttc ctaggggtga gggctgagcc agcagggtcc gtgcccagga    16620
gggatgcatg ggtggccaca gcccagcctg cactgatctt gtctgtcccc ttctttggaa    16680
ggaaggagcc ccaaaccagg gtgcaagaca gtgggtgggg gtgccttgag catgacctca    16740
agtgatttcc agccctgcc agtgctgact tctctgggga agggctggga cttccttctg    16800
ggctcaagtc acgacccttg gatggaattt cctgggagct tttctgtttt ttctggagtt    16860
ttcagttttt tcctaaccag acagggactt ggtacagaat ctcatattct aattatgcct    16920
aggagcagcc tctccccacc actcacagtg tttagcatgt gacaggaatc gattaaggca    16980
tgagtgatta aattaaagcc aggcattgac ttggatggtg taatattctg acatctgttt    17040
ggtgtcaaag gcacggggca ggcgcgttaa ttgaactgct tgcacctggc atttgaattg    17100
agccagagcg gggctaaagt cagtttgcct tcaccctgta aatggagggt ttctccggag    17160
cgtggatggt gggaggtatt tcagggtgta tgcataaccc ccaccctgac aatggcccat    17220
ctcttctcca gcgtggccag gtttgagtgc cagtcctggg tgtccagtgg ccccatagcc    17280
ttgcgtttta gtaaaatgct gcccccatta ccacctggtc tgtgcacttc ggtcactgga    17340
atttgccatc ttccagtccc gaatgtggca agccatggag ccttaagctc ttctccctcc    17400
acatcctgga acagacccgc cagtttcttc caggcattgc ctcagtttgc ccctctgttt    17460
ccagtcacac tctcaccagc gataaaatga ttttagacct tatcatctca ccctcggatc    17520
cttatggaaa caataatgag ttgttccctg tttcaattcc aaaattcata tccaatccgt    17580
tttgcatgcc attgccaaat tcctcccaga gcaaccccgt cacctgccct ggccctctcc    17640
aagtgtggtc ctgccatggg catcgcctgc taagccaagc tggcctcgag ctgcctgccc    17700
gggtccccac accttggctc acctccctgc ccagtcccgc ctcctgccag cctgccctgt    17760
ggctccttca tagatgccgt gctctttctg ccccttgctc acccatggca gccttgcccc    17820
tctctccctg ccccaccccc tatttaaatt gacctgacct tcctcagtgt ccatcttccc    17880
cgaagctttc cccagccttg gcactcaagg tccagaggct acgcgtttcc tctcacctgt    17940
ggcagcgccg tgctccccag tgcctcacag tttccttctt gccccgcttc ctgtgtagg     18000 actcatctgc ccacaggttg cacgtcctgt gagggcaagg actgtgtctt atgtgacttt    18060
ccttctccag tcacagagct gggcacatag atagctcaaa accctcttta ttaacacagt    18120
tggatgttga gaaatcaaac aggccaatgt caaatgagct ctccttattt aaatcaagtc    18180
agttctccac ctcctagcac tcagttccag tactctatat acatggaaat aataaaaaac    18240
acatttcctt tgaaacattc tataatcgtt cctttgccct acttcagacc aacttaacgc    18300
actccccatt ggtccaaatg agttttgcta tacgaagatg ctgataataa tagcagcagt    18360
ggattattct gctaaaacca ttgcctcgtt aatcctcagt cccgaggtgg ggattattat    18420
cctcattttg cagagaagca aactgagact cagagatttc acagctgggg agggagccag    18480
ctcatccctc tgtccaggcc caagctctct cccgcttgcc ttcctgcctc tgcaacctca    18540
```

```
gagcatcccc catctggttc tactgcctgt gctagtcgtg caggagccaa aagacacgtc    18600
tttagtgcta aggactggag aagccatgcc ctccagcctc tgtgaatggg tcatatgtaa    18660
catgagcctg gagaaattat ttgaaaccaa aggcaagcct ctaaaccagg ctgctgcttc    18720
atggcgccgg tgacggcaga accaaattta gtgctgtggg caggtccaca cttatcaaat    18780
agagaagctc attttcttc cggctcacat caagcatgaa aaatgttcac acataccccc    18840
cacacacaca tgctttccgg aggggtccat gtggctagag ctggaagat gtggatgaga    18900 ggagcctggc aggtaagccc agggaagatg acattcagct tcccagacag catctacagg    18960
gagaaattta attaaaagtg gggcggtttc cctgagcaag gcagacaaag tcagccctct    19020
actgttaaga aaagggtca cagtgagagg ggaggtgagg agactgagtc tgtattttct    19080
agtctgttgg gctacactac ctgatccccc ttcctcaaaa atccacttta ctttccccat    19140
gtctacacca atgtggttca cactctggga ccaggaaaag ggggagtgat ggggaacaga    19200
gaagggagga gctcacacag ctgaggctgg ggttatgcat atcgaattac ttagaatttg    19260
caacctcaca gggtactttc atggcgttga atacacttc ccacagccac cctccctcta    19320
actaaaagca agagtcattt ctcagttctg gtcttgcctc ccacgttctc ctccacattt    19380
aagaaaatcc accagctaca aagtgaagat accatatgtg atatcccacc ctagtttctg    19440
ttttatcagg gtttggagca ggtggagcag gcagagggat catttcagcc tataaattgt    19500
attaagggtg agtactgagt cattcttcaa gaaaagtttt agaagcatcc aaaactgaag    19560
ggtggagcca cctggagaca gtatcatcag tcctggcccc gagcatggcc tgcataggcc    19620
cccatggatc ccagcgggag ctgcagagtg cgggcacctt ggcacacagc cctgagtgca    19680
aaattaggag ctgggcagag ggcatctctc tgtcgccatt gggcagccca gggcacactg    19740
gtcatagcct tagaccacga acaccctgtg cccggggac agatgcaacc agtgtgccct    19800
gggctgccca atggcaacag agagatcgac acctggaccc catgtcacgg ggactccact    19860
actaaggctc ctaagactgc caccttccag tgggataagc cctgcctcct actgggccca    19920
caatgtgcag agaacacttg ggactacctg gctttctgga tacacaaata ttgatccaat    19980
ctggactaat tagaaggtca gtcccaataa caaatcgaag tcagctgggc gtgatggctc    20040
actcctataa tcccagcact ttgggaggct gaggtgggca gatcatttga agccagaagt    20100
tcaagaccag cctgggcaac atagcaaaac cctgtctcta ctaaaaatac aaataattag    20160
gctgggtgtg gtggctcatg cctgtaatcc caacagtttg ggaggctgag gcaggtggtc    20220
acctgaggtc aggagtttga gaccagcctg gccaacaggg tgaaacccg tgtctactaa    20280 aaacataaaa attagccaag catgatggca tgtgcctata atcctggcta ctaggaggc    20340 tgagacagga gagaatcgct tgaatccagg aggtggttgc agtgagctga gatggtgcca    20400
ctgcactcca gcctggttga cagagcaaga ctctgtctca aaaaaaaaa aaaaaaaaa    20460 aaaagccatg cctggtggag cactacgtgt aatctcagct atttgggagg ctgaggcacg    20520
agaatcactt gaacctggga ggcagtggtt gcagtgagct gagatcgcgc cactgcactc    20580
cagcctgggc gacagagtga gtgagactcc atttcaaaaa aataataaat ctgagtcact    20640
ttaatattgt tatttggatg tcaacctcta ggtgtttgag acaggagagt gatatggggg    20700
cactggaaac acacaggcac ggggtgtcct cacacttggg tagcccacac gatgtgatt    20760 cagggtgctg ggaggtcccc ccactcccca aattactaac aagtggatag tactttacag    20820
tttatatgat ctcatttgat tcttaacatg agcctgtgag tgaaaaattc cttcccctct    20880
tctacagatt aggacgttga gattcaggga ggttcagagg gattcaggga agtcaagtgg    20940
```

```
cacctggagt cccgtggcta atttgaggcc ggtaggggat tcgaacccag gatttgtgct   21000
tcttatgcct gggcttctgc tccctgggc atggtcttcc ccctagcttt cccattcact    21060
gctttagcct aggggtccta ccctttatta aactgccagt gcctcactgc ttttctcccc   21120
caaagacaaa aaaaaagtgt ttttgctttt gttttgtttt tcatgggcag agacctggaa   21180
tttcagcttg agaatttgtg ccatatgata aataaatcaa cagatggctt tttccttaaa   21240
aaaaaaaaaa aaaaaaacta agatgtattt gcagtgaggc ataatttgta ccaaaaagtg   21300
ctcaccacac tgtagtcatg ggggcaggag gcagccgcgg gtgaagggag aaatcttgga   21360
gtccaggcag ccccttctg ggctgaactg gggagctggg ggtgctgcca gccctgccag    21420
gttctcctag gaggcggcag ctcatatggc tgtgggagga ggcagaggga gcctcatatg   21480
cacccacatt tccagggatc tagaagacag aaggaggaaa accaccatca tgttaaagca   21540
gacagttagg taacacatcc tgtaatacaa gttatttttt ccacatctaa aggctaaaaa   21600
tagttgttag aatttaaaga taattggtaa atgagtttct atccttctag tttcacatca   21660
aatggaatca tgctgccttc acatcactag tgcccgttat ttgtgtttaa tttccacaat   21720
gttgtctaat tccactcttt gggcttcccc agggatccag cctccctcac tcgcccatcg   21780
cagggagatg ctttattcat ctttgtgtct tctgtgccgg gcatagcgca tggcacagaa   21840
taagcactca gtaattgatt cacgagtgaa taaatggatg agtgggtgag ttcaatattg   21900
actacaaaaa ccctaaggcc acactggtga gtggctgcgc ctgtagtccc agctgctggg   21960
gaatctgagg caggaggatc tcttgagccc aggagtttga aactagcctg gcgatatag    22020
cgagaacctg tctcaaatga caaaaacagg gccaggtgca gtggctcacg cctggaatcc   22080
cagcacttta ggaggccaag atgggaggat cacttgaggc caggagtccg agaccagcct   22140
gggcaacata gggagaccct gtctctacaa aaaatttttt aaaaattagc tgggcatggc   22200
ggtgtgcgct tgtagtccca gctactcagg aggctgaggc aggaggatca cttgagccca   22260
ggaaattgag gctgcagcga gccatgatgg caccactgca ctgcagcctg ggcgtcagaa   22320
cgagacctgc tctcaaaaaa acaaacaaac aacaaaaaaa aaggcttct taaagagact     22380
tgagaacaga aaggggaaca gatacataac ttatatattt atttgttcat cttccacct     22440
tcctggaggg tggaggggaa caggtctgta tttggagttt tgaatgctaa agtgggaat     22500
acatgtactg tttgccatga tctgttcaaa agttaagcca aatgccttag attctcctga   22560
aaactggaat gccactgtaa actataagcc ccacttcaaa gataaaagat cttgatgaac   22620
agggctgggt ctgtggactg ggcctctccc caccacacaa ggaagggtgg tgccagttga   22680
aggaaaatca cttaaatcct tgctgtctcc taataaggtg tggtcccagg tagggctgtc   22740
agaattagca aattaaaaca cagggcatct gtgaaaatta gaatttcaga taacaacaaa   22800
taattggcat aggctgcata atgtccctca aagatatcag gtcctaatct ccagaacctg   22860
taaatgtgat cttatttgga aaaggggtct ttgtagatgt ggttaaatta aggattttga   22920
gatgggggga ttatcctgta ttatctaggt aggtcctaaa tgcagtcaca ctcatccttg   22980
taagaggaag gaagagagag atggaaaaca cagaagagaa gacaatgtgg tgatggaggc   23040
agagattgga gtgaggtggc cacaagccaa ggactgctgg cagctaccag cagccagaaa   23100
agtccaggaa ccaattctct cttggagctc cagagggagt gtggccctgc tgacaccta     23160
gcttcaacct agtgatcctg attttggact ttggccttca gaagtgtgag ggaatgaata   23220
tctgttgttt taagccacca agtttatggt catttcctac agcagccaca ggaatcaaaa   23280
```

-continued

```
acagtaagta tgtcccatgc aatgtttgtg acacacacca aaaatattac ttgttgttca    23340
cctgaaattc aaatttaact gggtctcctg tattttattt ggccaaccta gttcccaggc    23400
ccaaagaaag aggcttttga aatttgcaag aaagctggtt ggagctgtca gaaagtggac    23460
tttgtaaaca cagtaccacc gaaccaattt gaactgtact acctctagac aaaagagagg    23520
gcagtcagac agttgttcgt gatttcttct ttcaacagtc atttgagcac ttactacaaa    23580
acagaagcta tgtgtaaggg tggaggcgtt agctgttaat caggacctcc aggctaagtt    23640
tctgtattag tccgttttca cgctgctgat aaagacatac ccgagactgg ggaatttaca    23700
aaagaaagag gtttaattgg acttacagtt ccaagtggct ggggaagcct cacaatcatg    23760
gcagaaggca aggaggagca agccacatct tacatggatg gcagcagaca gacagggaga    23820
gagagcttgt gcaggggaac tcctcttttt aaaaccatca gatctcgtta gacttattca    23880
ctatcaagag aacagcacag aaaagacctg cccccatgat tcagttactt cccaccagat    23940
ccctcccaca acatgtggga attcaagatg agatttgtta ccatatcagt taccaaccct    24000
tccagataaa tcacgtgaaa tatcgccatt aacagagtga gctcaggtgg ttcttcagtg    24060
catttctgat acctgaacct tccctgggaa tttcacagac catcaggctc tccacccttt    24120
gatagcagga tagcagggcc caggttctgc aggaggagat gttaccacag gcctgaaagg    24180
gagggagggg cagatgctac aggaagatgc tggctctgga ttcgctggag gagctttcaa    24240
gggaagtaga tacacactgt ctccatcatt tcatgtccat cacactctaa aatgctttgg    24300
acaagaagca aatgttaaag acaaatgtgg cccatttttcc tgtacaaaga gggctgctcc    24360
catgccaggc tattggcact ggtgggcatg aggcttctct gctgccctgg ccgggggggtt    24420
ctctcactca ccattggctc tctgacacct ggagagacca ccaccttgg gctttcatga    24480
tgctcacaga atccacactg ttggagcttt aaggagcctg gatcaactgg aacaggcagg    24540
gagtactagg acagcccagc attgccccaa aatatccagg cctgataaaa gagaaaaaca    24600
ggtagctcac aggaaaagga taaaaaaagg aggaggatt taacatgaaa aggtgcttga    24660
tctccctcat aataaaaaga ctgctgattc catccaggca agtgacagaa aaaaaaaatt    24720
taatttaaaa agactgctga taaaaccaca gcgagacact gctgctcagg gatctgaggg    24780
tgtgggcagc caggctgcca cgcatcatgg gtcggagagg aagaccacac ccctggagca    24840
gagggcggct gatctgtcag atgccctttg acagcacctc agcttccaag aattaaccct    24900
ttctatgtga gcagaggcat ccatgggggg acacactggt gaatcatctg ttatgtagaa    24960
gtctggaaaa catcaggatg gaactggtga aataagtgtg gcctctgacg gaatggagcg    25020
gtccgtctgc actgctgcgg gtgcccctca gatcctgtgg gtcagtgaga aaagcagtga    25080
ggaacaaggc aggtactgtg tactgtcctc tgcgtgcaag gaaggccagc gcatgcaaca    25140
gagtccacac agacatagcc taactctgga aggaagaatg agaatgcagt ttcagtggtg    25200
gcctctggtg gggagaaact gggtgaaggg agatgtcatt tccatttctc tactattaat    25260
tttgtattac catgcttaaa tgttacttt tacctttttt ttttttttg agacagggtc    25320
tctctctgtt gcccaggcag gagtgcagtg gtacaatcat ggttcactgc agcctgaacc    25380
tcccaggctc aagcaatcct cccacctcag cctcctgagt agctgggact ataggcacgc    25440
ataccaccgt gcccagctat tttttttaat caagatggag ttttctatg ttgcccaggc    25500
tggtctcaag ctcctggact caagcaatcc tcctgcctca gcctcccaaa gggctgagat    25560
taaaacgtga gtcaccctgc ccagccaatt gcttttaaa aaagattaaa tgcatgtata    25620
cgctcaggca tcagcacact tggaaaggat gaaaatatcc ggaagaaggg ttctttaaa    25680
```

```
aggctcctca agtgatgctg gcaggcatga cgaatgtccc tggtcacaaa agctctgatc   25740
tggcctaacc ctgtcatgtt agagactgga gtgcgtgtgt gtgcgcgcaa agtgtggggg   25800
gatgggggtg agtgtgtgtg gtgtgtaagc atgagtgtgt atgtgtgtgg tgtggggtg    25860 tgtgctgtgt gagcgtgtgt gagtctgtgt gtgtagtgtg tgtgtgaagt atgtggtgtg   25920
tatgtgtgac gtgaggtgtg tgtggtgtgt gagttgtgta tggtgtgtgc atgagcatgt   25980
gtgtgggcat gtgatgtgtg tgtggtgtgt aagcatgtgt gagtgtgtat gtttgagcat   26040
gtgtggtgtg ttgtgatatg tgtgtggtgt gtgagcatgt gtgtgtgatg tgtctgtgtg   26100
tggtgtgtgt gagcatgtgt gttgtgtgtg tggtgcatgt gtgtggcgtg tgagcgtgtg   26160
tgtgcattgt gtctgtgagc atgtgtgagt gtgtgtgtgt tcagcatata taaggcatgt   26220
aactgaacac agcactttag agggctctcc tggagtcaga gggggtgggt aggaggagaa   26280
gggaggtggg ctagtgtgct gaagtatcta ctccttgtca tagtctgtga cacccagac    26340 tagcccatga gccacccttgt tccctgcatt tccaatgaga cctcggtgga catgttccct   26400
gaggtgaggc tgactgatgt catttgacga tcttgatgcc aaatcctttt atatcaaaaa   26460
caaccagaac actctctttt ctcttagtgc tttcacccag atgaccacat ttcatcctcc   26520
cagccactct gggccaggtg gcactgctgg tttgaaaggg aggtctcccc tggagtaact   26580
tccgtgggcg gattcacacc ctgcccacag tcctgtccca gtcagccac catggtggtc    26640 tccggttcct ccagaattcc cgcttttcag ctcatcccca cattcccgga gggactgaga   26700
gcgcagcccc agggccctgc tctttggggg ccgtctctac acccagagaa gcagcaaggc   26760
attcctaggt ttctctttca gatgcagaac ttcagtgttc agagatgttc ccactggtcc   26820
tgagagggct cagttcagct ttaatgactg cgctgttgcg tgtgctctgc agagggcggg   26880
tggcccagcg tggctgactg cagttttcct gacgtggagc ccgagcctgc cccgctgttt   26940
attaattaag gatcactctg cttgcagaac cctgaactcc ccagaactgt gaggtgggag   27000
aaccccgaga ggccacctgg ccccacttcc cacctgctgc ccaaaccccc tctctgcctt   27060
cctgacagtc accccaactc ccagtgatcc ccatcaacca tctgacaagg ggactgagag   27120
ggaagagaaa ggaggggccc aaagaggaag gtaaaactgt cgggaacagc ccccaaatgt   27180
gtgacagcct tcagtggagt tgcccacttt ccctttttctc ctcctgcag gacctccctt    27240 ctccccagtc ctcccaact tctgaggtta cattgagaaa agtctgcaga gaggtgccag     27300
catcacaagg tgttaaggac cacgagtttg gcattttaac agatgccaga gccacttgag    27360 aaaatgtggta actaagccca gagaggtaca gttaacctcc ccagagtcac acagcaggtt   27420
catggcaaag ctggactagc acaggtgtcc ttcccctgca gatccccttc tgtgccccac     27480
atcacctccc tccagtgtct gggccacctg gagatgggcc ctcagactca cccggccaga   27540
ggtgccatct catgggagag gtctggccag gaagcatcga tatttgagat cccaagaaat    27600
gaagacttgg cctgtcagat gacagacttc ggtcatggga acacgtgatc tgttttacac    27660
atgcgtcccc tcagcagcag ctttccagaa cattcccact ttcttctgta gtgagaagaa    27720
ctctttccct gcagcctcct gcccaactcc tccttcagtg tctttgcttc agtgtctttg     27780
ataaaccatt ctgctttgca gagtgcgagc tctgccttgc agggttcgca tctgcctgtg    27840
ctgagtaacc aacgctaagg tcgagtggtc ggtcacctct cataagagct agggttgtct    27900
catgctgatg actaggactt gccctcaagg agaaaaataa atcaaaacaa agcaaaaac     27960 agcaaacatg catctcttaa agaaggctct gagtccaggt aaatttcctt ccactgaagc    28020
```

```
agccaggctg aattcgaatt atctttgccc ctgcttaaaa actaatgcaa attttcctag   28080
agaatatcca ctaattcctg gagggggcat gggcattcct gatgcccatg agaggaccat   28140
ttgctcttcc ctcagtatgc taaataacag aagcgacatt tgttgctgga aagtatcagt   28200
gaagttaata aggttttttct tgcccagggt gagggaacag ttcccaatga caaatgctgt   28260
atgggaaggg gctgtagaac tgccagcccc tttggtccat ccgtaaagtg aactctgtgg   28320
atcctggagg attccagcgt ctttttttttt ttttcttttt ttttaagaca gagccttgct   28380
gtcacccagg ctggagtgca gtggcacgat ctcagttcac tgcaacctcc gcctcccggg   28440
ttcaagcgat tctcatgtct cggcctcccg agcagcaaga ctacaggtgc gcaccaccat   28500
gcccgactaa ttttttgtatt attagtagag acggggtttt cactctgttg gccaggctgg   28560
tctcaaactc ctgaccctcag gtgatccacc cgcctcagcc tcccaaagtg ctgggattac   28620
aggcatgagc caccatgccc agccagcatc tttcattttt ctgtctgctt tggccctttc   28680
ctctctcact gtcttccttt tccatttcca aagtcagtcc atctcactat tagcacaaaa   28740
actgctagag cgcttgtcat tggtcatctc tccctgcacc tggctggtct gttcttggcc   28800
actgaagcgt ttcccccagc tgttgcttta atcattttat tgttattatg ccttacttaa   28860
gaaatggata tgagatgcat ttacctgtct cttcctgcca ctctgcagag ccagtaagat   28920
gtggtggaaa gggcccaggc tttggaggag ggctggctgg ggttggatct tggctgcccc   28980
ctactagctg tgtgaccttg ggtaagtagc tggacctctc tgagcctggt tcggaatcat   29040
agcacctctc tttcagggct gctgtaagga atagcagtgg tgtgtataaa gcagagcgca   29100
cagccagcaa ctggccccta gccacactgc tgagcaccta ctgtgataag ctgccattgt   29160
ggtgtgtgaa gcaaagggga acatgcctg ctgtagtgag cttcctgtag ggcaggttgt   29220
agaaccagag gtgggttcca aggttacaaa gggactctta gtgtattagt ctgttctcac   29280
attactataa agacctacct gagactggat catttataaa gaaagaggt ttaattggct   29340 cacattggct gggtgcggtg gctcacgcct gtaatcccag cattttggga ggccaaggcc   29400
ggcggatcac ttgaggtcag gaatttgaga ccagcctggc caacatggtg aaaccctgtc   29460
tcttctaaaa taaaatacaa aaattagctg gccatggtgg tgtgcgcctg aatcccagc   29520 tactcaggag gctgaggtgg aagaattgct tgagcccggg aggtggaggt tgcagtgagc   29580
caagatcgcc ccactgcact ctagcctggg cagcagactg agactctgtc tcaataaaaa   29640 aaaaaaaaa gaaaagaaaa agaattgcaa gaaataaatt attgtttatg agctatatgg   29700
tctgtggtac cttgttgtgg gactgggagt cttggcgtct ccctgaccct gcctgttgct   29760
gcagcaccgc tcagccctgc ctgctcccta cctgcctccc ctcggcctct cctgcctcca   29820
ccggccccct ggtgcctcct ctagagacag tcctcctggg accgattgtg ttctcactta   29880
cacgaggcat ccaggactac agataaccag aggaaggggc gccccccccg cctgccctcc   29940
tccctggcat cctcacgctg cagaggtcag agcctcatcc cagcccctta cctgccccta   30000
ctctgtggag aaccgtggtc agttcgccag gccggatcca cgaacggcct tgtggaagat   30060
ggtgagctca cacccagagc tggctccgat gaccctgtct cctttacatg tttctacctt   30120
cccctcccta ccttccccca ctgctgggcg cagagtggag gcagatgagg tttaaagctc   30180
agaagggctt aaacgggttg gggcgcagtg gctcatgcct gtaatcccgg cactttggga   30240
ggccaaggca gaggatcact tgagcccagg agttcgagac caacctgagc aacatagtga   30300
gaccgcgtct ctacaaaaaa taaaataaat aaaattagct ttgcagggtg gcatgcacct   30360
gcagtccctg ctactcagaa ggctgaggtg gaggatcgc ttgtgcccag gagtttgagg   30420
```

```
ctgcagtgag ctatgctggc accacagcac tccagcctga gtaacagaat gagatcctgt   30480
ctcaaaacaa acaaacaaac aaacaaaaga aggcttaaag ggggctccag gtgggcttgg   30540
cagcacaaag ctatgaagtt ctatcttaga cacaagttct gttactgggc ctttgcaggc   30600
tggcctgggt acctggctgc catagacagg gaaccttcca gatgagctgc aggcgtggag   30660
cacaggagcc agggtgctct tcctgggctc tgtccacagg cagaacgtac acagtctttg   30720
tacacgtccg gcggctctgg tgcctatttt tgtttgtgtt tttcttttgt ttgggggat    30780 ggatttggtt tcccccgagc cctctgtcct cctgtcacct ggctggtgct cggcaatgtt   30840
gaccagctgc ctggctggag ttggcagtgg ctaaggctgt gacagctaac atgttcctga   30900
gtcctctcat ttcttcacca taatgccctg ttgagtttgc agatactgtc tctgttttta   30960
tctcccgggg aaactgaggc tcagagtggc taggccacct tcccatggtc cctcagctca   31020
tgagggccac acagggcatt gcggtggcct tctcctcagc cttgaccctc cggccccagc   31080
attgctgcct caagggggtct cctctgctga gccgtgcacc ttctgcctgg cagctccaac  31140
tctgtggctg tgttcagtgg ctcagcactg ccccttgacc ctccctggcc ttctgcggat   31200
gccagactgg agcactctga caaggtctgg ggtggttgta tgggtcctgt gacctctata   31260
cacctcccag tgcctgggaa tcctgcagat acaccctcct tagccgtccc taaccataga   31320
ggacatttct gaggtccccg agagagtggg gcacccctgc aggatccaac tgctgggccc   31380
aggaaggata gcagcagcat gaggggttcc attagccaca aactcacggc atggaacctt   31440
cacccacctc gcccctcatc tgctgtttag cacctggcac gccgtgtata cttactgatt   31500
attacatttt aatggcaaat tatagtggca aacgtatgca tctttgcaca attgttgtac   31560
agcatgatga acaagtcatt aatagtaaag aataaatgtg aaagtgagaa aaatctgact   31620
gccaaagttt ttactccttc cttccctccc cagacttta aatgaaagtt tagggataat    31680
cccttagttg tcctgctagt aggacttgca attaaaagaa ttgggccaag aacacttcta   31740
cgcttctcct tttaggtttg ggtgtaaatt cggggtattt ctcactgatg aaagcctggt   31800
gcagggcaga ccgtgggaag cttcatttc cggaatggac catcaacatc ccttggagaa    31860
gaattctctt ctccagaccc agacctggtg tcctggcacc cattgggcaa gtgggtccta   31920
gaagacaaac ctggtcagag cctggaggct gcttagcatt ccccacgcac attagcagct   31980
cggagagctc aggaagccgc agcccctcct tgcctcacca gcctggatca ggacagcatc   32040
ccctggaaga cacacagggc ctggcctctg attacccagc ctggagggaa agctcaatcg   32100
agcatcatgt caccccggtgc ccccatgcag ggtggcactg tgagaccccc caagccaatg  32160
ataccacctc acaggagtgc aggcccattg tggccagatc atcttgactt tcaagataa    32220 atcagaaatc gtatttccat gagatatccc tatttgcaag tgatggtgac taaattagaa   32280 gttttttgaat attgtaacat gttcgtaggc tgtttgtctg gtttaaactc tatctggagg  32340
aattcaagct agacttcagg aataacttct tgaggcaagg attttgagac cttagggaaa   32400
gaaggacgtc ttgggggtat tctgactgtt gtcctcctgg aagggaagaa cagagaacta   32460
gaagactgcc cttagcgaag ttcaaagcac ctaagcccgg gacctcagc aagtgttctt    32520 gagtcacaga ttctccctga ggcgcctctt tctggctcca tagaatggct gattctgtaa   32580
ctcggtgagt ttgctttttt tttttcctcc atcacccagg ctggagtgca gtgaagctgg   32640
agtgccgtgg agcgatcact gcaacctctg tctcccaggt tcaagcaatt ctccttcctc   32700
agcctcccaa gtagctggga ttacaagcat gcagcaccac acctggctaa ttttttgtgtt  32760
```

-continued

| | | | | | |
|---|---|---|---|---|---|
| tttaatagag | acggcccgaa | gtgctaggat | tacaggcatg | agccaccgcg | ccagccata | 32820 |
| actctgtgac | tcttgttaca | aaggccttat | attttgctct | ttgagggtgg | ttttggtttg | 32880 |
| atgcctgttg | gttgccatct | tttaactagg | gatgttttat | caaaatgccc | agccaaagtg | 32940 |
| tccaaacaaa | ttatacctta | aagtttgaaa | atgtctggca | cttctaattc | aatgcctgtt | 33000 |
| gtgccaggca | ctgggctgct | gaggaactga | gtcccgtccc | tgcaggctag | ctagagaaca | 33060 |
| cacacacaca | cacacacaca | cacacacaca | gagtggtctt | acaagtcagt | tttatattct | 33120 |
| acctatatgc | aataaaggta | ttattatgtt | gaggtgcctt | gatataaaaa | tttttcttaa | 33180 |
| aggagaggat | gcctaaaaca | ggcattacct | gaaacctcct | ctctccagca | ttggttgtct | 33240 |
| tctgtcatga | ctcagggttt | tcactgagaa | tgggatggaa | atgtggtcta | aagataggc | 33300 |
| caatgttggg | actggatccc | ctctgggaag | tcagaccagg | ctaggcagg | tccttgaagc | 33360 |
| catcaggaaa | agcctctgga | gccagaaaca | aaacaaaaaa | aaaatggtgt | taactaaact | 33420 |
| cagtctcaaa | tcctgaatag | gactcaagtc | aagcaaaata | attaaaggag | ttagcaaagg | 33480 |
| gcaagtcaga | gagaccgagc | aacaccaatg | tcttccggga | gccctgtggc | gagtgacaga | 33540 |
| gcctggactc | tggagtagaa | ctcatcttgt | gtcttcttct | gccactcgtt | agctgggtga | 33600 |
| ccttgagcca | agcccttaa | cctcttggac | cctatgttct | tatctctaag | taggggctgg | 33660 |
| taatatcttc | ccctttgagg | aatgccctct | aaggggtgtt | gtgaagattc | ggtaaggtgg | 33720 |
| caggggtagg | actcctggcc | agaaacaggc | acataataaa | tgctaagtct | ctccttctct | 33780 |
| ccacctgctg | gatgctgtag | atactaagga | tttcgatgtg | aatgagacaa | accccctgcc | 33840 |
| ttccaggagc | ctttgagaat | cagagaacta | gacccatttc | cagaacaagg | ggatgcaggg | 33900 |
| tctggataaa | gttttgggga | tcaatagagc | agagggctcc | cagaggatcc | catagggttg | 33960 |
| actcctaact | caagggcatg | agacaacccc | caggaagggc | accctggaag | gggtccggct | 34020 |
| gtccctgatt | tacttgtggg | cactggggga | atgcccggag | ccatccagcc | ctcagggctc | 34080 |
| tgtgtgattc | tgggttcctc | ccataaaaga | taatcagatt | ctttcacgtt | aatgtctttc | 34140 |
| tccacctcat | tgcacatcat | gcagctattc | attgactcag | caagtatcag | ctttgcatgc | 34200 |
| gaccttggcc | tacccacttt | agcttttagt | aatagctccc | ttcttgaata | atacaaccag | 34260 |
| tggggaaaca | gaacctaact | cttacctctg | ggaggcttat | ttgcttttgag | aacatatgtc | 34320 |
| ctgcagtttt | gttcatatgg | cagtgaagtt | tcgtgcacac | actctagagc | caggcagcct | 34380 |
| gggttcaaag | cgcagctctg | ccaggtccta | actgcatgaa | tttgggcaag | tcgctcaacc | 34440 |
| tctccatgcc | tgagtttcct | catctgtaag | attggagcaa | tggtaatacc | tgctttttag | 34500 |
| ggttgagaag | agaattaaat | gaattaagat | gggtaaagtg | cttagagtgg | agctttgcaa | 34560 |
| gtagtaagtg | ctatgtaagt | gttcgattta | aaatgaaaga | cccttaaata | cattctttgt | 34620 |
| tcatttcaca | agcccttcat | ttcacaacct | tacatttcac | aaccaagctc | tgtctcccct | 34680 |
| ggaatccagc | cataactctg | ctcacaagtg | tgagacaggc | cccagcagag | ctgcacgaag | 34740 |
| aggagagaag | gcagccccc | agactcccaa | cccctgtcc | aagatggcaa | aaccagaaca | 34800 |
| cagcctctgt | accaccccag | caggtattca | gaatctgcaa | tctccaaagc | ccacttcaat | 34860 |
| tgtaaatgta | gagccacgtg | cgcttttaagt | cacctgtcac | tctggaggct | cttttgctca | 34920 |
| gttcctcacc | attagcaggg | atgacaggga | gtgcaggagt | gcggtcgact | cccagatatt | 34980 |
| ggagagcgct | gggctagctg | cccattctcc | cggcctccac | tcctctttgc | tgtccagcca | 35040 |
| tcacttgctc | tttgaaggca | aacaaaacag | aaaacagtgc | caaaagtatg | ggaagaaagc | 35100 |
| cagcttctcc | cctggggtgc | ctgtgatgcc | atgcccaccc | tccctgacca | cgcagcccct | 35160 |

```
gtggaccctc agggcccaa gcccccattt ccatcacatg cgtacaccca tgtgtgtcca    35220
tagccgccca tctcagtcaa taaggctgct cctgcccact tggaatagtg gtgacaacca   35280
ggagtggctt atgggaacta tcccaatggc ctgacagcat gtccgctgca aaccgctgag   35340
gtaggacact gccctcatgt ctagctgatc agcaagaggc gcagttgctt tcttaggtaa   35400
cattgctgct gtgtcctggc cattgctggg gggtggcact taatctacac cagatttttc   35460
cctcctgtat cttccaagct gcttggatct tggtgctgaa ttaggttgga ctttgtcttg   35520
tggggaaggg aggactatag accctcaacg taagcaatgg tcagactatt ctaagaaaac   35580
tcgccgaatt aaagcatgag gtaaatttag ttctgacttc tgtccacccc actgccactg   35640
tccccttta tcccatgatc ccttgctttt cttttcctcc tctctccta tctcttgtgt    35700
ttgacgcatg ataggaattc agaaatatat gtttgtggat tgtttattc acgtagcaaa    35760
ccatttcttg agtgcctacc atgggccagg tagaatgggc ggccccgggc tgcagtggtt   35820
tcttcagccc ctctccaggg tttacactgt gcaagacggt ttgtgatggg tcctcccatc   35880
gaggaccaca ctcttctttc tctgtgcccc ttggtcctca gtctctgacc ccacttcaaa   35940
ggcagcattc actcagggaa gctcccatac aatgctagtc agagtaaaag tttggacaaa   36000
ttgccaggaa gcagcttgtc agtatgcata aacagccttt aaaatattac tactctttga   36060
cccagaattt cacttctagg aatctgtcct aaggaagtag tcacatgcaa agatttatg    36120
taccaagatg ttcatcaaag tgttgtttta taacaggaag tctcagaagc tggataaata   36180
tccaacctct ggaaatggtt agatagaata gtatgtagcc attagaaaat tatgtctatg   36240
gggtttaaaa tgtcatggga aaacacttct gacataaaag agcatgagaa ctgtatattt   36300
agcataatct taactatgtt ttagaatgca caggaaaaaa atgtacaaac atattcatag   36360
tgatgtctct ggtggtagga ttatgatcag taagtacttc tgtctcttca tatttcctg    36420
tatttgataa tacatgcata tgttgttttt aaaataagaa aaattttaag tttaaaattg   36480
gagctgaaaa gtgttttag gtcaggcgag gtggctcaca cctgtaatag caccactttg    36540
ggaggctgag gcagtcagat cacttgagcc caggagttcg agaccagcct ggccaacatg   36600
gtgaaacccc atctctacta aaaataaaaa aattagccat gtgtggtggc acacatctgt   36660
aatcccagct acttgggagg ctgaggcatg agaattgctt gaacccagga ggtggaggtt   36720
gcagtgagcc aagatcgtgc cactgcactc tagtctgggc aacagagtaa gactctatgt   36780
caaagaaaaa aaaaaagaa agcctttt aaacagtagc agacataact atataatcct     36840
tactaagctg tcggtcaaat tttatttat atatttatt tattcattta ttattttag     36900
acagggtctc actctgttgc ccaggctgga gtacagtggc gtgatcatgg ctctcttcaa   36960
acttgacctc ccgggctcaa gtgatcctcc catcttagcc tcccaagtag atgggaccac   37020
aggtgcatac caccacacct ggctaatttt ttttatttt tattttaga gatggtgttt    37080
actatgttgc ccaggctagt ctcaaactcc tgggctcaag ctatcctccc acctcggcct   37140
cccgaagtgc tgggggttacc agcatgagcc actgtaccca gccctcaaat ttttaaaaat   37200
ctataagaga cattattgga caattagaga aattcacata tggacttata atagtatcag   37260
agtgtgtggt gtgatggttc tggagggaat ggacttttc tttggagaca ggcttttcta   37320
tgcccaccct tttatcttgc taacttatca tcatccaggt tccagcagaa acattacttc   37380
ccccaggaaa tttcttaagg gtgcagtatc atgatgtctg cagcaaattc tcaaatagct   37440
caggaaaaaa gtacgtgtgt ggtatgagtg tgtgtatgta tgtgtgtata tatatacaca   37500
```

```
tatatacaca tatatataca tatatgtgta tatatataca tatatgtgta tatatataca   37560
cacacataca catatatata cacacacaca tacatacatg tattttttata taattatata   37620 tgcagagagt gcaaatgttg ccaagttaaa gattggtgag tctaggtgaa gggaatatgg   37680
tatttattgt attatttgtg caacttttct taagtttgaa aattttcaaa acaaaaaatt   37740
ggaggaagaa ggcatgccag tctaccccaa gccctccatt ggaatgctga aaatctaaac   37800
aatgtgattt ggcaatttca tttcttttct gttgtgggcc agtagtcctt agatgttggg   37860 gaaggggta gtcgctgagg tgtggttgac ttaggatgga agaagcagaa gtcaagactc   37920
ccagggtcaa agtggtttgc tctgctgacc caagtgtggg aggcccagag tcagcgtttc   37980
aggtgtgcta attcagcatg gttctattca cggccaaagt ccaccctggg cacctctctg   38040
gcagcaatct tgggtgactc tactaaggcc aggcctccat gacccatgt ctggatccca   38100 tatctccacc tctcccactg tctcaggaac ggtgcttagc ttttttcttt ccctctcctg   38160
tcttctttgc cagcatgtag aaagttaaa taattcccct cttacaaca aaacaaaaca   38220 taccccttc agtcaaccac cctagctctc ttctcctttt cccagccaga ttttttttaaa   38280 agcatcctag gccaggcgcg gtgactcacg cctgtaattc cagcactttg ggaggccaag   38340
gtgggtggat cacaaggtca ggagatcgag accatcctgg ctaacatggt gaaaccccat   38400
ctctactaaa aatacaaaaa agtagccggg agtggtggca ggtgcctgta gtcccagcta   38460
ctcgggaggc tgaggcagga gaatggcgtg aacctggtag gcggaggttg cagtgagccg   38520
agatggcgcc actgcactcc agcctgggtg acagagtgag actccgtctc aggaaaaaaa   38580 aaaaaaaaa aaaaaaagc atcctcagca ctttggcaac tccatctcct cccaacatgt   38640
ccctgttact ggaatccagc caggactcag ccccgatctt tctactctaa ccagttgtct   38700
cagttaacaa ggacaggttt atgctgcagt gacaaacaag atcccaaatt cttgtggctt   38760
cacacatctg gcaccacctc atcttccagc cttaggagtc atctttagt tccttgaaaa   38820 ctctttacag ttttctgttg gggccttgtc atatactatt cccctggaat gttcttttcct   38880 atcccctccc tttcaccttg ctaacttgtg cccatcctcc aggtctcagc agaaacatca   38940
cttccttggg gaagttttct ccaacaccca cactacacag gtgtcccatc tacactccta   39000
tgactttgtg gtacttgtct cacttcattt tccactgcct tccccacaag gcacctgcac   39060
aagggcaagg accgtaccac tgtacctatg tcactcattg ctgtggtcac ctgcactctg   39120
gctgcctacc ttaactacac attagaatca cctgaggagc ttttaaagcc acaatgcaag   39180
actccaccct aggccaattg gatccaaatc cctggggtag ggccagacat cagtggagtt   39240
atatatacat atatatattt tgtttgtttg tttgtttgtt ttttgagaca gagttttgct   39300
ctgtcaccca ggctggagtg cagtggcgcg atcttggctc actgcaagct ccgcctctcg   39360
ggttcacacc attctcctgc ctcagcctcc tgagtggctg gaactacaag tgctcgccac   39420
cacgcccagc taatttttttt gtgtttttag tagagatggg gtttcaccgt gttagccagg   39480
atggtctcga tctcctgacc tcatgatctg cctgcctcat cagcctccca gagtgctggg   39540
attacaggca tgagccactg cacccggcca tcagtggata tatttttaaa gcactgcaga   39600
gaattctgtt gcatcagctt gagaaccact gatctgcctt gtgcttcaca tttaaaactt   39660 tttttaatg aataaataaa ccccaaaaaa ttaatctccc taagcctccc tagaagatag   39720
gatggtaagg atattttcct aggtaaaaat atgttaattt catatttcat gaaatttcat   39780
gtttcatttc aatcaagctc tgtcatacac cttacatggg gcaagccag tgcctgggca   39840 gggtgtaatt atactcatta cacaggcaag gaaaagtcac attaggtgat ggagcacaaa   39900
```

```
taggcagtta atggtttcag ggctagttag gatatgtttg tctttcaatt gcaagtaata    39960
gaagcccaaa gaaattggtt atttatataa tataattgat tggttcccaa atttgaaaaa    40020
ttcaggaata gacccagctt aggtacagct ggatccagtc actcaaacaa tgtcacaaag    40080 aacccttttga caggaatgta tcctgtgttg actctacttt gctctgagta gtctttcccc    40140
aggtgatgat aaaaatggtc atcatcgcca ggcttgtgtc ctgtttagta ggaatataca    40200
agaagagctc agtaaatgct ggccccacca ctaagcaaaa acaaaacttt tgttgttgtt    40260
attgttgttt taaataacag cttagacctt tcttctttcc ttgttattct ctttcatctg    40320
taatccagtt ttctacttct gaagtataga atgttctgat gatttattct tcattaccca    40380
caacttgcac atgtttattt aaaaatgcca ggattgcctg gccgttgtgt gctgttaacc    40440
tttgtttgct gttagtggat ccctgaagtt caggctccca ggggagcaga taatgggtat    40500
ccagttcctg caatatccac cctctggcaa gccaagttcc ttcctgggta aggttttgcc    40560
tacctgcatt cctagggaag tttctgggcc tgaccaccaa gccagctctg agaaggggtg    40620
cataagcccc accatgcttt ggctctgtcc ctatagaata ttttatgttg ttactgaaaa    40680
ctaaaggaag atgggtgcgg tggctcatgc ctgtaatccc agcactttgg gaggccaaga    40740
cagattgatc actcgatgcc aggagttcaa gaccagcctg gccaacatgg tgaaaccttg    40800
tctctacaaa aacaaacaa aacaaaaatt agccgggtat ggtggcatgc acctgtggta    40860
ccagctactc aagaggctga ggcacaagaa tctcttgaac ctgggaggta gaggttgcag    40920
tgagccgaga tcgcactact gcattccagc ctgggtgaca gagcaagatt ctgtctccaa    40980
aaaaaaaaaa aaaagaaaa ggaaagctaa aggagagaga ctaaaatgat atcaggttcc    41040
tggagaacaa acagacatga ttttgcttca tggcaggaca gccggaagaa gtgggattat    41100
atcctcacat tacaaataag aaaactgaga ctcagaatgg ttaagtcact tgtcccaggc    41160
cacacagcca gtaaattaca gaaacagaat ttgaacccaa atcttccagc tccaaagctt    41220
gtgttctttt cactacctcc tgcttaattt tttaatttct aagattagac ccttcatcta    41280
tccatgacac ctgcctgtca tcccctgaaa aaaggtgaac gccgttcaga aattttctta    41340
gcctgagctc actcccagtt cacttatttt tgctttgtca tggctgccca gtccccactt    41400
gtagaccagg aataggtcat ggctgcgggg actacacgct gtcgctgctg caagggccgg    41460
cctctgtttc cggggctgag tggggggccag acctgccagg agcaccatct tctgtgggtc    41520
ctgcctggat gtcacatccc ggccccaaga agtcactgca aaccttcgta ttattgagct    41580
tcacatccta gaatttgctg tcactgtggc tgctgcatga agttgtcctg agagaaacgg    41640
gcattgtcat taacagggaa attgatggtc tgggggaaaa gtcatcctca ttctcttgca    41700
gatctatggg tgattgagac tggctgatgt tgaagggggtt tctcagccat cgtgtgccat    41760
gttatggaac agtggtgtag ccagccattt gacacccagc gctgacccttt gtttaacaac    41820 ctcacctata tatgacaaaa tgattgtcag aaataatcgt gtaatgaaat gactgtaata    41880
atggccagaa aagaaacgca gatagtaaaa tgtttctctt gttgaactct gtacatataa    41940
ttgcaccagg attttttttca aataaaaagt aaatattata ctacaaaaaa gggaaaaagc    42000
acaagcattt attaaatagc tttctatatc tttctgagtt ttgatccttt gattgcagac    42060
tgatgtaata tttattgtaa atcattgctt ggttactaag tgaactttaa gaaaagtgag    42120
acgtctgcag aagttgccca taatttagca gctactgtat tgtaccattg atgtacggct    42180
ttattttctt gattaattat ttaaacaata taattcacaa ttttaaaata ataaatttcc    42240
```

-continued

```
acttaaaatg gtatttaaac tcagcaaaat atatcatcta tgagtaaaat ttgtatttac    42300
caagcaaaaa tattacagtt tgtggttcac atgctgtctc actgttttaa attttaaata    42360
caaaaactcc aagtaggctg ggtgtggtgg ctcacacctg taatcccagt actttgggag    42420
gctgaggcag gcatatcgct tgagttcagg agttcaagat tgcctgggc aacatagtga     42480 gatcctgtct ctactgaaaa caattagctg ggtgtggtgg cacatgcctg cggtcccagc    42540
tactcaggag gctgagatag gaggatcact tgaaccctgg gggacagagg ttgcagtgag    42600
gcaagattgc accactgcac tccagcctgg gtgacagatt gagaccctgt ctcaaaaaaa    42660
gaaaaaaaaa aaagaaacac aaaaactcca ggtggtcgca cagaatgaca ggactgaagt    42720
aacttagctc caatttctgt cttcataatc actgtcctac cattgtctgt gcttagaatc    42780
tacttgctta atgcaggaac atgtgttctc acagagatgg aaaatgcaaa tggcgccaga    42840
agcaagctgg aaattctgaa ccattaagaa tttactctct gccaggcacg gtggctcacg    42900
cctgtaatcc caggactttg ggaggctgag gcaggcagat catctgaggt caggagttca    42960
agaccagcct ggccaacatg gtgaaacttc atctctacaa aaatacaaaa attagccagg    43020
catgatggtg ggtgcctgta atcccagcta ctcgggaggc tgaggcagga gaatcgcttg    43080
cacctgagag gtggaggttg cagtgagccg agatctatct gcaccattgc acttcagcct    43140
gggagacaga gtaagactcc atctcaaaaa aaaaaaaaaa aaaaagaac ttactctcaa     43200 aataaatacg tgtggctgac tccacatatg gtagggccaa ctgtataact agaagttctc    43260
caaataactt ctgtggagaa aaaaagtttt attaaaggtt aactttttta aagtgctaac    43320 tagaaccta ctaacactga gatcgcacca attgtttata acttagacag gccgggtgc      43380 agtggctcat gcctataatc ccaacacttt gggaggccga ggcaggtgga tcacttgatg    43440
tcaggagttc gagaccagcc taaccaacat gatgaaaccc catctctact aaaaatacaa    43500
aaattagcca ggcacggtgg tacacgcctg taatcccagc tactggggag ggtgaggcag    43560
gagaatctct tgaacccagg aggcggagat tgcagtgggc caagatcgca ccattgcact    43620
ctagccccag caacaagagt gaaactctgt ttcaaacaaa caaacaaaaa aaaaaacctc    43680
ttggaccagg aaaatatttt ttaagggagg agtattttat cactggcatt gtttaggatt    43740
gcaggcacat gatgctaatg aaaagcagac taactattag ttggttttat tactgttttt    43800
gaactctctc tctcccttt tttttttttt gagacagagt ctctctctct gtcacccagg     43860
ctggaatgca gtgactgcag tctcagctca ctacatcctc tgcctcctca gttcaagtga    43920
ttctcgtgcc tcagcctccc gagtagctgg gattacaggg caccacacca ggctaagttt    43980
ttgtattttt agtagaggca gggtttcacc atgttgccca ggctggtctc aaactcctgg    44040
cctcaagcga tctgcccatc ttgacctccc aaagtgttgg gattacaggc gtgagccacc    44100
gtgcctagcc ctgtttttga actctctaga gacagtccag ccccttatta cttgtcctga    44160
ggcagctgct cccttcacct ggcccccgc attgtgttcc ggaccttgt cctggtggtg      44220 ctaaagaata tctctgtcga tcctttgggg actgggaaaa ctgaggccca gtgccacgcg    44280
atgccatttg ttcagggaag attaggtcat ctgctaggtc cccagtcact tgaccttctt    44340
cccagacagg aagaagctgc tctgggtctc tcagtgctcc acgtgtcttt gcacattgaa    44400
atgttttctg attttttttt ttttttttt gctgttacat ttacttttaa aaataacaa      44460 gcaataaaat gttacatttg agaaggttga aatgagaatt gatttgagtt aaattctagc    44520 agattttct tagaagaatg atatcatcat ctccagctac ctgcaattga tctactctga     44580
attaagaaag agacttccat ttgttgttta tattttgcac tcttgatgtg tttctttaaa    44640
```

```
ttatggtcat gggccaggtg taggagctca cacctgtaat cccagcacct tgggactctg   44700
aggagggagg atcactggag gccaggagtt caagacctcg tctgtacagt aaattttaaa   44760
aattagccag gcatggtagc attcacctgt agtcttagct acttgggagg ctgagatggg   44820
aggattgctt gagccagaac tttgaggcta cagtgagtta ttttcacgcc actgccctct   44880
agcctggctg acagagcaag acctgcctca aaaaataag taaaaataa attaaatttc   44940
aatcattagc agtcattagg atatttaaat acagtatgtt gaatcaaagt tacgcatgtg   45000
tgtatttttt tttccagaga gttgtttatc atgtgggttt taatttaact ttaaaaaaat   45060
gttgctggga cagttgccca aatggtatca tcagccattt ggttgagaac gtatgtcctg   45120
cgggctcctc tgtcactgga gttttgctag ctgacagcca ctggctagtt agagactgca   45180
gtcagcacag atgcaggcgt ggacttgcgc acgtaaccat gtcaatgcaa agccatcact   45240
tcttaaaaat tctgaacccct gctgtctgag atggtggtgc agcggataga actctgctct   45300
aagaggcagt agctaattcc atgtcttctt tgcccttgac tagctgagtg actttgcaca   45360
tggggcttgc ctctctgttg ccttgtctgc aaagtggaat catctttttcc ttgctagaca   45420
gaaggtggac cctggaccta tggccttttt gagtttcccc cccgcttctt agaaggacct   45480
ctgatcctac tgagtttaat acccacgggt taataattgg gaaaagcaaa ggaagcgctt   45540
ctgtttaggt aattatatgc atgttttttgt cttttttctgg ctggaaagat atccaagcca   45600
ctgggaaggt ccgtggctac ccagggtagc cctctctggg gagggctgct atatccaaga   45660
gccctcatg agaatttgaa aatcgaccat ggtagggcct gctgacttt tgacagctaat   45720
ggtgtgctga gaattgtccc tccaaagatg cctttccatt ccctcgggag agtctgggca   45780
gccctactg ggggctggga tgctggctct cccctcagcc tccacccccaa ctgctctctt   45840
ccctcctccc ctccccagcc ccctaatttc tctcacaagg ctttgttctg cagcaaccttt   45900
tcctaatgca gtcctggcct cttcgcagct tcattacata accttccgtg gactcctggt   45960
ccaaggatca ccccagaaag ccagtcagag gtaggcacgc agctggggtc catttactta   46020
ccttccccac cccctcggaa ctcagaggtg gtgcaggaat ttggactcca agaattaaca   46080
gctccaccac catcaccaga gccaaaactc aggatgcatg tgcttcatct gctgcttatt   46140
tccagctgag agccagtggt gccatggttc cttagggagc cggtcccctg atgccggctc   46200
ctggccccaa atctctctga tccgggctct tccagaatgt cttgtctcca ccatcgcctt   46260
tgaccaatgg tgtccctttg cctggtaatg tcccctttgc ctgatgatgg ccctgtcact   46320
cctctcttta gcacagagga ggctgtttca tcccttcaag cctgccctcc cttcaagtct   46380
tagctcaagt tcaccttctc cgcagagcct tctccaatct tcttgactac gtctcctctc   46440
agctccagca acctctgtct ctggcactga ttccttactt agctaagaga atcacagaca   46500
cttggggctc aggacaatct gctttctctc ttcttaccca tggccttgga ctgtgtgtac   46560
ctctttgtct ccactcccaa acccaacccc cagagggcag agagcatgtt gtctgtcccc   46620
ttgctcagca tgaagccatg cgtgtggtag atcggcagag ttccataact tgtgttgacc   46680
gagggtcac tttgctctga aattacccct gtgtccttca gtatttgcac agatagcttc   46740
ctggccagac cgaatatatc caagggcatg gcccacctct gctcctgttt ccaggtccct   46800
ggtgggggtt agttcatgcc ttcctcataa tctgcccact ggcctggtcc tcaaggtctt   46860
cccaactgct cagccagagt tgagaaaatg ggtcgctcca tcctgtttgt gtcgttctct   46920
ccttcctggc ccactctcct gcccacaggt atccaggggc tgcctgtagc attagaggac   46980
```

```
atacatgcac atgcgtgggc atgggacact cacgtagcct ccaagcacag catcaataat   47040
gcattctgtg ctttatagca tggaaagctg ctctaaactt tattacacag tggacatgtc   47100
tgaagcagct cccaaatcca cccctgagtg tgttggaatt ggcaagccta tcacttggga   47160
gtctagtttt tttgttcgtt aataatagat gcttcctgtg gccccagctt ggcaattttg   47220
atttaaagtg atcttaactg aagagactaa tggacgggtc tgaatttgtg ccttttaagc   47280
acaaagtatt gctcttaatt aactggattc tatcctttga gcaggcagag gccttccccc   47340
aagggcgtca ttaacgatcc acatctggac atcttccaaa gccttcttct gtttcaggcc   47400
aaccgcaggt gtgttcctga acacccagga ggctatgaga gccacatatg cctcccaaat   47460
acacacagtg tgcatgccca gggacataga gcagtgtgca aagtcccatt ccatctctct   47520
ccacctggga gaggatggct cttctgtctg attcatggct caaagtggta aaggagctcc   47580
ccactccccg tcccacgcct actcagagtc tgcaaatatg tatgcgatat gagagctcgt   47640
cagttagctg tcttcagtgt ggcgcacatt tgaggagtct gactcccctc cagcacaggc   47700
caatgtgcac tgctctccta tctttgtacc cccactgttg cactgtgcag aggttggagc   47760
catagaagta ccagagctgt gaaaggagag gcccctctc acctctgccc tggtctccat   47820
ccccactttc tctaggaagc tagtaggtgc tgacagggga gagaagggag gggaggggtc   47880
cagaaacagt ggctcatgcc tgcaatccta gcactttggg aggctgaggc aggaggatca   47940
tttgaggtca ggagtttgag accagcctgg gcaatgtagc aagaccctat ctctacaaaa   48000
agaaaaaatg taattagctg ggtgtggtgg tgggcacctg tagtcctagc tacttgggag   48060
gatgaggtgg gaggattgct tgagcccaag agtttgaggt tacagtaagc tgtgattgca   48120
ccactgcact ccagcctggg caacagagct gagaccctat ctcaaaaaaa gaaaaaaaaa   48180
aagaaaggag agagagagaa agaaaagaaa agaaaaaaaa aaagaagggg aagggaaagc   48240
ccagaagagt gtggggagag gaggcggccg tcattctggg gccctcagtg tgcacaacca   48300
gataacacat gctctgtggg cttttgtacc attttgcttg agcataaaga aaggaaggct   48360
gcccctaaat agaaagcact ctggaggcaa acaaatctga ctccaatcct ggccctgcca   48420
cttttcccagc tgaggactta gacaagcacc ctagcctctt ggacattctc agagccatct   48480
gctgcaagtg ggtgctgcca tacccacctt actgggcagg cttgggggac caagggtggt   48540
aaatggctca gtctttcatg atgcggccac acagcaggtg cgccatccag gtccatttct   48600
ttccttcctt tcccccaaat caagttgtca ttaaagtact agtccacatt aatgaaatca   48660
actgtattaa ttttctattt gctgctataa taaatcatca gaaatttagt ggcttaaacc   48720
aacacaaatg tattacctta cagttctgga ggccagaagc cctccatagg tgtcactggg   48780
ctgaaatcaa ggttttggca aggttgcggt cctttctgga gggtccaggg gagaatccat   48840
tttcttcctt tttccagctt ctaaaggttt catgcattcc ttggctcatg atcttctata   48900
gctatagtca gaaaatttt ccatcaatca tcttcaaagc cagcaatggc aggatgagtc   48960
ctcacatcac cttgctctga caccagttct ctgcctccct cttccacatg tcaggaccct   49020
catgattact ttgggctcac tctgataatc tgggatgatc tctctatttt agagtcagct   49080
gactgggaac cttaattcca tctacaaccc caattcctct ttgccatgta cagtgacata   49140
ttcacaggtt ctggggatta ggacgagcct gtctctgaaa ggctacttta catgaaaatt   49200
cattttttta attaagattt tttttttcctc ttgagacaag gtctcactct atggttcagg   49260
ctggagtgca gtggtatgat cacagctcac tgcagcctcg acgtctctgg gctcaggtga   49320
tcctcccacc tcagcttccc tagtagctgg aactacaggg gtgagccccc atgccagct   49380
```

```
aattttttt tttttttttt tttgagacag agtctcactc agtcacccag gctggtgtgc  49440
agtggtgcaa tctcagctca cagcaacctc cgcctcctgg gttcaagtga ttcttgtgcc  49500
tcagcctccc aaggagctgg gactacaggt gtgcaccacc acgcccgact aattttgta   49560
ttttagtaa  agatggggtt tcaccatgtt ggccaggctg gtctcaaact cctgatctca  49620
agtgatccac caacctcagc ctctcaaagt gctgggatta caggtgtaag ccaacatgcc  49680
cggccccagc taatttttaa atattttttt tgtagagatg gggttttacc attttgtcta  49740
ggctggtctt gaactcctgg gctcaagcaa acctcccacc ttggtctccc aaagtgctgg  49800
gattacagca tgagccactg cactcggcct aagagaaga  tttaataatt aatactttac  49860
aacaagatct ggaagaggtg ggatgagtaa ctaaatgagg atacaagtaa cccgggtcat  49920
atttgctaat accttggtc  acattgaact tgatatctta tcagatttc  ctaatcagct  49980
cctttagcag cagtgttgca gcatcttatc tcattttgtt ttttgttttt ttgcctagca  50040
catgcctgta aatcactgga ttgaggtgtt tagatgtttg ttgtcctttg gatgcttctt  50100
ataaatccat atttcatggc tccctggaaa gtgctatgca aatgataagc tgcaaggatg  50160
gaaaggaaat tgcagtgctc ctgaattgta aatgggcttt tacgaggagg tttctaatta  50220
ctcgctcttt ctcttgaact gaggagttga agtgtaggtg gcagatccat aacagataat  50280
catgtgtgtg atgtgacttc agcctgagcg tcgaggacca agtcacagag caggaacagc  50340
cactctccag tgtccttggg gctacgtctg aggagaacct gggatttcat atatgacctg  50400
cactggctgg ggggctctct tgacgtaacg tgttccctct gagcatgtta cagattctga  50460
cattcttatg ttccttctgt ggagagacat gtacttagtg acctaactca ctttagcata  50520
ttttgctca  tcgtttgtgt agcttaaagg aatcagataa ttaccccctc cccactactt  50580
tcggaagcac aaatgcaatg ccctagaatt gtactgggga ctcaaaaaga aaagagagta  50640
gtaaaatcta ttaaaggggga caaagacagc ctatatacta caagctttct attttttatgg 50700
cagagaatgc cattttctaa gtaaacagag aactgcattt gacctgcaat atcaaatgca  50760
tggatttgat gctttggaaa gcaactgttt tctgcgttaa tctgggtgtc ttccgtgaaa  50820
tgtcctcctg cctttggctt aaacactagc tttgtctaca gccattccat cctgaacctg  50880
cccaatcttg tctgaatcct ggtttcacca ctgacaagct gtgtgtcctt gggcaagtta  50940
cttcacctgt ctgtgcttca gagtcctcat ctgtgagttg gggaatctgg acagaatcta  51000
ccccataggg cgtagtgagg atgtgttgaa ttatcccaag tggctacaca gagtaagcac  51060
tcaaatgatg tcatcgttgt catgattgct gttaccagag cctagagttc attctgatac  51120
tcgagtctgt ggcccatcca gcccaggtaa ggaatagttg gaggagttgg gcatgttcag  51180
cttgaagagg agacgacagg ggatatggga tagttgaatc tgtgaagggc ccctgggat   51240
gaagaactgg catgttctgt gtggctccag ggcactgagc aggacccatt tgccaaagtc  51300
tcagggacac agtttctagc tatagacaga aaaattttct gtcactcaga ggatgaaaat  51360
agaatgagcc cccttaagag gtaatgagct ccctgtcatt ggaaggattc cagaagagct  51420
aggtaaccac tttaggtgct atcaagggc  ttttttcttt aaagtccttt ccaaaagctt  51480
ctgagattgc ataaacaata ggaagccatc ttggtgcttt aacacaaact ctccccagtg  51540
atgagggttg agccaaagcc agattggcaa gcagagagga gacttgtgta caaggagttc  51600
ctcgagtcaa ttgcttttc  cttgttctag ccagccagag ggctcctgtt ggaaaacagg  51660
agaccggaga ggctgaggcc tgaccaaacc agcttctgca ggccagctgg gaggccacaa  51720
```

```
ctcctaccta cgggaaaact gaagggcatc tctattttta gattagcaaa agaaaataaa   51780
tttaagtttg agtctccttt gcaactttta aaagacatct ttattgagat gatcattcac   51840
attctataaa attcccccac tttgagttac aattcagtgg ttttagtctt ccttgatgat   51900
tttgatggtc ttttcttaag gctcttggaa gacccagaag cctctcagac acaggtgggt   51960
gtggagggcg tagcacagag gcagacttct catttcctgg gtctcccctt taatgactct   52020
cagagacccc tccttccccc tgcccctggc ttctacccca ggggtgtaga gttttgccat   52080
tttccaagca gaacttcatt tcctcttctg tgtctacact cttttgtgctt ctttcttgcc   52140
agcttttttct cctttgcccg cccttccttc cttccttccc tccctccctc cttccctcct   52200
tccctctttc cctccttccc cccttccacc cttcccccct tccccccttc cctccttcct   52260
tccttccctc cttccttcct tcttcctgc cttccttcct tcctgccttc cttccttcct   52320
gccttccttc cttccttcct tccttccttc cttccttcct ggtatgtgac taatttctgt   52380
ttcaggacat aaatgttgtc caggctgttc tttggtcttt ctgttggata atggacattt   52440
ggcattgaga gaggctgctt tttctgaaat catgttcttg gggcccagaa cctaggtgtg   52500
tgcttctgac tttgttttct tcctgatcca aattctgata tgtccattta aattgatcta   52560
gacccacagg gcactgtggg acagatcctc agtggaacat gactctgtaa cgagagcatt   52620
ttgttttgtc aaaatgagaa catattattg cctttcatct gattgtaaac ataatacatg   52680
tttataaaac agtataatga gacaaaaatg tagacactaa taagggaaaa tctccctaat   52740
tgtatttctc ttcacagaga aagcccctgt tgggcatata tactctagtt tgtttatttg   52800
tttgactaca catatatgta ttcttttctt atgtataaaa attctgaaca tgcacatttc   52860
tgcaactact gttttcactt gatgatgcat ggacctctct agagtgtacg tttcttcttc   52920
cttacaaagc agttggcttc gcccagggta caccaggaca cggttttggc tctgtcccca   52980
gggtgtcacg ggaccagggg atgatctcac agggtctgcc atctgccctg cctggccgga   53040
ggctgcatcg agagggccaa ggggcaccac gtgtcgtggg tactgtcaaa caagagcctt   53100
cagagccttc cacagtcttt cttttgcttc ccagcattgc ttccccgctg gtggactctg   53160
aatctagaac tagctccagg cgcctctcca aattcagacg ggagctgggg cactattata   53220
atgcaaatct aggcaaagcc ctcccaatac caggatccag aatggggtgg ggccctttgc   53280
cctgaaaagc tgtttagttt gaaaatacaa acaggagaca gaaaagtttg gctaaattaa   53340
tggataaagt tttaacgatg gtaaccatag tagggttcat cgacagccag cgatggttct   53400
gaacacttga catgtattaa ctcacctaat ccccacattt tacagacaat gcaaaggagg   53460
ctctgggagg ttgagtgact tgccccaaag tcgcacagct cctaagtgaa ggattcggag   53520
tggactccag gcagcctggt ctgactccct gcactgcgct gtgcttatct ctggccccaa   53580
tgccgccatg cagaagtgtc tggggcact ttgtctctgt cagacagaat tcggagatgt   53640
gtatgcttgc cctggtatgg cacttctctt tttttgagac agaatctcac tctgtcaccc   53700
tggctggagt gcagtggcat gatctcagct cactgcaacc tccgcctccc aggttcaagc   53760
aattcttgtg cctcagcctc ccaagtagct gggattatag atgtgcacca tcgtgcctag   53820
ctaaatttt gtacttttag taaagatgtt gttttgctgt gttggccaag ctgatctcga   53880
acttttggcc tcaagtgatc tgcctacctc agcctcccaa agtgctggga ttacaggcat   53940
gagccaccat gcctggcagt gtggcacttc ttacgtgtgt tcagcggaca ctgtttatct   54000
tctgtccctc caagacggtg ctgagctcag gtcgttcatt actggcagac aactgctgat   54060
ttccaacaga attgccatcc tcttctcccc tgcgactttc agagtgtgac ctcagactca   54120
```

```
aaaattagaa gtgaaaacat cttaaaaact atcaccttttt cttcctaatc ctcctctccc   54180
ctccctgtct tccttgttgt ccccatctaa tgaactatca tggcaaaaag agcccatttc   54240
tggtcatttt ctgtggcctt tcaaactccc acctacccca ctgctcctgg gtgcattacc   54300
cgaaagctga gacttcagtg cagaaagtgc caggccctct gtcccccag atcgccttcc    54360 ttgtcttccc tgtgcttgcc tgtcacattg tgtgggttcc agcgctggaa ggaatgagga   54420
acagattctc tggttctcct tttgaagttt accttcgctc caccacttct gagaccttcc   54480
cggaagttgc cccttgtttc tctcctctcc agggctgccc cagagctgcc tctcacctct   54540
tcctgctgtc accccaccac catcagggca gaagttggga caaagcctct cctactggct   54600
cctgcttttc tcccttaggt ccagcctcct cttctccatc ttcaggagtc tccttctcca   54660
ctcacacgtc atgacttcag cacctcgcat cagtccagaa tatgactgct tgttcaagtg   54720
ccacctttct catgcatttt tttctagtga caatcacagc caccctgtgg ggcaggagtg   54780
tcatcatccc catgtttcaa atgaagaatt gcagttcaga gagggcaagt gactggccca   54840
gcctcaacag ctagccagtg gaccccacca gggcttctga ctccagtccg ggttcccttt   54900
ccacccaaat ccatggaggg agctgagccg agaacaggtg tccttcagga agacgtgaag   54960
ccaaagcctc cacctccaaa ctcagggggcc cagggagtcc aggcacccat ccactcacaa   55020
ggctggatat ggtgcattcc aggagagggg ttggggggcga gtggcctctc tgtgtacccg   55080
tggggataga tgcgcaagtg gcatcgccac atcgtgagtc ctggcttcat gggtgagctc   55140
caggtccaac gagaagccaa gcaggggcc cttcaagctc agctttgggc ccgggtcggg    55200
gtacagggta gagcgggcct ccccagcccc tgccatgagg ccaaggcagt gcatcgttcg   55260
cagcgtacat tcagaaacca aagcctagga gctggttatc attccggttt acagctgatg   55320
gaagagcagg tgcttccgag aacccacagt gctctttggc cagtgaccca agggtgcctc   55380
tgagaggcct cgcagcaccc ggaggtgctg ctgaggcaac gccctgactg taagaaggac   55440
cattcatcct cagagagtgg ccgtgatgct gctgcgacag tcccaccatc cctcccgact   55500
ctcactccca acagacttcc cactgtaaag ctgaactctc cagcaaatca cctctcgcca   55560
gactctctcc tcactctctc tgggtccact agaggttcct cagcctctct ttgccttggt   55620
tttcccagct gtaaaatgga gcaaagaggg cctatgtacc cacaaaggtg tggttggagc   55680
gactcctcct acattagggc ctcgagtggg gcttcatgat tggttggtgg aggtctccaa   55740
acccacccag tgccaccgaa ggctgagact gcagatgcaa tgccacaggt gtccttcctc   55800
agcctgggca gctgaacatc atgtgtaaaa cggggataat aagataataa cagccccttg   55860
cacctatgtg gctgtgagga ttaaacaaga taaatgtgta acagtgcctg gctatagaaa   55920
tatttactct tgttattaag ggaagaatat gtgtggctaa aaagggatcg aagatgtaaa   55980
agccaatccc tcccctctca gcatatttaa gggtaatgtt gagttggttt gtggaccatt   56040
tgctgcctgt tagagctgga aggtagggac cccctctcaa cagcgatgct acaaattata   56100
cccattggag gtcaaccaaa agacaaagct tattggctgg acatggtggc tcacacctgt   56160
aatcctagca ctttgggagg ccaaggcagg cggatcactt gagatcagga gttcgagacc   56220
agcctggcca acatggtgaa accccatccc tactaaaaat acaaaaatta gctgggcgtg   56280
gtggtgcaca cctgtaatcc cagctactca ggaggctgag gcaggagaat cactagaacc   56340
caggaggtga aggttgcagt gagccgagat cgcaccactg tactcaaacc gaggcaacag   56400
agggagacgc aatctcaaaa aaaagaaaaa aagacaaagc ttgttaatac cagcatattg   56460
```

```
ttaagggaat aaagtaggct gcagaacaac tggtgtaata tggtgccatg tagggaaaat   56520
tacatgtgtg cataggagag gggtctgcaa ggttgtgccc taagatgtta gagtggttcc   56580
tttgcttttc tcttttataa ttttgtattt gacttttaaa taaggaccat aaatcacttt   56640
tataaaatac attctctcca gcccctacta ctcctttaaa gaataagagt ggtttgccca   56700
agaaagacag ttttttttgc tctggttttc ttgattctga catcagagga aactccttct   56760
catccacttg gggctctggg ttcaggggat tcatttcagg cagattaaag tggtgaccag   56820
gggcattcgt ggacacaggg agggacagga gcaccatcag tttgtctcac acaaccactg   56880
tcatcctcac tgaaggctgt tgcctgatca aaaacagtat tgggccaggc acggtggctc   56940
acacctgtaa taccaccact tgggaggct gaggtgagtg gatcacttga ggtcaggagt   57000
tcgagatcaa cctggccaac atggtgaaac cttgtctcta ctaaaagttc aaaaattagc   57060
caggcgtggt gggtgcctgt agtcccagct acttgggagg ctgaggcagg agaattgctt   57120
gaacccgaga ggtagaggtt gcagtgagcc gagatggcac caccacactc cagcctgggc   57180
gaccgagggg gactctgtct taaaaaaaaa aaaaaaaaaa aaaatatat atatatatat    57240
atgtcaaaaa tggggtagtt tttagatcta tagtagttct aaaaacaaag gccatccaag   57300
catgacagat ttacaagcac tattggctat tccagtagtt acaatggagg agagaagctt   57360
ttagttaaaa caaacaaaca acacaacaaa cccagaaacc ttaggtcaaa accaaaattg   57420
tcctctcaga cacaatctgg gaattttctc atgacagtgg gcattagcca actgacatca   57480
gcagcaacca tccgtgtgca cacagtggca ccacctcctc ccaaaaagca gccttcatct   57540
atgccctcat acaatcgttg attattctct ttggattgag gcccggaatt atttaagttt   57600
cttcttgcca gcatgagtct ttcctttctg tatgctcctt atcttctctc tttaatttgg   57660
cagttctgct tgaaatctgg gtctttcatt agtagtagtt caatttggtt ccagaacatt   57720
ctgtggtgtg atgcaatgtg accagagctc acacttcaga gctcttcaag ggccagtctt   57780
actgagcacc tcccagtggc tgcctgtgtg ctgggcgcca cttgtggtgg gcaggagaga   57840
ggagggaca caaaggaga cacagctcct tcttagaagc tcaaagttgg ggaccagctg    57900
ccacagaaga gtatgtttag catctgagac accaagatcc agcgtcacaa gggtgtttat   57960
taagcctcct catctctttc tttttctttt ttttttttt tttcctcagg cagtcttact    58020
ctgtcaccca ggctggagtg cagtggcatg atctcggctc actgcatgca accaccacct   58080
cccgggttta agcaattctc ctgcctcagc ctccccagta gctgggatta caggtgccca   58140
ccaccacacc cagctaattt ttgtgttttt agtagagaca gggtttcacc atgttggtca   58200
ggctggtctc gaactcctga cctcagatga ttcacccacc tcggcctccc agtgtgctgg   58260
gattacaggt gtgagccacc gcgcctggcc ttgctgttga ttcatctata gtatgtttga   58320
cttgatgacc tccagttacc ttagacagag gttctcatct aagctccaac tttccatttc   58380
ctttgtcctc gtctttcccc ttaacccctc cacatttctc tcaaaatcac cccacttcta   58440
aaaaatactg tttatttttc ttttaaattt caaattatct atactcattg aaataaatca   58500
aaatagcatg gaataagcga aaaaaatgga tcccacccct cccactccc attccctagg    58560
gctaaccata gttaaccatt taatgactag gttttttgt tgttgttatt ttttatttat    58620
ttattttgag acagagtctt actctgtcac ccaggctgga gtgcagtggt gtgatctcgg   58680
ctcactgcaa cctctgcctc ccaggttcaa gcattctcct gcctctgcct cctgagtagc   58740
tgggattaca ggtgcctgcc accacacctg gctaattttt gtacttttgg tagagacagg   58800
gtttctcaat gttagccagg ctggtctcga actcctggcc tcaagtgatc tgcccacctt   58860
```

```
ggccttccaa aatactggga ttaaggtatg agccaccgca cccagccctc ctgggctctt    58920
ttcctttagt tgcactcgct ccccgctcct ggagtagagg gatttccgag agactgtggg    58980
ctccagcctt cacctaggcc caggactagg atgcctgccc taacatttat ctttatacct    59040
taaagcaaaa cagctggacc ataagcattc aagaacaaac tgtgaataag agaaagttc     59100 tcccaggaaa caagagcttt agttatgttg ggccagccct tatattcctt agctgttacc    59160
agtcactgct tgatttaatc tcggctatca cttggcctga caggtctgct gctggtgcca    59220
ggatgtctgg gttttgaagc ctggctccat tacatacttc ctgtgtgacc ttgggcaact    59280
tactcaacct gtctgttcct cagtttcccc agctgtatta tgtcagcata atagtttgtt    59340
gtgtgaatta aatgaggtaa taactggaaa tgcttcaaac atggttccta tcatgagaaa    59400
tcctgctttc cgcctaaatg tgctggaaaa ttcctggtgg tgcagaacag agaccagag    59460 caaaggaaag acagggtgca gaagccaaaa attaccttgg agaacaaagc gcatgttaag    59520 gttattttg gattctaggt ttatctctgc ttggtcttca gttacctaca agagatccat     59580
ttaggggatt tttgtttgtt tttaacgata gctttattga gatataattc atatgccata    59640
aaagtcactc ttttaaaatg tttccggtat attcacaagg ctgtgcagcc ttccctgtcc    59700
ttgattccag tctgagtttt taactgaagg gataaggagg accacgcttt ccccagacca    59760
gaaccgcggg ccaggggggcg attccgctga gtcaccgcgg gcgcctggtg cgcggcggcg    59820
gagcccggga ccttccttgg ctgccccta gcgagggccg cagcgcagcc tgagacaccc    59880
gccggggccg ctccacggcc gtcggattta gactggaagc tcggtccagg tccccagctt    59940
gatgcgcccg cggtgtagga gaccagcccg actcgagctt cccctgagcc cctggactct    60000
tgactccagc agggcctggg taatgaacgt cagctcccct ttcccaaagg ggttgctctg    60060
ttgggaaggc accgtttga tacagtagca tagagatggg ttttagcatc aaaatatcag     60120
aattcaagcc ttgctctctg cttactagct gtgtgaccct aaaaggtttt ctgaacgtct    60180
ctgagcttca gtttcctcat cattccttct cacggggtgg ttgtgagcat tacagagatc    60240
ctctctgtga agccccctgtg agtggctcat cctgagggct gaaataaaca tgttattaat    60300
aatccaaaac tggcaaggga tgttgactgg tccccctccc ttgcccaagg agctttctag    60360
aacctgagtt atcattacca aactgtactg ccttgagtaa gaaagttaga aggaatggga    60420
aggatggtgg caggtggagg aaggcggatt ggtcatcacc tccttgcagc aagaaacagc    60480
cccagatcgt gggaaaccta cagacctgct agacagacta ggagcaaaag ctggggctt     60540 aagaatcccc agggaggttc tcctgagaga gtagccagtt ggattttgta agcagagatt    60600
tgtttgggga ggaggtgaca acgtagggag cagaggggca aagctgtcgg gaatcctgcc    60660
ttgagggcag ggatgtgtgt tgggggagt tgggtcactg gggctcggtg gccttgggca     60720
agtttctacc tctcaggtcc tttacccacc taggtcgcc atcctgccca cctcacaggt     60780
tacagtgagc ctgatgcac tgtcatgggc aggtgcccag gaaatggca gacatgttcc      60840 aaacagcacg cagcattccc cagtgatgcc cagggtcacc ttggaggtgg gcgagatgcc    60900
tggggtttct cgtccacccc acaacacctc aggggacagc caaagctgtc ccttcaggta    60960
agctgcacag aagatgtgaa ctctgctgca aagactctat tctttgggag caaagggac     61020 ccagggtctc acctgcacat ccctgtccct gagggcctag gggttcttgg aggcccagc     61080 cttggcaaaa tgaggaagaa ggtgaaggtt gtctgggccc ctgccaggct ccttcctcgg    61140
ccacgcactc cccttcctgc acacacaccc ttctccctcc accccatctc cattgttgtc    61200
```

```
agaaaagtca caataaaaag gtccatattg tctagttccc atacttttaa ttttttaaaat    61260 tttatttatt tatttattta tgtattttt gagacagagt cttaacccag gctggagttc      61320
agtggcatga tctaggctca ctgcaacctc tccctcctgg gttcaagtga ttctcatgcc     61380
tcagcctccc gagtagctga gattacagat atgtgccact atgccagct aattttgta       61440 ttttagtag agacggggtt tcaccatgtt ggccaggctg gtctcgaact cctggcctca      61500
agtgatctgc ctgcctgagc ctccggaagt gctgggattt caggtgtgag ccaccgcact    61560
cggctccaca cttttcactt attaaaagac tgtggtgtcc atcaatggat gaatgaataa     61620
accaatgtgg actatccctc ccattaccca aggaatgaag cacggagccg tgccaagatc     61680
tggattcaca gtgaaagaag ccagtcacca aaagccacgt gctgtgtgac ttcccttata    61740
cgaaatatcc agaagagata catccatggt gacagaaagt agatgagcag ctggggactg    61800
gcgaagggga aaggggag cagctgtcta tgaggtccag cctttcttct gggtttggtg       61860
agaatgtttt ggaactagat agaggtgata gttgtacaac attgtgaatg tactaaatgc    61920
cactgaatca ttcattttaa atcgttcttt acgttgcatg aattttaagt caatcaaaaa    61980
cagttgtttg aaaagagaaa agcctatggg tagcggcagc agtgattgga tttatgattc    62040
gattccatgg ctcatccctc ccctgcctca cccctcgcc ctccgacgtc ttcttctttt      62100
actctgaact gttatctttg ttctcatctc tctctctctc tctcaaccct gcagacactt    62160 ttcccttct ttgtctgccc ccaccctcca gatttccgtg tctccagtgt ctccctacga    62220
ggcatgaatt gagactggga gggtgtgatt ctgaagaagg caccaacagt gactcagcta    62280
gccccttccc ccaccccgcc ccccgggcct caatttagct aaaaaaccac agggacggac    62340
tcaggaggca ataccttcc aagggtccct aaaaaatgtc ccattttagt gtccaggttt      62400
cactcaactt tagtgcctcc cctaaaatgt gttccttacc tcccacccca ctgcatctaa    62460
gtcactgcct gagaaaacag gattgaggaa aggagaaagg aagagagaga gagaggagga    62520
gagagagaga gagggaggaa ggctgatgga tttagaaaag aagaaaacaa gtggtctgag    62580
gaaaacagcc ttggtgtgtt tattttcctg tctgtgtatc gcttctcggc cttttggcta    62640
agatcaagtg tattttcctg tctgtgtgtc tcgcttagat tacagggatc tgtgggtgat    62700
gacacgtctg gtccaggctg cgtagtcacc tcaagggcat gcttattgat gtgttttca    62760 attcactatc tttgcatggg agtcccaggc caagaggcac agctgcgcca tttgtctgtt    62820
ggtttagata tcctttatcc agttcttcca gagaaatcat cctgcccttc tggaggaggt    62880
gggcagcagg ggtcagagat gggagggaaa ggaaggagcc aggtccttgg ctaggatgcc    62940
agggtcccct gcctctcacc tggcctgggc tggaggcctc ctgctgtcct gtcactgatc    63000 actacccgc cccagcctcc tgagttagaa gacacaggct aaagtagagt atttcttcat      63060 tgaaaaccc atacaaaata aaggttcata aaaataaaa atttagactg ggtgctgtgg      63120
ctcacacctg tgatcccagc actttgggag gccaaggcag gtggatcgct tgagccctgg    63180
ggttcatgac cagcctgggc aacatagtga aaccccatct ctacaaaaaa tacaaaaaat    63240
tagccaggca tggtggtgca tacctgtggt cccagcttct cagcctatgg acccacatag    63300
aatacaatgt cagcataaga agggagcccc ggggtcacca aatggtttgg gcggcaaaga    63360
acctgaaggt tgagagaagt ggcttggtta cccagctgtt ggatgtgaga cctggccact    63420
gcttcttcca tacccctagac ctgcaccctg acatctcaag taaaaagttg ggggatgttt   63480
tatggtccag gatgaaggaa gggcagtgag gggcagcgga gcatcacttt gcatttctgt    63540
ctgcctctta ctggctgtgt gacctggggc aggtaacttc ccagactcct gggaatcata    63600
```

```
acacctatga tgatgatgat gatgatgatg atgatgatga tgacacctac ctcaaggatt  63660
gccctgaagg gtcacagaga tgcctgcaag gcacctgcat ggagcaagcg ccccttctct  63720
ggcaggtgct gggtgagcac tacctgctgc caggccctgg ggctatggca ctgcgtgacc  63780
ctgcaagtcc tacctggcga agctgtcgtt cttgtgctca gtcagtgttg gttgtaagac  63840
tgagaagagt cacttcattt tgctctccag ggacatcttt ctgggtccta ttttctgcct  63900
atgtcaagta gcgcctcaag gatgctcctg aaaatgggct tgtctttctt aacatggcag  63960
gtaggtccca aagcattagc atggggcagc tgacctagcc cagccaatgc agtgcagtga  64020
ctcttgcaac cgagtctaat cagaaggtcc atgaacctac gagcatttcc tgtcccagga  64080
tcagggtgga ggctgagcct ccctgcttag agattcttcc catgcattcc acttttttcc  64140
ccaaaagaaa atattgaccc ttgagaggca cacagtttat ttattttgca tagtaaatag  64200
tagcctgtat tttaaggatg agttgatttc tgcatcagcc cctgtaggtc atcagccttc  64260
tattggtgca tctgactctc tctagccctg cagggatggt ggaggggag gggaaggagg  64320
gatctttatt ggaaaccagg acagtgagac tcattgccct gtcatctgct ctgtggtgct  64380
gaatgaggca gcccaacaga gaaataccct gagcgagcat ccccagcctc caaaacagtg  64440
gcgcattgcc ctgagtcctg ggaatgacct ttgattctcc tgctcctgac ttggaaccca  64500
tggaaacctc tagaagcagc tgaggaaaac ccaacatgaa aagcagaact ccacactgag  64560
aatataggag gtgatcggaa catacaatga ttcttgctaa gaccgattca cagttttct  64620
ttttttttcga tcgaagaaat actggagaag cctaaagaag gagtctaaaa actctggcac  64680
gtgggccaaa actgtccttg agctaagaat gattttcaca ttttaagtg gttgaaaat  64740
gaaataaaat aagatgatgt tttgtgcac atgaaagcta tgggaaattc aaattctaat  64800
atctataaat agtgttttat cagaacacag tcatgctcat ttatttatgc tcgatggctg  64860
cttcccgct acaattacgt tgagcagtta caacagagac cacgtgggcc acaaagcctt  64920
acaatattta ctatctggcc cttccagaa aaaatgtgc cgactcttga ccttaacctc  64980
agcaattgg gaggccgagg caggcggatc gcttgagctc tggagttcat gaccagcctg  65040
ggcaacatag taagactcca tctctacaaa aaatacaaaa cattagccag gcatggtggt  65100
gcacacctgt ggtcctagcc actcgggaga ctgaggtggg aggatcgcct gagcccagga  65160
agtcgaggct gcagtgagct gtgatggcac cactgcacct cagcctgggc gacagagcaa  65220
gaccttgtct ccaaataaat aaataatgca aagtaaaata aataaaacca tataaaaagg  65280
aatcaattta aaattataat gaaagctggc cgggcatggt ggctcacgcc tgtaatccca  65340
gcactttggg aggctgaggt gggtggatca cgaggccagg agatcgagac catcttggct  65400
aacacggtga acccccgtct ctactaaaaa tacaaaaaaa aaattagccg ggcacagtgg  65460
cgggcgcctg tagtcccagc tactcggag gctgaggcag gagaatgtct tgaacccggg  65520
aggtggagct tgcagtgagc cgagatcgtg ccacttgcag tccagcctgg gcgaagagc  65580
gagactccgt ctcaaaaaca aaacaaaaa caaaacaaa aaaaattat aatgaaagcc  65640
aaggggcata gtagaacaaa ttttctagag ctcattaagt caaatgagtc accagttagt  65700
aaaacgcagt cacggggaag agagggcagg attctttgaa gcagcggctc tcctaaaaac  65760
aacccaccct tgtccagctg ccttccctcc tgagggtgtt ccctttgact gtgtgacccc  65820
catccctat ttcccaaccg tccaagccca cctctagcat aatacgagct tttaatccct  65880
ctccctgacc ccaacccgat tttgaagccc agtctagtat tttctcaaat acacttcttg  65940
```

```
gctccattcc ttcctttcca tcacctctgc cttttcactg catgcttgga ccactgcagt   66000
cagctcccta tgaacagttg ctctctaccc atccaatcgg ccccgcctgc tgctgccaaa   66060
ttcaccgagg gcacctctgt ggtgctgcct gtggacaaag tccaagccag ccacctcacc   66120
cacctacagg tgagtgggga gcagccagcg tgtccagtgg tttacccat cgccacagac    66180 ttggtgatgt gtcgatgtgc agagaagggg tgttggcagc cacaacacaa gcaacccgc    66240 cccatgtgag atctaagatg ggcgtgctgg gagccacctc tgagaatcca acagaaggca   66300
gaggggagaa cggctcacac ggcacaaaca ctccttcctt ttttttttt ctttttcctt    66360 tttgaaagga gtctcactct attgcccagg caggagtgca gtggtgcaat ctcagctcac   66420
tgcaacctcc gcctcctagg ttcaagcgat tctccagcct cagcttccca agtagctggg   66480
attacaggta cactccacca tgcccggcta attttgtgt ttttagtaga acgggtttt     66540 ccctatgttg gccaggctgg tcttgagctc ctgacctcag gtgatctgcc tgccttggcc   66600
tcccaaagtg ctgggattac aggtgtgagc catgggcct agcctccttc catttaaatg    66660
tatgcctaat ttgcccattg agaacggctg agacgcattt taagtggcca gggtctactt   66720
agagttagtg ctcatgacca ggcccaggtc aagcctggct ggccagatgg tgcctttgac   66780
ctgctctgtc tctgtgcaaa ggaatgagct gaaggatggg ggtgcagtgt gtgggcagtg   66840
ggctggggct ggcaggactc agtgactaag ggaagagaac tttcctcact accagcctgt   66900
cttttcaggg caccgcgggg ggctttggga cttggtgatg aacacagcac agagagctgt   66960
ccagcatgcg ggtccctggc ttctcacact tcccaggctc cttcagaggc tctctccaaa   67020
gggagctgct ctctctagaa cccatgaatt tggaatatag caaccactg cattggggac     67080 cactgacctc aaacatagag accagagcaa atggggctca tcacgtgaaa ctcatctgga   67140
actctagcag gttcttttat atatatatat atatatatat attttttatt attatacttt   67200
aagttctagg gtacatgtgc acaacatgca ggtttgttac atatgtatac atgtgccatg   67260
ttggtgtgct gcaccatta attcatcatt tacattaggt atatctccta atgctatccc    67320
tccccactcc ccccacccca caacaggccc cagtgtgtga tgttcccctt cctgtgtcca   67380
agtgttctca ttgttcaatt cccacctacg agtgagaaca tgctgtgttt ggttttttg    67440 tccttgcgat agtttgctga gaatgatggt ttccagcttc atccatgtcc ctacaaagga   67500
catgaactca tcatttttta tggctgcata gtattccatg gtgtatatgt gccacatttt   67560
cttaatccag tctatcattg ttggacattt gggttggttc caagtctttg ctattgtgaa   67620
tagtgccgca ataaacatac gtgtgcatgt gtctttataa cagcatgatt tatattcctt   67680
tggttatata cccagtaatg agatggctgg gtcaaatggt atttctagtt ctagatccct   67740
gaggaatcgc cacactgtct tccacaatgg ttgaactagt ttacagtcct accaacagtg   67800
taaaagtgtt cctatttctc cacatcctct ccagcagctg ttgtttcctg acttttaat    67860 gatcgccatt ctaactggtg tgagatgtta tctcatggtg gttttgattt gcatttctct   67920
gatggccagt gatgatgagc attttttcac atgtctgttg gcgaactcta gcagcttctt   67980
ttcacaagtt catggagaga ggtttcccac tgagggaatc acatctgtct gatcaaaaga   68040
ggcttgggaa atggctctcc tgttcattcc ctgaaaacct ctgatggaac cactgccact   68100
gtggcagccc cagcactggc accccagcca tgattggtgc cccagccaca tctctgctgt   68160
gagccccaga gccctggtta attaatcatc cacgtgttga tggggagagg cccattcaca   68220
aaagcgacat aaagcccagg gagacgtggc cgtggcaaga agggtgtggg actacattcc   68280
gcccccaact gagagattca gaaaccagaa aaaaatggaa aaacatactg tgctcttggg   68340
```

```
tgggaaaact aaatatcatg aagggagcaa tttttatagt tttggcctat aatacaattc    68400
cagccgaaat cccagtggaa ctttgagaat ttgcaggaaa aaaaaaaatg tctaaagtac    68460
atctggaaga caaacttaca agaaggtcaa ataattttga aaaagaaaat gatatctaag    68520
cccacctaga gaataagact tgagatccaa agctaaatca ggaggctcta gcaaaattga    68580
cagataagca ggacagagtg catggtgcat tcacctgggg aagagggcag attggtctac    68640
aaataggcct gggtccactg actttagctg ttatatttgg ggagaaactt ttcaacctca    68700
ctccatctta aacctaaaaa tattccagat gaattaataa atataaaaaa ttagaccact    68760
aaaaatgtag aagaaaatgg atgatctttc tataccatag agcaatggaa taaatcacaa    68820
aggaaaacag atttgactat ataaaactta aaccctgccc atcaaaaacc atcagaaacc    68880
aaaataaaag gcaaccaact ggagaagata gttgccacaa atatgatcaa gggttaatgt    68940
tattcataaa ttaagagccc acacaagtca ttagaataag cactgagacc tgaacagaca    69000
agcaaaaaga atgagagtgg gtcggcgcgg cggctcatgc ctgtaatccc agcactttgg    69060
aaggctgaag caggcggatc acttgatccc aggagttcca acaccagcct gagcaacatg    69120
gtgaaaccct gcctctacaa aagtcataaa tattagccgg gtgtgatggc acacgcctgt    69180
agtcccagct actcaggagg ctgaggtggg tggatcactt gagcccggga ggtagagtct    69240
gcagtgagcc aagatcacac cgctgcactc cagctggagc aacagagtga daccctgact    69300 taaagaaaa aaaaaaaaa agaggagaaa aatgctgatc tcactagtaa ttaaaacatc    69360
aggccaggcg cagtggctca cacctttaat cccagcactc tgggaggctg aggcaggcag    69420
atcacttgag atcaggagtt ctagaccagc ttggccaaca tggtgaaatc ccgtctctac    69480
aaaaaataca aaaattcgcc aagcgtggtg gcacatgcct gtgatcccag ctactcggga    69540
ggctgagaca ggagaattgc ttgaacacgg gaggcagagg ttgcagtaag ctgagatcgt    69600
accattccag tccagcctgg gctacagagc gagactctgt cccagaaaaa attaaaacat    69660
cacatattta aacaactcta ggatatcatt taaaaaaaca ttaatagact gtttttttaga    69720 gcacttttag gttcacagtg aaactgagtg gaaggtacag agacttcccg tatgttccct    69780
gccctccacg tacagcctcc cccactgcca acgtcctgca ccagagtggt acacttgtta    69840
caaccaatga atcctcatta acatatcatt atcacccaag ttcatagttt acattagtaa    69900
aacatcatct ttcatctata agcacaaaaa ttttttggca tttatttagg tgtatgatta    69960
actcagtgtt gacaagactc acacttcata cccacttgca ctgcatctga gaagcaattg    70020
gtgtctacag ccgctacacc ctcaacaagc ccgatcttgt ttgaaaagca attggtgatg    70080
cttctcaaaa ttctatggac aaagtcagcc gggcatggtg gctcatgcct gtaatccta    70140 aactttggga ggccgaggca ggcagatcac ctgaggtctg gtgaaaccct gtctctacta    70200
aaaatgcaaa aattacccag gcatggtggc tgggcctgt aatcccagct actcgggagg    70260
ctgaggcagg agaatcgctt gaagcaagga ggcggaggtt tcagtgagcc aagattgcac    70320
cactgcactc cagcctgggt gacaagagtg aaactccatc taaaaaaaaa aaattatgga    70380
caaagttttt caaaaagata tttaatgcaa ctttatttgt aatattggaa catctgaggc    70440
catttcagtg ctaactatta ggggatggtt aggaaaatat ggtacatatg tggaaaggaa    70500
catttggtag ttagtgcccc tgatgtttac aaaggctttt agtgaccaac aaatgctcat    70560
gctataatct tatgtgaaaa aagcaagtag cataattgca actatatttt taatgcatag    70620
aataaaaggc tagaaggaaa tatcacagat ccttgacata cattcccaaa cctttgtaaa    70680
```

```
tccgcggatt catgaaaaca gacacatttg cacaagtgcc tgatcttttc tgttatacat   70740
tcattagaag tcaagccctg gtgccacaaa gtatctgcct tttcaaatgt gatcagaatg   70800
ttctcttttg cttcaaggcc atttttcacg aagcagtggc atttttgcct cttcatcaga   70860
gtcaccgtgt gccctggagg actgagaaca gcagagccgt tttaggatgg acagggcag    70920 ccaggaggat tgggctcact ccctactgag tgcctcactc ccgtacagcc cccatagagg   70980
aagaggggtg caaatttatt cctcagccag atggcatgtg ccgcctgtcc tggaatttca   71040
catcacttat gatggaccaa aattccaaaa gctgaatcca tgattgtcaa agtctggtat   71100
ggcaggatgt caacagtaat cgtttctggg cagagggatg attttctctt cccatcttgc   71160
tttgtataaa tacattttct ataataaggt tgtattactt ttctcatcaa gaaatagcaa   71220
agtactgttt tactcaaaat atgaatagag ccaggcatgg tggcagctta tgcctgtaat   71280
cccaacactt tgagaggcgg atatgggagg atcactttag cccaggagtt tgagaccagc   71340
ctgggcaaca tagtgagacc cccgtcccca ctcccccaaa gaaacccac aaagcattta    71400 tcctggatta ttcacagggg ccaaaaaaaa aaaaaattc aggcctccta tagccatgag   71460
ctacgaatat gaaatatgc aaatgtgtaa gaaaagccag cacatccgat ttttacttt     71520 actttcacac ctctgtccac catgttccaa gagaagaaac ttggtcattg aaaggaatag   71580
atcaaatcca agaacaaaa ccactgtgct cattaaactt cttagtgttc acaaagcttt    71640
agctgcaggt tgaatggggc aacccgaatt ggctggctca cctgggctgc agggagcaga   71700
gatcgcgaca ctgcactcca gcctgggcaa caaagcgaga ctctatctca aaaaaaaaaa   71760
agttcataaa ttcaaagtta tgaattattt ttaaaataat aataatttac aataaagatg   71820
aggacaaagt gtgagtaaat ggtggtttct atccagctct gttgagctga agtggcatct   71880
ccctgctggg gcttttgggg aagaagggtg tgtgttgctc ttcagatccc aagcctcatg   71940
cccctactgg gccctgtggg gtgcttctca gcccaccagg agagccaccg ttggaacaca   72000
cacgtggggg acctggtggg tgccggtgtg gtgaatgggg gccacagcct gactccagga   72060
agccagcaaa ctcggagctg gaggagtcag gacaccccg atgagtcaag agttggtttt    72120
gctgccagtt gacatctgat tgaaccatct cttcacttct ccgtgcctca ctttccttac   72180
cagacaggct ctgctgatgc tgtccctctc ctgttcagtc gtgccctcac cgttaaagag   72240
aaagagcaaa ctgctgggca gcagcattga tttttttaat gaagtggaaa gagagctggg   72300
aataacaagt cgggcccacc tcacctgcct cacctggtgg gtttatttgt tttgtttttt   72360 ttttttttgtt ttgagacaga gtttcaccct gtcacccagg ctggagtgca gtggtgtaat   72420
ctcagctcac tgcaacctcc acctgccagg ttcaattgat tctcctgcct cagcctcccc   72480
agtagctggg attacaggca cctgccacat gcctggctaa ttattgtatt tttagtagag   72540
atgggttttt accatgttgg ccaggctggt ctcgatctcc tgacctcagg tgatccaccc   72600
acctcggcct cccaaagtgc tgagatcaca ggcgtgagcc accatgcctg ccgtcacct    72660 ggtggtgttg aatatgaact gctgcggtgt tggtaaatta agcaagcaga tagatgtaaa   72720
taacgcttgg gcaggaatat ggagcacggg atgaggatgg gcggccaact gttagagagg   72780
gtagcaggga ggctgagatc tgcctgccat gaactgggag gagaggctcc tctctctctt   72840
cacccccact ctgcccccca acactcctca gaacttatcc tctcctcttc tttccccagg   72900
tgaactttga accaggatgg ctgagccccg ccaggagttc gaagtgatgg aagatcacgc   72960
tgggacgtac gggttggggg acaggaaaga tcagggggc tacaccatgc accaagacca    73020
agagggtgac acggacgctg gcctgaaagg ttagtggaca gccatgcaca gcaggcccag   73080
```

```
atcactgcaa gccaaggggt ggcgggaaca gtttgcatcc agaattgcaa agaaatttta   73140
aatacattat tgtcttagac tgtcagtaaa gtaaagcctc attaatttga gtgggccaag   73200
ataactcaag cagtgagata atggccagac acggtggctc acgcctgtaa tcccagcact   73260
ttggaaggcc caggcaggag gatcccttga ggccaggaat ttgagaccgg cctgggcaac   73320
atagcaagac cccgtctcta aaataattta aaaattagcc aggtgttgtg gtgcatgtct   73380
atagtcctag ctactcagga tgctgaggca gaaggatcac ttgagcccag gagttcaagg   73440
ttgcagtaag ctgtgattat aaaactgcac tccagcctga gcaacagagc aagaccctgt   73500
caaaaaaaaa agaaaagaaa aagaaagaaa agaaatttac cttgagttac ccacatgagt   73560
gaatgtaggg acagagattt tagggcctta acaatctctc aaatacaggg tacttttttga  73620 ggcattagcc acacctgtta gcttataaat cagtggtatt gattagcatg taaaatatgt   73680
gactttaaac attgcttttt atctcttact tagatcaggc ctgagtggcc tctctttagc   73740
aagagttggt tagccctggg attcttactg tagccacatt aataaacaac atcgacttct   73800
aaacattcta taataccatc ttttggccaa attgacttcg cctcttcctc tctctttcca   73860
aatgaaatgt gtttcatttc actgtcagac cacatggttg gggacccac  agagcacaca   73920 gccctccctc tgccttccca tgctggccct tcacccactg ctggagtgcc aggttggtcc   73980
aagggttgga ccaagttgtc tgaggttgtc tcaaggttgg tcgaggctgt ctccgcgctg   74040
ggttgtgcta caaggagccc ttctttccat gggtgtggct ggcagtgagt gctcacagca   74100
acagcccaca gtgcagcccg agggcaggat ggactcagtc cctgcctcca tacccatttc   74160
taaggaggca aaatggcaaa cactctactt ttctctttta atgctaaaaa taagaaaaca   74220
ccttgcagcc cagggtatgg gtagtgcatg gaagccgtgg agttgtgagg tgggaagtga   74280
cctctgctgg atatgtctat tcaggaagat tgctggagtg ggtggggtct ctgggaggtc   74340
ccctgagtgt gggaagctgg gaccaccagc tttctcgcac agggagtggc catcccagct   74400
tggagaggtt ccaggactgg ttgggaggca cgtttcagat ttctatctgt tgaatcagcg   74460
aagatattgg attatgagga atttgggaat taggaaagtg ggtgcaggtg ggttgggggt   74520
aggtgaagga agacatgggc gtattggggg agcaggggct gctcagaggt gttccagaag   74580
ctctgggtga ggaggtgaga gggaccgggg aatgcagctc ggcccagcct ccctgcctga   74640
ggtcagccat cacgtggtga tggcaagatg gaaatgtgct ttctgactgc tccagccagt   74700
gctgccagat tcagctcccc agggagggca cctgagaggc tccaagccag gagatctgtt   74760
ttctcctttg ttttgttttt ttttgttttg ttttgtttta ttatactttta agttctaggg  74820 tacatgtgca caacgtgcag gtttgttaca tatgtataca tgtgccatgt tggtgtgctg   74880
cacccatcaa cttgtcattt acattaggta tatctcctaa tgctatccct ccccctccc    74940 cccaccccct gttttctcct ttgaatcctt cttagaggcc gggtgcggtg gctcacgcct   75000
gtaatcccag cactttggga ggctgcggca ggaggattgc ttgagcccag gagttccaga   75060
ccagcctggg caacatagtg agacctcgtc tctacagata ataattttaa aaattatccg   75120
ggcatagtgg catgcaccta tagtcccagc tactcaagag gcagaggcag gaggatcact   75180
tgagcccagg aggcggaggt tgccgtgagc caagatccca ccactgcact ccagcctggg   75240
cgacagagac ccccatgtca aataataata ataataaata aatccttctc agtcccttcc   75300
tcactgtgtc cccctccact gaattttttcc acctcctctc ccacttcccc cactcccgct   75360
ttccctctcc ttctctcccc actccatctt tttctttctc tgctgtttct cgtccctccc   75420
```

```
tcctctccat cccacaacac tgcctaccct gtccctgccc caccctggtg ctcaggatgt   75480
gtgaagtgag gggtggtagc ccccaagacc tcaaccccga aggttagcct gttgaaacca   75540
ctttctccca gctgcccccc tggcagttgg tgctgctggg ggaaactggg attggggcc    75600 agattttgcc tcttttcctg acaaagagag atgaagagtt ctctcaccag gtgcctggga   75660
ctggggtgtg ggtgtcccag cctatcccag cgcatctgtt ctgcatcatg attaatagtg   75720
ctgctttcag ccgggcgcgg tggctcacac ctgtaatccc agcactttgg gaggctaagg   75780
tgggcagatc acaaggtcag gagttcgaga ccagcctggc caacatggtg aaacctcgtc   75840
tctactaaaa atacaaaaat taaccaggtg tggtggtggg tgcctgtagt cccagctact   75900
tgggaggctg aggcaggaga atcacttgaa tctgggaagc agaggttgca gtgagccaag   75960
atcgtgccac tgcactccag cctgggtgac agagcgagac tccgtcctaa aaaaaaagga   76020
gttttgctct gtcgcccagg ctggagtgta gtggcgccat tcggctcac cgcaacctgc    76080 gcctcccggg tgcaagcgat tctcctgcct cagcctccca agtagctagg attacaggcg   76140
cctaccacca cgcccggcca gttcttgtat ttttagaaga gacggggttt caccctgttg   76200
gccaggctcg tctgggactc ctgacctcag gtaatccgcc cacctcagcc tcccaaagtg   76260
ctgggattgc aggcatgagc caccgtgccc agtcaactcc ttctcaaaaa aaaaaaaata   76320
gtgctgcttt ctcttcaag tgtcctgatt tgggtgatag taaatgccac tctacttata    76380
agggatctac ctcagaatgc taattgggac atttttgtag cactctactg ttggcagcag   76440
gtgatgctca caacagcccg tgagggtgga tgacgtccgc ttcacagatg acaaaggagc   76500
ctcatgctca gaccgtgggc tgccagagca ggtccatggc tgcagcccca catgaccat    76560 atttccccct tgtcactctt tccaccaagc tcccttggaa cttcagttat taagctctct   76620
tgggtggaat ccaagttaga atcacaacat gtgcctcata tggattgtgc cagtgaaaaa   76680
tgacattcta tttagaggca gggcagcctg gcttagagtc agtttaaaat atgtattatg   76740
ctgcaacaaa tgtaccatga tcctgtaaga tgttcacaac aagggaactg gatgtggggt   76800
atactgtctg tactaacttc acaagttttc tgtaaatcta aaactgttcc aaaataacaa   76860
gttcgtttaa aattaactcc aggagaccag gtacggtagc taatgcctat aatcccagca   76920
cttcggaagg ctgaggcagg tggattgctt gagcccagga gtttgagaca gcctgggca   76980 acatggtgaa atcctgtctc taaaaaaaat cacaaaaatt agccaggtgt ggtgcgcat    77040 tcctgtagtc ccagctactt gcggggctga ggtgggagaa tcatctgagc ccaggagttt   77100
gaggctgcag tgagctgtga ttgtaccact gcactccaac ctgggcaaca gagcaagacc   77160
ctgtctcaaa aacaaaaat gaaataaagt ccaggaaaga agtaggtttt accactctta    77220
ttttctgaag agaaaactaa atttaatgtg taaagtgagg acaagttcac caagttagtg   77280
tttgagttgc ctaaatatg tttgctaaaa ctattcaaag ctttcacata aacatgatc     77340 agaagttcta tgccaaaaca tatgtgtgtg tatatatata tgcactatat atactgtata   77400
taaaaatgca aaatctaaat tgccaacctt ttagaaattg ctctgaaagg aaagcatttc   77460
aagataattt gcttacccaa agaatatact ttccaagaaa gcaagtaata cttaaggtgt   77520
tcataatcct catcaaatta attccttgcta ctgaaagctt acaaggagct gttttgatgt   77580
cgggtgtgac aggtttgact tggcagaagg tgtcacttta ctaacaacat tttaaataag   77640
tgacagaaga caagaaacta cacgttaaat gccagaacaa agagtgtcta agtggatgct   77700
aagagttgaa atatgctggg atacctgccc aagagagctg aaaagtagat gaaagttggt   77760
tacctataaa ctagtgcacc ctaatgaatt aaaaggtgtt gatgagttaa cttgttatgc   77820
```

```
cttccagata agacatgcaa atggggcttc ttcctccttc actacttcca agggatttaa    77880
caaggagacc aatgcaaatg ataaggactg tagggctcaa gctggggaca gattggggaa    77940 aggggggacca tcatgcccat atagatgtcc ctgtgccctg gcagtcaagg ctgctgaaaa    78000
ataacaaaac ccagaagtct gcgtgatgct gcctctccat ttgtccaaag ccttcttgcg    78060
gcagtttgca ggcttttgca aaagctccag gaccaaggag ctatgttcat gctggaagct    78120
tgttcaggat tagctgttct ttgtgggatg ggtgcagcca gggccaggtg tccagggaca    78180
gtgttttaac aaagggcatg aggtgtctga tctcacagtg gaactccact tgcctttttt    78240
tcatcttctc attctgcttc atgcacagaa ccagccccat cctgaaactg actctaaatt    78300
actcccgccc caggtggagt gcctttctcg gagttcaaca gagccttcct gtcgcccaag    78360
ggacaactcc actgaatgcc caagccacac ccaaaaccta acaagtaaaa accaaattct    78420
gtgctccccc atcctgggcc attcctggtt tctctactgc tgttggtgat accaccatca    78480
gcttgtccat catgaccctg ccagttcct cccacaaccc tccacagcac ccagggacct    78540
cacctccatt ccatccgaca cagatctcct caccacaaac cttggttttg caacagcagc    78600
catgagacct ttacaccctc cgcccttcat cctgtccccc actgaggccc cagagccatt    78660
ccttaaagca gcgcgccaca aactataacc cacaagccaa ttctggtacc cagcctgttt    78720
tgcacagcca gtgaactgac aatgatcttt tcatacagcc agaaaaacaa aacaaaacaa    78780 aaacaacaa aaaaaaccc caccattctg agcatgtgac ttccatgttc aagatgtctc    78840
atgttcagaa aggcccctgg aaaaggagga aggggagctg ggcacaaagg gagaccctct    78900
cagctgagct cctcccatcc agacattttc ctggacttcc tatccaatga cttcccttag    78960
cttcttatca gccaccctg tctgcccagg aggctggaag atgtggcctt ttaactgggc    79020
acagctctgt cctctatcat atcagggctc tgttcccaag gagggtagag agaatggaca    79080
ccaggtggac cctcagcagt ctgtgccaca gagggagtgt ttgcaatttc cagactaaaa    79140
gtccccatgt gcttgacggg gtatgtgact acaacgtgat gcttgacttt tcctcatatg    79200
accagagcca ctttgtccat ctggtacaat gtcagctatc tgctaggggc cctccaggat    79260
tcccagtcaa ttccatatct gcatcaccac cattggcact aaataaaata aaatactcaa    79320
gttcctgctg gtgagcatga gcagtgctac actgggccct tcaaccaagg tgacatgata    79380
atgactgaaa ataatcactg ccacttattg gggacgtctc atctgccagg catggtacaa    79440
agtgctttaa ataagcattc aacaatttca tgctgacaga agccctgtga gccagtggag    79500
ctactactat gcccattata caggggagaa aactgaggca gagagaggtt aggtaattcg    79560
ctcagcctca cacaaccaat aggtggtgga gccaggattt gggccccatc tgcctgactc    79620
tctagaggct ctatcttcca gtcttccaga gttgagtcta agccatgaat aggacaatta    79680
gacagcagag gaaacccatt cagccaccat gtgcatgaag agtaaggaat ttctgtcata    79740
cagaggggag tgaattcact gagctgagag ctgaggaacc attgatctga tggctgagac    79800
accactggga agactggaga ggcttttctg ggcatgcagt gccaggcaca ggaggagctg    79860
agggaagatg actaagaggt actggcaaag aattcagaaa ttctgatgga agctttacat    79920
gttaccatca catccatcca tctatccacc catccatcca cccatatctt cctccctcca    79980
cccaatcatg catacatcca gtcatctata caccacccac ccacccatcc atccatccat    80040
ccatcccttc atccatccca tcatccatcc aattatacat acatccaatc atatatctgt    80100
acataatcca ttcttccctc ggttcatcca tccatccatt catccatcca tccacccatc    80160
```

```
ccttccttca tccttcctat catccatcca atcatatatc tgtacataat ccattcttcc    80220
ctcggttcat ccatccatcc attcatccat ccatccaccc atcccttcct tcatccttcc    80280
tatcatccat ccaatcatac atatatccaa tcatacatct gcacatcacc agctcatcca    80340
tctatccatt tatccatcca tccttccttc catccatcat tcatccatca tacatacatc    80400
taaccataca tctctacatc attcattctt ccatcgattc atccaattat ccatcattcc    80460
ttcctccatc catcccatta tccatttgat catacatata tcatctatac atcatccatt    80520
catccatcca tccatccatc cacccatatc ttcatccaat caatcataca tacatcgaat    80580
catctacaca tcacccatcc atccatccat ccattcatct atccacccat ccatccatcc    80640
atccatccat tcatctatcc acccatccat ccatccatcc atccatccat ccatgtaacc    80700
atccagtcat atatccaatt acacatccat ccagttatac attcatacat gcatctaatc    80760
attcaattat acatacacac atccatataa ttctacatcc aattatacct ccatccaatt    80820
acacattcat acacccacct aataaattat taattcatat atccatccat ataattatac    80880
atcaattata catccatcta atcattcagt aattcaccca ccatccagtc atctatccaa    80940
taatacattc atccaatcat ccatccatcc atccacccat tcatccatcc atccgtccgt    81000
ccacccatca tggtatgagc catgatttac cacgatggtc cctgtggac agcccaggtg    81060 gggcagaact gaagggaagc ccagggctgc ccccataaac atttgcctcc tttacatgga    81120
tgagaactag atccacatgt ataaatcctc atgatttgaa ggtgctttta ccaacattca    81180
ctcatgggat tctcccagga gctctaggag gaggcaggta gagttgaggt catctcacgc    81240
attttacaga tgaggaaacg gaggccctga gaggcaggtc caaggccacc tgaccagaaa    81300
gaagtggaac tgggacttga acccagccat cttgcccctt ggtcccatgc tctctagcct    81360
gtaactcctg cttcctggtg gggcatctcc aggaggaccc tatcggctgg ccatgggcct    81420
gccctggagt cttttgctct gtgtggccat ccttcctccc tcaggagagt gtgtgctccc    81480
agagcacagg ctgtatcttc tgagcatttt gtcccttccc agtacctagc actcagctct    81540
gtatacattg ggctctcaag aattctcaac cttccagagt gtaaggcctt gacctgctca    81600
gccctggata ctgcatgatg cattgataag cccataaaat aaccagggca gattgactcc    81660
cagtggccaa agtgccacag ggaagggaca attcagccct tctaggagga ggaggaggta    81720
gttttctcat ttctattaag gcaacaaaag ctgccttact aaggacattc ttggtggagg    81780
gcgtgactgt caaccactgt gatcatttgg gcctctcttg cccaggcttc ccattctgaa    81840
aggacagttt tattgtaggt acacatggct gccatttcaa atgtaactca cagcttgtcc    81900
atcagtcctt ggaggtcttt ctatgaaagg agcttggtgg cgtccaaaca ccacccaatg    81960
tccacttaga agtaagcacc gtgtctgccc tgagctgact cctttccaa ggaagggggtt   82020 ggatcgctga gtgttttttcc aggtgtctac ttgttgttaa ttaatagcaa tgacaaagca    82080
gaaggttcat gcgtagctcg gctttctggt atttgctgcc cgttgaccaa tggaagataa    82140
acctttgcct caggtggcac cactagctgg ttaagaggca ctttgtcctt tcacccagga    82200
gcaaacgcac atcacctgtg tcctcatctg atggccctgg tgtggggcac agtcgtgttg    82260
gcagggaggg aggtgggggtt ggtccccttt gtgggtttgt tgcgaggccg tgttccagct    82320
gtttccacag ggagcgattt tcagctccac aggacactgc tccccagttc ctcctgagaa    82380
caaaaggggg cgctggggag aggccaccgt tctgagggct cactgtatgt gttccagaat    82440
ctcccctgca gaccccactg aggacggat ctgaggaacc gggctctgaa acctctgatg     82500
ctaagagcac tccaacagcg gaaggtgggc cccccttcag acgccccctc catgcctcca    82560
```

```
gcctgtgctt agccgtgctt tgagcctccc tcctggctgc atctgctgct cccctggct    82620
gagagatgtg ctcactcctt cggtgctttg caggacagcg tggtgggagc tgagccttgc    82680
gtcgatgcct tgcttgctgg tgctgagtgt gggcaccttc atcccgtgtg tgctctggag    82740
gcagccaccc ttggacagtc ccgcgcacag ctccacaaag ccccgctcca tacgattgtc    82800
ctcccacacc cccttcaaaa gccccctcct ctctctttct tcaggggcca gtaggtccca    82860
gagcagccat ttggctgagg aaggggcag gtcagtggac atctgatctt ggtttagtat     82920
ccttcatttt gggggctctg ggtgtggcct gggcctctgg actttggcca cggtgtttgt    82980
tccagcccct ctcctaacct gtcctttcca gacactcggc atctaggtta ttagcacctc    83040
gcatactttc tgacatgctc ctcagtcctg attttgacca tcttctcttg cttcccatct    83100
gtgtcagtca agactgcatt tggctgtaag aaacagaaac cccaactaac tgtggcattt    83160
acatgaagag gtttactttt ctcacataat cagatgtcta gacttggcca gcacctcaag    83220
ggtcattgat gctctcctgt ctttattttc tgtcatcttt agtggttgga ttgttgcctc    83280
atggttacaa agtggctgct gcacttccag gcatcacatc tgcctttgaa gcaggaacaa    83340
gttgcaaagt aaagtggcca aaagggccct gaaactaaat gtgtcccctt aggaaagcag    83400
gagttttctt gcaagtggca atcttctgct tatgtctcat tggccagagc tgggtcttac    83460
ggccacccct tgctgcgagc aaggctggga cattgagcat tttgccgtcc aacctctta    83520
gcagaataaa ccaaggggga agaacgttaa tagtggcttt tgagtcacta gttggcagta    83580
tctgcccctc tatctttcca tcctccccat ggagtttcaa ggttcctttc tcagtacttc    83640
ttcaggctct gcacgttcat ttggatcttg tgtcttgggg tgaaaaactg cccaagtgt    83700
ctccccaagc atccaccttt ggattaattt ggaaaatggc tgtcaagtgc ccgcctcttg    83760
cttggtataa tgctacagct ttagaggacg cagcaggcat gggccttgcc gctgaggttc    83820
ttagcctcat gagaatatcc agatcagatt ctcttggctc cttcttagag ccagtgatgc    83880
aagacacttc ctgctcatct tgtcgggacg gttttacaag ttgcctgcca tcctgagaaa    83940
gtctacaaaa cgatgccaga cctcatgcca gcttcccaag ccttgactct cagtgctccc    84000
tcaacaggat tctggaagaa tctcccaaac aagtcgcaat cccctctgga ccctgtgcag    84060
gcatgagact caagagcatt ggctcccacc cctggtggag gaacactgc tggggctggg     84120
atcttgcctg gttgctccgc ctgcacccaa gacaaccata attaaaatgt ccttcattga    84180
acttggaaag ccttcaaagc tgacaactcc ttatgtgtac ccggaaaggc ctgggagtgt    84240
gccagggcat tgctcgggag ggacgctgat ttggaagcat ttacctgatg agagactgac    84300
agcagctcct ggtagccgag ctttccctcc tgcctctgct gtgaaggtgg acccatccaa    84360
cagtcaaatg cctgactctg gacaggagcg gacctattta ttgccatgca agggactctg    84420
cacttttgaa ttgtgggtca tgggcttgga tttagggggtt agagctggga gaagtcttgg   84480
aagtcaccta gagatgacac tgccattttg cagatgagga aaccgtccaa tcaaaatgga    84540
ccaaggactt gcccaaagcc tcacagcaaa accataggcc cccgcactaa ccccagagtc    84600
cctgtgctgt cttaagaatc aaatagttgt aagcaatcat ctggttttca gtatttcttc    84660
ttttaaaatg cctggggcca tgcccagcag tctgttttcac tgcagcgttt acacagggct    84720
gccgggcttt cctggtggat gagctgggcg gttcatgagc cagaaccact cagcagcatg    84780
tcagtgtgct tcctggggag ctggtagcag gggctccggg ccctacttca gggctgcttt    84840
ctggcatatg gctgatcccc tcctcactcc tcctcccctgc attgctcctg cgcaagaagc    84900
```

```
aaaggtgagg ggctgggtat ggctcgtcct ggccctcta aggtggatct cggtggtttc   84960
tagatgtgac agcacccctta gtggatgagg gagctcccgg caagcaggct gccgcgcagc   85020
cccacacgga gatcccagaa ggaaccacag gtgagggtaa gccccagaga ccccaggca   85080 gtcaaggccc tgctgggtgc cccagctgac ctgtgacaga agtgagggag ctttgcgtgt   85140
ttatcctcct gtggggcagg aacatgggtg gattctggct cctgggaatc ttgggttgtg   85200
agtagctcga tgccttggtg ctcagttacc tccctggctg cctgccagcc tctcagagca   85260
tttagggcct tctggacttc tagatgctcc tcatcttgcc tcagtcagcg cgtcagttcc   85320
agagacttct ctgcagggtt ttctggggca ggtggtggca gacccgtgcc ttcttgacac   85380
ctgaggtcag tccacccctcc tgctcagact gcccagcaca gggtcacctc caaggggtg   85440 gaccccaaga tcacctgagc gcacagaggg tgcagatgac tggaccacac cttttggtga   85500
tcttaatgag gtggtcccag aggagctcag acatgcaatc tagcatccag ttctgggact   85560
ctgtctcctt ttcaaacgta ttcatgtaga acaggcatga cgagaatgcc ttgtcaacat   85620
gggtgatggg gaatcaatca gacagggcgc cgggctcaag gctgcagtca cccaagagtg   85680
gctcagccca ccaggccta ggaaacgcct gcacagcctg gagctcctgg agtcatttcc   85740
ttcatgtctt cttcactgca cttacgtaaa gatgccagcc attggtttgg tgatttggag   85800
ggtgcccagt tgcccaacaa gaaatgcaga agaggcctag ccaggatttc accagcagtg   85860
gagagtagag aagatgtggc cagaaaagag tttccttttcc ctcctaaaga tggtactccc   85920
tgcagctact ggggaagcct gcagcattct ctagggctct gtgtgttgag agcagcccca   85980
ccctggcccc ttctgagtgc atttctgctt tgtgacttga tccgtgaagt cccctgagat   86040
gggcagaggg gatgtcctcg aagctggggc agagcctcat ccttgaacgt gaaggacgtt   86100
tgaagactgt ggcatgatca caggatgaga tcacagggaa cttgagtttc tctcctcctc   86160
tcccttcaca gttatttcac tgagggaaat ccctcccctg cccagaatga aaactctagc   86220
caactcttga cttttccatc actccaaagt agttgaaagt acattagtct ccacagtggc   86280
aaaacagtgt gcaaaagcta ataattaga acagccagtc ccatgtgaca gtcaaagctt   86340
ctaactccat tcaaagttgc agccattccc ctcgagggct ggcagggagg ggaggggtaa   86400
gagaaacagg aaggttctta ctgagttggt cctggtgtga gctgcgtcac actccctgca   86460
gaggtttcaa ggagactctc tctctctctg tctccatggg gaccttattt gaattcttct   86520
actcttaccc cagcctgcca tctccagcta tcctcccctg aagagccctt ctgctgcgct   86580
ggattctggt ggccatgtca tctcctcggc cccgtgggag tctgaagatc tggctgcagc   86640
ctcacctctg aggtcctgct agttgccacc tcttaaacat gatctgaggc tcccatgcac   86700
tctgacctgt gcccacatgg ggcccacggg aaacacgctg gcaagcaaac tgtgggtgtg   86760
cagacggttc tcagggctgc agcacctgtc ctttgctctg cccccaaagc aaggccagcc   86820
catcttccat cctctagtgt tccttggtgg ggccctgacc acagtccacc aggtccctaa   86880
ccagagggga cacacaccag gtgtcctcaa tgtattgcct tgaaacagtt gtgctgggac   86940
tgtgatgggg ggtggccatg tagccacccc caccaccccc aagccactct ctccaaggaa   87000
atcctcctaa agatcccttt acatcctcca tgtggtgggg aggttctaga gttgggtgca   87060
tgtgtcttca gctactgaca atgcagacct tagttggcac ctcgctctgg cctatcctgt   87120
ttgctgttct tggcgctcca gtgaaactcc ccatgggcca tccagttggg gtgcagtgtg   87180 gccacccct tgcaggttcc tgccttgctg gagagcacag ggcctcctg gctcttgtaa   87240 aacactcccc atggtacaga gaggccagca gtgatgtgag gcccaacctc cctccatggt   87300
```

```
gttcccaagc agctcccttt ctggggtcaa ggggtggcaa agacagtgca gcgtccaatt   87360
tctgactcaa gccgggcctg gctatcgcag ctctgcactg tgtgtgacag caaggcaact   87420
cacccagtgc cgtggcagtg accgtgtccg aggaagcctc ctcacaccct ctgtctcaag   87480
gactctggca tttagctgga cttgctgtag ctctgagcct ttctgccatt gccatcacct   87540
tgtcagaaac tcaggccgaa tctgcactca gagttgtgcc caggcagttg agccaacact   87600
tgctcagcga tattgtcaca tgacaaggca ctgtcaccac tgggcgtcgt gggtagcgca   87660
gtgtcggctg gatggacccg gagggtgtct gtgtcatgct agtgctagtg atgggagccc   87720
cgtgagccca ttgcccgccc tcccatgccc tcagcagctg cctggggaca gccaatggcc   87780
tgggtgtttc tgaggctacc acatggcttc caggaaactc gagaaccttt ctctcccttg   87840
cctacactct tcacacaggc ctgtgctggc agcggtggg gatccggcat tcctatctta   87900
ggtgcagaaa gtgactgact cattgcaggc ctgggagata agactgatgg cccagccagc   87960
aagatgtatg gatttctcag aggcagtggc ctctgtcatt gtcctcagga aatgctggtg   88020
attctggtgg cctgaggtca atgcatgtca acgtggccaa cttgccttat aaacttttt   88080 tctggacaat tgcgtgcact gtcctgtaac agtgtcctgt tgtttatgat gcagaaatag   88140
gtgtttttaa agcctattga ttttggtact attaatgtgg tcaggaactt tctcagtctt   88200
tcttgtttgg ggtgagctgt ggcttcctaa acaggaaccc aagacacccc caaaagctgc   88260
tcaccagcac tgccagcctc cctcttacca agtagcaccc gttcaggaca ttctgcgaaa   88320
ggcatttgcc cagaagttgg gaggaaggaa atgtaacatt ttggggcacc taccatatgc   88380
caggcaccag gctaaacgtg ttcacacaaa ttctcttact aaccctcacc atccttctac   88440
aagacaaact agtatcttca tcttggggtt caagatgagg aaatggaggc tcagagaggt   88500
tgaatgaatg ccggtgcctg gatatgaacc ccatctgcct gactccgcaa cccaggcaaa   88560
gtctttcctt gaacttccca gcagccactg cttagacaca gcctcacaa ccatggctca   88620 gcagcaaatt gcttctctga cctcactcag cctgtgtgtc cttgttgagt gaggcattca   88680
ggaccctggt cccaaagtgg agaaagtctt tcctactagg tcatagctac acctgcatgt   88740
gggtgctgtg cctttttgttt agtgaacttt tatcaccagc atcctcagca atgacatttg   88800
cagagaagcc agagctgagg caccttggta ttcttgggat gtgactttcc tgaatgttta   88860
agggaaaatg cccgaaggta cagagagctt ggtttctagt aaacaataac tgtcttgctt   88920
ttacccccct tcatttgctg acacatacac cagctgaaga agcaggcatt ggagacaccc   88980
ccagcctgga agacgaagct gctggtcacg tgacccaagg tcagtgaact ggaattgcct   89040
gccatgactt gggggttggg gggagggaca tggggtgggc tctgccctga aaagatcatt   89100
tggacctgag ctctaattca caagtccagg agatttagg gagttggttc ttatcaaagg   89160
ttggctactc agatatagaa agagccctag tggttttttt ctaataccat ttctgggtaa   89220
ttcctaaggc atttagtgtt ctgaaagatg ctagccttgt ccagcctggg agttgagaat   89280
gaatgtctaa cagaaactct aggccgggcg tggtggctca cgcctctaat cccagcacta   89340
tgggagaccc aggtgggcag atcacctgag gtcaggagtt tgagaccagc ctggccaaca   89400
tgtgaaatcc tgtctcacta caaataaaaa aattagccgg gtgtggtggt aggtgcctat   89460
aatcccagct actcaggagg ctgaggcagg acaatcgctc gaacccagga ggtggacgtt   89520
gcagtgagcc gagatcgcat cattgcactc cagcctgggc aacaaaagca aaactccgtc   89580
tcaaaaaaaa aaagaaaact caaatatgtg tgacaggcga ttctcactgc aggctgccct   89640
```

```
gtggctgatc caggagcaag gccttaacca tgtcatcccc aagcgattgc ttgtaaactt    89700
tcttctgtgc agccttcaac ccttattatg attttcttct caggaaccaa actgctgtat    89760
tcaagaaagg cagctttgtg taatcattta tcataaatat cttaagaaaa atcctagaga    89820
ttcctaattt taggaaatgg gagacctatg gtactgatat aatgtgggct gggcttgttt    89880
tctgtcattt gctagataaa tgaacttgag agcctactgt aaaatgtgga agcttctaga    89940
ttgcagaagg gctggaaaga cactgttctt ttctcccgag tgatgggatc tgtccagtat    90000
ttagagctgc ctctgaggcc atctgattct aggagactct gcctcgttga ggatattttg    90060
aggcctaact acacattcct gcccccagag aggtcacagc ctatagcagg ctgatgtttc    90120
tcatgtcaca tggcacagaa aggcacattt tcgttctcag gctaacaaag agcttcaaaa    90180
actattagaa gggacagtgg ctataagaga agaacctcag tcaatgtgtg aaattaacta    90240
ggaacctggc tcctgtttct tttaggtcat gtttttcagc ttaggtaaaa ctagaggctt    90300
tgataaagca tgacctctag aaatcattgc ttttcataaa tggaagtggg tttgagtttt    90360
ttctactgat tgttagtgca ggtgatgtct acatgccccc agaacatatt ccatgcaaca    90420
aaaaaagccc aggtcaccgt ctttgctggg aacttgactt ttgtgctcac tgaattttaa    90480
gctttctgac agcagcctgg aatcatgagg gataaagta cctattagta agatggaaaa    90540
aggtgtttca ggttggagct gcagtctgtt gagagtaagc tatgggaagg cctgtatacg    90600
aggggtggac ttttcttctg taagtgtcca gagaccaggc ctcctgaaga gggcatgggg    90660
gcttaactta cctggactac tgtgtttaca atactcattt atcttgaact cctcctaacc    90720
cctgagaatt gctacattta gtatttgctg agtacttcct agcatcctag gaatcaata    90780 gaacattctc ccaaccaggc tgggtgcggt ggctcatgtc tgtaatccca gcactttggg    90840
aggccaaggt aggcagatcc cttgaggcca ggagtgcaag actagcctgg ctgacatggt    90900 gaaacccgt ctttactaaa aatacaaaag ttagccaggc atggtggtac acacctgtaa    90960
tcccagctac atgggaggag taggaggcag gagaattgct tgaacctggg aggtggaggt    91020
tgctgtgagc cgagatcatg ccactgcact ccagcctggg cgacagagtg agtgagactc    91080
tgtttaaaaa aaaaaaaaaa aaagaacatt ctcctaacct ggcttcttcc tccaggggtg    91140
taattaatca tgtcagtttc ctcattgata cacacacaca cacactacaa tcctgtatcc    91200
attacttttc aaggtacatt tactatttac gtttggggtc cttgtctctt ttttaatagt    91260
gtttcttaaa gtcttgtatt atatcagagt acagtaacat cccagtcaag agcactctag    91320
taagctctag gaggaaagcg acttccggaa ggcagtggag acctgtcctg ttggggcagc    91380 atagggggcag cccctgcctc tggtcagttc tggcgctcag gctcagggtt gcctctgggc    91440
tgttcttccc agagactgac aaagggctcc cataaggcac ctgcagagcc tgtgagaagc    91500
tgaagtcaat gttttcctga caccagttga tctgtgcagg atccattgat ttaaccacct    91560
gctgtgtggc atgcactgtg gtcgatgcca ggaacaggaa ttggaggggc ccatgagcat    91620
ggccagtatc acaggctgga ggtgctgctg cgctctgacc gggcctcttg gggatgagcc    91680
catgtcaacc accttgcctc cgatgggtc gggcccacag gttacctttg tgtgtccatg    91740
accacacctt cctccccgac ctcatccaaa tctctttctt ttccaagccc ctgaatcctt    91800
cagggctgca ggttttgttt aaagcagagc tggtgagttg cataggttgt tgcgttggga    91860
ctagatgggg tgttcaaaga gttgggagtt aaaaaacata aagggtattt attaggagaa    91920
ccaaggagtg taattctcct gttcttaata tgcggccagg ttaatgaatg tcacgtgaat    91980
gaaccagaaa aaaatgaagt gtgcccttga tcagctgggt tggtgtgcag caagctgtgt    92040
```

```
gaccagggga cagcagtggt cctgagggcc gtcactgtct gccgtgcaga gcccttcctc    92100 ccacggggc  ctacctcacc tgtgccaagg gcttgtctgt ggtcagtgac ctggatagat    92160
ctgaatgggg cttctttttc gaggagtctt atggcaggtc tctcagtaaa gactccattc    92220
ttgatgatca cacattttgg attttccaaa tctgtcagag aatgggcttg aggcggggtt    92280
tgtgggcact agtttcactg gtttcattta ccaaaaaggg gagcagaagt caagtatggt    92340
ggctcatccc tgtaatccca gaggcaagag aattgcttga gcccaggagt tcgagaccag    92400
cctgagcaac ataaggagac cccgtctcca caaaaatgaa aaataacatt ttagtcagac    92460
gtggtggcat gcatctgtgg tcccagctgc ttgggaggt gagatgggag ggttgtttga     92520
gccctggagt taaagttgca atgagctgtg attgcaccac tgcactctag cctgggtgac    92580
agaacgagac cctgtctcaa aaaaaaaaaa aagaaagaa aaaaggaaa aaaaaactc       92640 atgcctgtaa tcccagcact ttggggaccg gggtgggcag atcacgaggt caggagatca    92700
agactatcct agccaacatg gtgaaacccc gtttctacta aaaatacaaa aattagccag    92760
gtgtggtggc acgtgcctgt aatcccagtt actcgggagg ctgaggcagg agaatcgctt    92820
gaaccaggga gtcagaggtt gcagtgagct gagatcgtgc cactgtactc cagcctgggc    92880
gacagagtga gactctgtct caaaccaaaa aaaagggtg gggggcgggg gcaggagaac     92940
agtgagaggt agggagagga aaggggattc tcgctacacc caaaccagat accatctaga    93000
ggctagaatc tttgggaggc tcaaattccc tagaaagcag gagaagcttc tgtagccctc    93060
ccgctttccc agtagattaa gcccaggcg gctccagatg tgtgacatgc tctgtgccca     93120
accagagccc atcataggca gaggaataac acccacacca gaagggccct cggaggtcac    93180
cacgtccaag aaccctcttt acagatgagg aaactgaggc ccagagaggg gagagccacc    93240
tagcgagctg gtggcggcta gaccaggaga gctgtcattc caagcaagca aaggcaacga    93300
gacgagccca gagctgtgct cccatctctt tgttaggggg cctgggatgc cctctcagtg    93360
tcattttgtc caggatgatg ctccctctct taagcgatta atgcgccctt gctaacctt    93420 tgctatcgct gcctcttcaa accagaggag ttgagagttc cgggccggca gaggaaggcg    93480
cctgaaaggc ccctggccaa tgagattagc gcccacgtcc agcctggacc ctgcggagag    93540
gcctctgggg tctctgggcc gtgcctcggg gagaaagagc cagaagctcc cgtcccgctg    93600
accgcgagcc ttcctcagca ccgtcccgtt gcccagcgc ctcctccaac aggaggccct     93660
caggagccct ccctggagtg gggacaaaaa ggcggggact gggccgagaa gggtccggcc    93720
tttccgaagc ccgccaccac tgcgtatctc cacacagagc ctgaaagtgg taaggtggtc    93780
caggaaggct tcctccgaga gccaggcccc ccaggtctga gccaccagct catgtccggc    93840
atgcctgggc ctcccctcct gcctgagggc cccagagagg ccacacgcca accttcgggg    93900
acaggacctg aggacacaga gggcggccgc cacgcccctg agctgctcaa gcaccagctt    93960
ctaggagacc tgcaccagga ggggccgccg ctgaagggg caggggcaa agagaggccg      94020 gggagcaagg aggaggtgga tgaagaccgc gacgtcgatg agtcctcccc ccaagactcc    94080
cctccctcca aggcctcccc agcccaagat gggcggcctc cccagacagc cgccagagaa    94140
gccaccagca tcccaggctt cccagcgag ggtgccatcc ccctccctgt ggatttcctc     94200
tccaaagttt ccacagagat cccagcctca gagcccgacg ggcccagtgt agggcgggcc    94260
aaagggcagg atgcccccct ggagttcacg tttcacgtgg aaatcacacc caacgtgcag    94320
aaggagcagg cgcactcgga ggagcatttg ggaagggctg catttccagg ggcccctgga    94380
```

```
gaggggccag aggcccgggg cccctctttg ggagaggaca caaagagggc tgaccttcca    94440
gagccctctg aaaagcagcc tgctgctgct ccgcggggga agcccgtcag ccgggtccct    94500
caactcaaag gtctgtgtct tgagcttctt cgctccttcc ctggggacct cccaggcctc    94560
ccaggctgcg ggcactgcca ctgagcttcc aggcctcccg actcctgctg cttctgacgt    94620
tcctaggacg ccactaaatc gacacctggg tgcagctgct ccactccctc ggcctcctcc    94680
cgtgctcagg ctgtggccgc acgcgcccct cacgcttgcc cgccactctg catgtcacca    94740
gcacccccgc tccgtgctcc ccaccttgtt tgactctctg gccacttgat tgtccacaa    94800 cggcccatca gcccacagga ggtttggtgg gtgccttcca ccgacaggat gacgggtgcc    94860
ctcatggtgt ctagaactct ccaaccctcc catgtaggca taagcagccc cactttgcag    94920
atgaggaaac ggaggctcag agaagtacag taacttgccg aaggccaatg agtagtaagt    94980
gacagagcca ggtttgggat ccaggtaggt tgtctctgaa agacacgcct gtcctgcatc    95040
ccacaacgcc tcccaggagg tgctggagtg tggacgccta acacagagat gtgcagggca    95100
cacacagcag gtgacacaca cagcatccag aggtggccca gagctcatgc tgtgcctttg    95160
gcccagtgcc ctgcccccac ccactctgcc ttgtggcagg aagacaagga gcagacacaa    95220
gatctccctg gtccacatgc caccacctcc ctctgcagag acaagggga tcctcatgct     95280 ggcattggag ggggttgagc agggcccacc ttgagccctc aggagcacga ccacagcagc    95340
cctgcaggga gggattggtg ggaggagagt cccaagtatc agggagagga gagttggtgt    95400
cccacaggag acctcagagc cacaaggcga gcttgttcat aaatttggga cccttagcat    95460
ttcacagtta tttgcagagc ccagaaatgg atgttactga agctcacagt tgcaagcatc    95520
tgttaaattt ttattagatt ttacttttag ggaaaacttt gaaatgctat aaagaagcct    95580
gtgtttaaaa gttaagacag aggctggggg cgatggctca cgcctgtaat ctcagcactt    95640
tgggaggcca aggcaggtgg atcatttgag gttaggagtt cgagaccagc ctggccaaca    95700
tggtgagacc ctgtctctac taaaattaca aaaaattagc tgggcgtggt ggcgggcacc    95760
tgtagtccca gctactgggg aggctgaagc aggataagtg cttgaaccca ggaggcggag    95820
gttacagtga gccaagatca caccactgta ccctaagcct gggcgacaga gtgagactct    95880
gtctcaaaaa ataaaataaa ataaagttaa gagagaaaaa aatatatcct atatcctttg    95940
ttaaattcca aaacagtagg ggacaaataa ctgacttgac aggttactac aatatttcct    96000
gaaatgatgt tttcttgaat actggcctac tagaggttca taggtgtgtt tggattaaaa    96060
aagagttcca tggcccagtg actggggaa aaaaataaaa gactaaagta agttaaacag    96120
gcttttctgc tgcaggactt gtcagagcct ttaatgtact aatggccatt gtgaccctct    96180
gagaaggtca cagagtgggt ttcccaaact tacttgattc tacctgctaa catttcctgg    96240
aggaagtttg ggaaatgccg atttagcaga ttcttttgtt gtgccgtgga tggtgctggt    96300
tgatgtgggc aaaacaaaga acacgtgagt cagatccgcc tggggctctt actaaagtgc    96360
aggttcccag gtgccacttt aggcttacag acccagttgt ggggtaagcc tgggagtctt    96420
ttagcaggtg attctgccac atagtatagt tggaaaacct ctgggcatac tcattgctgg    96480
tccctctaga aatccaggtg acaatagcca atgagaagct ccaagagacc cagttgtcca    96540
tggggtagag ggaatgtgat attgaaacca agaagaaaa tctatgatca gttttcagca    96600
gtgactgtca agagaaggag aagggtgagt tagcgctgat gctggctgac aggtcagcgg    96660
gttggtttca ccaaggagtg tgatgaaggc tgatgttgtc tgtgggaatg tatgatggta    96720
actggtttgt agctaatttg gggaagcagt gagaattcgt gcccttttgaa gaccagtaag    96780
```

```
tggcaagaaa cccaccaggc ctggctcagg gctgggctgg gcttggctcg tctcagagca    96840 gctgggctg gtggccaaag ccaccattag tgaggggcag gccctggggg tacaaccagc    96900
aactagggga caaagacaac cctgccagcc tctcctattc tggaggcgtg tgaccagaaa    96960
tggagatggg ttggtcagca taagatggcc aggaaggtgg aaatcaggac tgctggcaat    97020
ctagccacat gggcagggga gccgggtggt tccaggcagt ttccaaggcc aagagggtga    97080
gcaggcacct cacagggaat cagggccaag cctggctgca gtgtgagac aatgcaccca     97140 cccccatcct tggatcttgc aggaggctgg gtcctcactg agctaccaac atccatggcc    97200
ctgaggcttt taaaacaccc atccatggag tggggctggt cccagtgggg tgaggctgac    97260
cctggcagaa acagggcagg agcctgtggg ttagggagac tgcaccttcc ttagatagcc    97320
tccatgccat catgtccccg tgacagtttc tgctgcgtcc cctctgcatg gtcccaccct    97380
cggccagcct gctgccccct cttgccaggt tgcgctaatc agtgacccca gtgtgctgtg    97440
ttgatactaa caatgcgagg cctagcagat tcaagggaaa agagaaccaa ctgggttttcc   97500 accagaccca actaaacaaa catggaccta tcccagagaa atccagcttc accacagctg    97560
gctttctgtg aacagtgaaa atggagtgtg acaagcattc ttattttata ttttatcagc    97620
tcgcatggtc agtaaaagca aagacgggac tggaagcgat gacaaaaaag ccaaggtaag    97680
ctgacgatgc cacggagctc tgcagctggt caagtttaca gagaagctgt gctttatgtc    97740
tgattcattc tcatatataa tgtggggagt atttgtcact aaagtacagc tgtcatttaa    97800
agtgctttgt attttggggc aggcttttaa aaagtccagc atttattagt tttgatactt    97860
accccaggga agagcagttg gcaggttcat gaagtcatgc tcctaattcc agctttctta    97920
gtgtactttc agtgagaccc tgacagtaaa tgaaggtgtg tttgaaaacc aaacccagga    97980
cagtaaatga aggtgtgttt gaaaaccagc cctaggacag taaatgaagc catcttctca    98040
ctgcataaac tgcacccaga tctttgccca tccttctcag tatttcactt cacccattgt    98100
ttactgtctc aatgactggg gaaatgtctg gggaaatgct cccgtaattg cacagtggcg    98160
tttttcctgg aaaatcccac catggctcta gataagacct atttttctta aaggtatcta    98220
aaatttccag cataaattct gtctgaaaca cctgaatttt aatcagtact ggagcccgga    98280
gggcatctcc agttgccaca tagctctgag cattcagtgg tgtgttgagg gctgctcccg    98340
gaagtgcctg cagagtcagg gctccccagc ctcatctagt gaggcagtgg aagggcctgt    98400
ggggatttgg agagctggcc tgggtctctg aagtgatagt gacagctgct tgtcaatcac    98460
ggtgcacatt tagtgccggg ggcagggggc agggaatacc agcctcatgc atgcatgcat    98520
tcatttgttc cttccttcat tcattcattc agtacacatg ggtacaacat ccctgccctg    98580
gagttgccca gagtctaggg agggaaaga tctattaccc tgggcctcgg ccagctgggg     98640
agtgctgctg gtggagaggg gccgtgtgca gcgagggaag gaggagtcgt caataccccc    98700 acccagctt tgctttcttg tcatcagccc caggccccca gctgtgtcc ctcctctccc      98760 attgctactt catctcctgg gtcctcctta ccaagcctga ccacacagag ggccttggcc    98820
gcttccatgg ggaattggaa agcaataaga tagcatcccc tagaagccca gtgaagtctg    98880
ggacaggacc cttctctgag ctctgacttg ctcttggaaa cacttcgagg cttagcctcc    98940
ccactttgtt tcccaagagt gtgacctgtt cccctccaaa cacccccttc tcctccaggg    99000
ccatgcccac ccgtcaaaat cccccacggg caggacgaac tgtgggtgtc agtcaccatc    99060
tatcctgcat cctggttcca gggcccccccc cagccccgcc tccataggga caggcgtgca   99120
```

-continued

```
gacacccgtc cctggctgct tcctcttgtg gaatgggttc aaaagtaagc agtgttgttt    99180
acactgacaa actgaaaaaa aaagaaaaag agataacatt ggaggcttgg cacagtggct    99240
catgcctgta atcccagcac tttgggaggc taaggtggga ggatgtcccc agcccaagag    99300
ttctagacca gcctgggcaa catagcaaga ccccatctca aaaaaaaat ttaattggcc     99360
aggcagaggt gggaggatca cttgaaccca aagggtggag gctgcagtga gccgtgatgg    99420
caccactgca ctccagccag ggcaacagag ggagaccctg tctctaaaac aaacaaacaa    99480
acaaacaaac aaagagtta acattggcca gattaggatt caccagatag tgttaatatt     99540
agtttgattt gagactttaa tcagaaagca catgtgtggt gggggtgggt gtaacctaag    99600
tcaggtagaa tctttccaac ttggggggggg cacactcctg attgtagcca tatgagtctg    99660
tcagtgtggt ggaagagacc atgggttaat gggcaggtaa aaaagcacct tgcctggaat    99720
tgagtagaaa gtaaggccct tcagaccccg tgacacactt ggggacattt tcttgagtaa    99780
catcctaaga ttcatgtacc ttgatgatct ccatcaactt actcatgtga agcacctta     99840
aaccagtcgt ctccaaattc aggggcacag taacatccaa caggctggag aaagaacgta    99900
ctagaacttc cattcctttt tcatgtcctc ttctaaaagc tttgtcaggg ccaggcgcgg    99960
tggctcacgc ctgtaatccc agcactttgg gaggccgaga cgggtggatc acgaggtcag   100020
gagatcgaga ccatcctggc taacacagtg aaaccccatc tctactaaaa atacaaaaaa   100080
acgagccggg cgtggtggtg ggcgcctgta gtcccagcta ctcgggaggc tgaggcagga   100140
gaatggcgtg aacccaggag gcagagcttg cagtgagccg agattgcacc actgcagtcc   100200
agcctgggcg acagagcgag actccgtctc aaaaaagaaa agaaaaaga aaagaactg     100260
tgattgggga ggacggtcac tttcctgttc ttactgatca gaagggatat aagggtacc    100320
tgattcaaac agcctggaga tcactgcttt caaccattac ctgccttatt tattttagt    100380
tactgtcctt ttttcagttt gtttccctcc tccatgtgct gactttatt ttgatttat     100440
ttatgtttat gttaagaca tccacacgtt cctctgctaa aaccttgaaa ataggcctt     100500
gccttagccc caaacacccc actcctggta gctcagaccc tctgatccaa ccctccagcc   100560
ctgctgtgtg cccagagcca ccttcctctc ctaaacacgt ctcttctgtc acttcccgaa   100620
ctggcagttc tggagcaaag gagatgaaac tcaaggtaag gaaaccacct tgaaaagaa    100680
ccaggctgct ctgctgtggt ttgcaaatgt gggtttgtt tatttgtttt ttagcctcaa    100740
agacctttct tcaaatgagt tctggcatag aagcaccgtg taaaatagtt agaattctgg   100800
gcaaagggga aaagagagct gggggccatc cctctcagca ccccacaggc tctcatagca   100860
gcagctccta agacacctgg tgggaccttg gtttcgaaat cgctactcta aggctgggca   100920
cggtggctca cacctgtaat cccagctctt taggaggccg aggagggtgg atcacctgag   100980
atcaggagtt cgagaccagc ctggctaaca tggcaaaacc ctgtctctac taaaaataca   101040
aaaattagcc gggcgtggtg ttatgcgtgg tggtaatcgc agctactcgg gaggctgagg   101100
cacaaggatt gcttgaaccc cagaggcaga ggttgtagtt agctccagct tgggcgacag   101160
agcaagaccc tgtcgcaaaa attgtttaaa aaacaaaccc aaaattgcta ctctcattgg   101220
gttcctttgc ccattcctga ttttggcaag agaaatgctt ccagattgcc ctgatctggg   101280
taggacagca tcacgccata gcaacactgc cccgtgagct cactgccccc tcaactagct   101340
tgtggtcctt ggttaatgtc agtttctttt ttgagtttgt gttatgtcta agggtcatct   101400
gctgggtaac ggaacccagg gactgcccta gtccctagac tgtgccatgc ccgactctgc   101460
cagctttgtc agtgatgctg gtgctcgcct cctcgggtgc tcgcctggtc tgagcacacc   101520
```

```
caaggagttc ttgaggcctt agggttgttt gcgagagaat gaaagaacac gacctagctc    101580
tctttagcat ccttggtcag gttcaacact gcccccaggg gcctctggtg gagccaacca    101640
ccatcagcca aataaatcca taattagagt cagaaaatgg atgtctgcat atgtgtagtg    101700
cactaatgtc ctgccgatga ttgacatgga gtggagagtg acctgatcat tgctgtgagc    101760
tctgctggcc ttggcacaac tcatgctgat aactaatgca cacagttcct ctgggaggaa    101820
atgtcctcag ggaacttgga gtttgggtgg ggatgtgggt ttgtgtgccc agcaagccct    101880
tgtggttgta gcagacacta gtggcatcta ggaggcaaag ggtcacccca gtcttagcca    101940
cgttttgagt caaggtggcg gagtggggct ggtgttgact cttggtggca gtaacttttc    102000
ccaatggtga aaacccctc tatcatgttt catttacagg gggctgatgg taaaacgaag    102060
atcgccacac cgcggggagc agcccctcca ggccagaagg gccaggccaa cgccaccagg    102120
attccagcaa aaccccgcc cgctccaaag acaccaccca gctctggtaa gagaacgtt      102180 ctcttgaatc ttagaggaag ctgaagctct cagaggtaca gccttcattt taggaggcct    102240
taggccactg agaatgaata acccctggca gctggtcagc agcttgcagt ttactaagca    102300
ctggagtctt cattgccttc tcagtccttt tgatttctga ggcaaatgtt gaatccctac    102360
cttttttttt tttttcttt tgagacagag tttcgctttt gttatccagg ccggagtgca     102420
gtggtgtgat ctcagctcac tgcatcctcc acctcccagg ttcaagcgat tctcctacct    102480
cagcctccct agtagctggg attacaggca cctgccacta tgcccggcta atttttttgta   102540 tttttagtag agacagggtt tcaccatgtt ggccaggctg gtctcgaacg cctgacctca    102600
ggtgatccac ctgcctcggc ctcccaaagt gctgggatta caggcatgag ccaccactcc    102660
cagcctgaat cctcactttt tatcaatgaa gaaattgagg ctgattctgc agcatgataa    102720 aaaaaatac agaaaaagga aaaaaagaa agaaatcgag cctctgagag tttgcttgac      102780
tgagtctaac cagctcattt taaacccgag gaaaatgcag tcacatgact actaagtggc    102840
agctctcgga gcctctctgg ccccaagtcc agggttccat agaggcagcc ccagcatggc    102900
atgttttcag tccccaaatg agactctgga gacaaatgtc tctggagaca gagcagcagc    102960
ctggataagt cacaatgggt gacgtcactc agggctcaac ccctgggcag cttaacttgc    103020
tagggacgtt aggagtctgc tgcaaaacct gagggtctta gctgagcagt cacaggctgg    103080
gcccgttgcc ctgggctcct gtgagtaaaa cccagtcaat tttgagtacc cagtaaggca    103140
tccattgagt tattttgcag ccaggagtgc tattaagaac agtcgcggct gggcgtggtg    103200
gctcatgcct gtaatcccag cactttggga ggccaaggtg ggcggatcac ctgaggtcag    103260
gagttcgaga ccagcttggc caacatggca aaaccccgtc tctaataaaa atacaaaata    103320
attagctggg cgtggtggcg ggcgcctgta atcccagctt tcaggaggg tgaggaagga     103380 gaatcacttg aacccaggag gcagaggttg cagtgagctg agatcgcacc attgcactcc    103440
agcctggatg acaaaagtga gattccttct caaaaaaaaa aaaaaaaaa cagtcgtcct    103500 ctttggggat tagggacagc ctgcctgcct gcccgagcac ttctctcttc cattgcccca    103560
gtgaagtatt ccaggcccct gggtttagac tctgcaccat gtagggggtgt ctgacctgca   103620 cttgctcctt ggtggcacgg gcagcctatg gcacttgctg cgggctgtga ccaaagcctg    103680
gcctggatct tggatcttgg tgactctgct tctccctggc ctgagggagc tgcccagagc    103740
ctgcccacca cctgctgcgt gtctttgcgg tggcatttct cgcacacatg ccgtgcggtg    103800 gcaccccaa ggatggccat tcactaaggc ccattgtttt tgtcttttcg cttcgtgttt      103860
```

```
tctggcctgg tgttttttctc atatacatgt gatccaggga taattcccag aattttgaca  103920
ggattttaag tagcgtttgg atcctgctgt ttttttttca cttaacatcg ggccagttga  103980
ctcacactct gttttttgtt gttgttttttt tgagacggag tctcactgtg tcacccaggc  104040
tgaagtgcag tggcacaatc ttggcatact gcaacctctg cttcccaaat tcaagcagtt  104100
ttcctgcctc agcctcctga gtagctggga ctacaggcac aggccaccac gccctgctaa  104160
tttttgtatt tttagtaaag acagggtttc accattttgg ccagcctagt ctcgaactcc  104220
tgacctcaag tgatccgccc acctcggcct cccaaagtgc tgggattaca ggggactcac  104280
actttgtaac aacctgaaac aacgtgatgc atttcccttt gggtcttacc tgctcttcgg  104340
tggctgcctg caggtggaga gaccctcccc cttgggcccc tcgaccttgt ttcagaatgg  104400
ggcccctgct gggccagctg tgggtgcctg ccacgtgaag gactcattaa ggccctgttt  104460
aagcctgatg ataataaggc tttcgtggat ttttctcttt aagcgactaa gcaagtccag  104520
agaagaccac cccctgcagg gcccagatct gagagaggta ctcgggagcc tacttcgctg  104580
ggagcagcct ccctttgcgt gtgtggccat tcactggctt gtgtttctag agccgggagg  104640
acccttttct gcaatgcagg gttcacacag ggttcgcagc ctgaagatgg agcagtccga  104700
attctcttcc ctgtgcagtt tgcgcagctg tgttttgtctg atgggctttc taatcctgtg  104760
tgctctcctt gacttcaggg acaatggcat tacaggcatg agccaccatg cctggctgtc  104820
tccctatgtt tcagatgaag acataggctt aaggaggtca ggtgacttgc ccacgaccac  104880
tctgtaaata gaggcatga aaagtatttg gagccaccac caccaagccc actggtcacc  104940
ctgggtctct gaagtcaggg aggcaggagg atgggaggtc tgaggaggca gagaggctga  105000
gcctggaggc cctggaggcc gaggccccat ctgttgtttc cttatgtgga aaataagagg  105060
cttcatttgt cctattgcca cagagcgtac tacttcagga acatccaaga catgaaatc  105120 cgcagggcac ggtggctcac gtctataatc ccggcacttt gggaggttga ggtgggagaa  105180
tcgcttgagg ccagaagttc aagaccagcc tgagcaacat agtcagaccc cgtctctata  105240
aaaaacatta ttttttaaaaa agacatggaa gtcaaattct aaaaactggt gctggctggg  105300
tgcggtggct catgcctata atcccagcac tttgggaggc cgaggcgggt ggatcacctg  105360
aggtcaggag ttcaagacca gcctggccaa catggtaaaa cctctactaa agaaatcttt  105420
actgaaaata caaaaatcca gtctctacta aaataagtct ctactaaaaa tacaaaaatt  105480
agccaggcgt ggtgctgcac acctgtaata tcagctactc gggaggctga ggcaggagac  105540
tcgcttgatc ccatgcagcg gaggttcag tgagccgaga tcacgccatt gcactccagc  105600
ctgggcatca gaataagact ccgtctcaaa aaaaaaacca caaaaaaaca aacaacaac  105660 aaaagaaaac tagtgcttat tcgtcactgg ccaagctgcc cattggctac atgggtgctt  105720
caaagagctg cccttctcca ggtctggcca gcaggtatgt gttacagcaa atgcctgggg  105780
cagcggcagg ggcattgctg cgggaagctt ctggacttgc aggaaagcta agttctcaga  105840
ctgcagggga gctaagcaca cctcggcaca gggtgaggcc tgcggttctc agacttcagt  105900
ctttgtggag cttgagaaaa atgaggcttt gcaggtccca cccctagaga ttctgctcta  105960
tccactcttg aaggggatcg agaaatttgc attttgcaac tcccactttc ctccttgaaa  106020
gctccggaga ttctgacgca gggttccgtg ggccacactt tggaaaatac agacccatga  106080
gatagaatac cagactgttg aagtgtaacg ggggcctggg aagtgcagta acagaagcaa  106140
gtttgagggt aaaggacacc cagaggaggg agggacagca tctgcatgga gaggagaaga  106200
gaccccccag cagcttccag ggtgttggaa gggtgcgcta gtaactgcta tgcatggcag  106260
```

```
gtggggaact gtacgtcagg gcacagcagc atgaagcggt atggctcgtg tggacagcta  106320
gggacaggca ggcgtggagc aggcatcctg ttctgaaggc caaatcccac agaggagcca  106380
gggtgctggc aggagccctg aactagccga acagctgaac agctgaacat tcaccctgtg  106440
gggaaagggt cagaagcgtc caggcttgag ggcacagctg ggtctcgtca ctgcatcacc  106500
cttatttagg ataaaggccc tgaagaattg tattagaggt tggcaaagca tatctaccac  106560
ctcctggagc cacgctggcc gcagggatta taattatttc cattttcaaa ttaaggcctc  106620
tgagctcaga gagggaagt tacttgtctg aggccacaca gcttgttgga gcccatctct  106680
tgacccaaag actgtggagc cgagttggcc acctctctgg gagcgggtat tggatggtgg  106740
ttgatggttt tccattgctt tcctgggaaa ggggtgtctc tgtccctaag caaaaaggca  106800
gggaggaaga gatgcttccc cagggcagcc gtctgctgta gctgcgcttc caacctggct  106860
tccacctgcc taacccagtg gtgagcctgg gaatggaccc acgggacagg cagcccccag  106920 ggcctttttct gaccccaccc actcgagtcc tggcttcact cccttccttc cttcccaggt  106980
gaacctccaa aatcagggga tcgcagcggc tacagcagcc ccggctcccc aggcactccc  107040
ggcagccgct cccgcacccc gtcccttcca accccaccca cccgggagcc caagaaggtg  107100
gcagtggtcc gtactccacc caagtcgccg tcttccgcca agagccgcct gcagacagcc  107160
cccgtgccca tgccagacct gaagaatgtc aagtccaaga tcggctccac tgagaacctg  107220
aagcaccagc cgggaggcgg gaaggtgaga gtggctggct gcgcgtggag gtgtgggggg  107280
ctgcgcctgg agggtaggg ctgtgcctgg aagggtaggg ctgcgcctgg aggtgcgcgg  107340
ttgagcgtgg agtcgtggga ctgtgcatgg aggtgtgggg ctccccgcac ctgagcaccc  107400
ccgcataaca ccccagtccc ctctggaccc tcttcaagga agttcagttc tttattgggc  107460
tctccactac actgtgagtg ccctcctcag gcgagagaac gttctggctc ttctcttgcc  107520
ccttcagccc ctgttaatcg dacagagatg gcagggctgt gtctccacgg ccggaggctc  107580
tcatagtcag ggcacccaca gcggttcccc acctgccttc tgggcagaat acactgccac  107640
ccataggtca gcatctccac tcgtgggcca tctgcttagg ttgggttcct ctggattctg  107700
gggagattgg gggttctgtt ttgatcagct gattcttctg ggagcaagtg ggtgctcgcg  107760
agctctccag cttcctaaag gtggagaagc acagacttcg ggggcctggc ctggatccct  107820
ttccccattc ctgtccctgt gcccctcgtc tgggtgcgtt agggctgaca tacaaagcac  107880
cacagtgaaa gaacagcagt atgcctcctc actagccagg tgtgggcggg tgggtttctt  107940
ccaaggcctc tctgtggccg tgggtagcca cctctgtcct gcaccgctgc agtcttccct  108000
ctgtgtgtgc tcctggtagc tctgcgcatg ctcatcttct tataagaaca ccatggcagc  108060
tgggcgtagt ggctcacgcc tataatccca gcactttggg aggctgaggc aggcagatca  108120
cgaggtcagg agttcgagac caacctgacc aacagggtga aacctcgtct ctactaaaaa  108180
tacaaaaata cctgggcgtg gtggtggtgc gcgcctataa tcccagctac tcaggaggct  108240
gaggcaggag aatcgcttga acccaggagg cagaggttgc agtgagccga gatagtgcca  108300
ctgcactcca gtttgagcaa cagagcgaga ctctgtctca aaacaaaata aaacaaacca  108360 aaaaaccca ccatggctta gggcccagcc tgatgacctc attttcact tagtcacctc  108420 tctaaaggcc ctgtctccaa atagagtcac attctaaggt acggggtgt tgggagggg  108480 ggttagggct tcaacatgtg aatttgcggg gaccacaatt cagcccagga ccccgctccc  108540
gccacccagc actggggagc tggggaaggg tgaagaggag gctgggggtg agaaggacca  108600
```

```
cagctcactc tgaggctgca gatgtgctgg gccttctggg cactgggcct cggggagcta   108660 ggggctttc tggaaccctg ggcctgcgtg tcagcttgcc tccccacgc aggcgctctc     108720 cacaccattg aagttcttat cacttgggtc tgagcctggg gcatttggac ggagggtggc   108780
caccagtgca catgggcacc ttgcctcaaa ccctgccacc tcccccacc caggatcccc    108840 cctgccccg aacaagcttg tgagtgcagt gtcacatccc atcgggatgg aaatggacgg    108900
tcgggttaaa agggacgcat gtgtagaccc tgcctctgtg catcaggcct cttttgagag   108960
tccctgcgtg ccaggcggtg cacagaggtg gagaagactc ggctgtgccc cagagcacct   109020
cctctcatcg aggaaaggac agacagtggc tcccctgtgg ctgtggggac aagggcgag    109080 ctccctggaa cacaggaggg agggaaggaa gagaacatct cagaatctcc ctcctgatgg   109140
caaacgatcc gggttaaatt aaggtccggc cttttcctgc tcaggcatgt ggagcttgta   109200
gtggaagagg ctctctggac cctcatccac cacagtggcc tggttagaga ccttgggaa    109260 ataactcaca ggtgacccag ggcctctgtc ctgtaccgca gctgagggaa actgtcctgc   109320
gcttccactg gggacaatgc gctccctcgt ctccagactt ccagtcctc attcggttct    109380 cgaaagtcgc ctccagaagc ccatcttgg gaccaccgtg actttcattc tccagggtgc    109440
ctggccttgg tgctgcccaa gaccccagag gggccctcac tggccttttcc tgccttttct   109500 cccattgccc acccatgcac ccccatcctg ctccagcacc cagactgcca tccaggatct    109560
cctcaagtca cataacaagc agcacccaca aggtgctccc ttcccctag cctgaatctg    109620 ctgctccccg tctggggttc cccgcccatg cacctctggg ggccctggg ttctgccata    109680 ccctgccctg tgtcccatgg tggggaatgt ccttctctcc ttatctcttc ccttcccta    109740 aatccaagtt cagttgccat ctcctccagg aagtcttcct ggattcccct ctctcttctt    109800
aaagcccctg taaactctga ccacactgag catgtgtctg ctgctcccta gtctgggcca    109860
tgagtgaggg tggaggccaa gtctcatgca ttttttgcagc ccccacaaga ctgtgcaggt   109920
ggccggccct cattgaatgc ggggttaatt taactcagcc tctgtgtgag tggatgattc    109980
aggttgccag agacagaacc ctcagcttag catgggaagt agcttccctg ttgaccctga   110040
gttcatctga ggttggcttg gaaggtgtgg gcaccatttg gcccagttct tacagctctg    110100
aagagagcag caggaatggg gctgagcagg gaagacaact ttccattgaa ggccccttc    110160 agggccagaa ctgtccctcc caccctgcag ctgccctgcc tctgcccatg aggggtgaga   110220
gtcaggcgac ctcatgccaa gtgtagaaag gggcagacgg gagccccagg ttatgacgtc   110280
accatgctgg gtggaggcag cacgtccaaa tctactaaag ggttaaagga gaaagggtga   110340
cttgactttt cttgagatat tttgggggac gaagtgtgga aaagtggcag aggacacagt   110400
cacagcctcc cttaaatgcc aggaaagcct agaaaaattg tctgaaacta aacctcagcc   110460
ataacaaaga ccaacacatg aatctccagg aaaaagaaa aagaaaaatg tcatacaggg    110520
tccatgcaca agagccttta aaatgacccg ctgaagggtg tcaggcctcc tcctcctgga   110580
ctggcctgaa ggctccacga gcttttgctg agacctttgg gtccctgtgg cctcatgtag   110640
tacccagtat gcagtaagtg ctcaataaat gtttggctac aaaagaggca agctggcgg    110700 agtctgaaga atccctcaac cgtgccgaa cagatgctaa caccaaaggg aaaagagcag    110760
gagccaagtc acgtttggga acctgcagag gctgaaaact gccgcagatt gctgcaaatc   110820 attggggaa aaacggaaaa cgtctgtttt ccccttttgtg cttttctctg ttttcttctt    110880
tgtgcttttc tctgttttca ggatttgcta cagtgaacat agattgcttt ggggcccaa    110940 atggaattat tttgaaagga aaatgcagat aatcaggtgg ccgcactgga gcaccagctg   111000
```

```
ggtagggta gagattgcag gcaaggagga ggagctgggt ggggtgccag gcaggaagag   111060
cccgtaggcc ccgccgatct tgtgggagtc gtgggtggca gtgttccctc cagactgtaa   111120
aagggagcac ctggcgggaa gagggaattc ttttaaacat cattccagtg cccgagcctc   111180
ctggacctgt tgtcatcttg aggtgggcct ccctgggtg actctagtgt gcagcctggc   111240
tgagactcag tggccctggg ttcttactgc tgacacctac cctcaacctc aaccactgcg   111300
gcctcctgtg caccctgatc cagtggctca ttttccactt tcagtccag ctctatccct   111360
atttgcagtt tccaagtgcc tggtcctcag tcagctcaga cccagccagg ccagcccctg   111420
gttcccacat ccccttttgcc aagctcatcc ccgcccgtgtt tggcctgcgg gagtgggagt   111480
gtgtccagac acagagacaa aggaccagct tttaaaacat tttgttgggg ccaggtgtgg   111540
tggctcacac ctaatcccaa cacctgggga ggccaaggca gaaggatcac ttgagtccag   111600
gagttcaaga ccagcctggg caacataggg agaccctgtc tctacaattt ttttttttaat   111660
tagctgggcc tgttggcact ctcctgtagt tccagctact ctagaggctg aggtgggagg   111720
actgcttgag cctgggaggt cagggctgca atgagccatg ttcacaccac tgaacgccag   111780
cctgggcgag accctgtatc aaaaaagtaa agtaaaatga atcctgtacg ttatattaag   111840
gtgccccaaa ttgtacttag aaggatttca tagtttaaaa tacttttgtt atttaaaaaa   111900
ttaaatgact gcagcatata aattaggttc ttaatggagg ggaaaaagag tacaagaaaa   111960
gaaataagaa tctagaaaca aagataagag cagaaataaa ccagaaaaca caaccttgca   112020
ctcctaactt aaaaaaaaaa atgaagaaaa cacaaccagt aaaacaacat ataacagcat   112080
taagagctgg ctcctggctg ggcgcggtgg cgcatgcctg taatcccaac actttgggag   112140
gccgatgctg gaggatcact tgagaccagg agttcaaggt tgcagtgagc tatgatcata   112200
ccactacacc ctagcctggg caacacagtg agactgagac tctattaaaa aaaaaatgct   112260
ggttccttcc ttatttcatt ccttattca ttcattcaga caacatttat ggggcacttc   112320
tgagcaccag gctctgtgct aagagctttt gccccccaggg tccaggccag gggacagggg   112380
caggtgagca gagaaacagg gccagtcaca gcagcaggag gaatgtagga tggagagctt   112440
ggccaggcaa ggacatgcag ggggagcagc ctgcacaagt cagcaagcca gagaagacag   112500
gcagacccctt gtttgggacc tgttcagtgg cctttgaaag gacagccccc acccggagtg   112560
ctgggtgcag gagctgaagg aggatagtgg aacactgcaa cgtggagctc ttcagagcaa   112620
aagcaaaata aacaactgga ggcagctggg gcagcagagg gtgtgtgttc agcactaagg   112680
ggtgtgaagc ttgagcgcta ggagagttca cactggcaga agagaggttg gggcagctgc   112740
aagcctctgg acatcgcccg acaggacaga gggtggtgga cggtggccct aagagaggc   112800
tcagttcagc tggcagtggc cgtgggagtg ctgaagcagg caggctgtcg gcatctgctg   112860
gggacggtta agcagggtg agggcccagc ctcagcagcc cttcttgggg ggtcgctggg   112920
aaacatagag gagaactgaa gaagcaggga gtcccaggtt ccatgcaggg cgagagaaa   112980
gttgctcatg tggggcccag gctgcaggat caggagaact ggggaccctg tgactgccag   113040
cggggagaag ggggtgtgca ggatcatgcc cagggaaggg cccagggggcc caagcatggg   113100
ggggcctggt tggctctgag aagatggagc taaagtcact ttctcggagg atgtccaggc   113160
caatagttgg gatgtgaaga cgtgaagcag cacagagcct ggaagcccag gatggacaga   113220
aacctacctg agcagtgggg cttttgaaagc cttgggggcgg ggggtgcaat attcaagatg   113280
gccacaagat ggcaatagaa tgctgtaact ttcttggttc tgggccgcag cctgggtggc   113340
```

```
tgcttccttc cctgtgtgta ttgatttgtt tctcttttt gagacagagt cttgctgggt   113400
tgcccaggct ggagtgcagt ggtgcgatca tagctcactg cagccttgaa gtcctgagct   113460
caagagatcc ttccacctca gcctcctgag tagttgggac cacaggcttg caccacagtg   113520
cccaactaat ttcttatatt ttttgtagag atggggtttc actgtgtcgc ccaggatggt   113580
cttgaactcc tgggctcaag tgatcctcct gcctcagcct cgcaaattgc tgggattaca   113640
ggtgtgagcc accatgcccg accttctctt tttaagggcg tgtgtgtgtg tgtgtgtgtg   113700
tgggcgcact ctcgtcttca ccttccccca gccttgctct gtctctaccc agtcacctct   113760
gcccatctct ccgatctgtt tctctctcct tttaccctc ttcctccct cctcatacac     113820
cactgaccat tatagagaac tgagtattct aaaaatacat tttatttatt tatttgaga   113880
cagagtctca ctctgtcacc caggctggag tgcagtggtg caatctcggc tcactgcaac   113940
ctccgcctcc caggttgaag caactctcct gcctcagcct ccctagtagc tgggattaca   114000
agcacacacc accatgccta gcaaatttt atattttag tagaggagga gtgtcaccat     114060
gtttgccaag ctggtctcaa actcctggcc tcaggtgatc tgcctacctt ggtctcccaa   114120
agtgctggga ttacaggtgt gagccaccac gcctgccctt aaaaatacat tatatttaat   114180
agcaaagccc cagttgtcac tttaaaaagc atctatgtag aacatttatg tggaataaat   114240
acagtgaatt tgtacgtgga atcgtttgcc tctcctcaat cagggccagg gatgcaggtg   114300
agcttgggct gagatgtcag accccacagt aagtgggggg cagagccagg ctgggaccct   114360
cctctaggac agctctgtaa ctctgagacc ctccaggcat ctttcctgt acctcagtgc     114420
ttctgaaaaa tctgtgtgaa tcaaatcatt ttaaaggagc ttgggttcat cactgtttaa   114480
aggacagtgt aaataattct gaaggtgact ctaccctgtt atttgatctc ttctttggcc   114540
agctgactta acaggacata gacaggtttt cctgtgtcag ttcctaagct gatcaccttg   114600
gacttgaaga ggaggcttgt gtgggcatcc agtgcccacc ccgggttaaa ctcccagcag   114660
agtattgcac tgggcttgct gagcctggtg aggcaaagca cagcacagcg agcaccaggc   114720
agtgctggag acaggccaag tctgggccag cctgggagcc aactgtgagg cacggacggg   114780
gctgtggggc tgtggggctg caggcttggg gccaggagg gagggctggg ctctttggaa     114840
cagccttgag agaactgaac ccaaacaaaa ccagatcaag gtctagtgag agcttagggc   114900
tgctttgggt gctccaggaa attgattaaa ccaagtggac acacacccc agccccacct     114960
caccacagcc tctccttcag ggtcaaactc tgaccacaga catttctccc ctgactagga   115020
gttcctgga tcaaaattgg gagcttgcaa cacatcgttc tctcccttga tggttttgt     115080
cagtgtctat ccagagctga agtgtaatat atatgttact gtagctgaga aattaaattt   115140
caggattctg atttcataat gacaaccatt cctcttttct ctcccttctg taaatctaag   115200
attctataaa cggtgttgac ttaatgtgac aattggcagt agttcaggtc tgctttgtaa   115260
ataccctgt gtctattgta aaatctcaca aaggcttgtt gccttttttg tggggttaga     115320
acaagaaaaa gccacatgga aaaaaattt cttttttgtt tttttgtttg cttgtttttt     115380
tgagacagag tttcactctg tcgcccaggc tggagtgcag tggtgcgatc tccgcccact   115440
gcaagctcca cctcccgggt tcatgctatt ctcctgtctc agcctcccaa gtagctggga   115500
ctgcaggtgc ccgccaccac acctggctaa tttttttgta ttttagtag agacgggtt     115560
tcaccgtgtt agccaggatg gtctcaatct cctgacctcg tcatctgcct gcctcggcct   115620
cccaaagtgc tgagattaca ggcgtgagcc accgtgcccg gccagaaaaa acatttcta     115680
agtatgtggc agatactgaa ttattgctta atgtcctttg attcatttgt ttaatttctt   115740
```

```
taatggatta gtacagaaaa caaagttctc ttccttgaaa aactggtaag ttttctttgt   115800
cagataagga gagttaaata acccatgaca tttcccttt  tgcctcggct tccaggaagc   115860
tcaaagttaa atgtaatgat cactcttgta attatcagtg ttgatgccct tcccttcttc   115920
taatgttact ctttacattt tcctgcttta ttattgtgtg tgttttctaa ttctaagctg   115980
ttcccactcc tttctgaaag caggcaaatc ttctaagcct tatccactga aaagttatga   116040 ataaaaatg  atcgtcaagc ctacaggtgc tgaggctact ccagaggctg aggccagagg   116100
accacttgag cccaggaatt tgagacctgg gctgggcagc atagcaagac tctatctcca   116160
ttaaaactat ttttttttat ttaaaaaata atccgcaaag aaggagttta tgtgggattc   116220
cttaaaatcg gagggtggca tgaattgatt caaagacttg tgcagagggc gacagtgact   116280
ccttgagaag cagtgtgaga aagcctgtcc cacctccttc cgcagctcca gcctgggctg   116340
aggcactgtc acagtgtctc cttgctggca ggagagaatt tcaacattca ccaaaaagta   116400
gtattgtttt tattaggttt atgaggctgt agccttgagg acagcccagg acaactttgt   116460
tgtcacatag atagcctgtg ctacaaact  ctgagatcta gattcttctg cggctgcttc   116520
tgacctgaga aagttgcgga acctcagcga gcctcacatg gcctccttgt ccttaacgtg   116580
gggacggtgg gcaagaaagg tgatgtggca ctagagattt atccatctct aaaggaggag   116640
tggattgtac attgaaacac cagagaagga attacaaagg aagaatttga gtatctaaaa   116700
atgtaggtca ggcgctcctg tgttgattgc agggctattc acaatagcca agatttggaa   116760
gcaacccaag tgtccatcaa cagacaaatg gataaagaaa atgtggtgca tatacacaat   116820
ggaatactat tcagccatga aaaagaatga gaatctgtca tttgaaacaa catggatgga   116880
actggaggac attatgttaa gtgaaataag ccagacagaa ggacagactt cacatgttct   116940
cacacatttg tgggagctaa aaattaaact catggagata gagagtagaa ggatggttac   117000
cagaggctga ggagggtgga ggggagcagg gagaaagtag ggatggttaa tgggtacaaa   117060
aacgtagtta gcatgcatag atctagtatt ggatagcaca gcagggtgac gacagccaac   117120
agtaatttat agtacattta aaacaacta  aaagagtgta actggactgg ctaacatggt   117180
gaaaccccgt ctctactaaa aatacaaaaa ttagctgggc acggtggctc acgcctgtaa   117240
tcccagcact ttgggaggcc gaggcgggcc gatcacgagg tcaggagatc gagaccatcc   117300
tagctaacat ggtgaaaccc cgtctctact acaaatacaa aaaaagaaa  aaattagccg   117360 ggcatggtgg tgggcgcctg tagtcccagc tactcgggag gctgaggcag gagaatggcg   117420
tgaacccggg aggcggagct tgcagtgagc cgagatcgcg ccactgcact ccagcctggg   117480
cgacaaggca agattctatc tcaaaaaaat aaaaataaaa taaaataaaa taataaaata   117540
aaataaaata aaataaaata aaataaataa aataaaatgt ataattggaa tgtttataac   117600
acaagaaatg ataaatgctt gaggtgatag atacccccatt caccgtgatg tgattattgc   117660
acaatgtatg tctgtatcta aatatctcat gtaccccaca agtatataca cctactatgt   117720
acccatataa atttaaaatt aaaaaattat aaaacaaaaa taaataagta aattaaaatg   117780
taggctggac accgtggttc acgcctgtaa tcccagtgct tgtgaggct  gaggtgagag   117840 aatcacttga gcccaggagt ttgagaccgg cctgggtgac atagcgagac cccatcatca   117900
caaagaattt ttaaaaatta gctgggcgtg gtagcacata ccggtagttc cagctacttg   117960
ggagaccgag gcaggaggat tgcttgagcc caggagttta aggctgcagt gagctacgat   118020
ggcgccactg cattccagcc tgggtgacag agtgagagct tgtctctatt ttaaaaataa   118080
```

```
taaaaagaat aaataaaaat aaattaaaat gtaaatatgt gcatgttaga aaaaatacac 118140
ccatcagcaa aaaggggta aaggagcgat ttcagtcata attggagaga tgcagaataa 118200
gccagcaatg cagtttcttt tattttggtc aaaaaaaata agcaaaacaa tgttgtaaac 118260
acccagtgct ggcagcaatg tggtgaggct ggctctctca ccagggctca cagggaaaac 118320
tcatgcaacc cttttagaaa gccatgtgga gagttgtacc gagaggtttt agaatattta 118380
taactttgac ccagaaattc tattctagga ctctgtgtta tgaaaataac ccatcatatg 118440
gaaaaagctc ctttcagaaa gaggttcatg ggaggctgtt tgtatttttt ttttctttgc 118500
atcaaatcca gctcctgcag gactgtttgt attattgaag tacaaagtgg aatcaataca 118560
aatgttggat agcaggggaa caatattcac aaaatggaat gggacatagt attaaacata 118620
gtgcttctga tgaccgtaga ccatagacaa tgcttaggat atgatatcac ttcttttgtt 118680
gttttttgta ttttgagacg aagtctcatt ctgtcaccca ggctggagtt cagtggcgcc 118740
atctcagctc actgcaacct ccatctcccg ggttcaagct attctccttc ctcaacctcc 118800
cgagtagctg ggttgcgcac caccatgcct ggctaacttt tgtattttta gtacagacgg 118860
ggtttcacca cgttggccag gctgctcttg aactcctgac gtcaggtgat ccaccagcct 118920
tgacctccca aagtgctagg attacaggag ccactgtacc cagcctagga tatgatatca 118980
cttcttagag caagatacaa aattgcatgt gcacaataat tctaccaagt ataggtatac 119040
aggggtagtt atatataaat gagacttcaa ggaaatacaa caaaatgcaa tcgtgattgt 119100
gttagggtgg taagaaaacg gttttttgctt tgatgagctc tgttttttaa aatcgttata 119160
ttttctaata aaaatacata gtcttttgaa ggaacataaa agattatgaa gaaatgagtt 119220
agatattgat tcctattgaa gattcagaca agtaaaatta aggggaaaaa aaacgggatg 119280
aaccagaagt caggctggag ttccaacccc agatccgaca gcccaggctg atggggcctc 119340
cagggcagtg gtttccaccc agcattctca aaagagccac tgaggtctca gtgccatttt 119400
caagatttcg gaagcggcct gggcacggct ggtccttcac tgggatcacc acttggcaat 119460
tatttacacc tgagacgaat gaaaaccaga gtgctgagat tacaggcatg gtggcttacg 119520
cttgtaatcg gctttgggaa gccgaggtgg gctgattgct tgagcccagg agtttcaaac 119580
tatcctggac aacatagcat gacctcgtct ctacaaaaaa tacaaaaaat ttgccaggtg 119640
tggtggcatg tgcctgtggt cccagctact tgggaggctg aagtaggaga atccctgag 119700 ccctgggaag tcgaggctgc actgagccgt gatggtgtca ctgcactcca gcctgggtga 119760
caaagtgaga ccctatctca caagaaaaa aaacaaaaca aaaacccaa agcacactgt 119820 ttccactgtt tccagagttc ctgagaggaa aggtcaccgg gtgaggaaga cgttctcact 119880
gatctggcag agaaaatgtc cagtttttcc aactccctaa accatggttt tctatttcat 119940
agttcttagg caaattggta aaaatcattt ctcatcaaaa cgctgatatt ttcacacctc 120000
cctggtgtct gcagaaagaa ccttccagaa atgcagtcgt gggagaccca tccaggccac 120060
ccctgcttat ggaagagctg agaaaaagcc ccacgggagc atttgctcag cttccgttac 120120
gcacctagtg gcattgtggg tgggagaggg ctggtgggtg gatggaagga gaaggcacag 120180 ccccccttg cagggacaga gccctcgtac agaagggaca ccccacattt gtcttcccca 120240
caaagcggcc tgtgtcctgc ctacggggtc agggcttctc aaacctggct gtgtgtcaga 120300
atcaccaggg gaactttttca aaactagaga gactgaagcc agactcctag attctaattc 120360
taggtcaggg ctagggctg agattgtaaa aatccacagg tgattctgat gcccggcagg 120420
cttgagaaca gccgcaggga gttctctggg aatgtgccgg tgggtctagc caggtgtgag 120480
```

```
tggagatgcc ggggaacttc ctattactca ctcgtcagtg tggccgaaca cattttttcac  120540 ttgacctcag gctggtgaac gctccctct ggggttcagg cctcacgatg ccatccttt  120600 gtgaagtgag gacctgcaat cccagcttcg taaagcccgc tggaaatcac tcacacttct  120660
gggatgcctt cagagcagcc ctctatccct tcagctcccc tgggatgtga ctcgacctcc  120720
cgtcactccc cagactgcct ctgccaagtc cgaaagtgga ggcatccttg cgagcaagta  120780
ggcgggtcca gggtggcgca tgtcactcat cgaaagtgga ggcgtccttg cgagcaagca  120840
ggcgggtcca gggtggcgtg tcactcatcc ttttttctgg ctaccaaagg tgcagataat  120900
taataagaag ctggatctta gcaacgtcca gtccaagtgt ggctcaaagg ataatatcaa  120960
acacgtcccg ggaggcggca gtgtgagtac cttcacacgt cccatgcgcc gtgctgtggc  121020
ttgaattatt aggaagtggt gtgagtgcgt acacttgcga gacactgcat agaataaatc  121080
cttcttgggc tctcaggatc tggctgcgac ctctgggtga atgtagcccg gctccccaca  121140
ttcccccaca cggtccactg ttcccagaag cccttcctc atattctagg agggggtgtc  121200
ccagcatttc tgggtccccc agcctgcgca ggctgtgtgg acagaatagg gcagatgacg  121260
gaccctctct ccggacctg cctgggaagc tgagaatacc catcaaagtc tccttccact  121320
catgcccagc cctgtcccca ggagcccat agcccattgg aagttgggct gaaggtggtg  121380
gcacctgaga ctgggctgcc gcctcctccc ccgacacctg gcaggttga cgttgagtgg  121440 ctccactgtg gacaggtgac ccgtttgttc tgatgagcgg acaccaaggt cttactgtcc  121500
tgctcagctg ctgctcctac acgttcaagg caggagccga ttcctaagcc tccagcttat  121560
gcttagcctg cgccacccctc tggcagagac tccagatgca aagagccaaa ccaaagtgcg  121620
acaggtccct ctgcccagcg ttgaggtgtg cagagaaat gctgcttttg gcccttttag  121680
atttggctgc ctcttgccag gagtggtggc tcgtgcctgt aattccagca ctttgggaga  121740
ctaaggcggg aggttcgctt gagcccagga gttcaagacc agcctgggca acaatgagac  121800
ccctgtgtct acaaaaagaa ttaaaattag ccaggtgtgg tggcacgcac ctgtagtccc  121860
agctacttgg gaggctgagg tgggaggatt gcctgagtcc gggaggcgga agttgcaagg  121920
agccatgatc gcgccactgc acttcaacct aggcaacaga gtgagacttt gtctcaaaaa  121980
acaatcatat aataatttta aaataaatag atttggcttc ctctaaatgt ccccggggac  122040
tccgtgcatc ttctgtggag tgtctccgtg agattcggga ctcagatcct caagtgcaac  122100
tgacccaccc gataagctga ggcttcatca tccctggcc ggtctatgtc gactgggcac  122160
ccgaggctcc tctcccacca gctctcttgg tcagctgaaa gcaaactgtt aacaccctgg  122220
ggagctggac gtatgagacc cttggggtgg gaggcgttga ttttttgagag caatcacctg  122280 gccctggctg gcagtaccgg gacactgctg tggctccggg gtgggctgtc tccagaaaat  122340
gcctggcctg aggcagccac ccgcatccag cccagagggt ttattcttgc aatgtgctgc  122400
tgcttcctgc cctgagcacc tggatcccgg cttctgccct gaggcccctt gagtcccaca  122460
ggtagcaagc gcttgccctg cggctgctgc atggggctaa ctaacgcttc ctcaccagtg  122520
tctgctaagt gtctcctctg tctcccacgc cctgctctcc tgtcccccca gtttgtctgc  122580
tgtgagggga cagaagaggt gtgtgccgcc cccaccctg cccgggccct tgttcctggg  122640
attgctgttt tcagctgttt gagctttgat cctggttctc tggcttcctc aaagtgagct  122700
cggccagagg aggaaggcca tgtgcttttct ggttgaagtc aagtctggtg ccctggtgga  122760
ggctgtgctg ctgaggcgga gctggggaga gagtgcacac gggctgcgtg gccaacccct  122820
```

```
ctgggtagct gatgcccaaa gacgctgcag tgcccaggac atctgggacc tccctggggc    122880
ccgcccgtgt gtcccgcgct gtgttcatct gcgggctagc ctgtgacccg cgctgtgctc    122940
gtctgcgggc tagcctgtgt cccgcgctct gcttgtctgc ggtctagcct gtgacctggc    123000
agagagccac cagatgtccc gggctgagca ctgccctctg agcaccttca caggaagccc    123060
ttctcctggt gagaagagat gccagcccct ggcatctggg ggcactggat ccctggcctg    123120
agccctagcc tctccccagc ctgggggccc cttcccagca ggctggccct gctccttctc    123180
tacctgggac ccttctgcct cctggctgga ccctggaagc tctgcagggc ctgctgtccc    123240
cctccctgcc ctccaggtat cctgaccacc ggccctggct cccactgcca tccactcctc    123300
tcctttctgg ccgttccctg gtccctgtcc cagccccct cccctctca cgagttacct      123360
cacccaggcc agagggaaga gggaaggagg ccctggtcat accagcacgt cctcccacct    123420
ccctcggccc tggtccaccc cctcagtgct ggcctcagag cacagctctc tccaagccag    123480
gccgcgcgcc atccatcctc cctgtccccc aacgtccttg ccacagatca tgtccgccct    123540
gacacacatg ggtctcagcc atctctgccc cagttaactc cccatccata aagagcacat    123600
gccagccgac accaaaataa ttcgggatgg ttccagttta gacctaagtg aaggagaaa     123660
ccaccacctg ccctgcacct tgttttttgg tgaccttgat aaaccatctt cagccatgaa    123720
gccagctgtc tcccaggaag ctccagggcg gtgcttcctc gggagctgac tgataggtgg    123780
gaggtggctg ccccccttgca ccctcaggtg accccacaca aggccactgc tggaggccct   123840
ggggactcca ggaatgtcaa tcagtgacct gcccccagg ccccacacag ccatggctgc     123900
atagaggcct gcctccaagg gacctgtctg tctgccactg tggagtccct acagcgtgcc    123960
ccccacaggg gagctggttc tttgactgag atcagctggc agctcagggt catcattccc    124020
agagggagcg gtgccctgga ggccacaggc ctcctcatgt gtgtctgcgt ccgctcgagc    124080
ttactgagac actaaatctg ttggtttctg ctgtgccacc tacccacccT gttggtgttg    124140
ctttgttcct attgctaaag acaggaatgt ccaggacact gagtgtgcag gtgcctgctg    124200
gttctcacgt ccgagctgct gaactccgct gggtcctgct tactgatggt ctttgctcta    124260
gtgctttcca gggtccgtgg aagcttttcc tggaataaag cccacgcatc gaccctcaca    124320
gcgcctcccc tctttgaggc ccagcagata ccccactcct gcctttccag caagattttt    124380
cagatgctgt gcatactcat catattgatc acttttttct tcatgcctga ttgtgatctg    124440
tcaatttcat gtcaggaaag ggagtgacat ttttacactt aagcgtttgc tgagcaaatg    124500
tctgggtctt gcacaatgac aatgggtccc tgttttttccc agaggctctt ttgttctgca   124560
gggattgaag acactccagt cccacagtcc ccagctcccc tggggcaggg ttggcagaat    124620
ttcgacaaca catttttcca ccctgactag gatgtgctcc tcatggcagc tgggaaccac    124680
tgtccaataa gggcctgggc ttacacagct gcttctcatt gagttacacc cttaataaaa    124740
taatcccatt ttatccttttt tgtctctctg tcttcctctc tctctgcctt tcctcttctc    124800
tctcctcctc tctcatctcc aggtgcaaat agtctacaaa ccagttgacc tgagcaaggt    124860
gacctccaag tgtggctcat taggcaacat ccatcataaa ccaggtagcc ctgtggaagg    124920
tgagggttgg gacgggaggg tgcaggggggt ggaggagtcc tggtgaggct ggaactgctc    124980
cagacttcag aaggggctgg aaaggatatt ttaggtagac ctacatcaag gaaagtgttg    125040
agtgtgaaac ttgcgggagc ccaggaggcg tggtggctcc agctcgctcc tgcccaggcc    125100
atgctgccca agacaaggtg aggcgggagt gaagtgaaat aaggcaggca cagaaagaaa    125160
gcacatattc tcggccgggc gctgtggctc acgcctgtaa ttccagcact tgggaggcc     125220
```

```
aaggtgggtg gatcatgagg tcaggagatt gagaccatcc tggctaacac agtgaaaccc  125280
cgtctctact aaaaatacaa aaaattagcc gggcgtggtg gtgggcgcct gtagtcccag  125340
ctactccgga ggctgaggca ggaaaatggc gtgaacccgg aaggcggagc ttgcagtgag  125400
cggagtgagc agagatcgcg ccactgcact ccagcctggg cgacagagcg agactccgtc  125460
tcaaaaaaaa aaagcacatg ttctcgcttc tttgtgggat ccaggagata gagaatagaa  125520
ggatggttac cagaggctgg gaagggtagt gaggggatgg tggggggatg gtcaatgggt  125580
acaaaaaaaa tagaataaga cctagtattt gatagtgcaa cagggtgact atagtcaata  125640
ataatttaat tgtacattta aaaataacta aagatagcc gggtgcagtg gcttacgtct  125700
gtaatcccag tactttggga ggctgaggtg ggcgtttgag accagcctgg ccaacatggt  125760
gaaaccccat ctctactaaa aatacaaaaa ttagccaggc atggtggcgg cgcctgtaa  125820 tcccagctac tcgggaggct gaggcaggag aatcacttga acctgggagg cagaggttgc  125880
agtgagccga gatcttgcca ctgcactcca gcctgggtga cagtgaaact ccgtctcaaa  125940
aataaaaata aaaatacagc tgggcacggt ggctcacgcc tgtaatccca gcactttggg  126000
aggccgaggc gagcggatca caaggtcagg agatatagac catcctggct aacacggtga  126060
aacccggtct ctactaaaaa tacaaaaaat tagccaggcg tggtggcagg tgcctatagt  126120
cccagctact cacaaggctg aggcaggaga atggcatgaa cctgggaggc ggagcttgca  126180
gtgagccgag attgtgccac tgcactccag cctgggcgag agagtgagac tccgtctcaa  126240
aacaaaaaca aaaacaaaaa caaaacaaa cacacaacaa aaacctaaaa gaatataaat  126300
ggattgtttg taacacaaag gacaaatgtt tgaggggatg gatacccat tttccatgat  126360 gtgattatta tacattgtgt gtctgtatca aaacatctca tgagcccat aaatatatac  126420 acctaactat gtacccacaa aaattaaaaa aatatatttt ttaaggtgaa gagggaggcg  126480
agatgctggc cttaacccct aacccgttgt tctccctgca agctgtccac agggcctctc  126540
agactcgagg ttcagctata tggatgcatg agcttggtcc ccagccaaca tgggagacac  126600
ttcaccatcg gcagcagcta cagcacagga accctgggtc actgccatgt cccctctgtg  126660
actttgttta aacagaaaat gatgctctgg gccggctgtg gtggcccaca cctataatcc  126720
cagcaccttg ggaggcgggg gtgggcagat tgcctgaggt caggagttgg agatcagcct  126780
ggccgacatg gcgaaacccc atgtctacta aaaatacaaa aactagccag gcatggtggc  126840
acatgcctgt aatcccagct acttgggagg ctgaagcagg agaatcactt gaacccagga  126900
ggcagaggct gagtgagcca agatcgtgcc aatgcactcc agcttgggtg agggagtgag  126960
actccgtctc aaaaaaaaaa aaaagaaag aaaagaaaa gaaagtgatc ctactggaac  127020
catgcttact cccctcccca cctcacactg tgtagaaatt agtgctgtcg gccaggcgcg  127080
gtggctcatg cctgtaatcg cagcactttg ggaggccaag gcaggcggat cacgaggtca  127140
ggagatcaag accatcctgg ctaacacagt gaaaccctgt ctctactaaa aatacaaaaa  127200
attagccggg catggtggca ggcacctgta gtcccaacta cttgggaggc tgaggcagga  127260
gaatggcatg aacctgggag gcggagcttg cagtgagcca agatcgcgcc actgcatacc  127320
agcctaggtg acagagtgag actcagcaaa aaaagaaaga aagaaagaaa gaaatcagtg  127380
ctgtctatac ttctttctgc agtgatggaa atattctgta tctgtgctgt ccagtatagt  127440
agccactagc tacatgtggc acttgaaaca tggctggtac agttgaggaa gagtggctgc  127500
catatcggac gacacagcta tagattctgt cacccccacc cgagagtcca gagcggggac  127560
```

```
ttctgcctta ggccctattc agggctgatt tttacttgaa cccttactgt gggaagagaa    127620
ggccatgaga agttcagtct agaatgtgac tccttatttt ctggctccct tggacacttt    127680
gtgggattta gtctccctgt ggaaagtatt ccacaagtgg tgccactacc ccagctgtga    127740
gagcagctgg gagctgcttt tgtcatcttt ccctggaaag tcctgtgggc tgtctcttcc    127800
tcatgccttg tcccatgctt gggcatggtg tcaagcgtca ggagggagaa agggtcctta    127860
tttatttatt tagagaggga cccttcttct gttcccaggc tggagtgcag tggtgcgatc    127920
tcggctcact gcaacctccg cctcctgggt tcaagtgatt ctcctgcctc agcctcctga    127980
gtagctgaga ttacaggcac atgccaacat gcccggctaa tttttttttt ttttttttt    128040 tttttttttt tttttttttt gagatggagt tgtactctca ttgcccaggc tggaatgtaa    128100
tggcacaatc tcggctcact gcaacctcca cctcctggat tcaagcaatt ctcctgtctc    128160
agcttcccaa gtagctggga ttacaggtgc ccgccaccat gctcaactaa tttttgtatt    128220 tttttttag tagagacgag gtttcaccat gttggtcaga ctggtctcaa actcctgacc    128280
tcaggtgatc cacctgcctc ggcctcccaa agtgctagga ttacaggcat gagccaccac    128340
gcccggcctg aaagggttct tatttagtgt gcatttgac attcaattta attccaaggt    128400
cttgtggggt catggtttac aggatgttga tatagaaaag acttcactta atgggccggg    128460
cgcagtggct catgcctgta atcccagcac tttgggaggc cgaggcaggc agatcaggag    128520
gtcaggagat tgagaccatc ctggctaaca cagtgaaacc ccatctctac tgaaaataca    128580
aaaaattagc tgggcgtggt ggcaggcacc tgtagtccca gccactcggt tggctgaggc    128640
aggagaatgg catgaacccg ggaggcggag cttgcagtga cagagacca tgccactgca    128700 ctccagcctg ggcgacagag caagactctg tctcaagaaa aaaaaaaaa aacagacttt    128760 acttactgga agccaaccaa tgtatattta gagtaatttt tcctgggctg agctgtcatt    128820
tacttttgca gtatctcaag aagaagagtt tacagtgtaa atatttgatg cacactttga    128880
ttatatagat gaagcaaact attttcaaga gctttgcaag gacttacttg tatccaaaca    128940
ccattctaaa aggagtctta cctacttcta aaggctggtc tctacttgga accacttgct    129000
tggccctggt tcaagtcctg ctgcaaacct ggaagtcctg tcattgtctt cttccctcca    129060
gagcagtggc acccaatcta atttttgctg tgccccagca gccctggca cttttgccctg    129120 tagactgcag acctcatgta atgtatgtta agtccacaga accacagaag atgatggcaa    129180
gatgctcttg tgtgtgttgt gttctaggag gtggccaggt ggaagtaaaa tctgagaagc    129240
ttgacttcaa ggacagagtc cagtcgaaga ttgggtccct ggacaatatc cccacgtcc    129300 ctggcggagg aaataaaaag gtaaaggggg tagggtgggt tggatgctgc ccttgggtat    129360
atgggcatta atcaagttga gtggacaaag gctggtccag ttcccagagg aggaaaacag    129420
aggcttctgt gttgactggc tggatgtggg ccctcagcag catccagtgg gtctccactg    129480
cctgtctcaa tcacctggag ctttagcacg tttcacacct gggccccaac ctggagaggc    129540
tgaccaatgg gtctcagggg cagctcggtt gctggagttt ttgttttat ttattttat    129600 gtatttaagg cagggtctct gtattagtcc attctcacac tgctaataaa gacatacca    129660 agactgggta atttataaag gaaagaggtt taatggactc acagttccac atggctgggg    129720
aggcctcaaa atcatggcgg aaggcaaagg agaagcaaag gcatttctta catggcgaca    129780
ggcaagagag cgtgtgcagg ggaactccca tttataaaac catcagacct catgagattt    129840
attcactatc atgagaacag catgggaaag acccgcccc atgattcagt tacctcccac    129900
tgggtccctc ccatgacaca tggaattatg ggagctacaa ttcaagatga gatttgggtg    129960
```

```
gggacacagc caaaccatat cagtctccct ctgtcatcca ggctggagtg cactggcatg   130020
atctcggctc actgcagcct ctacctccct gggtcaggtg atcttcccac ctcagcctcc   130080
caggtagctg gaactacagg tacctgccac tatgcctggc taaatatttt gtatttcctg   130140
tggagacgag gttttgccac gttgcccagg ctggtcttga actcctgagg tcaagcaata   130200
tgcccacctc ggcctcccaa ggtgctggga ttacaggtgt gagccacagt gctcggccta   130260
agtcactgca gttttaaaag ctcccaggtg attcttcagt gcagtcaaaa gtgagaactg   130320
gctgggtgcg gtggctcatg cctgtaatcc cagcaccttg ggaggcgaag gtgggcagat   130380
ggcttgaggt caggagttca agaccagcct ggccaacatg gtaaaacccc atctctacta   130440
aaaatacaaa agttagctgg gtgtggtggt gcgtgcctgt aatcccagct acttgggagg   130500
ctgaggcatg agaattgctt gaacccaggg gacagaggtt gtagtgagcc gagatcgtgc   130560
cactgcactc cagcctgggc aacagagtga gattccatct cacaaaaaaa aaaaaaagcg   130620
agaaccactg tcctaggccc tgatgtttgc aggcaactaa aaaaggaagt ggacatcccc   130680
agtcagctgt ggcgcaccaa gaacaagtca tgggaacata acctaatttt ctaaatgggt   130740
tactaggcac ttagagcaaa acaatgatgc cgaaatcctg atttcagcaa agcctctgcc   130800
tgcctgtctt ggaagtatcc acatgaggct gctggggcct tggtgtcccc agcagtttct   130860
agtctctagg tcttgctgtg ggtgtctgtg cagtgagggt gtgtgtggcg ctgggtgagc   130920
tctgtctagg cctggcacag gatgcggtct ggtagctgct gcttctcttc tgcagaagcg   130980
cagccaagca ccctctgggg tttcaggccc acacccagcc tgaagttctg ggagtggctc   131040
actttccaac cttcagggtc tcccagcagc tgactgggga gtggtggagg gaaaagggat   131100
tgtattagtc cgttttcacg ccgctgatga agacataccc gatactgggc agtctaaaag   131160
atagaggtct gatggactca cagttccacg tgactgggga ggcctgacaa tcatggtgga   131220
aggtgaaagg cttgtctcac acggtggcag acaagagaaa agagcttgtg caggggaact   131280 ccccttata aaaccatcag atctcgggag acttattcac tatcatgaga acagcacggg   131340
aaagaccctc ctctatgatt caattacctc ccaccaggtc cctcccacaa catgtaggaa   131400
ttgtgggaac tacaattcaa gatgacattt gggtgggac acagccaaac catatcaggg   131460
cgtcccagaa agggtatagg gtctgagacc caagtcagca tgagaaagta tgcttctcat   131520
ggtggcccag ttgggtggaa gtggcagccg ggccgtcttt ccaccaggcc actcaagtag   131580
cagctgagag acccctgccc tggccagtcc ccgccctccc ctcttgccac tgcctctggt   131640
tctgaacaga tgggcaccct catcttgtat ttgtgattaa tgtctaacaa tgtagttttg   131700
tgagaagggt ttgctgatac agccttgctg cagatgctgc gaactgtggc ctggggcaga   131760
ccttacctcc agacacgccc tgaggcaggg gagggcactg gcccgtagct ggccgagagc   131820
tctcgggttg cgcgacaggg atacttttca gcggctgggt cgctatccaa agtgagaaaa   131880
cgaggaggga ccaggaggct gtccgcctca agagatgtgg gggccaggtc cagttatctg   131940
gggaagcagt aagcttctct gctgtttcta accccaggcc tcccctggtc taaggcaggg   132000
cctcccagcc tcggggcact ttaaagatat ctgggcctgg cccatcccc acagtctgac    132060 tgagtgggtc tggatagggc ctgagcattg gtgatttcct gggtgaaagg aggccctca    132120 cagtctctgg aagcttctct gtgttaggaa aagctctggg cttgactctg ctttgaaagt   132180
caagatccgc aaatcctctc agcctcagtt tctccttcag caagatgaaa tggaaatgct   132240
gtacctacgt cccggggtgg ttgtgagacc caaaaaagac aatgttctgg aaggttcctg   132300
```

```
gtgcgttgca gtcctctaag aacctgagtt agagccacgc tgagtctcag cttcttggct   132360
ccttctgttt caaactcgtc catgtgatag ctcaggaagg gtaggcaggg ccctgccccc   132420
tactcagaaa acaccatcct ggtcctgggg atccccgcag cattagtccc ctgttttccc   132480
agtgtattga gaaaaattgc taacaagcag tggggcacac caccagcctc ctgggttcct   132540
ttcagtttgg ggattttttgg acattcccag gaatgtctta aaaaacactt caaaaaacat   132600
taacataaat attttttatca aagcctgtat taaatggtct ttcaagaaaa tacagtaaca   132660
ggtcaggcat ggtggctcat gcctgtaacc ccagcacttt gggaggccaa ggcaggcaga   132720
tcacctgaaa tcaggagttc aagaccaacc tggccaacac agccaaatcc catctctaca   132780
aaaaatacaa aaattagctg ggtgtggtgg cacacacctg tagtcccagc tacttgggag   132840
gccgaggcag gagaattgct tgatcccgga ggcggaggtt gcagtgagcc gagatcgtgc   132900
cactgcactc cagcgtgggt gacaaggtga atctttgtct caaaaaaaaa aaaaaaaaaa   132960
agataaaata cagtatacag taatagagaa caatcctttt ttcaaagtag tgaccccaaa   133020
tgaacaaaat atgcatctag cttaaatgcg aacctggttt tctctacgcc cattcaagcc   133080
cctgcaatag gggcccttca ccccgcatcc atggactcct aaaattatat ggaaaatggc   133140
tgtgtgtgag tgtggatgga catgtgcaca catattttttg ctttaccag atgctcaaag   133200 agcctaggac ccaaaaaggg ctgagaatga ccgtgtcggc cacttcaggg tcatcaggaa   133260
ttgctgtgca ctgctcactt ctccagtgaa cactttctgc ttctgtgttt cctggtatcc   133320
tttgggactc ctggctaggt catgtgtttc tctactttca aagggcttc agccaggcac   133380 gatggcatga gcctgtagtc ccagttgctc tggaggttaa ggtgggaaga ttgcttgagc   133440
ccaggaattt gaggccagcc tgggcaagta gataggtaga tgattgatag atagatagat   133500 agataaaatag atggatagat aagtcgctag acagtcatcc atccacccat ccacacataa   133560
aaaggccttt gtcatgtcat gttttgtggc ccacctgcca gtgttgccca cagttgctgc   133620
ccctccaaac tcatcagtca ctggcaaaca ggaggaatgt gtggctcatg tctgggcatc   133680
agtggctgtg ggagacatcc ttgatcttct ccagcttctc cttccacatt ttccttttgca  133740 atctggcaat atctattaaa ataaaatgtg catgccttttt gacctaagag cttcacttct   133800
aggacccact tacacgtgtg tgacatgatg ttcatacggg ttttatttatc tgaggttgtt   133860 catacacacc attgcctgta atcactaaag gcgggagcag cctacacatc catccacaga   133920
ggagtagatg ccttttggta catccgtggc gacggaatac taagcagcct gtgtatctat   133980
acactcacac gtgtttgttt atgtgtggaa tatctctgga gggtacacaa gaaacttaaa   134040
atgatcactg tctctgggga gggtacctgg gtgcctggga ggcaggtcag ggaaggagtg   134100
ggcacaggta ttaccaattg gaagacaata aaaacaacag ctcctggcca ggcgcagtgg   134160
ctcacgcctg taatggcagc actctgagag gctgaggcgg gcagattgct tgcgtccagg   134220
agttcaagac cagcctgggc aacatagcaa accccgtttc tattaaaaaa tacaaaaaat   134280
tagccaggtg tggtggcatg cacctgtaat cccagctact cgggaggctg aggtgggaga   134340
atcacctgag cctgggaggt caaggctgca gtgaggtgag attgtgccac cgcactctag   134400
cctgggcgat agagcaagac cctgtctcaa aaacaaacaa aaaacagtcc ctggcactct   134460
gggccaggcc tggcagggca gttggcaggg ctggtctttc tctggcactt catctcaccc   134520
tccctccctt cctcttcttg cagattgaaa cccacaagct gaccttccgc gagaacgcca   134580
aagccaagac agaccacggg gcggagatcg tgtacaagtc gccagtggtg tctgggggaca   134640 cgtctccacg gcatctcagc aatgtctcct ccaccggcag catcgacatg gtagactcgc   134700
```

```
cccagctcgc cacgctagct gacgaggtgt ctgcctccct ggccaagcag ggtttgtgat   134760
caggcccctg gggcggtcaa taattgtgga gaggagagaa tgagagagtg tggaaaaaaa   134820
aagaataatg acccggcccc cgccctctgc ccccagctgc tcctcgcagt tcggttaatt   134880
ggttaatcac ttaacctgct tttgtcactc ggctttggct cgggacttca aaatcagtga   134940
tgggagtaag agcaaatttc atctttccaa attgatgggt gggctagtaa taaatatttt   135000
aaaaaaaaac attcaaaaac atggccacat ccaacatttc ctcaggcaat tccttttgat   135060 tctttttttct tccccctcca tgtagaagag ggagaaggag aggctctgaa agctgcttct   135120
gggggatttc aagggactgg gggtgccaac cacctctggc cctgttgtgg gggtgtcaca   135180
gaggcagtgg cagcaacaaa ggatttgaaa cttggtgtgt tcgtggagcc acaggcagac   135240
gatgtcaacc ttgtgtgagt gtgacggggg ttggggtggg gcgggaggcc acggggagg    135300 ccgaggcagg ggctgggcag aggggagagg aagcacaaga agtgggagtg ggagaggaag   135360
ccacgtgctg gagagtagac atccccctcc ttgccgctgg gagagccaag gcctatgcca   135420
cctgcagcgt ctgagcggcc gcctgtcctt ggtggccggg ggtgggggcc tgctgtgggt   135480
cagtgtgcca ccctctgcag ggcagccgt gggagaaggg acagcgggta aaagagaag    135540 gcaagctggc aggagggtgg cacttcgtgg atgacctcct tagaaaagac tgaccttgat   135600
gtcttgagag cgctggcctc ttcctccctc cctgcagggt aggggcctg agttgagggg    135660 cttccctctg ctccacagaa accctgtttt attgagttct gaaggttgga actgctgcca   135720
tgattttggc cactttgcag acctgggact ttagggctaa ccagttctct ttgtaaggac   135780
ttgtgcctct tgggagacgt ccacccgttt ccaagcctgg gccactggca tctctggagt   135840
gtgtgggggt ctgggaggca ggtcccgagc ccctgtcct tcccacggcc actgcagtca   135900
cccctgtctg cgccgctgtg ctgttgtctg ccgtgagagc ccaatcactg cctatacccc   135960
tcatcacacg tcacaatgtc ccgaattccc agcctcacca ccccttctca gtaatgaccc   136020
tggttggttg caggaggtac ctactccata ctgagggtga aattaaggga aggcaaagtc   136080
caggcacaag agtgggaccc cagcctctca ctctcagttc cactcatcca actgggaccc   136140
tcaccacgaa tctcatgatc tgattcggtt ccctgtctcc tcctcccgtc acagatgtga   136200
gccagggcac tgctcagctg tgaccctagg tgtttctgcc ttgttgacat ggagagagcc   136260
ctttcccctg agaaggcctg gccccttcct gtgctgagcc cacagcagca ggctgggtgt   136320
cttggttgtc agtggtggca ccaggatgga agggcaaggc acccagggca ggcccacagt   136380
cccgctgtcc cccacttgca ccctagcttg tagctgccaa cctcccagac agcccagccc   136440
gctgctcagc tccacatgca tagtatcagc cctccacacc cgacaaaggg gaacacaccc   136500
ccttggaaat ggttctttc ccccagtccc agctggaagc catgctgtct gttctgctgg    136560
agcagctgaa catatacata gatgttgccc tgccctcccc atctgcaccc tgttgagttg   136620
tagttggatt tgtctgttta tgcttggatt caccagagtg actatgatag tgaaaagaaa   136680
aaaaaaaaaa aaaaaggacg catgtatctt gaaatgcttg taaagaggtt tctaacccac   136740
cctcacgagg tgtctctcac ccccacactg ggactcgtgt ggcctgtgtg gtgccaccct   136800 gctgggcct cccaagtttt gaaaggcttt cctcagcacc tggacccaa cagagaccag    136860 cttctagcag ctaaggaggc cgttcagctg tgacgaaggc ctgaagcaca ggattaggac   136920
tgaagcgatg atgtccccctt ccctacttcc ccttggggct ccctgtgtca gggcacagac   136980
taggtcttgt ggctggtctg gcttgcggcg cgaggatggt tctctctggt catagcccga   137040
```

```
agtctcatgg cagtcccaaa ggaggcttac aactcctgca tcacaagaaa aaggaagcca 137100
ctgccagctg gggggatctg cagctcccag aagctccgtg agcctcagcc acccctcaga 137160
ctgggttcct ctccaagctc gccctctgga ggggcagcgc agcctccac caagggccct 137220
gcgaccacag cagggattgg gatgaattgc ctgtcctgga tctgctctag aggcccaagc 137280
tgcctgcctg aggaaggatg acttgacaag tcaggagaca ctgttcccaa agccttgacc 137340
agagcacctc agcccgctga ccttgcacaa actccatctg ctgccatgag aaaagggaag 137400
ccgcctttgc aaaacattgc tgcctaaaga aactcagcag cctcaggccc aattctgcca 137460
cttctggttt gggtacagtt aaaggcaacc ctgagggact tggcagtaga aatccagggc 137520
ctcccctggg gctggcagct tcgtgtgcag ctagagcttt acctgaaagg aagtctctgg 137580
gcccagaact ctccaccaag agcctccctg ccgttcgctg agtcccagca attctcctaa 137640
gttgaaggga tctgagaagg agaaggaaat gtggggtaga tttggtggtg gttagagata 137700
tgcccccctc attactgcca acagtttcgg ctgcatttct tcacgcacct cggttcctct 137760
tcctgaagtt cttgtgccct gctcttcagc accatgggcc ttcttatacg gaaggctctg 137820
ggatctcccc cttgtggggg caggctcttg gggccagcct aagatcatgg tttagggtga 137880
tcagtgctgg cagataaatt gaaaaggcac gctggcttgt gatcttaaat gaggacaatc 137940
cccccagggc tgggcactcc tcccctcccc tcacttctcc cacctgcaga gccagtgtcc 138000
ttgggtgggc tagataggat atactgtatg ccggctcctt caagctgctg actcacttta 138060
tcaatagttc catttaaatt gacttcagtg gtgagactgt atcctgtttg ctattgcttg 138120
ttgtgctatg ggggagggg ggaggaatgt gtaagatagt taacatgggc aaagggagat 138180
cttggggtgc agcacttaaa ctgcctcgta acccttttca tgatttcaac cacatttgct 138240
agagggaggg agcagccacg gagttagagg cccttggggt ttctcttttc cactgacagg 138300
cttttcccagg cagctggcta gttcattccc tccccagcca ggtgcaggcg taggaatatg 138360
gacatctggt tgctttggcc tgctgccctc tttcaggggt cctaagccca caatcatgcc 138420
tccctaagac cttggcatcc ttccctctaa gccgttggca cctctgtgcc acctctcaca 138480
ctggctccag acacacagcc tgtgcttttg gagctgagat cactcgcttc accctcctca 138540
tctttgttct ccaagtaaag ccacgaggtc ggggcgaggg cagaggtgat cacctgcgtg 138600
tcccatctac agacctgcgg cttcataaaa cttctgattt ctcttcagct ttgaaaaggg 138660
ttaccctggg cactggccta gagcctcacc tcctaataga cttagcccca tgagtttgcc 138720
atgttgagca ggactatttc tggcacttgc aagtcccatg atttcttcgg taattctgag 138780
ggtgggggga gggacatgaa atcatcttag cttagctttc tgtctgtgaa tgtctatata 138840
gtgtattgtg tgttttaaca aatgatttac actgactgtt gctgtaaaag tgaatttgga 138900
aataaagtta ttactctgat taaataaggt ctccattcat ggattccaag acaagaaag 138960
tcatatagaa tgtctatttt ttaagttctt tcccacgcac ccttagataa tttagctcag 139020
aacaggaaat gatagtatta ataaaagctg gacatcagga ttaacagctc tctctgggc 139080
cctgaaggtg agagttctca gacttgctca tttgcagttg cttctttgtg atgctggcaa 139140
accatcctag tcccattcaa agggcaatac aaagccttgt ggctgacctc acgatgcagc 139200
actcagttg caagaccggc accagtgtat gcaaacctga gaaggttggg gatgaggata 139260
tgggatcttt catccctgga aatttagtcc agaggcctgg ggctggagca gaacaccaag 139320
ccaatcagct taatgaatgg cttagattcc tgctaggttt gcagagctgc cttctttcct 139380
ttggtacctt attatagatt gaggagtatt tctgctaaac caagataggg ataaccagat 139440
```

```
agcatcttca tagcaatgcc acaaaggaaa acaaaaacaa aacagtaatc catcatatta 139500
ttccttagta actatgccaa ggtcatgata ctgaatcctt agattgtttc aaaatactac 139560
ttttctttgc tcttcctgat gtgtttgcca ccgcaggcag atgtttaagt aaaacagatt 139620
ttaactgcag ctacaaaagc agcaacaggc cagcaaaaga gaagtgctat ctcagagagc 139680
atggctttca gagccacaag agacagcctc actggctgtt tcagcttgac tgccatgcaa 139740
agaagagagc agagggagaa ccagccccac ccacttattc atcttgtaca aaaaaaaagc 139800
acctaccagc ctaggctaca tagtgagaca ctatctccac aaaaaaccca cgaaaactag 139860
ctgggtatgg tggcacatgc ctacagtccc agctactggt aaggctgtgg tgggaggatc 139920
tcttgaggcc aggaaggaga tccaggctgc agtgagccaa gattgcacca ctgcactcca 139980
gtctggacaa tcgagcaaga tcccatctca aacaataaaa aaaaaaagcg tgtaacctcc 140040
tcagaagaaa gatgttataa tctcaggcag caggcaagaa ccaatccagg ctctaagcaa 140100
attatgtatc tcactgaccc caccaaacct cagaaaaatt taacagtgag aagcaaaatc 140160
tcctttaaag agcaacttag aacagataga aaatatcata cagctgactt cactagagag 140220
aaagtgcatc aactgctttc actcaacaaa agaaaaaag atgatcaa tgcagatccc 140280 ctctcctcct ggcagcccctt accctcagtg aaaagccacc accattctct ctctggtggc 140340
catcagatca acctgcggcg ttcccacaag acagaatgga gattttccaa ggtatagagc 140400
aagtcagagt accccaaaga acggcggcag agagccagct ccgaaactgc caacactacc 140460
atgcatacac agttcagtaa gtcaagaaag gcctggtaca cagcattctg taactttttt 140520
ttttattttt ttcaattttt ccttctttttt tttttttaag cactagtctg tgctttgcga 140580
acagaatcaa gacattaaca aagatcagct tctctgaaga aaagcatttc tatagaacaa 140640
agacagctac atgtttcgct gccattacac agctccaaag caggaaaaga aaatatttac 140700
aaaatacaag gttttttttt tccatttttt gtttttgttt ttttttcaa tgctaaaagg 140760 gttattcaga attttcaacc ttataaatag aagaagcact ttatgcatag ggatatggtg 140820
cattattgta tttttttta aagaaacaat gacaaaccct ttaacttgca aacagaaaaa 140880
aaaatcacta atgttgaaaa ttgtgaaaaa accccaacca ttaa         140924
```

<210> SEQ ID NO 305
<211> LENGTH: 6816
<212> TYPE: DNA
<213> ORGANISM: Homo sapiens

<400> SEQUENCE: 305

```
ggacggccga gcggcagggc gctcgcgcgc gcccactagt ggccggagga gaaggctccc    60
gcggaggccg cgctgcccgc cccctcccct ggggaggctc gcgttccgc tgctcgcgcc   120 tgcgccgccc gccggcctca ggaacgcgcc ctcttcgccg gcgcgcgccc tcgcagtcac   180
cgccacccac cagctccggc accaacagca gcgccgctgc caccgccac cttctgccgc   240 cgccaccaca gccaccttct cctcctccgc tgtcctctcc cgtcctcgcc tctgtcgact   300
atcaggtgaa ctttgaacca ggatggctga gccccgccag gagttcgaag tgatggaaga   360
tcacgctggg acgtacgggt tgggggacag gaaagatcag gggggctaca ccatgcacca   420
agaccaagag ggtgacacgg acgctggcct gaaagaatct ccctgcaga cccccactga   480 ggacggatct gaggaaccgg gctctgaaac ctctgatgct aagagcactc caacagcgga   540
agatgtgaca gcacccttag tggatgaggg agctcccggc aagcaggctg ccgcgcagcc   600
```

```
ccacacggag atcccagaag gaaccacagc tgaagaagca ggcattggag acaccccag      660
cctggaagac gaagctgctg gtcacgtgac ccaagagcct gaaagtggta aggtggtcca    720
ggaaggcttc ctccgagagc caggccccc aggtctgagc caccagctca tgtccggcat    780
gcctggggct cccctcctgc ctgagggccc cagagaggcc acgccaac cttcggggac     840
aggacctgag gacacagagg gcggccgcca cgccctgag ctgctcaagc accagcttct    900
aggagacctg caccaggagg ggccgccgct gaaggggca gggggcaaag agaggccggg    960
gagcaaggag gaggtggatg aagaccgcga cgtcgatgag tcctcccccc aagactcccc  1020
tccctccaag gcctcccag cccaagatgg gcggcctccc cagacagccg ccagagaagc   1080
caccagcatc ccaggcttcc cagcggaggg tgccatcccc ctccctgtgg atttcctctc  1140
caaagtttcc acagagatcc cagcctcaga gcccgacggg cccagtgtag ggcgggccaa  1200
agggcaggat gccccctgg agttcacgtt tcacgtggaa atcacaccca acgtgcagaa   1260
ggagcaggcg cactcggagg agcatttggg aagggctgca tttccagggg cccctggaga  1320
ggggccagag gcccggggcc cctctttggg agaggacaca aaagaggctg accttccaga  1380
gccctctgaa aagcagcctg ctgctgctcc gcggggaag cccgtcagcc gggtccctca   1440
actcaaagct cgcatggtca gtaaaagcaa agacgggact ggaagcgatg acaaaaaagc  1500
caagacatcc acacgttcct ctgctaaaac cttgaaaaat aggccttgcc ttagccccaa  1560
acaccccact cctggtagct cagaccctct gatccaaccc tccagccctg ctgtgtgccc  1620
agagccacct tcctctccta aatacgtctc ttctgtcact tcccgaactg cagttctgg   1680
agcaaaggag atgaaactca aggggctga tggtaaaacg aagatcgcca caccgcgggg  1740
agcagcccct ccaggccaga agggccaggc caacgccacc aggattccag caaaaacccc  1800
gcccgctcca aagacaccac ccagctctgc gactaagcaa gtccagagaa gaccaccccc  1860
tgcagggccc agatctgaga gaggtgaacc tccaaaatca ggggatcgca gcggctacag  1920
cagccccggc tccccaggca ctcccggcag ccgctcccgc accccgtccc ttccaacccc  1980
acccacccgg gagcccaaga aggtggcagt ggtccgtact ccacccaagt cgccgtcttc  2040
cgccaagagc cgcctgcaga cagccccgt gcccatgcca gacctgaaga atgtcaagtc  2100
caagatcggc tccactgaga acctgaagca ccagccggga ggcgggaagg tgcagataat  2160
taataagaag ctggatctta gcaacgtcca gtccaagtgt ggctcaaagg ataatatcaa  2220
acacgtcccg ggaggcggca gtgtgcaaat agtctacaaa ccagttgacc tgagcaaggt  2280
gacctccaag tgtggctcat taggcaacat ccatcataaa ccaggaggtg gccaggtgga  2340
agtaaaatct gagaagcttg acttcaagga cagagtccag tcgaagattg gtccctgga   2400
caatatcacc cacgtccctg gcggaggaaa taaaaagatt gaaacccaca agctgacctt  2460
ccgcgagaac gccaaagcca agacagacca cggggcggag atcgtgtaca gtcgccagt   2520
ggtgtctggg gacacgtctc cacggcatct cagcaatgtc tcctccaccg gcagcatcga  2580
catggtagac tcgccccagc tcgccacgct agctgacgaa gtgtctgcct ccctggccaa  2640
gcagggtttg tgatcaggcc cctggggcgg tcaataattg tggagaggag agaatgagag  2700
agtgtggaaa aaaaagaat aatgaccggg ccccgccct ctgccccag ctgctcctcg     2760
cagttcggtt aattggttaa tcacttaacc tgcttttgtc actcggcttt ggctcgggac  2820
ttcaaaatca gtgatgggag taagagcaaa tttcatcttt ccaaattgat gggtgggcta  2880
gtaataaaat atttaaaaaa aaacattcaa aaacatggcc acatccaaca tttcctcagg  2940
caattccttt tgattctttt ttcttccccc tccatgtaga agagggagaa ggagaggctc  3000
```

```
tgaaagctgc ttctggggga tttcaaggga ctgggggtgc caaccacctc tggccctgtt    3060 gtggggtgt cacagaggca gtggcagcaa caaaggattt gaaacttggt gtgttcgtgg     3120
agccacaggc agacgatgtc aaccttgtgt gagtgtgacg ggggttgggg tggggcggga    3180
ggccacgggg gaggccgagg caggggctgg gcagagggga gaggaagcac aagaagtggg    3240
agtgggagag aagccacgt gctggagagt agacatcccc ctccttgccg ctgggagagc     3300
caaggcctat gccacctgca gcgtctgagc ggccgcctgt ccttggtggc cggggtgggg    3360
ggcctgctgt gggtcagtgt gccaccctct gcagggcagc ctgtgggaga agggacagcg    3420
ggtaaaaaga gaaggcaagc tggcaggagg gtggcacttc gtggatgacc tccttagaaa    3480
agactgacct tgatgtcttg agagcgctgg cctcttcctc cctccctgca gggtagggg     3540 cctgagttga ggggcttccc tctgctccac agaaaccctg ttttattgag ttctgaaggt    3600
tggaactgct gccatgattt tggccacttt gcagacctgg gactttaggg ctaaccagtt    3660
ctctttgtaa ggacttgtgc ctcttgggag acgtccaccc gtttccaagc ctgggccact    3720
ggcatctctg gagtgtgtgg gggtctggga ggcaggtccc gagcccctg tccttcccac     3780 ggccactgca gtcaccccgt ctgcgccgct gtgctgttgt ctgccgtgag agcccaatca    3840
ctgcctatac ccctcatcac acgtcacaat gtcccgaatt cccagcctca ccaccccttc    3900
tcagtaatga ccctggttgg ttgcaggagg tacctactcc atactgaggg tgaaattaag    3960
ggaaggcaaa gtccaggcac aagagtggga ccccagcctc tcactctcag ttccactcat    4020
ccaactggga ccctcaccac gaatctcatg atctgattcg gttccctgtc tcctcctccc    4080
gtcacagatg tgagccaggg cactgctcag ctgtgaccct aggtgtttct gccttgttga    4140
catggagaga gcccttttccc ctgagaaggc ctggcccctt cctgtgctga gcccacagca    4200
gcaggctggg tgtcttggtt gtcagtggtg gcaccaggat ggaagggcaa ggcacccagg    4260
gcaggcccac agtcccgctg tcccccactt gcacccctagc ttgtagctgc caacctccca   4320
gacagcccag cccgctgctc agctccacat gcatagtatc agccctccac acccgacaaa    4380
ggggaacaca ccccccttgga aatggttctt ttccccagt cccagctgga agccatgctg     4440
tctgttctgc tggagcagct gaacatatac atagatgttg ccctgccctc cccatctgca    4500
ccctgttgag ttgtagttgg attttgtctgt ttatgcttgg attcaccaga gtgactatga   4560
tagtgaaaag aaaaaaaaa aaaaaaaagg acgcatgtat cttgaaatgc ttgtaaagag     4620
gtttctaacc caccctcacg aggtgtctct caccccccaca ctgggactcg tgtggcctgt   4680
gtggtgccac cctgctgggg cctcccaagt tttgaaaggc tttcctcagc acctgggacc    4740
caacagagac cagcttctag cagctaagga ggccgttcag ctgtgacgaa ggcctgaagc    4800
acaggattag gactgaagcg atgatgtccc cttccctact tccccttggg gctccctgtg    4860
tcagggcaca gactaggtct tgtggctggt ctggcttgcg gcgcgaggat ggttctctct    4920
ggtcatagcc cgaagtctca tggcagtccc aaaggaggct tacaactcct gcatcacaag    4980
aaaaaggaag ccactgccag ctgggggggat ctgcagctcc cagaagctcc gtgagcctca   5040
gccacccctc agactgggtt cctctccaag ctcgccctct ggaggggcag cgcagcctcc    5100
caccaagggc cctgcgacca cagcagggat tgggatgaat tgcctgtcct ggatctgctc    5160
tagaggccca agctgcctgc ctgaggaagg atgacttgac aagtcaggag acactgttcc    5220
caaagccttg accagagcac ctcagcccgc tgacctttgca caaactccat ctgctgccat    5280
gagaaaaggg aagccgccctt tgcaaaacat tgctgcctaa agaaactcag cagcctcagg    5340
```

```
cccaattctg ccacttctgg tttgggtaca gttaaaggca accctgaggg acttggcagt    5400
agaaatccag ggcctcccct ggggctggca gcttcgtgtg cagctagagc tttacctgaa    5460
aggaagtctc tgggcccaga actctccacc aagagcctcc ctgccgttcg ctgagtccca    5520
gcaattctcc taagttgaag ggatctgaga aggagaagga aatgtggggt agatttggtg    5580
gtggttagag atatgccccc ctcattactg ccaacagttt cggctgcatt tcttcacgca    5640
cctcggttcc tcttcctgaa gttcttgtgc cctgctcttc agcaccatgg ccttcttat     5700
acggaaggct ctgggatctc cccttgtgg ggcaggctct tggggccagc ctaagatcat    5760
ggtttagggt gatcagtgct ggcagataaa ttgaaaaggc acgctggctt gtgatcttaa    5820
atgaggacaa tcccccagg gctgggcact cctcccctcc cctcacttct cccacctgca    5880
gagccagtgt cctgggtgg gctagatagg atatactgta tgccggctcc ttcaagctgc    5940
tgactcactt tatcaatagt tccatttaaa ttgacttcag tggtgagact gtatcctgtt    6000
tgctattgct tgttgtgcta tggggggagg ggggaggaat gtgtaagata gttaacatgg    6060
gcaaagggag atcttggggt gcagcactta aactgcctcg taacccttt catgatttca    6120
accacatttg ctagagggag ggagcagcca cggagttaga ggcccttggg gtttctcttt    6180
tccactgaca ggctttccca ggcagctggc tagttcattc cctccccagc caggtgcagg    6240
cgtaggaata tggacatctg gttgctttgg cctgctgccc tctttcaggg gtcctaagcc    6300
cacaatcatg cctccctaag accttggcat ccttccctct aagccgttgg cacctctgtg    6360
ccacctctca cactggctcc agacacacag cctgtgcttt tggagctgag atcactcgct    6420
tcaccctcct catctttgtt ctccaagtaa agccacgagg tcggggcgag ggcagaggtg    6480
atcacctgcg tgtcccatct acagacctgc agcttcataa aacttctgat ttctcttcag    6540
ctttgaaaag ggttaccctg ggcactggcc tagagcctca cctcctaata gacttagccc    6600
catgagtttg ccatgttgag caggactatt tctggcactt gcaagtccca tgatttcttc    6660
ggtaattctg agggtggggg gagggacatg aaatcatctt agcttagctt tctgtctgtg    6720
aatgtctata tagtgtattg tgtgttttaa caaatgattt acactgactg ttgctgtaaa    6780
agtgaatttg gaaataaagt tattactctg attaaa                              6816
```

<210> SEQ ID NO 306
<211> LENGTH: 776
<212> TYPE: PRT
<213> ORGANISM: Homo sapiens

<400> SEQUENCE: 306

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110
```

```
Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Lys His Pro Thr
                405                 410                 415

Pro Gly Ser Ser Asp Pro Leu Ile Gln Pro Ser Pro Ala Val Cys
            420                 425                 430

Pro Glu Pro Pro Ser Ser Pro Lys Tyr Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
            500                 505                 510

Pro Ala Gly Pro Arg Ser Glu Arg Gly Glu Pro Lys Ser Gly Asp
        515                 520                 525

Arg Ser Gly Tyr Ser Ser Pro Gly Ser Pro Gly Thr Pro Gly Ser Arg
```

```
                530                 535                 540
Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ser Ala Lys Ser
                565                 570                 575

Arg Leu Gln Thr Ala Pro Val Pro Met Pro Asp Leu Lys Asn Val Lys
            580                 585                 590

Ser Lys Ile Gly Ser Thr Glu Asn Leu Lys His Gln Pro Gly Gly Gly
        595                 600                 605

Lys Val Gln Ile Ile Asn Lys Lys Leu Asp Leu Ser Asn Val Gln Ser
    610                 615                 620

Lys Cys Gly Ser Lys Asp Asn Ile Lys His Val Pro Gly Gly Gly Ser
625                 630                 635                 640

Val Gln Ile Val Tyr Lys Pro Val Asp Leu Ser Lys Val Thr Ser Lys
                645                 650                 655

Cys Gly Ser Leu Gly Asn Ile His His Lys Pro Gly Gly Gly Gln Val
            660                 665                 670

Glu Val Lys Ser Glu Lys Leu Asp Phe Lys Asp Arg Val Gln Ser Lys
        675                 680                 685

Ile Gly Ser Leu Asp Asn Ile Thr His Val Pro Gly Gly Gly Asn Lys
    690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735

Asp Thr Ser Pro Arg His Leu Ser Asn Val Ser Ser Thr Gly Ser Ile
            740                 745                 750

Asp Met Val Asp Ser Pro Gln Leu Ala Thr Leu Ala Asp Glu Val Ser
        755                 760                 765

Ala Ser Leu Ala Lys Gln Gly Leu
    770                 775

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gcccttctgg cctggagggg                                                 20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tggcccttct ggcctggagg                                                 20

<210> SEQ ID NO 309
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 309
gctggtgctt caggttctca                                              20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tcaggtcaac tggtttgtag                                              20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
tgctcaggtc aactggtttg                                              20

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
ttgctcaggt caactggttt                                              20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ccttgctcag gtcaactggt                                              20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
ccctcttcta catggagggg                                              20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 315
ttctccctct tctacatgga                                                20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
cttctccctc ttctacatgg                                                20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
ccttctccct cttctacatg                                                20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
caaatccttt gttgctgcca                                                20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
tcaaatcctt tgttgctgcc                                                20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tggctccacg aacacaccaa                                                20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
gtggctccac gaacacacca            20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
tgtggctcca cgaacacacc            20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
ctgtggctcc acgaacacac            20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
cctgtggctc cacgaacaca            20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gcctgtggct ccacgaacac            20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
tgcctgtggc tccacgaaca            20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ctgcctgtgg ctccacgaac                                               20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
tctgcctgtg gctccacgaa                                               20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gtctgcctgt ggctccacga                                               20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
cgtctgcctg tggctccacg                                               20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
tcgtctgcct gtggctccac                                               20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
atcgtctgcc tgtggctcca                                               20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
catcgtctgc ctgtggctcc                                              20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
acatcgtctg cctgtggctc                                              20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gacatcgtct gcctgtggct                                              20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
tgacatcgtc tgcctgtggc                                              20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ttgacatcgt ctgcctgtgg                                              20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gttgacatcg tctgcctgtg                                              20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
aggttgacat cgtctgcctg 20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
aaggttgaca tcgtctgcct 20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
caaggttgac atcgtctgcc 20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
acaaggttga catcgtctgc 20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
cacaaggttg acatcgtctg 20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
acacaaggtt gacatcgtct 20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
cacacaaggt tgacatcgtc 20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
tcacacaagg ttgacatcgt                                                20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
ctcacacaag gttgacatcg                                                20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
actcacacaa ggttgacatc                                                20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
cactcacaca aggttgacat                                                20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
acactcacac aaggttgaca                                                20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
cacactcaca caaggttgac                                                20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
tcacactcac acaaggttga                                              20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
gtcacactca cacaaggttg                                              20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
cgtcacactc acacaaggtt                                              20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
ccgtcacact cacacaaggt                                              20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
ccccgtcaca ctcacacaag                                              20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
cccttctccc acaggctgcc                                              20

```
<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
catcaaggtc agtcttttct                                                   20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
ccaaccttca gaactcaata                                                   20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
tccaaccttc agaactcaat                                                   20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
ttccaacctt cagaactcaa                                                   20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gttccaacct tcagaactca                                                   20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
agttccaacc ttcagaactc                                                   20

<210> SEQ ID NO 364
```

<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 364
cagttccaac cttcagaact                   20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 365
gcagttccaa ccttcagaac                   20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 366
gtcccaggtc tgcaaagtgg                   20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 367
aagtcccagg tctgcaaagt                   20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 368
aaagtcccag gtctgcaaag                   20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 369
ggcacaagtc cttacaaaga                   20

<210> SEQ ID NO 370
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
aggcacaagt ccttacaaag                                              20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
tcaccctcag tatggagtag                                              20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
ttcaccctca gtatggagta                                              20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
tttcaccctc agtatggagt                                              20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
atttcaccct cagtatggag                                              20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
aatttcaccc tcagtatgga                                              20

<210> SEQ ID NO 376
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 376
ccttaatttc accctcagta                                                     20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
cccttaattt caccctcagt                                                     20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
tcccttaatt tcaccctcag                                                     20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
ttcccttaat ttcaccctca                                                     20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
cttcccttaa tttcaccctc                                                     20

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
actcttgtgc ctggactttg                                                     20

<210> SEQ ID NO 382
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 382
cactcttgtg cctggacttt                                              20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
ccactcttgt gcctggactt                                              20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
cccactcttg tgcctggact                                              20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
tcccactctt gtgcctggac                                              20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
gtcccactct tgtgcctgga                                              20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
ggtcccactc ttgtgcctgg                                              20

<210> SEQ ID NO 388
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 388
gggtcccact cttgtgcctg                                                   20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
gtgccctggc tcacatctgt                                                   20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
agtgccctgg ctcacatctg                                                   20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
cagtgccctg gctcacatct                                                   20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
gcagtgccct ggctcacatc                                                   20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
agcagtgccc tggctcacat                                                   20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 394
tgagcagtgc cctggctcac                                              20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gcatggcttc cagctgggac                                              20

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
agctgctcca gcagaacaga                                              20

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
tatatgttca gctgctccag                                              20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gtatatgttc agctgctcca                                              20

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
tgtatatgtt cagctgctcc                                              20

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
gcagggcaac atctatgtat                                              20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
ggcagggcaa catctatgta                                              20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
gggcagggca acatctatgt                                              20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
tcactctggt gaatccaagc                                              20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
gtcactctgg tgaatccaag                                              20

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
agtcactctg gtgaatccaa                                              20

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
tagtcactct ggtgaatcca                                               20

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
atagtcactc tggtgaatcc                                               20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
catagtcact ctggtgaatc                                               20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
tcatagtcac tctggtgaat                                               20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
ctggtctctg ttgggtccca                                               20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
atcctgtgct tcaggccttc                                               20

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
aatcctgtgc ttcaggcctt                                           20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ctaatcctgt gcttcaggcc                                           20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
cctaatcctg tgcttcaggc                                           20

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
tcctaatcct gtgcttcagg                                           20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
gtcctaatcc tgtgcttcag                                           20

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
agtcctaatc ctgtgcttca                                           20

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
cagtcctaat cctgtgcttc                                         20

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
tcagtcctaa tcctgtgctt                                         20

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
ttcagtccta atcctgtgct                                         20

<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
cttcagtcct aatcctgtgc                                         20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
gcttcagtcc taatcctgtg                                         20

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
ggagttgtaa gcctcctttg                                         20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
gctctggtca aggctttggg                                         20

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
tgctctggtc aaggctttgg                                          20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
gtgctctggt caaggctttg                                          20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ggtgctctgg tcaaggcttt                                          20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
tgaggtgctc tggtcaaggc                                          20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
tttctcatgg cagcagatgg                                          20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
tgctgagttt ctttaggcag                                          20

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
ctgctgagtt tctttaggca                                        20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
gctgctgagt tctttaggc                                         20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
ggctgctgag tttctttagg                                        20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
aggctgctga gtttctttag                                        20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
gaggctgctg agtttcttta                                        20

<210> SEQ ID NO 436
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
tgaggctgct gagtttcttt                                        20

```
<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
ctgccaagtc cctcagggtt                                                      20

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
actgccaagt ccctcagggt                                                      20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
tactgccaag tccctcaggg                                                      20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
ctactgccaa gtccctcagg                                                      20

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
tctactgcca agtccctcag                                                      20

<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
ttctactgcc aagtccctca                                                      20

<210> SEQ ID NO 443
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
tttctactgc caagtccctc                                                   20

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
atttctactg ccaagtccct                                                   20

<210> SEQ ID NO 445
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
gatttctact gccaagtccc                                                   20

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
ggatttctac tgccaagtcc                                                   20

<210> SEQ ID NO 447
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
tggatttcta ctgccaagtc                                                   20

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
ctggatttct actgccaagt                                                   20

<210> SEQ ID NO 449
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
atcttaggct ggccccaaga                                              20

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
tgatcttagg ctggccccaa                                              20

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
tttatctgcc agcactgatc                                              20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
atttatctgc cagcactgat                                              20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
aatttatctg ccagcactga                                              20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
tatatcctat ctagcccacc                                              20

<210> SEQ ID NO 455
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 455
gtatatccta tctagcccac                                                   20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
agtatatcct atctagccca                                                   20

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
aaccccaagg gcctctaact                                                   20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
gcaaccagat gtccatattc                                                   20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
ggcttaggac ccctgaaaga                                                   20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
ggcatgattg tgggcttagg                                                   20

<210> SEQ ID NO 461
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 461
aggcatgatt gtgggcttag                                                     20

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
gtaacccttt tcaaagctga                                                     20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
ggtaaccctt ttcaaagctg                                                     20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
gggtaaccct tttcaaagct                                                     20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
agggtaaccc ttttcaaagc                                                     20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
cagggtaacc cttttcaaag                                                     20

<210> SEQ ID NO 467
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 467
ccagggtaac cctttcaaa                                                    20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
cccagggtaa ccctttcaa                                                    20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
gcccagggta acccttttca                                                   20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
tgctcaacat ggcaaactca                                                   20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tcctgctcaa catggcaaac                                                   20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
gtcctgctca acatggcaaa                                                   20

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 473
cccgtacgtc ccagcgtgat                                               20

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
ggccagcgtc cgtgtcaccc                                               20

<210> SEQ ID NO 475
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
ccatgcgagc tgataaa                                                  17

<210> SEQ ID NO 476
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
gcatcgtcag cttacct                                                  17

<210> SEQ ID NO 477
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
ctttgctttt actgacc                                                  17

<210> SEQ ID NO 478
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
tcaactggtt tgtagac                                                  17

<210> SEQ ID NO 479
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 479
ccttgctcag gtcaactggt                                                    20

<210> SEQ ID NO 480
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
ggttgacatc gtctgcctgt                                                    20

<210> SEQ ID NO 481
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
gtcccactct tgtgcctgga                                                    20

<210> SEQ ID NO 482
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
gacatcgtct gcctgtggct                                                    20

<210> SEQ ID NO 483
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
cccactcttg tgcctggact                                                    20

<210> SEQ ID NO 484
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
gtcccaggtc tgcaaagtgg                                                    20

<210> SEQ ID NO 485
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 485
gtctgcctgt ggctccacga                                                  20

<210> SEQ ID NO 486
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
agtcactctg gtgaatccaa                                                  20

<210> SEQ ID NO 487
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
cggaagguca gcuugugggu                                                  20

<210> SEQ ID NO 488
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
gugucuccaa ugccugcuuc uucagcuggu                                       30

<210> SEQ ID NO 489
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
ucaacugguu uguagacuau                                                  20

<210> SEQ ID NO 490
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
uaugauggau guugccuaau                                                  20

<210> SEQ ID NO 491
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
```

```
gggcucagcc auccugguuc                                          20
```

<210> SEQ ID NO 492
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492

```
uuuccuccgc cagggacg                                            18
```

<210> SEQ ID NO 493
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493

```
gucuuugcuu uuacugacca                                          20
```

<210> SEQ ID NO 494
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494

```
uuuuuuguca ucgcuuccag                                          20
```

<210> SEQ ID NO 495
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495

```
accaguugac cugagcaagg                                          20
```

<210> SEQ ID NO 496
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496

```
acaggcagac gaugucaacc                                          20
```

<210> SEQ ID NO 497
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
uccaggcaca agaguggggac                                    20

<210> SEQ ID NO 498
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
agccacaggc agacgauguc                                     20

<210> SEQ ID NO 499
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
aguccaggca caagaguggg                                     20

<210> SEQ ID NO 500
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
ccacuuugca gaccugggac                                     20

<210> SEQ ID NO 501
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
ucguggagcc acaggcagac                                     20

<210> SEQ ID NO 502
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
uuggauucac cagagugacu                                     20

<210> SEQ ID NO 503
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
guccacuaac cuuucaggcc agcgu                               25

```
<210> SEQ ID NO 504
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
gcaucgucag cuuaccuugg cuuuu                                           25

<210> SEQ ID NO 505
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
ccaugcgagc ugauaaaaua uaaaa                                           25

<210> SEQ ID NO 506
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
gacuauuugc accuggagau gagag                                           25
```